(12) United States Patent
Lee et al.

(10) Patent No.: US 10,426,762 B2
(45) Date of Patent: *Oct. 1, 2019

(54) INHIBITORS OF HEPATITIS C VIRUS POLYMERASE

(71) Applicant: COCRYSTAL DISCOVERY, INC., Bothell, WA (US)

(72) Inventors: Sam S. Lee, Lynnwood, WA (US); Wang Shen, San Mateo, CA (US); Xiaoling Zheng, Fremont, CA (US); Irina C. Jacobson, Sammamish, WA (US)

(73) Assignee: COCRYSTAL PHARMA, INC., Bothell, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/618,418

(22) Filed: Jun. 9, 2017

(65) Prior Publication Data

US 2017/0273962 A1   Sep. 28, 2017

Related U.S. Application Data

(63) Continuation of application No. 14/407,993, filed as application No. PCT/US2013/046758 on Jun. 20, 2013, now Pat. No. 9,707,215.

(60) Provisional application No. 61/662,078, filed on Jun. 20, 2012.

(51) Int. Cl.
| | | |
|---|---|---|
| *C07D 417/14* | (2006.01) | |
| *A61K 31/4436* | (2006.01) | |
| *A61K 45/06* | (2006.01) | |
| *A61K 31/4355* | (2006.01) | |
| *A61K 31/4439* | (2006.01) | |
| *A61K 31/444* | (2006.01) | |
| *A61K 31/4709* | (2006.01) | |
| *A61K 31/497* | (2006.01) | |
| *A61K 31/5025* | (2006.01) | |
| *A61K 31/519* | (2006.01) | |
| *C07D 409/04* | (2006.01) | |
| *C07D 409/14* | (2006.01) | |
| *C07D 413/14* | (2006.01) | |
| *C07D 471/04* | (2006.01) | |
| *C07D 487/04* | (2006.01) | |
| *C07D 491/048* | (2006.01) | |

(52) U.S. Cl.
CPC ...... *A61K 31/4436* (2013.01); *A61K 31/4355* (2013.01); *A61K 31/444* (2013.01); *A61K 31/4439* (2013.01); *A61K 31/4709* (2013.01); *A61K 31/497* (2013.01); *A61K 31/5025* (2013.01); *A61K 31/519* (2013.01); *A61K 45/06* (2013.01); *C07D 409/04* (2013.01); *C07D 409/14* (2013.01); *C07D 413/14* (2013.01); *C07D 417/14* (2013.01); *C07D 471/04* (2013.01); *C07D 487/04* (2013.01); *C07D 491/048* (2013.01)

(58) Field of Classification Search
CPC .................................................... C07D 417/14
USPC ...................................... 546/269.7; 514/342
See application file for complete search history.

(56) References Cited

U.S. PATENT DOCUMENTS

| | | |
|---|---|---|
| 6,350,458 B1 | 2/2002 | Modi |
| 6,881,741 B2 | 4/2005 | Chan Chun Kong et al. |
| 6,887,877 B2 | 5/2005 | Chan Chun Kong et al. |
| 6,936,629 B2 | 8/2005 | Chan Chun Kong et al. |
| 7,402,608 B2 | 7/2008 | Chan Chun Kong et al. |
| 7,569,600 B2 | 8/2009 | Denis et al. |
| 8,771,665 B2 | 7/2014 | Lee et al. |
| 2003/0181798 A1 | 9/2003 | Al-Ali |
| 2007/0177298 A1 | 8/2007 | Jaatinen et al. |
| 2007/0293484 A1 | 12/2007 | Guan et al. |
| 2009/0018456 A1 | 1/2009 | Hung |
| 2009/0136448 A1 | 5/2009 | Corfield et al. |

(Continued)

FOREIGN PATENT DOCUMENTS

| | | |
|---|---|---|
| GB | 2463784 A | 3/2010 |
| WO | WO-1996/029075 A1 | 9/1996 |

(Continued)

OTHER PUBLICATIONS

Appleby et al., "Viral RNA polymerase inhibitors", Chapter 23 (pp. 527-546) In: Cameron et al. (eds.), Viral Genome Replication, Springer Science+Business Media (2009).

(Continued)

*Primary Examiner* — Patricia L Morris
(74) *Attorney, Agent, or Firm* — Marshall, Gerstein & Borun LLP

(57) ABSTRACT

The present invention provides, among other things, compounds represented by the general Formula I: and pharmaceutically acceptable salts thereof, wherein X, Y, $R^2$, and $R^3$ are as defined in classes and subclasses herein and compositions (e.g., pharmaceutical compositions) comprising such compounds, which compounds are useful as inhibitors of hepatitis C virus polymerase, and thus are useful, for example, as medicaments for the treatment of HCV infection.

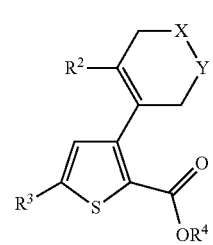

8 Claims, No Drawings

(56) References Cited

U.S. PATENT DOCUMENTS

2010/0145236 A1  6/2010  Greenberg et al.
2011/0201382 A1  8/2011  Hsiao
2012/0156933 A1  6/2012  Kreger et al.

FOREIGN PATENT DOCUMENTS

| | | |
|---|---|---|
| WO | WO-2002/100846 A1 | 12/2002 |
| WO | WO-2002/100851 A2 | 12/2002 |
| WO | WO-2004/052879 A1 | 6/2004 |
| WO | WO-2004/052885 A1 | 6/2004 |
| WO | WO-2006/072347 A2 | 7/2006 |
| WO | WO-2006/119646 A1 | 11/2006 |
| WO | WO-2008/017688 A1 | 2/2008 |
| WO | WO-2008/043791 A2 | 4/2008 |
| WO | WO-2008/058393 A1 | 5/2008 |
| WO | WO-2008/059042 A1 | 5/2008 |
| WO | WO-2008/125599 A1 | 10/2008 |
| WO | WO-2009/000818 A1 | 12/2008 |
| WO | WO-2012/083105 A1 | 6/2012 |

OTHER PUBLICATIONS

Bartenschlager et al., Replication of the hepatitis C virus in cell culture, Antiviral Res., 60(2):91-102 (2003).
Biswal et al., Crystal structures of the RNA-dependent RNA polymerase genotype 2a of hepatitis C virus reveal two conformations and suggest mechanisms of inhibition by non-nucleoside inhibitors, J. Biol. Chem., 280(18):18202-10 (2005).
Chan et al., Discovery of thiophene-2-carboxylic acids as potent inhibitors of HCV NS5B polymerase and HCV subgenomic RNA replication. Part 1: Sulfonamides, Bioorg. Med. Chem. Letter. 14(3):793-6 (2004).
Ghany et al., An update on treatment of genotype 1 chronic hepatitis C virus infection: 2011 practice guideline by the American Association for the Study of Liver Diseases, Hepatology, 54(4):1433-44 (2011).
Gubert et al., A convenient synthesis of parent and 2-substituted octahydro-2H-pyrazino[1,2-a]-pyrazines, Synthesis, 22(44):318 (1991).
Hodgson, The Sandmeyer reaction, Chem. Rev., 40(2):251-77 (1947).
Huang et al., "Hepatitis C virus related assays", Chapter 2, pp. 56-57, In: Tan et al. (eds.), Hepatitis C: Antiviral Drug Discovery and Development, Caister Academic Press (2011).
International Preliminary Report on Patentability, International Application No. PCT/US2013/046758, dated Dec. 23, 2014.
International Search Report and Written Opinion, International Application No. PCT/US2013/046758, dated Nov. 15, 2013.
Li et al., Allosteric inhibitors of hepatitis C polymerase: discovery of potent and orally bioavailable carbon-linked dihydropyrones, J. Med. Chem., 50(17):3969-72 (2007).
Li et al., Discovery of (R)-6-cyclopentyl-6-(2-(2,6-diethylpyridin-4-yl)ethyl)-3-((5,7-dimethyl-[1,2,4]triazolo[1,5-a]pyrimidin-2-yl)methyl)-4-hydroxy-5,6-dihydropyran-2-one (PF-00868554) as a potent and orally available hepatitis C virus polymerase inhibitor, J. Med. Chem., 52(5):1255-8 (2009).
Lohmann et al., Replication of subgenomic hepatitis C virus RNAs in a hepatoma cell line, Science, 285(5424):110-3 (1999).
McKercher et al., Specific inhibitors of HCV polymerase identified using an NS5B with lower affinity for template/primer substrate, Nucleic Acids Res., 32(2):422-31 (2004).
Morrison et al., In HCV, protease race heats up with combo therapy looming, In Vivo: The Business & Medicine Report, 27(5):42-7 (May 2009).
Powdrill et al., Inhibitors of the Hepatitis C Virus RNA-Dependent RNA Polymerase NS5B, Viruses, 2(10):2169-95 (2010).
Rautio et al., Prodrugs: design and clinical applications, Nat. Rev. Drug Discov., 7(3):255-70 (2008).
Suzuki et al., Recent advances in the cross-coupling reactions of organoboron derivatives with organic electrophiles, 1995-1998, J. Organometallic Chem., 576:147-68 (1999).
Tan (ed.), Hepatitis C Viruses: Genomes and Molecular Biology, Norfolk, UK: Horizon Bioscience (2006).
Wang et al., Non-nucleoside analogue inhibitors bind to an allosteric site on HCV NS5B polymerase. Crystal structures and mechanism of inhibition, J. Biol. Chem., 278(11):9489-95 (2003).
Woerz et al., Hepatitis C virus replicons: dinosaurs still in business?, J. Viral Hepat., 16(1):1-9 (2009).
Yang et al., Cyclic amide bioisosterism: strategic application to the design and synthesis of HCV NS5B polymerase inhibitors, Bioorg. Med. Chem. Lett., 20(15):4614-9 (2010).

INHIBITORS OF HEPATITIS C VIRUS POLYMERASE

The invention provides compounds, compositions, and methods for the treatment of hepatitis C virus infection in humans.

BACKGROUND

Hepatitis C virus (HCV) is an enveloped, positive-sense, single-stranded RNA virus, of the genus *Hepacivirus*, belonging to the family Flaviviridae. Infection by HCV is a leading cause of liver disease and cirrhosis in humans. Transmission occurs primarily by way of percutaneous exposure to infected blood, typically involving use of injected drugs or injury with objects contaminated with blood, but is also associated with sexual contact with infected partners. Thanks to viral testing, risk of transmission by blood transfusion or by transplant is extremely low. Infection is often asymptomatic, or symptoms are mild, and about 15-20% of infected persons are able to clear the virus without treatment. However, infection in the remaining 80-85% of infected persons develops into persistent infection, which may be life-long, causing liver disease, which can lead to cirrhosis and hepatocellular carcinoma. HCV infection is the most common chronic blood-borne disease in the United States, affecting about 4 million people and causing about 12,000 deaths per year. "Evaluation of Acute Hepatitis C Infection Surveillance—United States, 2008," *MMWR*, Nov. 5, 2010, 59(43). Approximately 170 million persons around the world have chronic hepatitis C infection. Chen et al., *Int J Med Sci*, 2006, 3(2):47-52. Personal consequences of HCV infection include decreased life expectancy, chronic debilitating liver disease and possibly liver cancer, and risk of infection of sexual partners and health care workers. Economic consequences of chronic HCV infection in the United States are exceedingly large. Direct medical costs have been estimated at $10.7 billion per year for the 10-year period 2010-2019, with societal costs projected to be $54.2 billion, and the cost of morbidity from disability projected to be $21.3 billion. Id.

The hepatitis C virus has been intensively studied, and much is known about its genetics and biology. For an overview of this subject, see Tan, Ed., *Hepatitis C Viruses: Genomes and Molecular Biology*, Horizon Bioscience, Norfolk, UK (2006). HCV has a simple genome that resides in a single open reading frame of about 9.6 kb. The genome is translated in the infected cell to yield a single polyprotein consisting of about 3000 amino acids, which is then proteolytically processed by host and viral enzymes to produce at least 10 structural and non-structural (NS) proteins. The virus is diversified in infected humans into 16 different antigenically and/or genetically identifiable subtypes or genotypes, some of which are further subdivided into subtypes.

HCV rapidly mutates as it replicates, and is believed to exist as a viral quasispecies, meaning that it mutates rapidly as it replicates to generate many competing genetic varieties of the virus having comparable evolutionary fitness. This intrinsic generation of many varieties in a single infected person makes it very difficult to isolate a single variety for development of a vaccine, and is believed to be associated with the difficulty in developing a vaccine, development of resistance of the virus to specific pharmaceuticals, and persistence of the virus in the host. It is possible that the virus able to develop into immunologically distinct quasispecies under the pressure of the immune response of the host, thereby allowing it to survive and persist.

Another factor making it difficult to develop treatments for HCV infection is the narrow range of hosts and a notoriously difficult problem of propagating the virus in cell culture. Most research has been done using pseudoparticle systems. Pseudoparticles consist primarily of nucleocapsids surrounded by a lipid envelope and contain HCV glycoprotein complexes. These pseudoparticles have been used to elucidate the early stages of the viral replication cycle and receptor binding, and to study neutralizing antibodies. Notwithstanding, pseudoparticles have a significant limitation in that they cannot recapitulate the full replication cycle. Other systems described for investigation of HCV include culture of subgenomic RNAs in Huh-7 cells, and culture in primary human hepatocytes, and surrogate models such as the bovine viral diarrhea virus (BVDV).

Significant research has also been done in synthetic RNA replicons, which self-amplify in human hepatoma cells and recapitulate much, but not all, of the HCV replication cycle. Heretofore, such replicons have been subgenomic, and have also been unable to yield infectious viral particles. Moreover, such a replicon system appears to function only using the 1b genotype of HCV (HCV1b). More recently, HCV cell culture has become possible through the isolation of the JFH-1 clone (HCV 2a). While its uniqueness remains incompletely understood, JFH-1 replicates to high levels in Huh-7 (hepatocellular carcinoma) cells and other cell types in culture, and produces infectious particles. Serial passage of JFH-1 has caused it to become genetically conditioned to cell culture conditions and it may no longer be representative of clinical isolates of the virus, but the viral particles are apparently functional virions, insofar as they are infectious in culture and in inoculated animals bearing human liver xenografts. Apparently, the efficiency of JFH-1 replication depends significantly upon the NS5B gene of the clone. Replacement with NS5B genes from other genotypes is difficult. Woerz et al., 2009, *J Viral Hepat*, 16(1):1-9. Other replicon systems have been developed with various replication markers and for different HCV genotypes, including HCV 1a and HCV 2a. See, Huang et al., "Hepatitis C Virus-related Assays," Chapter 2 in *Hepatitis C: Antiviral Drug Discovery and Development*, S-L Tan and Y He, eds., Caister Academic Press (2011), at pp 56-57.

Currently there no treatment that is effective to cure HCV infection. Palliative treatments include reduction of circulating virus. This may be accomplished through blood filtration, e.g., by double filtration plasmapheresis, lectin affinity plasmapheresis, or a combination of the two methods, but this treatment requires repetitive application and may best be used in conjunction with standard-of-care pharmaceutical treatment.

Approved pharmaceutical treatments include injection of interferon, typically pegylated versions including peginterferon alfa-2a (Pegasys®) or peginterferon alfa-2b (PegIntron®). Clinical use of pegylated interferon was approved by FDA in 2001. Ribavirin (e.g., Ribasphere®, Virazole®, Copegus®, Rebetol®), a guanosine analog that has broad-spectrum activity against viruses, is used to treat HCV infection, but appears not to be effective against HCV when used as a monotherapy. Current standard-of-care therapy includes administering peginterferon in combination with ribavirin. This regimen is limited because of side effects (e.g., flu-like symptoms, leukopenia, thrombocytopenia, depression, and anemia) and only moderate efficacy; success is dependent in part on the genotype predominating in the patient. See Ghany et al., *Hepatology*, 2011, 54(4):1433-44.

Numerous alternative pharmaceutical approaches to treatment of HCV infection are now in research and development. For example, recombinant and modified interferon molecules have also been the subject of development programs, including, e.g., recombinant alfa interferon (BLX-883; Locteron®; Biolex/Octoplus) and albinterferon alfa 2b (Zalbin®; Human Genome Sciences).

The HCV protein NS3-4A, a serine protease, which is an enzyme essential for replication of the virus, has been the subject of intensive pharmaceutical research. A number of companies are seeking to develop inhibitors of this enzyme. Some of the earlier molecules are telaprevir (Incivek®, VX-950; Vertex) and boceprevir (Victrelis®, SCH503034; Merck & Co.), each of which has been approved for use. These various molecules may be useful as single therapeutics, but some are also being investigated in combination with interferon/ribavirin therapies and/or compounds that may be effective against HCV via other mechanisms. However, viral resistance to individual protease inhibitors is believed to occur easily. Morrison and Haas, *In Vivo*, May 2009, 42-47.

The NS5B polymerase of HCV is also undergoing study. This protein is an RNA-dependent RNA polymerase (RdRp), which is essential for the synthesis of viral RNA, and consequently, for the completion of the viral life cycle. An overview of the NS5B protein is available at Chapter 10 of Tan, supra.

Many groups are currently working on developing inhibitors of the NS5B polymerase. Wang et al. (*J Biol Chem* 2003, 278(11), 9489-95) report that certain non-nucleoside molecules bind to an allosteric site on the polymerase, interfering with a conformational change required for activity. Biswal et al. (*J Biol Chem*, 2005, 280(18), 18202-10) report crystal structures indicating that the NS5B polymerase exhibits two conformations, with a gross structure resembling the classical fingers, palm, and thumb domains of other polymerases. This paper also show cocrystal structures for two inhibitors bound to the polymerase, and offers hypotheses on the mechanism of polymerase inhibition. Li et al. (*J Med Chem*, 2007, 50(17):3969-72) report on some dihydropyrone compounds that are said to be orally available allosteric inhibitors. See also Li et al., *J Med Chem*, 2009, 52:1255-58.

Inhibitors of NS5B may be classified broadly into three groups: nucleoside analogues (NI), non-nucleoside analogues (NNI), and pyrophosphate compounds (PPi). See, Powdrill et al., *Viruses*, 2010, 2:2169-95 and Appleby et al., "Viral RNA Polymerase Inhibitors," Chapter 23 in *Viral Genome Replication*, Cameron et al., eds., Springer Science+Business Media 2009.

Nucleoside analogue compounds (NI), which bind at the enzyme active site and compete with natural nucleoside triphosphates, interfere with viral RNA synthesis. A number of these compounds have entered clinical trials. Nucleoside inhibitors include, for example, IDX184 (Idenix), RG7128 (RO5024048; Pharmasset/Roche).

Non-nucleoside inhibitors, by contrast, appear to bind at allosteric sites on NS5B—of which about 4 are known. Id. NNI compounds include, for example, filibuvir (Pfizer), tegobuvir (GS 9190; Gilead), VX-222 (Vertex), A-837093 (Abbott), ABT-072 (Abbott), ABT-333 (Abbott), and PF-868554 (Pfizer).

Also among the non-nucleoside inhibitors of NS5B are a series of thiophene-2-carboxylic acids and derivatives thereof. See, e.g., Chan et al., *Bioorg Med Chem Lett*, 2004, 14, 793-96; International patent publications WO 02/100846 A1, WO 02/100851 A2, WO 2004/052879 A2, WO 2004/052885 A1, WO 2006/072347 A2, WO 2006/119646 A1, WO 2008/017688 A1, WO 2008/043791 A2, WO 2008/058393 A1, WO 2008/059042 A1, WO 2008/125599 A1, and WO 2009/000818 A1. See also U.S. Pat. Nos. 6,881,741 B2, 7,402,608 B2, and 7,569,600 B2. See also, Yang et al., *Bioorg Med Chem Lett* 2010, 20, 4614-19, relating to some bioisosteres of such compounds. Other similar compounds are described, for example, in U.S. Pat. Nos. 6,887,877 B2 and 6,936,629 B2.

Pyrophosphate compounds (PPi) mimic natural pyrophosphates released during nucleotidyl transfer reactions.

Various NI and NNI compounds have shown safety or efficacy in clinical trials, but none has yet reached approval for use in treating humans. PPi compounds, by contrast, are generally in the investigational stage.

There remains a profound need for more effective pharmaceutical therapies, including medicaments that are useful as single agents or in combination with other active agents, for the treatment of hepatitis C infection in humans.

SUMMARY OF THE INVENTION

The present invention provides compounds represented by the general Formula I:

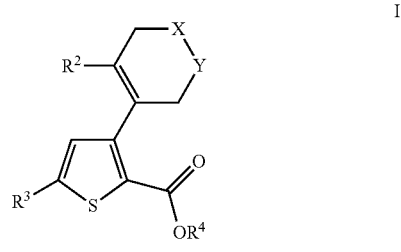

and salts (e.g., pharmaceutically acceptable salts) thereof, wherein X, Y, $R^2$, $R^3$, and $R^4$ are as defined in classes and subclasses herein and compositions (e.g., pharmaceutical compositions) comprising such compounds, which compounds are useful as inhibitors of hepatitis C virus polymerase, and thus are useful, for example, as medicaments for the treatment of HCV infection.

In certain other embodiments, the invention provides pharmaceutical compositions comprising a compound of the invention, wherein the compound is present in an amount effective to inhibit HCV polymerase activity. In certain other embodiments, the invention provides pharmaceutical compositions comprising an inventive compound and optionally further comprising an additional therapeutic agent. In yet other embodiments, the additional therapeutic agent is an agent for the treatment of HCV infection.

In yet another aspect, the present invention provides methods for inhibiting HCV polymerase activity in a subject or a biological sample, comprising administering to the subject, or contacting the biological sample with an effective inhibitory amount of a compound of the invention. In still another aspect, the present invention provides methods for treating any disorder constitutively associated with HCV infection or replication or involving HCV polymerase activity, comprising administering to a subject in need thereof a therapeutically effective amount of a compound of the invention.

DETAILED DESCRIPTION

In another aspect, the invention provides compounds according to Formula 1:

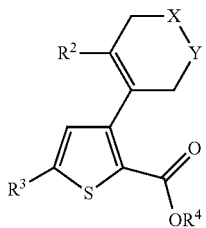

and salts and solvates thereof,
wherein:
one of X and Y is —CH$_2$— and the other is —NR$^1$—;
R$^1$ is —C$_{5-6}$hydroxyalkyl, —S(O)$_2$—C$_{0-4}$alkyl-R$^O$, —C$_{0-4}$alkyl-R$^O$, —C$_{0-3}$alkyl-C(O)—C$_{0-4}$alkyl-R$^O$, —C$_{0-3}$alkyl-C(O)O—C$_{0-4}$alkyl-R$^O$;
wherein:
R$^M$ and R$^N$ are independently hydrogen, —C$_{1-4}$alkyl, or R$^M$ and R$^N$ together with the atoms to which they are attached can form a 4- to 6-membered ring; and
R$^O$ is (a) a 5- to 7-membered cycloalkyl or heterocycloalkyl group, substituted with a —C$_{1-3}$alkyl, aryl, —O-aryl, or —NR$^M$R$^N$ moiety, (b) a 7-membered cycloalkyl or heterocycloalkyl group [optionally substituted with a hydroxyl], or (c) a 6- to 10-membered aryl or a 5- to 10-membered heteroaryl group, in each case monocyclic or bicyclic, and substituted with one to three moieties independently selected from —C$_{1-4}$alkyl, halogen, —NR$^M$R$^N$, —C$_{1-4}$haloalkyl, —C$_{1-4}$alkoxy, —C$_{1-4}$hydroxyalkyl, cyano, —O-aryl, and aryl, provided that at least one such substitution is —C$_{1-4}$alkoxy, —C$_{1-4}$hydroxyalkyl, cyano, or —O-aryl;
R$^2$ is —C$_{1-5}$alkyl optionally substituted with 1-5 halogens, —C$_{1-5}$alkoxy, —C$_{5-7}$cycloalkyl-C$_{0-3}$alkyl in which the alkyl is optionally substituted with 1-3 halogens, —C$_{1-4}$alkyl-C$_{3-5}$cycloalkyl, or phenyl optionally substituted with 1 or 2 halogens or —C$_{1-3}$alkyl groups optionally substituted with 1-3 halogens;
R$^3$ is —R$^A$—R$^B$ or halo;
wherein R$^A$ is ethynyl or is a phenyl or pyridinyl moiety optionally substituted with one or two Z, in which each Z is independently halogen, —C$_{1-3}$alkyl, —C$_{1-3}$haloalkyl, —C$_{1-3}$alkoxy, or cyano; and
wherein R$^B$ is hydrogen, —C$_{1-6}$alkyl, —C$_{0-3}$alkyl-NR$^M$R$^N$, —NHC$_{1-3}$alkyl-R$^Q$, —N(R$^U$)C(O)—R$^Q$, —C(O)NR$^U$R$^Q$, carboxyl, —C$_{2-6}$alkenyl, —C$_{2-6}$alkynyl, —C$_{0-3}$alkyl-C$_{3-6}$cycloalkyl, —C$_{1-4}$alkoxy, -methyl-(C$_{1-4}$alkoxy)$_{1-2}$, —C$_{0-3}$alkyl-NR$^S$R$^T$, —C$_{3-7}$cycloalkyl-C$_{0-3}$alkyl-R$^Q$, —C$_{0-4}$alkyl-R$^Q$, —C$_{2-6}$alkynylR$^Q$, or —C$_{2-4}$alkenyl-R$^Q$;
wherein R$^Q$ is a 5- to 9-membered monocyclic or bicyclic aryl or heteroaryl or a 3- to 7-membered cycloalkyl or heterocycloalkyl, optionally substituted with one or two R$^Z$, in which each R$^Z$ is independently —C$_{1-3}$alkyl, —C$_{1-3}$alkoxy, or —NR$^M$R$^N$;
R$^S$ and R$^T$ are each independently hydrogen or —C$_{1-4}$alkyl, or one of R$^S$ and R$^T$ is hydrogen and the other is —C(O)-5- to 9-membered aryl or heteroaryl; and
R$^U$ is hydrogen or —C$_{1-4}$alkyl;
provided that, when R$^A$ is phenyl, then R$^B$ appears at the para or meta position relative to the thiophene moiety; and R$^4$ is hydrogen, —C$_{1-4}$alkyl, —C$_{1-4}$alkyl-OC(O)O—C$_{1-4}$alkyl, —C$_{1-4}$alkyl-OC(O)—C$_{1-4}$alkyl, —C$_{1-4}$alkyl-OC(O)O—C$_{3-6}$cycloalkyl, 5-methyl-2-oxo-[1,3]dioxol-4-ylmethyl-, —C$_{0-3}$alkyl-C$_{5-6}$aryl, or —C$_{0-4}$alkyl-NR$^V$R$^W$; and
R$^V$ and R$^W$ are independently hydrogen or —C$_{1-4}$alkyl.

In another aspect, the invention provides compounds according to Formula I:

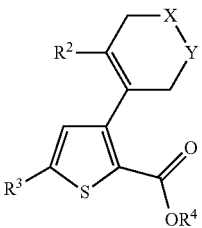

and salts and solvates thereof,
wherein:
one of X and Y is —CH$_2$— and the other is —NR$^1$—;
R$^1$ is hydrogen, —C$_{1-4}$alkyl, —C$_{1-6}$hydroxyalkyl, —C$_{1-4}$haloalkyl, —C$_{1-4}$alkyl-O—C$_{1-4}$alkyl, —S(O)$_2$—C$_{0-4}$alkyl-R$^O$, —C$_{0-4}$alkyl-S(O)$_2$—C$_{1-4}$alkyl, —C$_{0-4}$alkyl-S(O)$_2$—NR$^M$R$^N$, —C$_{2-4}$alkyl-NR$^M$R$^N$, —C$_{0-4}$alkyl-R$^O$, —C$_{0-3}$alkyl-C(O)C$_{1-4}$alkyl, —C$_{0-3}$alkyl-C(O)—C$_{1-4}$hydroxyalkyl, —C$_{0-3}$alkyl-C(O)—C$_{0-4}$alkyl-R$^O$, —C(O)O—C$_{1-4}$alkyl, —C$_{0-3}$alkyl-C(O)O—C$_{0-4}$alkyl-R$^O$, —C$_{0-4}$alkyl-C(O)OH, or —C$_{0-3}$alkyl-C(O)—C$_{0-4}$alkyl-NR$^M$R$^N$;
wherein:
R$^M$ and R$^N$ are independently hydrogen, —C$_{1-4}$alkyl, or R$^M$ and R$^N$ together with the atoms to which they are attached can form a 4- to 6-membered ring; and
R$^O$ is a 5- to 7-membered cycloalkyl or heterocycloalkyl group, optionally substituted with a hydroxyl, —C$_{1-3}$alkyl, aryl, —O-aryl, or —NR$^M$R$^N$ moiety, or is a 6- to 10-membered aryl or a 5- to 10-membered heteroaryl, in each case monocyclic or bicyclic, and optionally substituted with (a) one to three moieties independently selected from —C$_{1-4}$alkyl, halogen, —NR$^M$R$^N$, —C$_{1-4}$haloalkyl, —C$_{1-4}$alkoxy, —C$_{1-4}$hydroxyalkyl, cyano, —O-aryl, and aryl, or (b) a 6-membered aryl or 5-6 membered heteroaryl, optionally substituted with one to three moieties independently selected from —C$_{1-4}$alkyl, halogen, and —NR$^M$R$^N$;
R$^2$ is —C$_{1-5}$alkyl, —C$_{1-5}$alkoxy, —C$_7$cycloalkyl, C$_{5-7}$cycloalkyl substituted with halo or spirocycloalkyl, or aryl;
R$^3$ is —R$^A$—R$^B$ or halo;
wherein R$^A$ is ethynyl or is a phenyl or pyridinyl moiety optionally substituted with one or two Z in which each Z is independently halogen, —C$_{1-3}$alkyl, —C$_{1-3}$haloalkyl, —C$_{1-3}$alkoxy, or cyano; and
wherein R$^B$ is hydrogen, —C$_{1-6}$alkyl, —C$_{0-3}$alkyl-NR$^M$R$^N$, —NHC$_{1-3}$alkyl-R$^Q$, —N(R$^U$)C(O)—R$^Q$, —C(O)NR$^U$R$^Q$, carboxyl, —C$_{2-6}$alkenyl, —C$_{2-6}$alkynyl, —C$_{0-3}$alkyl-C$_{3-6}$cycloalkyl, —C$_{1-4}$alkoxy, -methyl-(C$_{1-4}$alkoxy)$_{1-2}$, —C$_{0-3}$alkyl-NR$^S$R$^T$, —C$_{3-7}$cycloalkyl-C$_{0-3}$alkyl-R$^Q$, —C$_{0-4}$alkyl-R$^Q$, —C$_{2-6}$alkynylR$^Q$, or —C$_{2-4}$alkenyl-R$^Q$;

wherein $R^Q$ is a 5- to 9-membered monocyclic or bicyclic aryl or heteroaryl or a 3- to 7-membered cycloalkyl or heterocycloalkyl, optionally substituted with one or two $R^Z$, in which each $R^Z$ is independently —$C_{1-3}$alkyl, —$C_{1-3}$alkoxy, oxo, or —$NR^MR^N$;

$R^S$ and $R^T$ are each independently hydrogen or —$C_{1-4}$alkyl, or one of $R^S$ and $R^T$ is hydrogen and the other is —C(O)-5- to 9-membered aryl or heteroaryl; and $R^U$ is hydrogen or —$C_{1-4}$alkyl;

provided that, when $R^A$ is phenyl, then $R^B$ appears at the para or meta position relative to the thiophene moiety; and $R^4$ is hydrogen, —$C_{1-4}$alkyl, —$C_{1-4}$alkyl-OC(O)O—$C_{1-4}$alkyl, —$C_{1-4}$alkyl-OC(O)—$C_{1-4}$alkyl, —$C_{1-4}$alkyl-OC(O)O—$C_{3-6}$cycloalkyl, 5-methyl-2-oxo-[1,3]dioxol-4-ylmethyl-, —$C_{0-3}$alkyl-$C_{5-6}$aryl, or —$C_{1-4}$alkyl-$NR^VR^W$; and $R^V$ and $R^W$ are independently hydrogen or —$C_{1-4}$alkyl.

In some embodiments, the invention provides compounds in which $R^2$ is —$C_{1-5}$alkyl substituted with 1-5 halogens. In some embodiments, $R^2$ is phenyl substituted with 1 or 2 halogens or —$C_{1-3}$alkyl groups optionally substituted with 1-3 halogens.

In another aspect, the invention provides compounds according to Formula I:

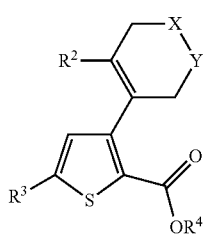

I and salts and solvates thereof,
wherein:
one of X and Y is —$CH_2$— and the other is —$NR^1$—;
$R^1$ is hydrogen, —$C_{1-4}$alkyl, —$C_{1-6}$hydroxyalkyl, —$C_{1-4}$haloalkyl, —$C_{1-4}$alkyl-O—$C_{1-4}$alkyl, —$S(O)_2$—$C_{0-4}$alkyl-$R^O$, —$C_{0-4}$alkyl-$S(O)_2$—$C_{1-4}$alkyl, —$C_{0-4}$alkyl-$S(O)_2$—$NR^MR^N$, —$C_{2-4}$alkyl-$NR^MR^N$, —$C_{0-4}$alkyl-$R^O$, —$C_{0-3}$alkyl-C(O)$C_{1-4}$alkyl, —$C_{0-3}$alkyl-C(O)—$C_{1-4}$hydroxyalkyl, —$C_{0-3}$alkyl-C(O)—$C_{0-4}$alkyl-$R^O$, —C(O)O—$C_{1-4}$alkyl, —$C_{0-3}$alkyl-C(O)O—$C_{0-4}$alkyl-$R^O$, —$C_{0-4}$alkyl-C(O)OH, or —$C_{0-3}$alkyl-C(O)—$C_{0-4}$alkyl-$NR^MR^N$;
wherein:
$R^M$ and $R^N$ are independently hydrogen, —$C_{1-4}$alky, or $R^M$ and $R^N$ together with the atoms to which they are attached can form a 4- to 6-membered ring; and
$R^O$ is a 5- to 7-membered cycloalkyl or heterocycloalkyl group, optionally substituted with a hydroxyl, —$C_{1-3}$alkyl, aryl, —O-aryl, or —$NR^MR^N$ moiety, or is a 6- to 10-membered aryl or a 5- to 10-membered heteroaryl, in each case monocyclic or bicyclic, and optionally substituted with (a) one to three moieties independently selected from —$C_{1-4}$alkyl, halogen, —$NR^MR^N$, —$C_{1-4}$haloalkyl, —$C_{1-4}$alkoxy, —$C_{1-4}$hydroxyalkyl, cyano, —O-aryl, and aryl, or (b) a 6-membered aryl or 5-6 membered heteroaryl, optionally substituted with one to three moieties independently selected from —$C_{1-4}$alkyl, halogen, and —$NR^MR^N$;

$R^2$ is —$C_{1-5}$alkyl, —$C_{5-7}$cycloalkyl-$C_{0-3}$alkyl in which the alkyl is optionally substituted with 1-3 halogens, —$C_{5-7}$cycloalkenyl-$C_{0-3}$alkyl in which the alkyl moiety is optionally substituted with 1-3 halogens, —$C_{1-4}$alkyl-$C_{3-5}$cycloalkyl, or phenyl optionally substituted with 1 or 2 halogens or —$C_{1-3}$alkyl groups optionally substituted with 1-3 halogens;

$R^3$ is —$R^A$—$R^B$;

wherein $R^A$ is ethynyl or is a phenyl substituted with $Z_m$ in which m=1 or 2 and each Z is independently halogen, —$C_{1-3}$alkyl, —$C_{1-3}$haloalkyl, —$C_{1-3}$alkoxy, or cyano, provided, however, that, if m=1, then Z is not a halogen, and if m=2, then at least one Z is not a halogen; and wherein $R^B$ is hydrogen, —$C_{1-6}$alkyl, —$C_{0-3}$alkyl-$NR^MR^N$, —$NHC_{1-3}$-alkyl-$R^Q$, —$N(R^U)C(O)$—$R^Q$, —$C(O)NR^UR^Q$, carboxyl, —$C_{2-6}$alkenyl, —$C_{2-6}$alkynyl, —$C_{0-3}$alkyl-$C_{3-6}$cycloalkyl, —$C_{1-4}$alkoxy, -methyl-$(C_{1-4}$alkoxy$)_{1-2}$, —$C_{0-3}$alkyl-$NR^SR^T$, —$C_{3-7}$cycloalkyl-$C_{0-3}$alkyl-$R^Q$, —$C_{0-4}$alkyl-$R^Q$, —$C_{2-6}$alkynyl$R^Q$, or —$C_{2-4}$alkenyl-$R^Q$;

wherein $R^Q$ is a 5- to 9-membered monocyclic or bicyclic aryl or heteroaryl or a 3- to 7-membered cycloalkyl or heterocycloalkyl, optionally substituted with one or two $R^Z$, in which each $R^Z$ is independently —$C_{1-3}$alkyl, —$C_{1-3}$alkoxy, oxo, or —$NR^MR^N$;

$R^S$ and $R^T$ are each independently hydrogen or —$C_{1-4}$alkyl, or one of $R^S$ and $R^T$ is hydrogen and the other is —C(O)-5- to 9-membered aryl or heteroaryl; and $R^U$ is hydrogen or —$C_{1-4}$alkyl;

provided that, when $R^A$ is phenyl, then $R^B$ appears at the para or meta position relative to the thiophene moiety;

$R^4$ is hydrogen, —$C_{1-4}$alkyl, —$C_{1-4}$alkyl-OC(O)O—$C_{1-4}$alkyl, —$C_{1-4}$alkyl-OC(O)—$C_{1-4}$alkyl, —$C_{1-4}$alkyl-OC(O)O—$C_{3-6}$cycloalkyl, 5-methyl-2-oxo-[1,3]dioxol-4-ylmethyl-, —$C_{0-3}$alkyl-$C_{5-6}$aryl, or —$C_{1-4}$alkyl-$NR^VR^W$; and $R^V$ and $R^W$ are independently hydrogen or —$C_{1-4}$alkyl.

In another aspect, the invention provides compounds according to Formula VI:

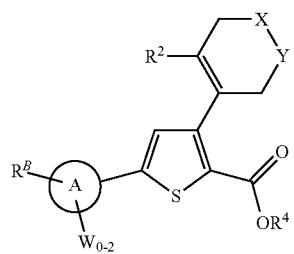

VI and salts and solvates thereof,
wherein:
one of X and Y is —$CH_2$— and the other is —$NR^1$—;
$R^1$ is hydrogen, —$C_{1-4}$alkyl, —$C_{1-6}$hydroxyalkyl, —$C_{1-4}$haloalkyl, —$C_{1-4}$alkyl-O—$C_{1-4}$alkyl, —$S(O)_2$—$C_{0-4}$alkyl-$R^O$, —$C_{0-4}$alkyl-$S(O)_2$—$C_{1-4}$alkyl, —$C_{0-4}$alkyl-$S(O)_2$—$NR^MR^N$, —$C_{2-4}$alkyl- NR$^M$R$^N$, —C$_{0-4}$alkyl-R, —C$_{0-3}$alkyl-C(O)C$_{1-4}$alkyl, —C$_3$alkyl-C(O)—C$_{0-4}$hydroxyalkyl, —C$_{0-3}$allyl-C(O)—C$_{0-4}$alkyl-R$^O$, —C(O)O—C$_{1-4}$alkyl, —C$_{0-3}$alkyl-C(O)O—C$_{0-4}$alkyl-R$^O$, —C$_{0-4}$alkyl-C(O)OH, or —C$_{0-3}$alkyl-C(O)—C$_{0-4}$alkyl-NR$^M$R$^N$;

wherein:

R$^M$ and R$^N$ are independently hydrogen, —C$_{1-4}$alkyl, or R$^M$ and R$^N$ together with the atoms to which they are attached can form a 4- to 6-membered ring; and R$^O$ is a 5- to 7-membered cycloalkyl or heterocycloalkyl group, optionally substituted with a hydroxyl, —C$_{1-3}$alkyl, aryl, —O-aryl, or —NR$^M$R$^N$ moiety, or is a 6- to 10-membered aryl or a 5- to 10-membered heteroaryl, in each case monocyclic or bicyclic, and optionally substituted with (a) one to three moieties independently selected from —C$_{1-4}$alkyl, halogen, —NR$^M$R$^N$, —C$_{1-4}$haloalkyl, —C$_{1-4}$alkoxy, —C$_{1-4}$hydroxyalkyl, cyano, —O-aryl, and aryl, or (b) a 6-membered aryl or 5-6 membered heteroaryl, optionally substituted with one to three moieties independently selected from —C$_{1-4}$alkyl, halogen, and —NR$^M$R$^N$;

R$^2$ is —C$_{1-5}$alkyl optionally substituted with 1-5 halogens, —C$_{1-5}$alkoxy, —C$_{5-7}$cycloalkyl-C$_{1-3}$alkyl in which the alkyl is optionally substituted with 1-3 halogens, —C$_{5-7}$cycloalkenyl-C$_{0-3}$alkyl in which the alkyl moiety is optionally substituted with 1-3 halogens, —C$_{1-4}$alkyl-C$_{3-5}$cycloalkyl, or phenyl optionally substituted with 1 or 2 halogens or —C$_{1-3}$alkyl groups optionally substituted with 1-3 halogens;

R$^3$ is -A-R$^B$;

wherein the A ring is 2-, 3-, or 4-pyridinyl, in which each Z is independently halogen, —C$_{1-3}$alkyl, —C$_{1-3}$haloalkyl, —C$_{1-3}$alkoxy, or cyano; and wherein R$^B$ is hydrogen, —C$_{1-6}$alkyl, —C$_{0-3}$alkyl-NR$^M$R$^N$, —NHC$_{1-3}$alkyl-R$^Q$, —N(R$^U$)C(O)—R$^Q$, —C(O)NR$^U$R$^Q$, carboxyl, —C$_{2-6}$alkenyl, —C$_{2-6}$alkynyl, —C$_{0-3}$alkyl-C$_{3-6}$cycloalkyl, —C$_{1-4}$alkoxy, -methyl-(C$_{1-4}$alkoxy)$_{1-2}$, —C$_{0-3}$alkyl-NR$^S$R$^T$, —C$_{3-7}$cycloalkyl-C$_{0-3}$alkyl-R$^Q$, —C$_{0-4}$alkyl-R$^Q$, —C$_{2-6}$alkynylR$^Q$, or —C$_{2-4}$alkenyl-R$^Q$;

wherein R$^Q$ is a 5- to 9-membered monocyclic or bicyclic aryl or heteroaryl or a 3- to 7-membered cycloalkyl or heterocycloalkyl, optionally substituted with one or two R$^Z$, in which each R$^Z$ is independently —C$_{1-3}$alkyl, —C$_{1-3}$alkoxy, oxo, or —NR$^M$R$^N$; and R$^S$ and R$^T$ are each independently hydrogen or —C$_{1-4}$alkyl, or one of R$^S$ and R$^T$ is hydrogen and the other is —C(O)-5- to 9-inembered aryl or heteroaryl;

R$^4$ is hydrogen, —C$_{1-4}$alkyl, —C$_{1-4}$alkyl-OC(O)O—C$_{1-4}$alkyl, —C$_{1-4}$alkyl-OC(O)—C$_{1-4}$alkyl, —C$_{1-4}$alkyl-OC(O)O—C$_{3-6}$cycloalkyl, 5-methyl-2-oxo-[1,3]dioxol-4-ylmethyl-, —C$_{0-3}$alkyl-C$_{5-6}$aryl, or —C$_{1-4}$alkyl-NR$^V$R$^W$; and R$^V$ and R$^W$ are independently hydrogen or —C$_{1-4}$alkyl.

The general Formula VI includes, for example, compounds of general Formulas VIa-VIf:

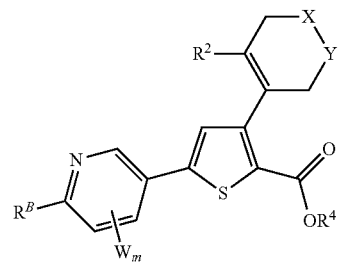

VIa

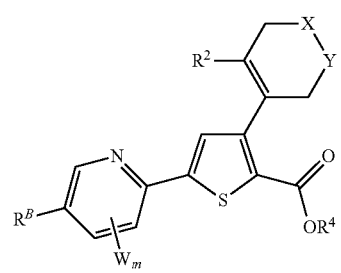

VIb

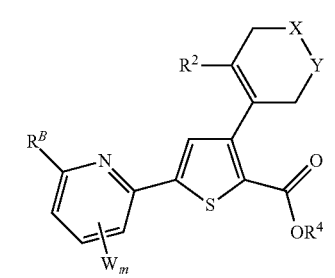

VIc

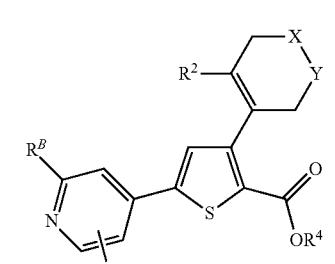

VId

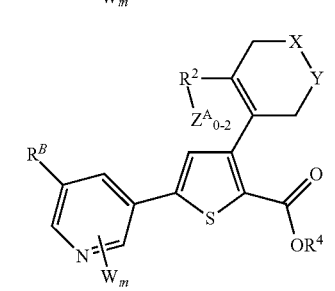

VIe

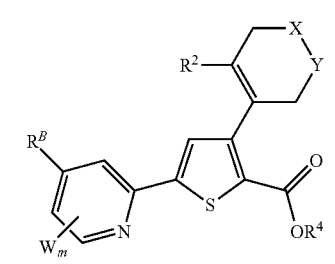

VIf and salts (e.g., pharmaceutically acceptable salts) and solvates thereof, in which m=0, 1, or 2, and any of the attached functional groups may be as otherwise set forth herein for compounds of Formula I. In some embodiments, these compounds have general Formula VIa. In some embodiments, these compounds have general Formula VIb. In some embodiments, Z occurs once, and is a halogen. In some embodiments Z occurs once and is —$C_{1-3}$alkyl, —$C_{1-3}$haloalkyl, —$C_{1-3}$alkoxy, or cyano. In some embodiments, Z occurs twice, in which each Z is independently halogen, —$C_{1-3}$alkyl, —$C_{1-3}$haloalkyl, —$C_{1-3}$alkoxy, or cyano.

In another aspect, the invention provides compounds according to Formula 1:

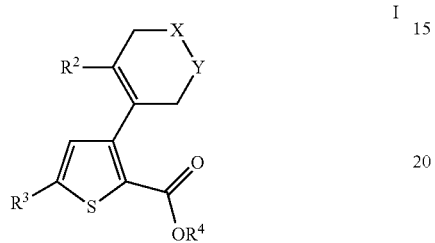

and salts and solvates thereof,
wherein:
one of X and Y is —$CH_2$— and the other is —$NR^1$—;
$R^1$ is hydrogen, —$C_{1-4}$alkyl, —$C_{1-6}$hydroxyalkyl, —$C_{1-4}$haloalkyl, —$C_{1-4}$alkyl-O—$C_{1-4}$alkyl, —$S(O)_2$—$C_{0-4}$alkyl-$R^O$, —$C_{0-4}$alkyl-$S(O)_2$—$C_{1-4}$alkyl, —$C_{0-4}$alkyl-$S(O)_2$—$NR^MR^N$, —$C_{2-4}$alkyl-$NR^MR^N$, —$C_{0-4}$alkyl-$R^O$, —$C_{0-3}$alkyl-$C(O)C_{1-4}$alkyl, —$C_{0-3}$alkyl-$C(O)$—$C_{1-4}$hydroxyalkyl, —$C_{0-3}$alkyl-$C(O)$—$C_{0-4}$alkyl-$R^O$, —$C(O)O$—$C_{1-4}$alkyl, —$C_{0-3}$alkyl-$C(O)O$—$C_{0-4}$alkyl-$R^O$, —$C_{0-4}$alkyl-$C(O)OH$, or —$C_{0-3}$alkyl-$C(O)$—$C_{0-4}$alkyl-$NR^MR^N$;
wherein:
$R^M$ and $R^N$ are independently hydrogen, —$C_{1-4}$alkyl, or $R^M$ and $R^N$ together with the atoms to which they are attached can form a 4- to 6-membered ring; and
$R^O$ is a 5- to 7-membered cycloalkyl or heterocycloalkyl group, optionally substituted with a hydroxyl, —$C_{1-3}$alkyl, aryl, —O-aryl, or —$NR^MR^N$ moiety, or is a 6- to 10-membered aryl or a 5- to 10-membered heteroaryl, in each case monocyclic or bicyclic, and optionally substituted with (a) one to three moieties independently selected from —$C_{1-4}$alkyl, halogen, —$NR^MR^N$, —$C_{1-4}$haloalkyl, —$C_{1-4}$alkoxy, —$C_{1-4}$hydroxyalkyl, cyano, aryl, —O-aryl, and aryl, or (b) a 6-membered aryl or 5-6 membered heteroaryl, optionally substituted with one to three moieties independently selected from —$C_{1-4}$alkyl, halogen, and —$NR^MR^N$;
$R^2$ is —$C_{1-5}$alkyl optionally substituted with 1-5 halogens, —$C_{1-5}$alkoxy, —$C_{5-7}$cycloalkyl-$C_{0-3}$alkyl in which the alkyl is optionally substituted with 1-3 halogens, —$C_{5-7}$cycloalkenyl-$C_{0-3}$alkyl in which the alkyl moiety is optionally substituted with 1-3 halogens, —$C_{1-4}$alkyl-$C_{3-5}$cycloalkyl, or phenyl optionally substituted with 1 or 2 halogens or —$C_{1-3}$alkyl groups optionally substituted with 1-3 halogens;
$R^3$ is —$R^A$—$R^B$ or halo;
wherein $R^A$ is ethynyl or is a phenyl or pyridinyl moiety optionally substituted with one or two Z in which each Z is independently halogen, —$C_{1-3}$alkyl, —$C_{1-3}$haloalkyl, —$C_{1-3}$alkoxy, or cyano; and
wherein $R^B$ is hydrogen, —$C_{1-6}$alkyl, —$C_{0-3}$alkyl-$NR^MR^N$, —$NHC_{1-3}$alkyl-$R^Q$, —$N(R^U)C(O)$—$R^Q$, —$C(O)NR^UR^Q$, carboxyl, —$C_{2-6}$alkenyl, —$C_{2-6}$alkynyl, —$C_{0-3}$alkyl-$C_{3-6}$cycloalkyl, —$C_{1-4}$alkoxy, -methyl-$(C_{1-4}$alkoxy$)_{1-2}$, —$C_{0-3}$alkyl-$NR^SR^T$, —$C_{3-7}$cycloalkyl-$C_{0-3}$alkyl-$R^Q$, —$C_{0-4}$alkyl-$R^Q$, —$C_{2-6}$alkynyl$R^Q$, or —$C_{2-4}$alkenyl-$R^Q$;
wherein $R^Q$ is a 5- to 9-membered monocyclic or bicyclic aryl or heteroaryl or a 3- to 7-membered cycloalkyl or heterocycloalkyl, optionally substituted with $R^Z_n$ in which n=1 or 2, and each $R^Z$ is independently —$C_{1-3}$alkyl, —$C_{1-3}$alkoxy, oxo, or —$NR^MR^N$, provided, however, that, if n=1, then the $R^Z$ is not —$C_{1-3}$alkyl or —$NR^MR^N$, and if n=2, then at least one $R^Z$ is not —$C_{1-3}$alkyl or —$NR^MR^N$; and
$R^S$ and $R^T$ are each independently hydrogen or —$C_{1-4}$alkyl, or one of $R^S$ and $R^T$ is hydrogen and the other is —C(O)-5- to 9-membered aryl or heteroaryl; and
$R^U$ is hydrogen or —$C_{1-4}$alkyl;
provided that, when $R^A$ is phenyl, then $R^B$ appears at the para or meta position relative to the thiophene moiety; and
$R^4$ is hydrogen, —$C_{1-4}$alkyl, —$C_{1-4}$alkyl-OC(O)O—$C_{1-4}$alkyl, —$C_{1-4}$alkyl-OC(O)—$C_{1-4}$alkyl, —$C_{1-4}$alkyl-OC(O)O—$C_{3-6}$cycloalkyl, 5-methyl-2-oxo-[1,3]dioxol-4-ylmethyl-, —$C_{0-3}$alkyl-$C_{5-6}$aryl, or —$C_{1-4}$alkyl-$NR^VR^W$; and
$R^V$ and $R^W$ are independently hydrogen or —$C_{1-4}$alkyl.
In one aspect, representative compounds of general Formula 1, and particularly general Formula Ia, include, for example:
5-(3-methyl-4-(thiazole-4-carboxamido)phenyl)-3-(1-methyl-5-(4-methylcyclohexyl)-1,2,3,6-tetrahydropyridin-4-yl)thiophene-2-carboxylic acid;
5-(3-methoxy-4-(thiazole-4-carboxamido)phenyl)-3-(1-methyl-5-(4-methylcyclohexyl)-1,2,3,6-tetrahydropyridin-4-yl)thiophene-2-carboxylic acid;
5-(3-cyano-4-(thiazole-4-carboxamido)phenyl)-3-(1-methyl-5-(4-methylcyclohexyl)-1,2,3,6-tetrahydropyridin-4-yl)thiophene-2-carboxylic acid;
5-(3-ethyl-4-(thiazole-4-carboxamido)phenyl)-3-(1-methyl-5-(4-methylcyclohexyl)-1,2,3,6-tetrahydropyridin-4-yl)thiophene-2-carboxylic acid;
3-(1-methyl-5-(4-methylcyclohexyl)-1,2,3,6-tetrahydropyridin-4-yl)-5-(4-(thiazole-4-carboxamido)-3-(trifluoromethyl)phenyl)thiophene-2-carboxylic acid;
5-(4-(5-methoxypyrazolo[1,5-a]pyrimidin-2-yl)phenyl)-3-(1-methyl-5-(4-methylcyclohexyl)-1,2,3,6-tetrahydropyridin-4-yl)thiophene-2-carboxylic acid;
3-(1-methyl-5-(4-methylcyclohexyl)-1,2,3,6-tetrahydropyridin-4-yl)-5-(4-(4-methyl-5-oxo-4,5-dihydropyrazolo[1,5-a]pyrinidin-2-yl)phenyl)thiophene-2-carboxylic acid;
5-(3-methyl-4-(pyrazolo[1,5-a]pyrimidin-2-yl)phenyl)-3-(1-methyl-5-(4-methylcyclohexyl)-1,2,3,6-tetrahydropyridin-4-yl)thiophene-2-carboxylic acid;
3-(1-methyl-4-(4-methylcyclohexyl)-1,2,5,6-tetrahydropyridin-3-yl)-5-(3-methyl-4-(thiazole-4-carboxamido)phenyl)thiophene-2-carboxylic acid;
3-(1-(2-hydroxyethyl)-4-(4-methylcyclohexyl)-1,2,5,6-tetrahydropyridin-3-yl)-5-(3-methyl-4-(thiazole-4-carboxamido)phenyl)thiophene-2-carboxylic acid;

3-(1-((1-methyl-1H-pyrazol-4-yl)methyl)-4-(4-methylcyclohexyl)-1,2,5,6-tetrahydropyridin-3-yl)-5-(3-methyl-4-(thiazole-4-carboxamido)phenyl)thiophene-2-carboxylic acid;

3-(4-(4,4-difluorocyclohexyl)-1-methyl-1,2,5,6-tetrahydropyridin-3-yl)-5-(4-(thiazole-4-carboxamido)phenyl)thiophene-2-carboxylic acid;

3-(5-(2,4-dichlorophenyl)-1-methyl-1,2,3,6-tetrahydropyridin-4-yl)-5-(4-(thiazole-4-carboxamido)phenyl)thiophene-2-carboxylic acid;

3-(1-methyl-5-(p-tolyl)-1,2,3,6-tetrahydropyridin-4-yl)-5-(4-(thiazole-4-carboxamido)phenyl)thiophene-2-carboxylic acid;

5-(6-aminopyridin-3-yl)-3-(1-methyl-5-(4-methylcyclohexyl)-1,2,3,6-tetrahydropyridin-4-yl)thiophene-2-carboxylic acid;

3-(1-methyl-5-(4-methylcyclohexyl)-1,2,3,6-tetrahydropyridin-4-yl)-5-(6-(thiazole-4-carboxamido)pyridin-3-yl)thiophene-2-carboxylic acid;

3-(5-cycloheptyl-1-methyl-1,2,3,6-tetrahydro-pyridin-4-yl)-5-phenyl-thiophene-2-carboxylic acid;

3-[5-(4-chloro-phenyl)-1-methyl-1,2,3,6-tetrahydro-pyridin-4-yl]-5-phenyl-thiophene-2-carboxylic acid;

3-(1-methyl-5-pentyl-1,2,3,6-tetrahydro-pyridin-4-yl)-5-phenyl-thiophene-2-carboxylic acid;

and salts (e.g., pharmaceutically acceptable salts) and solvates thereof.

In another aspect, the invention provides compounds represented by the general Formula I:

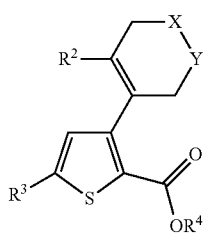

I and salts and solvates thereof,
wherein:
one of X and Y is —CH$_2$— and the other is —NR$^1$—;
R$^1$ is hydrogen, —C$_{1-4}$alkyl, —C$_{1-6}$hydroxyalkyl, —C$_{1-4}$haloalkyl, —C$_{1-4}$alkyl-O—C$_{1-4}$alkyl, —S(O)$_2$—C$_{0-4}$alkyl-R$^O$, —C$_{0-4}$alkyl-S(O)$_2$—C$_{1-4}$alkyl, —C$_{0-4}$alkyl-S(O)$_2$—NR$^M$R$^N$, —C$_{2-4}$alkyl-NR$^M$R$^N$, —C$_{0-4}$alkyl-R$^O$, —C$_{0-3}$alkyl-C(O)C$_{1-4}$alkyl, —C$_{0-3}$alkyl-C(O)—C$_{0-4}$hydroxyalkyl, —C$_{0-3}$alkyl-C(O)—C$_{0-4}$alkyl-R$^O$, —C(O)O—C$_{1-4}$alkyl, —C$_{0-3}$alkyl-C(O)O—C$_{0-4}$alkyl-R$^O$, —C$_{0-4}$alkyl-C(O)OH, or —C$_{0-3}$alkyl-C(O)—C$_{0-4}$alkyl-NR$^M$R$^N$;
wherein:
R$^M$ and R$^N$ are independently hydrogen, —C$_{1-4}$alky, or R$^M$ and R$^N$ together with the atoms to which they are attached can form a 4- to 6-membered ring; and
R$^O$ is a 3- to 7-membered cycloalkyl or 5- to 7-membered heterocycloalkyl, or is a 6- to 10-membered aryl or a 5- to 10-membered heteroaryl, in each case monocyclic or bicyclic;
R$^2$ is —C$_{1-5}$alkyl, —C$_{1-5}$alkoxy, —C$_{5-7}$cycloalkyl-C$_{0-3}$alkyl, —C$_{5-7}$cycloalkenyl-C$_{0-3}$alkyl, —C$_{1-4}$alkyl-C$_{3-5}$cycloalkyl, or phenyl;
R$^3$ is —R$^A$—R$^B$ or halo;

wherein R$^A$ is an ethynyl, or is a phenyl or pyridinyl moiety; and
wherein R$^B$ is hydrogen, —C$_{1-6}$alkyl, —C$_{0-3}$alkyl-NR$^M$R$^N$, —NHC$_{1-3}$alkyl-R$^Q$, —N(R$^U$)C(O)—R$^Q$, —C(O)NR$^U$R$^Q$, carboxyl, —C$_{2-6}$alkenyl, —C$_{2-6}$alkynyl, —C$_{0-3}$alkyl-C$_{3-6}$cycloalkyl, —C$_{1-4}$alkoxy, -methyl-(C$_{1-4}$alkoxy)$_{1-2}$, —C$_{0-3}$alkyl-NR$^S$R$^T$, —C$_{3-7}$cycloalkyl-C$_{0-3}$alkyl-R$^Q$, —C$_{0-4}$alkyl-R$^Q$, —C$_{2-6}$alkynylR$^Q$, or —C$_{2-4}$alkenyl-R$^Q$;
wherein R$^Q$ is a 5- to 9-membered monocyclic or bicyclic aryl or heteroaryl or a 3- to 7-membered cycloalkyl or heterocycloalkyl;
R$^S$ and R$^T$ are each independently hydrogen or —C$_{1-4}$alkyl, or one of R$^S$ and R$^T$ is hydrogen and the other is —C(O)-5- to 9-inmembered aryl or heteroaryl; and
R$^U$ is hydrogen or —C$_{1-4}$alkyl;
provided that, when R$^A$ is phenyl, then R$^B$ appears at the para or meta position relative to the thiophene moiety; and
R$^4$ is hydrogen, —C$_{1-4}$alkyl, —C$_{1-4}$alkyl-OC(O)O—C$_{1-4}$alkyl, —C$_{1-4}$alkyl-OC(O)—C$_{1-4}$alkyl, —C$_{1-4}$alkyl-OC(O)O—C$_{3-6}$cycloalkyl, 5-methyl-2-oxo-[1,3]dioxol-4-ylmethyl-, —C$_{0-3}$alkyl-C$_{5-6}$aryl, or —C$_{1-4}$alkyl-NR$^U$R$^V$; and
R$^V$ and R$^W$ are independently hydrogen or —C$_{1-4}$alkyl.

In some embodiments, the invention provides compounds of Formula I, in which X is —NR$^1$— and Y is —CH$_2$—. Thus, the invention provides compounds represented by the general Formula II:

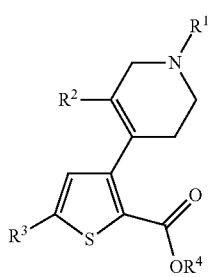

II and salts (e.g., pharmaceutically acceptable salts) and solvates thereof, in which any of the attached functional groups may be as otherwise set forth herein for compounds of Formula I.

In some embodiments, the invention provides compounds of Formula I in which X is —CH$_2$— and Y is —NR$^1$—. Thus, the invention provides compounds represented by the general Formula III:

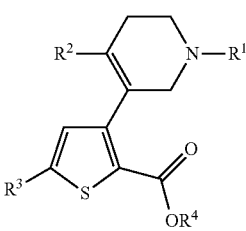

III and salts (e.g., pharmaceutically acceptable salts) and solvates thereof, in which any of the attached functional groups may be as otherwise set forth herein for compounds of Formula I.

In some embodiments, the invention provides compounds of Formula I, in which $R^O$ is a 3- to 7-membered cycloalkyl or 5- to 7-membered heterocycloalkyl, optionally substituted with a hydroxyl, —$C_{1-3}$alkyl, aryl, —O-aryl, or —$NR^M R^N$.

In some embodiments, the invention provides compounds of Formula I, in which $R^O$ is a 6- to 10-membered aryl or a 5- to 10-membered heteroaryl, in each case monocyclic or bicyclic, substituted with one to three moieties independently selected from —$C_{1-4}$alkyl, halogen, —$NR^M R^N$, —$C_{1-4}$haloalkyl, —$C_{1-4}$alkoxy, —$C_{1-4}$hydroxyalkyl, cyano, —O-aryl, and aryl.

In some embodiments, the invention provides compounds of Formula I, in which $R^O$ is a 6-membered aryl or 5-6 membered heteroaryl, substituted with one to three moieties independently selected from —$C_{1-4}$alkyl, halogen, and —$NR^M R^N$.

In some embodiments, the invention provides compounds of Formula I in which $R^A$ is ethynyl.

In some embodiments, the invention provides compounds of Formula I in which $R^A$ is ethynyl, and $R^B$ is selected from —$C_{1-6}$alkyl, and —$C_{0-3}$alkyl-$C_{3-6}$cycloalkyl.

In some embodiments, the invention provides compounds of Formula I in which Ra is phenyl. In some embodiments, the invention provides compounds of Formula I in which $R^A$ is phenyl and $R^B$ appears at the para position relative to the thiophene moiety. In some embodiments, the invention provides compounds of Formula I, in which $R^A$ is phenyl and $R^B$ is —$C_{2-6}$alkynyl-$R^Q$, or —$C_{2-4}$alkenyl-$R^Q$.

In some embodiments, the invention provides compounds of Formula I, in which $R^A$ is ethynyl and $R^B$ is hydrogen, —$C_{1-6}$alkyl, —$C_{3-7}$cycloalkyl-$C_{0-3}$alkyl-$R^Q$.

In some embodiments, the invention provides compounds of Formula I in which $R^A$ is phenyl and $R^B$ is selected from —$NHC_{1-3}$alkyl-$R^Q$, —NHC(O)—$R^Q$, —C(O)NH—$R^Q$, —$C_{0-4}$alkyl-$R^Q$, or —$C_{2-4}$alkenyl-$R^Q$.

In some embodiments, the invention provides compounds of Formula I in which $R^A$ is a phenyl or pyridinyl, substituted with one or two Z in which each Z is independently halogen, —$C_{1-3}$alkyl, —$C_{1-3}$haloalkyl, —$C_{1-3}$alkoxy, or cyano.

In some embodiments, the invention provides compounds of Formula 1, in which $R^Q$ is a 5- to 9-membered monocyclic or bicyclic aryl or heteroaryl or a 3- to 7-membered cycloalkyl or heterocycloalkyl, substituted with one or two —$C_{1-3}$alkyl, —$C_{1-3}$alkoxy, oxo, or —$NR^M R^N$.

In some embodiments, the invention provides compounds of Formula I, in which $R^2$ is —$C_{1-5}$alkyl, substituted with 1-5 halogens. In some embodiments, the invention provides compounds of Formula I, in which $R^2$ is —$C_{5-7}$cycloalkyl-$C_{0-3}$alkyl, in which the alkyl is substituted with 1-3 halogens. In some embodiments, the invention provides compounds of Formula I, in which $R^2$ is —$C_{5-7}$cycloalkenyl-$C_{0-3}$alkyl, in which the alkyl moiety is substituted with 1-3 halogens. In some embodiments, the invention provides compounds of Formula I, in which $R^2$ is phenyl, substituted with 1 or 2 halogens or —$C_{1-3}$alkyl groups optionally substituted with 1-3 halogens.

In some embodiments, the invention provides compounds of Formula I in which $R^2$ is —$C_{5-7}$cycloalkyl-$C_{0-3}$alkyl in which the alkyl is optionally substituted with 1-3 halogens. In some embodiments, the invention provides compounds of Formula I in which $R^2$ is -cyclohexylmethyl. Accordingly, the general Formula I encompasses compounds of general Formula IV:

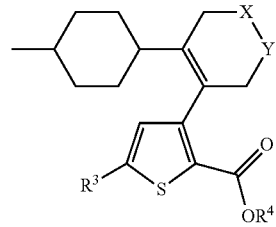

and salts (e.g., pharmaceutically acceptable salts) and solvates thereof, in which any of the attached functional groups may be as otherwise set forth herein for compounds of Formula I. In some embodiments, the invention provides compounds of Formula I in which $R^2$ is —$C_{1-5}$alkyl, or $R^2$ is —$C_{5-6}$cycloalkyl-$C_{0-3}$alkyl in which the alkyl is optionally substituted with 2-3 halogens, or $R^2$ is —$C_7$cycloalkyl-$C_{0-3}$alkyl in which the alkyl is optionally substituted with 1-3 halogens, or $R^2$ is —$C_{5-6}$cycloalkenyl-$C_{0-3}$alkyl in which the alkyl is optionally substituted with 2-3 halogens, or $R^2$ is —$C_7$cycloalkenyl-$C_{0-3}$alkyl in which the alkyl is optionally substituted with 1-3 halogens. In some embodiments, the invention provides compounds of Formula I in which $R^2$ is phenyl optionally substituted with 1 or 2 moieities independently selected from halogens and —$C_{1-3}$alkyl groups optionally substituted with 1-3 halogens.

In some embodiments, the invention provides compounds of Formula I in which $R^A$ is phenyl, optionally substituted with 1 or 2 Z moieties, in which each Z is independently halogen, —$C_{1-3}$alkyl, —$C_{1-3}$haloalkyl, —$C_{1-3}$alkoxy, or cyano. Accordingly, the general Formula I encompasses compounds of general Formula V:

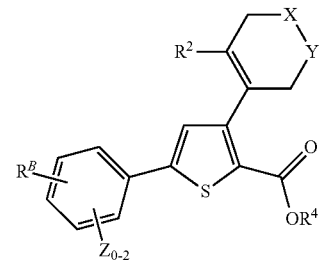

and salts (e.g., pharmaceutically acceptable salts) and solvates thereof, in which any of the attached functional groups may be as otherwise set forth herein for compounds of Formula I.

The general Formula V includes, for example, compounds of general Formulas Va and Vb:

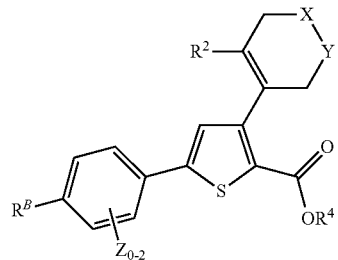

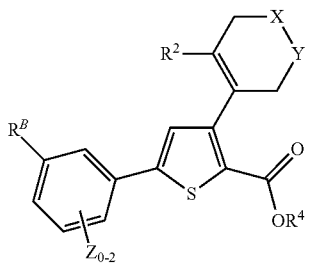

and salts (e.g., pharmaceutically acceptable salts) and solvates thereof, in which any of the attached functional groups may be as otherwise set forth herein for compounds of Formula I. In some embodiments, these compounds have general Formula Va. In some embodiments, these compounds have general Formula Vb. In some embodiments, Z occurs once, and is a halogen. In some embodiments 7 occurs once and is —$C_{1-3}$alkyl, —$C_{1-3}$haloalkyl, —$C_{1-3}$ alkoxy, or cyano. In some embodiments, Z occurs twice, in which each Z is independently halogen, —$C_{1-3}$alkyl, —$C_{1-3}$haloalkyl, —$C_{1-3}$alkoxy, or cyano.

In some embodiments, the invention provides compounds of Formula I in which:
$R^1$ is hydrogen, —$C_{1-4}$alkyl, —$C_{1-3}$alkyl-$C_{3-6}$cycloalkyl, —$C_{1-4}$hydroxyalkyl, —$C_{2-4}$alkyl-$NR^MR^N$, —$C_{1-4}$alkyl ester, or —$C_{1-3}$alkyl-$C_{6-10}$aryl; and
$R^M$ and $R^N$ are independently hydrogen, —$C_{1-4}$alkyl, or $R^M$ and $R^N$ together with the atoms to which they are attached can form a 4- to 6-membered ring.

In some embodiments, the invention provides compounds of Formula I in which $R^1$ is —$C_{1-4}$alkyl, —$C_{1-3}$alkyl-$C_{3-6}$cycloalkyl, —$C_{1-4}$hydroxyalkyl, or —$C_{2-4}$alkyl-$NR^MR^N$.

In some embodiments, the invention provides compounds of Formula I in which $R^B$ is —$C_{1-6}$alkyl, —$C_{3-6}$cycloalkyl, —$C_{1-4}$alkoxy, or -methyl-($C_{1-4}$alkoxy)$_{1-2}$.

In some embodiments, the invention provides compounds of Formula I in which $R^1$ is —$C_{1-4}$ alkyl.

In some embodiments, the invention provides compounds of Formula I in which $R^1$—$C_{1-4}$alkyl-$R^O$, in which $R^O$ is (optionally substituted) pyridine, pyrazole, or dioxolane.

In some embodiments, the invention provides compounds of Formula I in which $R^4$ is phenyl and in which $R^B$ is —NH—$R^Q$ or —NHC(O)—$R^Q$ and appears at the para position relative to the thiophene moiety. In some specific embodiments, $R^4$ is phenyl and $R^B$ is —NHC(O)—$R^Q$ and appears at the para position relative to the thiophene moiety, and $R^Q$ is a 5-9 membered heteroaryl, optionally substituted with $C_{1-4}$alkyl, and $R^4$ is optionally substituted with one or more of $C_{1-4}$alkyl $C_{1-4}$alkoxy, cyano, halogen, and $C_{1-4}$haloalkyl (e.g., trifluromethyl).

In some embodiments, the invention provides compounds of Formula I, in which $R^Q$ contains a 5- to 9-membered aryl or heteroaryl moiety selected from among furyl, isoxazolyl, oxazolyl, phenyl, pyrazolyl, pyridinyl, thiazolyl, thiophenyl, or tetrahydrofuranyl in each case optionally substituted with —$C_{1-4}$alkyl. In some embodiments, $R^Q$ is —$C_{1-3}$alkoxy.

In some embodiments, the invention provides compounds of Formula I in which $R^4$ is ethynyl and wherein $R^B$ is —$C_{1-6}$alkyl, —$C_{3-6}$cycloalkyl, —$C_{1-4}$alkoxy, or -methyl-($C_{1-4}$alkoxy)$_{1-2}$.

In some embodiments, the invention provides compounds of Formula I in which $R^B$ is not hydrogen, but may be any of the other groups described herein for that moiety. For example, the invention provides compounds of Formula V, such as compounds of Formula Va or Formula Vb in which $R^B$ is not hydrogen, but may be any of the other groups described herein for that moiety. Thus, in some embodiments, for example, in compounds of Formula V, $R^B$ is —$C_{1-6}$alkyl, —$C_{0-3}$alkyl-$NR^MR^N$, —$NHC_{1-3}$alkyl-$R^Q$, —$N(R^U)C(O)$—$R^Q$, —$C(O)NR^UR^Q$, carboxyl, —$C_{2-6}$alkenyl, —$C_{2-6}$alkynyl, —$C_{2-6}$alkynyl$R^Q$, —$C_{0-3}$alkyl-$C_{3-6}$cycloalkyl, —$C_{1-4}$alkoxy, -methyl-($C_{1-4}$alkoxy)$_{1-2}$, —$C_{0-3}$alkyl-$NR^SR^T$, —$C_{3-7}$cycloalkyl-$C_{0-3}$alkyl-$R^Q$, —$C_{0-4}$alkyl-$R^Q$, or —$C_{2-4}$alkenyl-$R^Q$; wherein:
$R^Q$ is a 5- to 9-membered monocyclic or bicyclic aryl or heteroaryl or a 3- to 7-membered cycloalkyl or heterocycloalkyl, optionally substituted with one or two —$C_{1-3}$alkyl or —$NR^MR^N$;
$R^S$ and $R^T$ are each independently hydrogen or —$C_{1-4}$ alkyl, or one of $R^S$ and $R^T$ is hydrogen and the other is —C(O)-5- to 9-membered aryl or heteroaryl; and
$R^U$ is hydrogen or —$C_{1-4}$alkyl.

In some embodiments, for example, in compounds of Formula V, when $R^B$ is hydrogen, then $R^1$ is —$C_{1-4}$alkyl, —$C_{1-4}$alkyl-$C_{3-7}$cycloalkyl, —$C_{0-3}$alkyl-$C_{5-7}$heterocycloalkyl, —$C_{1-4}$hydroxyalkyl, —$C_{1-4}$haloalkyl, —$C_{1-4}$ alkyl-O—$C_{1-4}$alkyl, —$S(O)_2C_{1-4}$alkyl, —$S(O)_2$—$R^P$, —$S(O)_2C_{5-7}$aryl-$C_{0-3}$alkyl, —$C_{1-4}$alkyl-$S(O)_2R^L$, —$C_{2-4}$alkyl-$NR^MR^N$, —$C_{0-3}$alkyl-C(O)—$C_{0-4}$alkyl-$R^P$, —C(O) O—$C_{1-4}$alkyl; wherein
$R^L$ is —$C_{1-4}$alkyl, —$C_{3-5}$cycloalkyl, —$NR^MR^N$;
$R^M$ and $R^N$ are independently hydrogen, —$C_{1-4}$alkyl, or $R^M$ and $R^N$ together with the atoms to which they are attached can form a 4- to 6-membered ring; and
$R^O$ is a 5- to 6-membered cycloalkyl or heterocycloalkyl, 5- to 7-membered aryl, or 5- to 10-membered heteroaryl group, optionally substituted with a hydroxyl, —$C_{1-3}$alkyl, aryl, O-aryl, or —$NR^MR^N$.

In some embodiments, for example, in compounds of Formula V, when $R^B$ is hydrogen, then $R^1$ is hydrogen, —$C_{1-4}$alkyl, —$C_{1-3}$alkyl-$C_{3-6}$cycloalkyl, —$C_{1-4}$hydroxyalkyl, —$C_{2-4}$alkyl-$NR^MR^N$, —$S(O)_2C_{1-4}$alkyl, —$S(O)_2$ $C_{4-7}$aryl, —$S(O)_2C_{6-10}$aryl-$C_{1-3}$alkyl, —$C_{1-4}$alkyl ester, —$C_{1-4}$alkyl-$S(O)_2R^L$, or —$C_{1-3}$alkyl-$C_{6-10}$aryl; wherein
$R^L$ is —$C_{1-4}$alkyl, —$C_{3-5}$cycloalkyl, or —$NR^MR^N$; and
$R^M$ and $R^N$ are independently hydrogen, —$C_{1-4}$alkyl, or $R^M$ and $R^N$ together with the atoms to which they are attached can form a 4- to 6-membered ring.

In some specific sets of embodiments, the compounds of general Formula V include compounds wherein $R^3$ is unsubstituted phenyl, $R^4$ is hydrogen or —$C_{1-4}$alkyl, X is —$NR^1$—, and Y is —$CH_2$—. In such cases, $R^2$ is other than —$C_{5-6}$cycloalkyl-$C_{1-3}$alkyl, or in some cases is other than —$C_6$cycloalkyl-$C_1$alkyl. In some embodiments, provided herein are methods of inhibiting hepatitis C virus polymerase using a compound of Formula V wherein $R^3$ is unsubstituted phenyl $R^4$ is hydrogen or —$C_{1-4}$alkyl, —$NR^1$—, and Y is —$CH_2$—, -and $R^2$ is —$C_{5-6}$cycloalkyl-$C_{1-3}$alkyl, or in some cases is —$C_6$cycloalkyl-$C_1$alkyl.

In some embodiments, the compounds of general Formula V specifically exclude compounds having a structure:

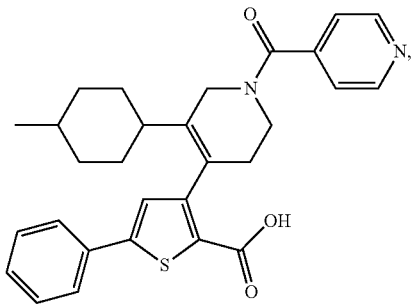

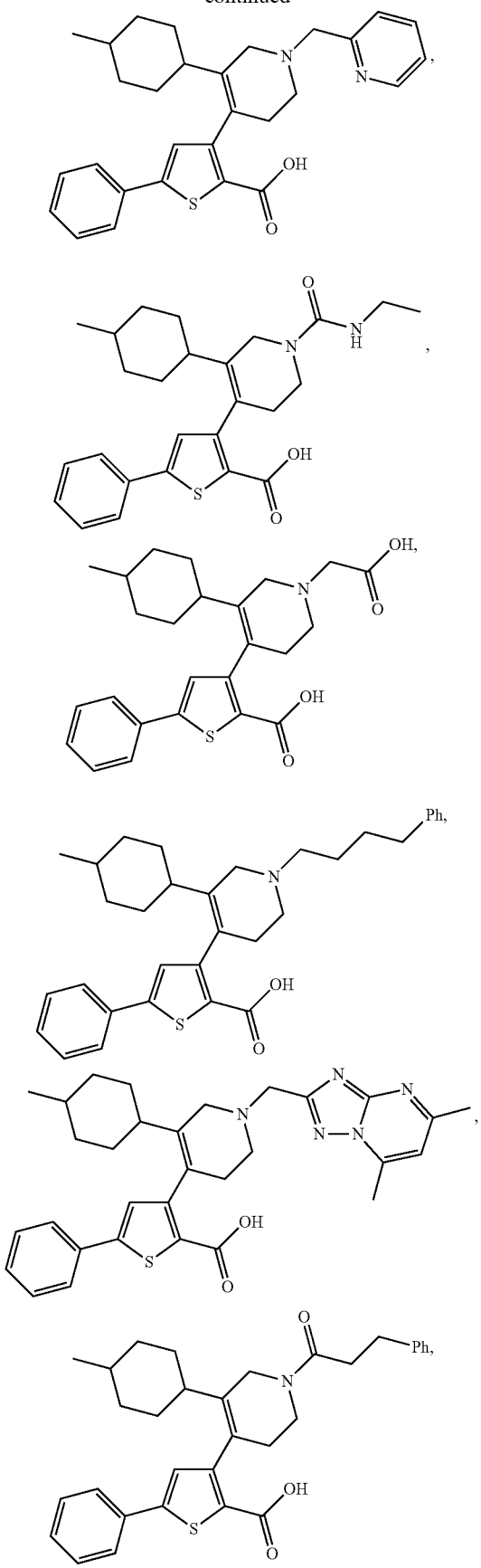
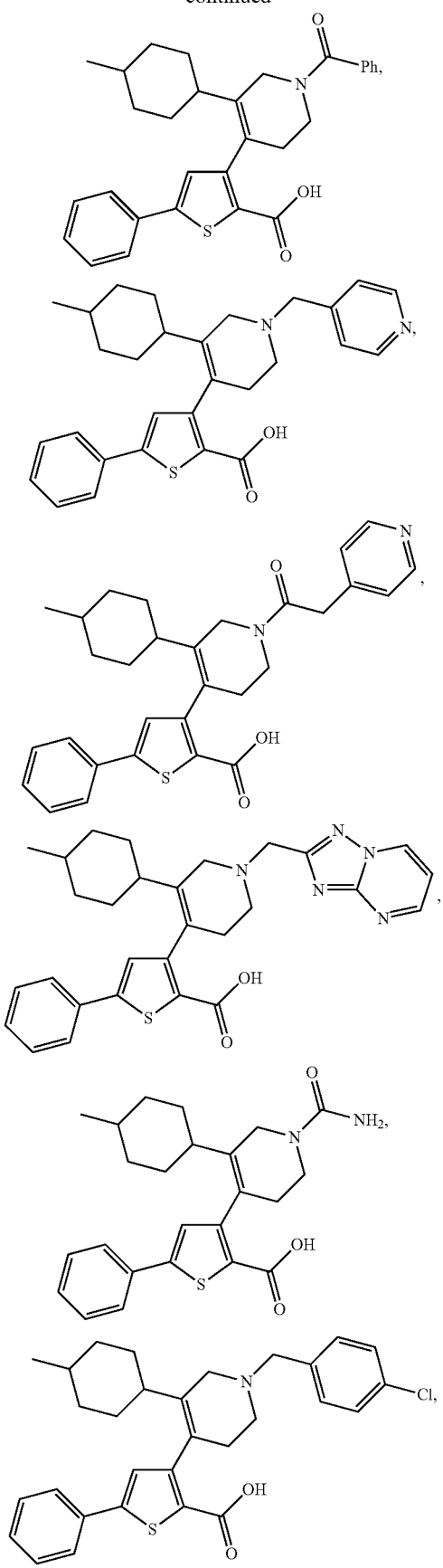

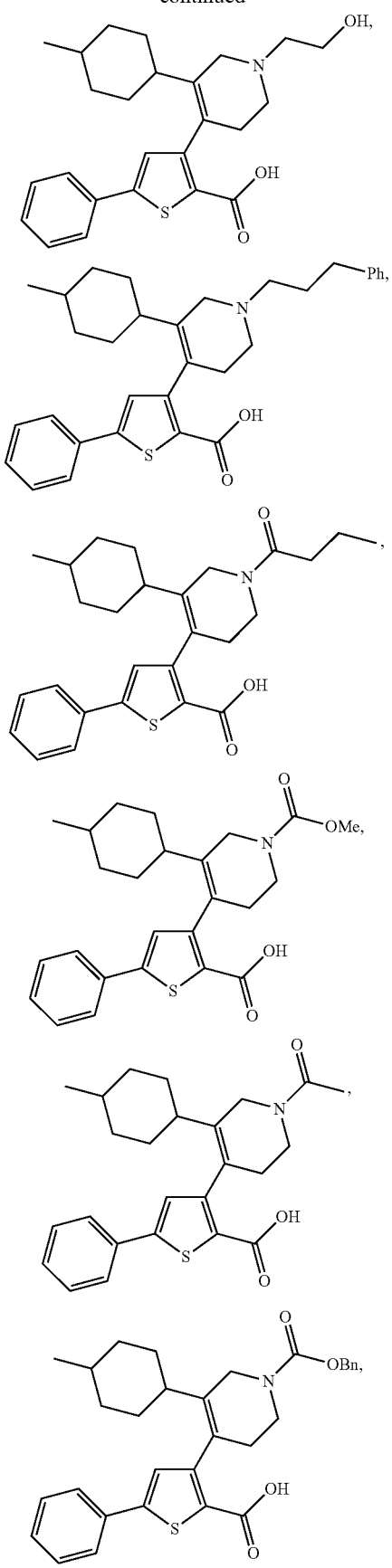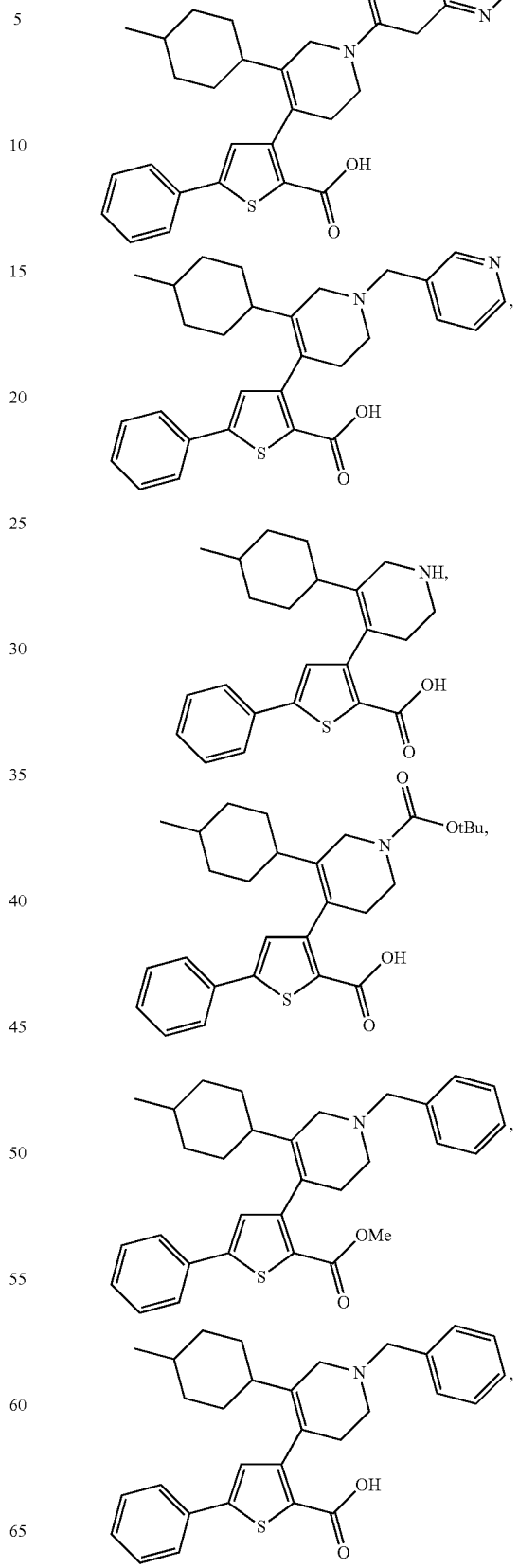

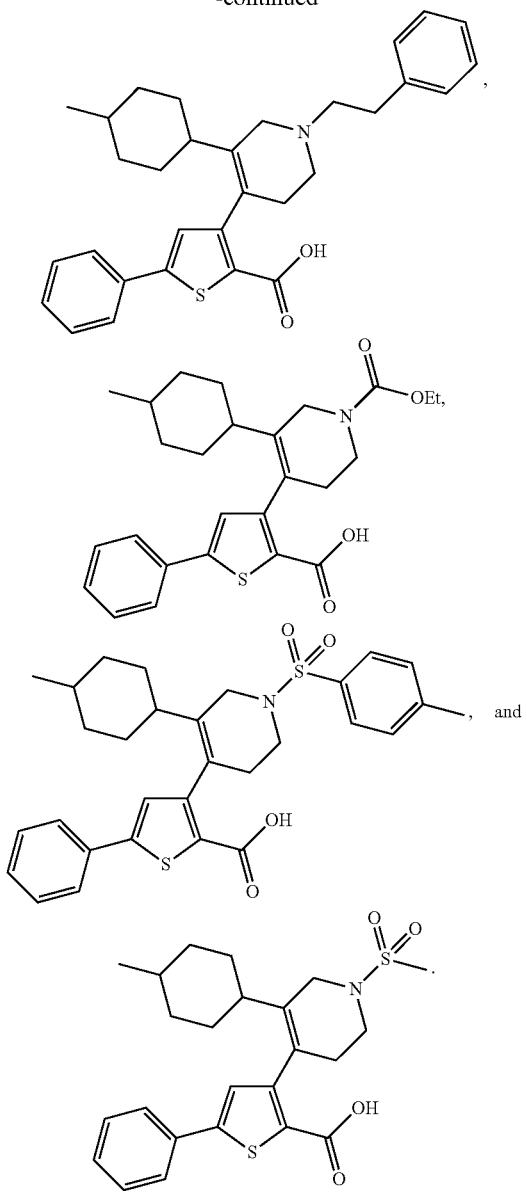

In some embodiments, provided herein are methods of inhibiting hepatitis C virus polymerase using the specific compounds of Formula V noted directly above in this same paragraph, while in other embodiments, provided are methods of inhibiting hepatitis C virus polymerase using a compound of Formula V that is not one of the specific compounds noted directly above in this same paragraph.

In one aspect, the invention provides compounds of Formula I in which $R^4$ is hydrogen. Thus, general Formula I encompasses compounds of general Formula Ia:

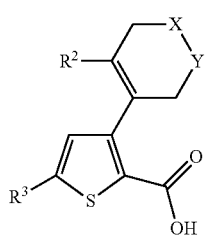

Ia including salts (e.g., pharmaceutically acceptable salts) and solvates thereof,
wherein:
one of X and Y is —CH$_2$— and the other is —NR$^1$—;
$R^1$ is hydrogen, —C$_{1-4}$alkyl, —C$_{1-6}$hydroxyalkyl, —C$_{1-4}$haloalkyl, —C$_{1-4}$alkyl-O—C$_{1-4}$alkyl, —S(O)$_2$—C$_{0-4}$alkyl-R$^O$, —C$_{0-4}$alkyl-S(O)$_2$—C$_{1-4}$alkyl, —C$_{0-4}$alkyl-S(O)$_2$—NR$^M$R$^N$, —C$_{2-4}$alkyl-NR$^M$R$^N$, —C$_{0-4}$alkyl-R$^O$, —C$_{0-3}$alkyl-C(O)C$_{1-4}$alkyl, —C$_{0-3}$alkyl-C(O)—C$_{1-4}$hydroxyalkyl, —C$_{0-3}$alkyl-C(O)—C$_{0-4}$alkyl-R$^O$, —C(O)O—C$_{1-4}$alkyl, —C$_{0-3}$alkyl-C(O)O—C$_{0-4}$alkyl-R$^O$, —C$_{0-4}$alkyl-C(O)OH, or —C$_{0-3}$alkyl-C(O)—C$_{0-4}$alkyl-NR$^M$R$^N$;
wherein:
$R^M$ and $R^N$ are independently hydrogen, —C$_{1-4}$alkyl or $R^M$ and $R^N$ together with the atoms to which they are attached can form a 4- to 6-membered ring; and
$R^O$ is a 3- to 7-membered cycloalkyl or 5- to 7-membered heterocycloalkyl group, optionally substituted with a hydroxyl, —C$_{1-3}$alkyl, aryl, —O-aryl, or —NR$^M$R$^N$ moiety, or is a 6- to 10-membered aryl or a 5- to 10-membered heteroaryl, in each case monocyclic or bicyclic, and optionally substituted with (a) one to three moieties independently selected from —C$_{1-4}$alkyl, halogen, —NR$^M$R$^N$, —C$_{1-4}$haloalkyl, —C$_{1-4}$alkoxy, —C$_{1-4}$hydroxyalkyl, cyano, aryl, —O-aryl, and aryl, or (b) a 6-membered aryl or 5-6 membered heteroaryl, optionally substituted with one to three moieties independently selected from —C$_{1-4}$alkyl, halogen, and —NR$^M$R$^N$;
$R^2$ is —C$_{1-5}$alkyl optionally substituted with 1-5 halogens, —C$_{1-5}$alkoxy, —C$_{5-7}$cycloalkyl-C$_{0-3}$alkyl in which the alkyl is optionally substituted with 1-3 halogens, —C$_{5-7}$cycloalkenyl-C$_{0-3}$alkyl in which the alkyl moiety is optionally substituted with 1-3 halogens, —C$_{1-4}$alkyl-C$_{3-5}$cycloalkyl, or phenyl optionally substituted with 1 or 2 halogens or —C$_{1-3}$alkyl groups optionally substituted with 1-3 halogens;
$R^3$ is —R$^A$—R$^B$ or halo;
wherein $R^A$ is an ethynyl, a phenyl or pyridinyl moiety optionally substituted with one or two Z in which each Z is independently halogen, —C$_{1-3}$alkyl, —C$_{1-3}$haloalkyl, —C$_{1-3}$alkoxy, or cyano; and
wherein $R^B$ is hydrogen, —C$_{1-6}$alkyl, —C$_{0-3}$alkyl-NR$^M$R$^N$, —NHC$_{1-3}$alkyl-R$^Q$, —N(R$^U$)C(O)—R$^Q$, —C(O)NR$^U$R$^Q$, carboxyl, —C$_{2-6}$alkenyl, —C$_{2-6}$alkynyl, —C$_{0-3}$alkyl-C$_{3-6}$cycloalkyl, —C$_{1-4}$alkoxy, -methyl-(C$_{1-4}$alkoxy)$_{1-2}$, —C$_{0-3}$alkyl-NR$^S$R$^T$, —C$_{3-7}$cycloalkyl-C$_{0-3}$alkyl-R$^Q$, —C$_{0-4}$alkyl-R$^Q$, —C$_{2-6}$alkynylR$^Q$, or —C$_{2-4}$alkenyl-R$^Q$;
wherein $R^Q$ is a 5- to 9-membered monocyclic or bicyclic aryl or heteroaryl or a 3- to 7-membered cycloalkyl or heterocycloalkyl, optionally substituted with one or two —C$_{1-3}$alkyl, —C$_{1-3}$alkoxy, oxo, or —NR$^M$R$^N$;
$R^S$ and $R^T$ are each independently hydrogen or —C$_{1-4}$alkyl, or one of $R^S$ and $R^T$ is hydrogen and the other is —C(O)-5- to 9-membered aryl or heteroaryl; and
$R^U$ is hydrogen or —C$_{1-4}$alkyl;
provided that, when $R^A$ is phenyl, then $R^B$ appears at the para or meta position relative to the thiophene moiety.

In some embodiments, disclosed herein are compounds of general Formula I wherein $R^A$ is phenyl, $R^B$ is —C$_{0-4}$alkyl-R$^Q$ or —N(H)C(O)—R$^Q$, and R$^Q$ is a 5-membered monocyclic heteroaryl or 9-membered bicyclic heteroaryl. Further provided are methods of inhibiting hepatitis C virus polymerase using one or more of these specific compounds of Formula I.

In another aspect, the invention provides compounds of general Formula Ia:

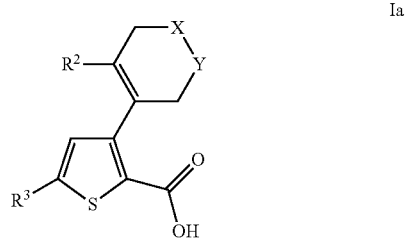

including salts (e.g., pharmaceutically acceptable salts) and solvates thereof, wherein:
one of X and Y is —CH$_2$— and the other is —NR$^1$—;
R$^1$ is hydrogen, —C$_{1-4}$alkyl, —C$_{1-3}$alkyl-C$_{3-6}$cycloalkyl, —C$_{1-4}$hydroxyalkyl, —C$_{2-4}$alkyl-NR$^M$R$^N$, —S(O)$_2$C$_{1-4}$alkyl, —S(O)$_2$C$_{4-7}$aryl, —S(O)$_2$C$_{6-10}$aryl-C$_{1-3}$alkyl, —C$_{1-4}$alkyl ester, —C$_{0-4}$alkyl-S(O)$_2$—C$_{1-4}$alkyl, —C$_{0-4}$alkyl-S(O)$_2$—NR$^M$R$^N$, or —C$_{1-3}$alkyl-C$_{6-10}$aryl;
wherein R$^M$ and R$^N$ are independently hydrogen, —C$_{1-4}$alkyl, or R$^M$ and R$^N$ together with the atoms to which they are attached can form a 4- to 6-membered ring;
R$_2$ is —C$_{5-6}$cycloalkyl, —C$_{5-6}$cycloalkyl-C$_{1-3}$alkyl, —C$_{5-6}$cycloalkenyl, or —C$_{5-6}$cycloalkenyl-C$_{1-3}$alkyl; and
R$^3$ is —R$^A$R$^B$ or halo;
wherein R$^A$ is phenyl or ethynyl, and
wherein R$^B$ is hydrogen, —C$_{1-6}$alkyl, —NHR$^Q$, carboxyl, —C$_{2-6}$alkenyl, —C$_{2-6}$alkynyl, —C$_{2-6}$alkynylR$^Q$, —C$_{4-6}$cycloalkyl, —C$_{1-4}$alkoxy, -methyl-(C$_{1-4}$alkoxy)$_{1-2}$, —C$_{1-3}$alkyl-NR$^S$R$^T$, —C$_{6-10}$aryl, or —C$_{5-10}$heteroaryl;
wherein R$^Q$ is hydrogen, —C(O)-5- to 9-membered heteroaryl, or —C(O)C$_{1-3}$alkyl; and
R$^S$ and R$^T$ are each independently hydrogen, or C$_{1-3}$alkyl, one of R$^S$ and R$^T$ is hydrogen and the other is —C(O)-5- to 9-membered aryl or heteroaryl;
provided that if R$^A$ is phenyl, then R$^B$ appears at the para or meta position relative to the thiophene moiety.

In another aspect, representative compounds of general Formula I, and particularly general Formula Ia, include, for example:
5-(3-chloro-4-(thiazole-4-carboxamido)phenyl)-3-(1-methyl-5-(4-methylcyclohexyl)-1,2,3,6-tetrahydropyridin-4-yl)thiophene-2-carboxylic acid;
3-(1-((1-methyl-1H-pyrazol-4-yl)methyl)-5-(4-methylcyclohexyl)-1,2,3,6-tetrahydropyridin-4-yl)-5-(4-(thiazole-4-carboxamido)phenyl)thiophene-2-carboxylic acid;
3-(1-(2-hydroxyethyl)-4-(4-methylcyclohexyl)-1,2,5,6-tetrahydropyridin-3-yl)-5-(4-(thiazole-4-carboxamido)phenyl)thiophene-2-carboxylic acid;
3-(1-((2,2-dimethyl-1,3-dioxolan-4-yl)methyl)-4-(4-methylcyclohexyl)-1,2,5,6-tetrahydropyridin-3-yl)-5-(4-(thiazole-4-carboxamido)phenyl)thiophene-2-carboxylic acid;

3-(1-(2,3-dihydroxypropyl)-4-(4-methylcyclohexyl)-1,2,5,6-tetrahydropyridin-3-yl)-5-(4-(thiazole-4-carboxamido)phenyl)thiophene-2-carboxylic acid;
3-(1-(2-hydroxyethyl)-4-(4-methylcyclohexyl)-1,2,5,6-tetrahydropyridin-3-yl)-5-(4-(pyrazolo[1,5-a]pyrimidin-2-yl)phenyl)thiophene-2-carboxylic acid;
3-(1-(2,3-dihydroxypropyl)-4-(4-methylcyclohexyl)-1,2,5,6-tetrahydropyridin-3-yl)-5-(4-(pyrazolo[1,5-a]pyrimidin-2-yl)phenyl)thiophene-2-carboxylic acid;
3-(1-((1-methyl-1H-pyrazol-4-yl)methyl)-4-(4-methylcyclohexyl)-1,2,5,6-tetrahydropyridin-3-yl)-5-(4-(thiazole-4-carboxamido)phenyl)thiophene-2-carboxylic acid;
3-(1-((1-methyl-1H-pyrazol-4-yl)methyl)-4-(4-methylcyclohexyl)-1,2,5,6-tetrahydropyridin-3-yl)-5-(4-(pyrazolo[1,5-a]pyrimidin-2-yl)phenyl)thiophene-2-carboxylic acid;
3-(1-((1,3-dimethyl-1H-pyrazol-4-yl)methyl)-4-(4-methylcyclohexyl)-1,2,5,6-tetrahydropyridin-3-yl)-5-(4-(thiazole-4-carboxamido)phenyl)thiophene-2-carboxylic acid;
5-(3-fluoro-4-(thiazole-4-carboxamido)phenyl)-3-(1-methyl-4-(4-methylcyclohexyl)-1,2,5,6-tetrahydropyridin-3-yl)thiophene-2-carboxylic acid;
3-(5-cyclohexyl-1-methyl-1,2,3,6-tetrahydro-pyridin-4-yl)-5-{4-[(thiazole-4-carbonyl)-amino]-phenyl}-thiophene-2-carboxylic acid;
3-(5-cyclopentyl-1-methyl-1,2,3,6-tetrahydro-pyridin-4-yl)-5-phenyl-thiophene-2-carboxylic acid;
3-(4-cyclohexyl-1-methyl-1,2,5,6-tetrahydro-pyridin-3-yl)-5-{4-[(thiazole-4-carbonyl)-amino]-phenyl}-thiophene-2-carboxylic acid;
3-(5-cyclohexyl-1-methyl-1,2,3,6-tetrahydro-pyridin-4-yl)-5-(3,3-dimethyl-but-1-ynyl)-thiophene-2-carboxylic acid;
and salts (e.g., pharmaceutically acceptable salts) and solvates thereof.

The invention further provides compounds that can be useful as prodrugs. For example, the carboxyl group on the central thiophene moiety of the compounds of Formula Ia may be modified to any of a variety of promoieties using conventional techniques. For example, a carboxyl moiety in a compound of Formula Ia may be replaced by or modified to a corresponding amides, carbamates, carbonates, or esters, provided that biotransformation processes can yield the appropriate carboxyl form of the parent compound. Ideally the prodrug form will, upon biotransformation, yield the parent compound in a high recovery ratio, and will be non-toxic or have no significant safety concerns.

Accordingly, in one aspect, there are provided compounds of Formula I in which the carboxyl group attached to the central thiophene of a compound is esterified, e.g., the group —C(O)OH is replaced by the group —C(O)O—R$^P$, wherein R$^P$ is —C$_{1-4}$alkyl, —C$_{1-4}$alkyl-OC(O)O—C$_{1-4}$alkyl, 5-methyl-2-oxo-[1.3]dioxol-4-ylmethyl, or —C$_{1-4}$alkyl-NR$^U$R$^V$, wherein R$^U$ and R$^V$ are independently hydrogen or —C$_{1-4}$alkyl.

In some aspects, compounds of Formula are contemplated as described herein wherein R$^4$ is other than hydrogen.

In some embodiments, prodrug forms of a compound of Formula I can have reduced potency for inhibition of HCV polymerase. Alternatively, such prodrug forms can have an IC$_{50}$ against HCV polymerase that is at least 50-fold, at least 100-fold, at least 150-fold, at least 200-fold, or at least 500-fold higher than the IC$_{50}$ of the corresponding unmodified carboxyl form of the compound.

General Preparation of Compounds

The compounds of the invention may be prepared by any suitable synthetic route, using chemical techniques and apparatus known to the skilled organic chemist. Details of the syntheses of exemplary compounds are provided in the Examples below. General outlines of such synthetic processes are provided to aid the understanding of the invention.

General Scheme 1 shows a preparation of compounds within Formula 1. Commercially available methyl 3-aminothiophene-2-carboxylate 1 can be transformed into methyl 3-iodothiophene-2-carboxylate 2 by the Sandmeyer reaction [see Hodgson H. H., *Chem. Rev.* 1947, 40(2):251-77], such as sequential treatment with tert-butyl nitrite and diiodomethane. A Suzuki reaction [see Suzuki, A. *J. Organometallic Chem.* 1999, 576:147-68] of 2 with pyridineboronic acid 3 affords 4. Palladium catalyzed coupling of 4 with an organo-metallic compound 5 (such as alkylzinc, or alkenylboronic acid) results in 6. Alkylation of pyridine in 6 is achieved by stirring with an alkyl halide, such as an alkyl iodide or alkyl bromide, in an inert solvent (such as acetonitrile). Reduction of 7 is effected by sodium borohydride in methanol to give the tetrahydropyridine 8. Deprotonation of 8 with a strong base (such as LDA) in THF at low temperature (−78 to −40° C.) is followed by addition of iodine to give 9. Suzuki coupling of 9 with a boronic acid gives 10, which is saponified to give final compound 10a. Alternatively, Sonogashira coupling [see Chinchilla R. and Nijera C., *Chem. Rev.* 2007, 107(3):874-922] of 9 with an alkyne results in 11, which is further saponified to yield final compound 11a. Suitable substitution of appropriate pyridineboronic acids can be used to prepare compounds of Formula I in which the nitrogen of the final tetrahydropyridine appears in the alternative position, i.e., X=—CH— and Y=—N—.

General Scheme 2 shows an alternative preparation of compound 6 in Scheme 1, when $R^2$ is a cyclic alkyl group. Treatment of a cyclic ketone 12 with a strong base such as LDA at low temperature (such as 0° C. to −70° C.), then quenched with N,N-bis(trifluoromethanesulfonyl)-aniline results in 13. Palladium-catalyzed reaction of 13 with a diboronate results in the desired cyclic alkenylboronic acid 5a. Suzuki coupling of 5a with 4 gives 6a. The cyclic alkene can be saturated with hydrogen gas under 50 psi, to give the cyclic alkane 6b.

General Scheme 2 - Preparation of Cyclic-Alkene and Cyclic Alkyl Groups

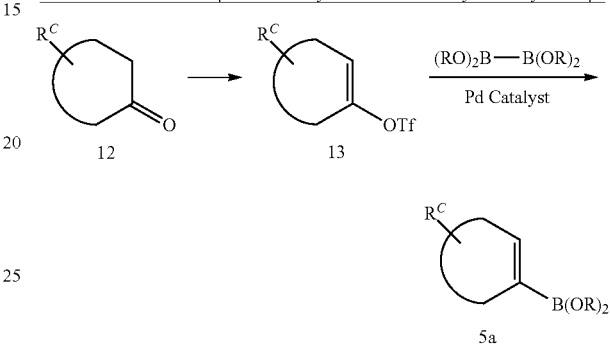

General Scheme 1 - Synthesis of Compounds of Formula II

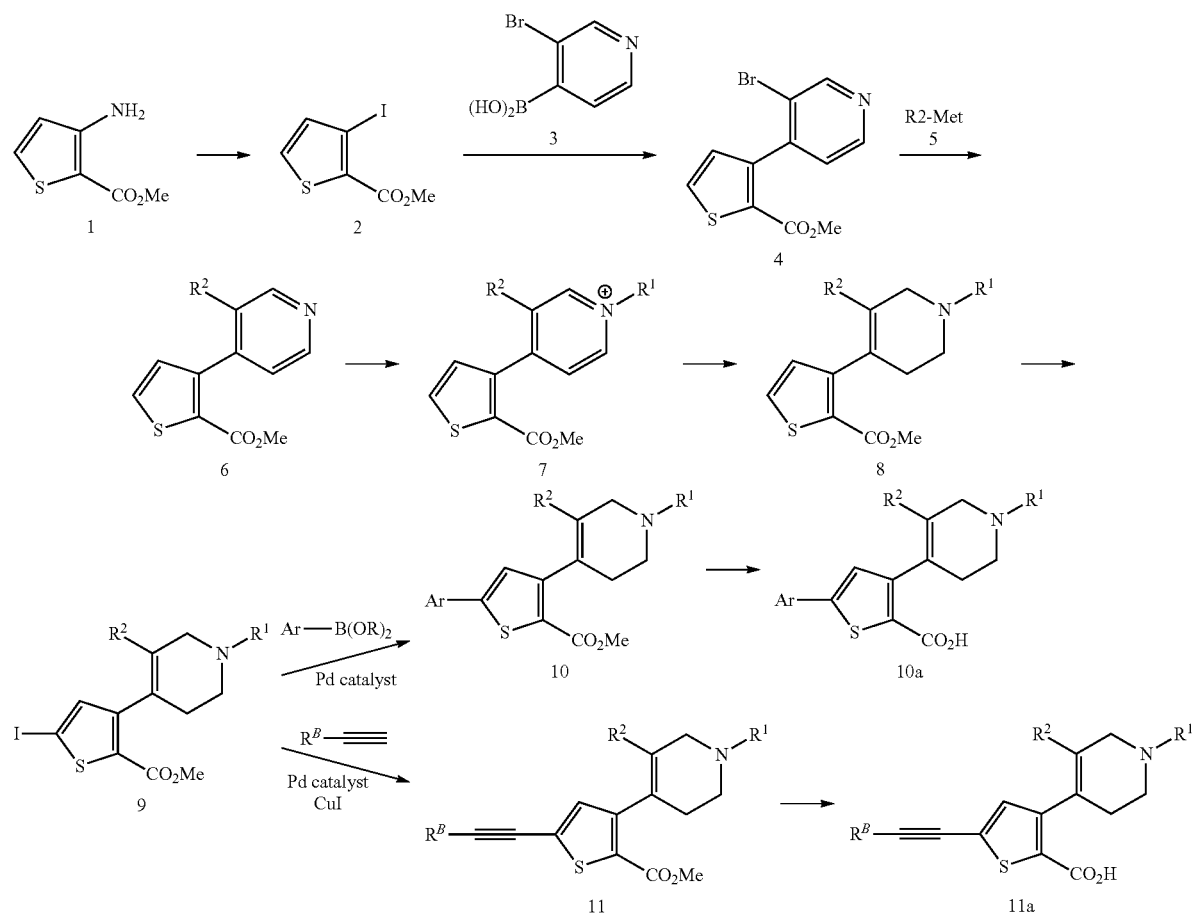

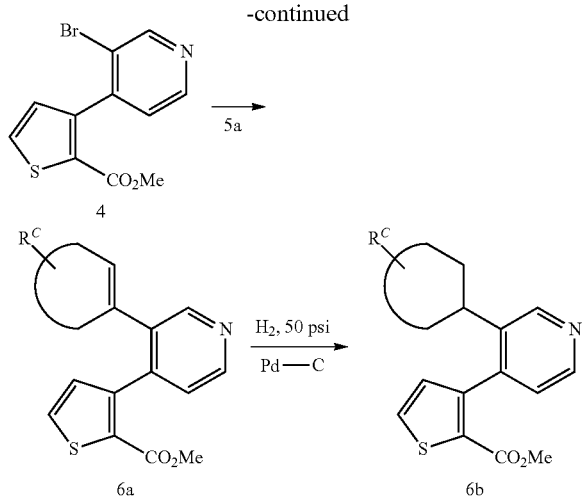

Alternatively, $R^1$ in compounds of formula 10 and 11 (General Scheme 1) can be prepared according to General Scheme 3. Compound 14 (e.g., a compound of Formula I in which $R^1$=benzyl) is treated with 1-chloroethyl chloroformate [see Gubert et al., *Synthesis,* 1991, 22(44):318], to give the cyclic secondary amine 15. The secondary amine 15 may be further derivatized with reductive amination, reaction with an acylchloride, reaction with a sulfonyl chloride, reaction with a chloroformate, or reaction with a carbamoyl chloride, followed by hydrolysis of the corresponding ester to give, respectively, final compound 16a, or 16b, or 16c, or 16d, or 16e.

In General Scheme 3, $R^D$ is hydrogen, —$C_{0-2}$alkyl, —$C_{0-2}$alkyl-$C_{3-6}$cycloalkyl, —$C_{1-3}$hydroxyalkyl, or —$C_{0-3}$alkyl-$C_{6-10}$aryl; and $R^E$ is hydrogen, or —$C_{1-4}$alkyl; or $R^D$ and $R^E$ together with the nitrogen to which they are attached can form a 4- to 6-membered ring.

General Scheme 3 - Derivatization of Tetrahydropyridines

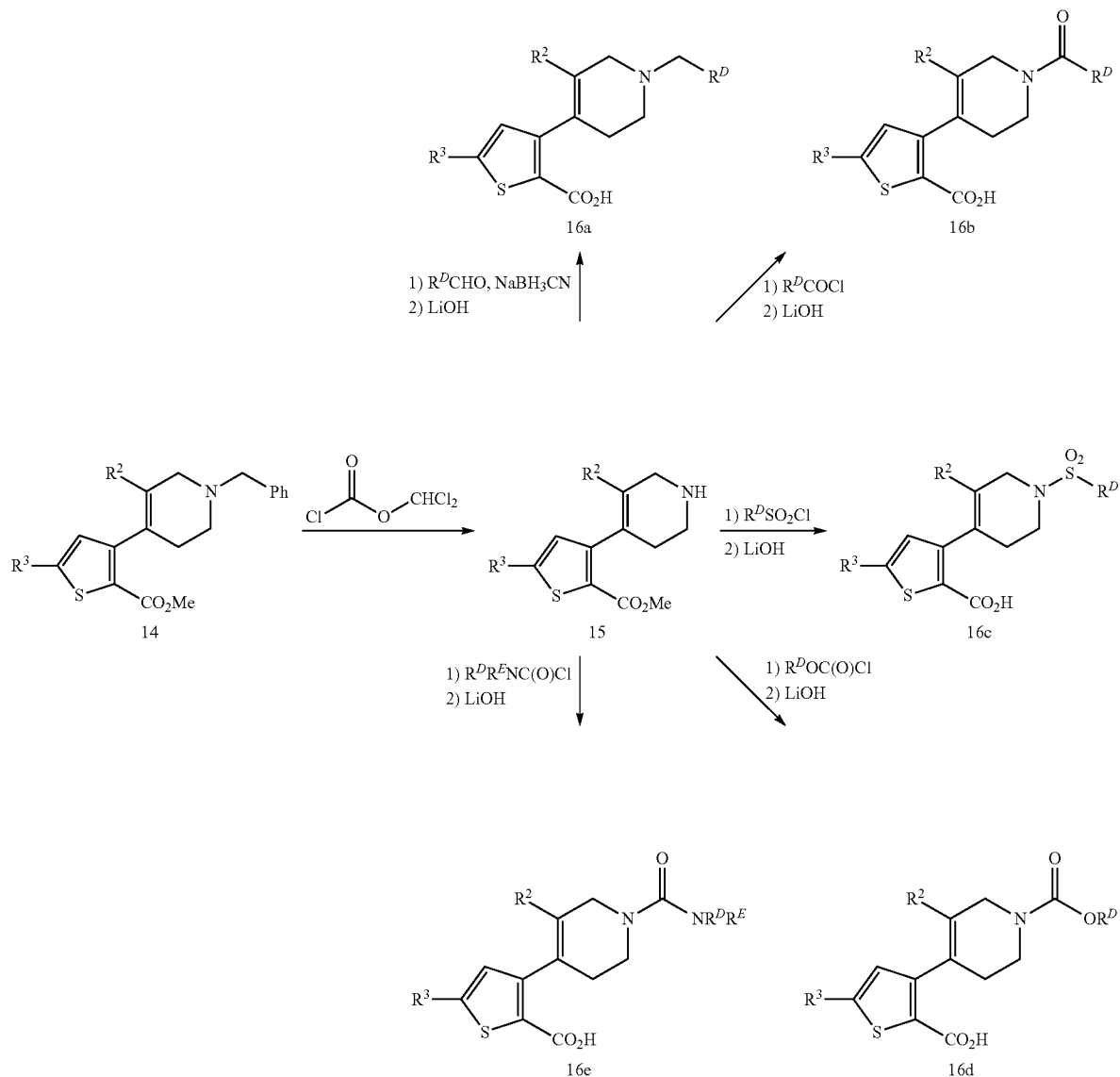

In General Scheme 4, compound 3 prepared (from General Scheme 1) can be reacted with $R^{2B}X$, where $R^{2B}$ is a cycloalkenyl and X is triflate (OTf) or iodide (I), under Suzuki reaction conditions. The resulting pyridinyl bromide 17 can be converted to boronic acid derivative 18 via either a Suzuki reaction with a diboronate compound or a sequential treatment with butyllithium and a trialkylborate. Suzuki reaction between the boronic acid derivative 18 and iodide 2 from Scheme 1 produces 19. Optionally, 19 with cycloalkenyl $R^{2B}$ can be converted to 20 with cycloalkanyl $R^{2B}$ via hydrogenation under moderate pressure. Methylation of pyridine can be followed by reduction with reagent such as sodium borohydride to give the tetrahydropyridine 22. Deprotonation of 22 by a base such as LDA is followed by quenching the anion with iodine to give 23. "N"-demethylation of 23 can be accomplished with known methods (Wuts, P. G. M.; Greene, T. W., 2007, *Greene's Protective Groups in Organic Synthesis*, $4^{th}$ Ed. Hoboken, N.J.: Wiley-Interscience) to give 24. Installation of $R^{1B}$ on 24 to yield 25 can be achieved with many methods, such as reductive amination of ketones and aldehydes, acylation with acid chloride and chloroformates, sulfonylation with sulfonyl chlorides, alkylation with alkyl halides, etc. Compound 25 can be converted via a palladium catalyzed reaction such as a Suzuki reaction, Negishi reaction, Sonogashira reaction, Heck reaction, Stille reaction, or Buchwald-Hartwitz amination to 26. Saponification of 26 provides the acid 27.

General Scheme 4 - General Preparation of Compounds of Formula III

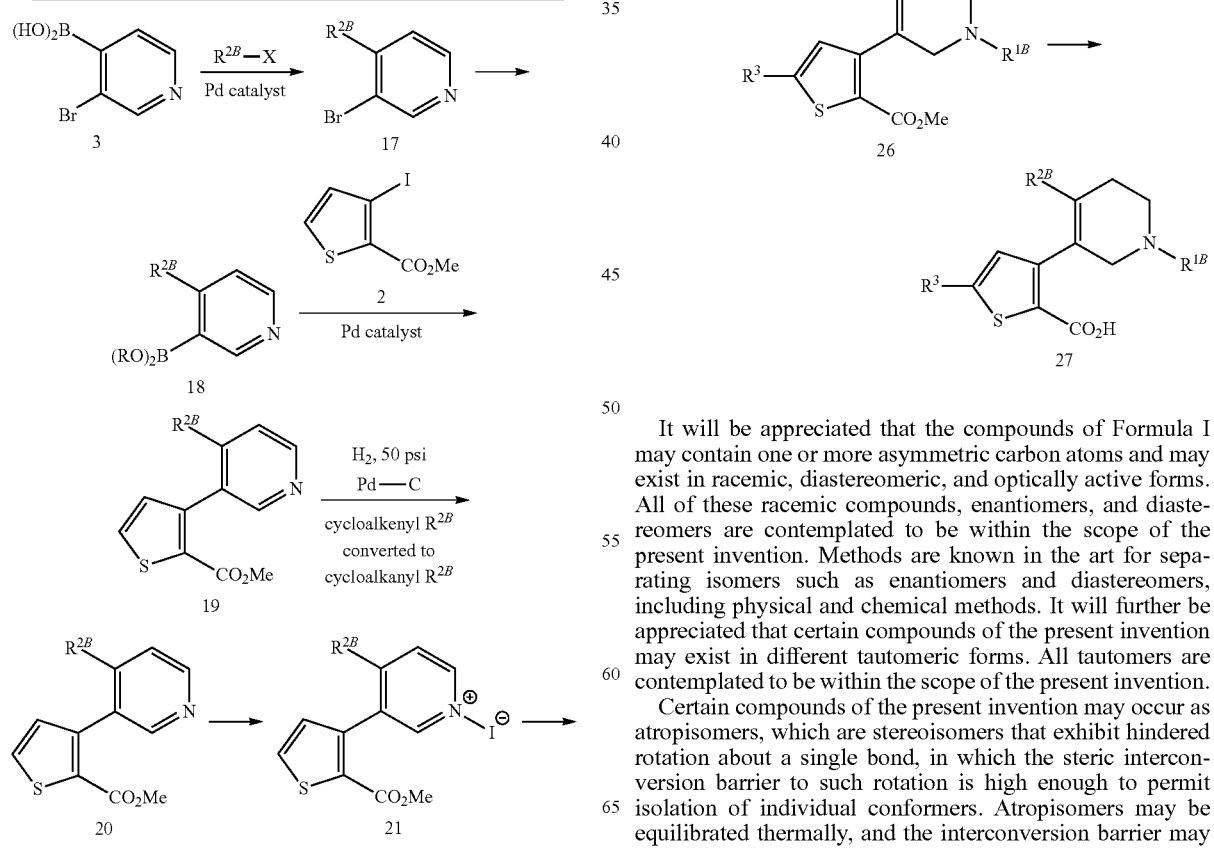

It will be appreciated that the compounds of Formula I may contain one or more asymmetric carbon atoms and may exist in racemic, diastereomeric, and optically active forms. All of these racemic compounds, enantiomers, and diastereomers are contemplated to be within the scope of the present invention. Methods are known in the art for separating isomers such as enantiomers and diastereomers, including physical and chemical methods. It will further be appreciated that certain compounds of the present invention may exist in different tautomeric forms. All tautomers are contemplated to be within the scope of the present invention.

Certain compounds of the present invention may occur as atropisomers, which are stereoisomers that exhibit hindered rotation about a single bond, in which the steric interconversion barrier to such rotation is high enough to permit isolation of individual conformers. Atropisomers may be equilibrated thermally, and the interconversion barrier may be measured kinetically.

The present invention also includes isotopically-labeled compounds of Formula I. The isotopically-labeled compounds are identical to the compounds of this invention, but for being manufactured to replace one or more atoms with another isotope of the same element. For example, a selected atom may be changed from a naturally abundant isotope to a rare isotope. Exemplary isotopes that can be incorporated into compounds of the invention include isotopes of hydrogen, carbon, nitrogen, oxygen, sulfur, chlorine, such as $^2$H, $^3$H, $^{11}$C, $^{13}$C, $^{14}$C $^{13}$N, $^{15}$O, $^{17}$O, $^{35}$S, $^{18}$F, $^{36}$Cl. Certain isotope-labeled compounds (e.g., $^3$H and $^{14}$C) are useful in compound or substrate tissue distribution studies. Certain heavier isotopes (e.g., $^2$H) may afford therapeutic advantages resulting from possible greater metabolic stability.

Also included within the present invention are salts, (e.g., pharmaceutically acceptable salts) of the compounds of Formula I, and particularly compounds of Formula Ia. Any salt that is consistent with the overall stability and utility of the compounds of Formula I may be provided using conventional methods. Suitable salts include, without limitation, salts of acidic or basic groups that can be present in the compounds provided herein. Under certain acidic conditions, the compound can form a wide variety of salts with various inorganic and organic acids. Acids that can be used to prepare pharmaceutically acceptable salts of such basic compounds are those that form salts comprising pharmacologically acceptable anions including, but not limited to, acetate, benzenesulfonate, benzoate, bicarbonate, bitartrate, bromide, calcium edetate, camsylate, carbonate, chloride, bronmide, iodide, citrate, dihydrochloride, edetate, edisylate, estolate, esylate, fumarate, gluceptate, gluconate, glutamate, glycollylarsanilate, hexylresorcinate, hydrabamine, hydroxynaphthoate, isethionate, lactate, lactobionate, malate, maleate, mandelate, mesylate (methylenesulfonate), methylsulfate, muscate, napsylate, nitrate, panthothenate, phosphate/diphosphate, polygalacturonate, salicylate, stearate, succinate, sulfate, tannate, tartrate, teoclate, triethiodide and pamoate. Under certain basic conditions, the compound can form base salts with various pharmacologically acceptable cations. Non-limiting examples of such salts include alkali metal or alkaline earth metal salts and, particularly, calcium, magnesium, sodium, lithium, zinc, potassium and iron salts, as well as tetraalkylammonium salts. General information regarding pharmaceutically acceptable salts may be found in Stahl P H, and Wermuth C G, eds., *Handbook of Pharmaceutical Salts: Properties, Selection and Use*, 2002, Wiley-VCH/VHCA Weinheim/Zürich.

The present invention also relates provides hydrates and other solvates of the compounds of Formula I. Thus, hydrates and other solvates of the compounds of Formula I and hydrates and other solvates of the salts of the compounds of Formula I are included within the scope of the present invention.

Esters, including pharmaceutically acceptable esters, of the compounds of Formula (I) are included within the scope of the present invention. Esters include stable carboxylic acid esters —COOR, for example, in which R is selected from optionally substituted straight or branched chain alkyl, alkoxyalkyl, aralkyl, aryloxyalkyl, aryl; or for example, —CH$_2$OC(O)R' or —CH$_2$OCO$_2$R' in which R' is alkyl (e.g., R' is tert-butyl). Unless otherwise specified, any alkyl moiety present in such esters suitably contains 1 to 6 carbon atoms, preferably 1 to 4 carbon atoms.

If there should be, in this specification, a discrepancy between a depicted structure and a name given to that structure, the depicted structure is to be accorded more weight. In addition, if the stereochemistry of a structure or a portion of a structure is not indicated with conventionally accepted notation, for example, bold or dashed lines, the structure or portion thereof is to be interpreted as encompassing all stereoisomers of such structure.

A compound of Formula I and its salts (e.g., pharmaceutically acceptable salts) may exist in crystalline forms, which may appear as different polymorphs or pseudopolymorphs. As used herein, crystalline "polymorphism" means the ability of a crystalline compound to exist in different crystal structures. Polymorphism generally can occur as a response to changes in temperature, pressure, or both. Polymorphism can also result from variations in the crystallization process. Polymorphs can be distinguished by various physical characteristics known in the art such as x-ray diffraction patterns, solubilities, and melting points. Polymorphism may result from differences in crystal packing (packing polymorphism) or differences in packing between different conformers of the same molecule (conformational polymorphism). As used herein, crystalline "pseudopolymorphism" means the ability of a hydrate or solvate of a compound to exist in different crystal structures. The pseudopolymorphs of the instant invention may exist due to differences in crystal packing (packing pseudopolymorphism) or due to differences in packing between different conformers of the same molecule (conformational pseudopolymorphism). The present invention comprises all polymorphs and pseudopolymorphs of the compounds of Formula I and their pharmaceutically acceptable salts.

A compound of Formula I and its salts or solvates may also exist as amorphous solids. As used herein, an amorphous solid is a solid in which there is no long-range order of the positions of the atoms in the solid. This definition applies as well when the crystal size is two nanometers or less. Additives, including solvents, may be used to create the amorphous forms of the instant invention. The instant invention comprises all amorphous forms of the compounds of Formula I and their salts, (e.g., pharmaceutically acceptable salts) and solvates.

In one aspect the invention provides a composition comprising a compound according to Formula I or a salt (e.g., a pharmaceutically acceptable salt) or solvate thereof. Such compositions may further comprise at least one further component, such as a pharmaceutically acceptable carrier or excipient.

Methods of Use

In another aspect, the invention provides a method for treating a hepatitis C virus infection in a host, comprising administering to the host a therapeutic amount of at least one compound according to Formula I, or a pharmaceutically acceptable salt thereof. There is likewise provided a compound according to Formula I or a pharmaceutically acceptable salt of such compound, for use in the treatment of a HCV infection in a host. In some embodiments, the method further comprises administering to the host at least one other therapeutically active agent selected from the group consisting of interferons, ribavirin, taribavirin, nucleoside HCV polymerase inhibitors, non-nucleoside HCV polymerase inhibitors, HCV NS3-4A protease inhibitors, HCV NS5A inhibitors, HCV entry inhibitors, HCV NS3 inhibitors, and HCV NS4B inhibitors. In some embodiments, the compound may be used for preventing HCV infection in a host. In some embodiments, the compound may be used to limit infection in a host. In some embodiments, the host is a human subject. In some embodiments, the compound is a compound of Formula Ia. In some embodiments, the HCV genotype is 1, or the HCV genotype is 1a, or the HCV genotype is 1b.

In another aspect, the invention provides a method for treating a hepatitis C virus reactivation in a host, comprising administering to the host a therapeutic amount of at least one compound according to Formula I, or a pharmaceutically acceptable salt thereof. There is likewise provided a compound according to Formula I or a pharmaceutically acceptable salt of such compound, for use in the treatment of a HCV infection in a host. In some embodiments, the method further comprises administering to the host at least one other therapeutically active agent selected from the group consisting of interferons, ribavirin, taribavirin, nucleoside HCV polymerase inhibitors, non-nucleoside HCV polymerase inhibitors, HCV NS3-4A protease inhibitors, HCV NS5A inhibitors, HCV entry inhibitors, HCV NS3 inhibitors, and HCV NS4B inhibitors. In some embodiments, the compound may be used for preventing HCV infection in a host. In some embodiments, the compound may be used to linmit infection in a host. In some embodiments, the host is a human subject. In some embodiments, the compound is a compound of Formula Ia. In some embodiments, the HCV genotype is 1, or the HCV genotype is 1a, or the HCV genotype is 1b.

In another aspect, the invention provides a method for inhibiting or reducing the activity of hepatitis C virus polymerase in a host, comprising administering to the host a therapeutic amount of at least one compound according to Formula I or a pharmaceutically acceptable salt thereof. There is likewise provided a compound according to Formula I, or a pharmaceutically acceptable salt of such compound, for use in inhibiting or reducing the activity of HCV polymerase in a host. In some embodiments, the method further comprises administering to the host at least one other therapeutically active agent selected from the group consisting of interferons, ribavirin, taribavirin, nucleoside HCV polymerase inhibitors, non-nucleoside HCV polymerase inhibitors, HCV NS3-4A protease inhibitors, HCV NS5A inhibitors, HCV entry inhibitors, HCV NS3 inhibitors, and HCV NS4B inhibitors. In some embodiments, the host is a human subject. In some embodiments, the compound is a compound of Formula Ia. In some embodiments, the HCV genotype is 1, or the HCV genotype is 1a, or the HCV genotype is 1b.

In a further aspect, the invention provides a method for inhibiting or reducing hepatitis C virus polymerase replication in a host, comprising administering to the host a therapeutic amount of at least one compound according to Formula I or a pharmaceutically acceptable salt thereof. There is likewise provided a compound according to Formula I, or a pharmaceutically acceptable salt of such compound, for use in inhibiting or reducing HCV polymerase replication in a host. In some embodiments, the method further comprises administering to the host at least one other therapeutically active agent selected from the group consisting of interferons, ribavirin, taribavirin, nucleoside HCV polymerase inhibitors, non-nucleoside HCV polymerase inhibitors, HCV NS3-4A protease inhibitors, HCV NS5A inhibitors, HCV entry inhibitors, HCV NS3 inhibitors, and HCV NS4B inhibitors. In some embodiments, the host is a human subject. In some embodiments, the compound is a compound of Formula Ia. In some embodiments, the HCV genotype is 1, or the HCV genotype is 1a, or the HCV genotype is 1b.

In another aspect, the invention provides a method of treating HCV-associated liver cirrhosis, chronic liver disease, hepatocellular carcinoma, cryoglobulinaemia, and/or liver fibrosis in a host, which comprises administering to the host a therapeutic amount of at least one compound according to Formula I or a pharmaceutically acceptable salt thereof. There is likewise provided a compound according to Formula 1, or a pharmaceutically acceptable salt of such compound, for use in HCV-associated liver cirrhosis, chronic liver disease, hepatocellular carcinoma, cryoglobulinaemia, and/or liver fibrosis in a host. In some embodiments, the method further comprises administering to the host at least one other therapeutically active agent selected from the group consisting of interferons, ribavirin, taribavirin, nucleoside HCV polymerase inhibitors, non-nuclcoside HCV polymcrase inhibitors, HCV NS3-4A protease inhibitors, HCV NS5A inhibitors, HCV entry inhibitors, HCV NS3 inhibitors, and HCV NS4B inhibitors. In some embodiments, the host is a human subject. In some embodiments, the compound is a compound of Formula Ia. In some embodiments, the HCV genotype is 1, or the HCV genotype is 1a, or the HCV genotype is 1b.

In another aspect, the invention provides a use of a compound according to Formula I or a pharmaceutically acceptable salt thereof in the manufacture of a medicament for treating a hepatitis C virus infection in a host. In some embodiments, the host is a human subject. In some embodiments, the compound is a compound of Formula Ia. In some embodiments, the HCV genotype is 1, or the HCV genotype is 1a, or the HCV genotype is 1b.

In another aspect, the invention provides a use of a compound according to Formula I or a pharmaceutically acceptable salt thereof in the manufacture of a medicament for inhibiting or reducing the activity of hepatitis C virus polymerase in a host. In some embodiments, the host is a human subject. In some embodiments, the compound is a compound of Formula Ia. In some embodiments, the HCV genotype is 1, or the HCV genotype is 1a, or the HCV genotype is 1b.

In another aspect, the invention provides a use of a compound according to Formula I or a pharmaceutically acceptable salt thereof in the manufacture of a medicament for inhibiting or reducing hepatitis C virus polymerase replication in a host. In some embodiments, the host is a human subject. In some embodiments, the compound is a compound of Formula Ia. In some embodiments, the HCV genotype is 1, or the HCV genotype is 1a, or the HCV genotype is 1b.

The invention provides, in a further aspect, a combination comprising at least one compound of Formula I or a pharmaceutically acceptable salt thereof together with at least one other active agent, especially interferon, ribavirin, and/or an additional anti-HCV agent. In some embodiments, the compound is a compound of Formula 1a. In some embodiments, the HCV genotype is 1, or the HCV genotype is 1a, or the HCV genotype is 1b.

In a further aspect of the present invention there is provided a compound chosen from compounds of Formula I or a pharmaceutically acceptable salt thereof for use in human or veterinary medical therapy, particularly in the treatment or prevention of viral infection, particularly flavivirus infection, for example, HCV infection. In some embodiments, the compound is a compound of Formula Ia. In some embodiments, the HCV genotype is 1, or the HCV genotype is 1a, or the HCV genotype is 1b.

In another aspect, the invention provides for the use of a compound of Formula I or a pharmaceutically acceptable salt thereof in the manufacture of a medicament for the treatment and/or prophylaxis of viral infection, particularly HCV infection. In some embodiments, the compound is a compound of Formula Ia. In some embodiments, the HCV genotype is 1, or the HCV genotype is 1a, or the HCV genotype is 1b.

In yet another aspect, the invention provides methods for inhibiting HCV polymerase activity in a biological sample, comprising contacting the biological sample with an effective inhibitory amount of a compound of Formula I or a pharmaceutically acceptable salt thereof. In some embodiments, the biological sample is a blood, tissue, or other fluid sample. In some embodiments, the biological sample is a culture of host cells, e.g., hepatocytes, or hepatocellular carcinoma cells, infected with HCV. For a survey of biological assay systems in which the compounds of the invention may be demonstrated, see, Huang et al., "Hepatitis C Virus-related Assays," Chapter 2 in *Hepatitis C: Antiviral Drug Discovery and Development*, S-L Tan and Y He, eds., Caister Academic Press (2011).

Such methods may be useful in research or in the clinic, for example, in the identification of HCV genotypes amenable to inhibition with the compounds of the invention or the identification of subjects who may beneficially be treated using compounds or compositions of the invention. In some embodiments, the compound is a compound of Formula Ia. In some embodiments, the HCV genotype is 1, or the HCV genotype is 1a, or the HCV genotype is 1b.

In various of the embodiments of the methods, set forth above, of using the compounds of the invention for treatment or prevention of HCV infection or the sequelae of such infection, the HCV may be genotypically unidentified. In other embodiments, the HCV is HCV genotype 1, optionally HCV genotype 1a or 1b. In other embodiments, the HCV may be selected from among other HCV genotypes, including HCV genotypes 2 and/or 3.

Without intending to be bound by theory, it is believed that the compounds of Formula I that exhibit inhibition of HCV replication or infectivity derive their activity through interaction with or binding to an allosteric site controlling the conformation of the HCV NS5B protein, and thereby inhibiting viral RNA synthesis in the host cell. It is believed that the compounds of Formula I that exhibit inhibition of HCV replication or infectivity interact with or bind to the NNI II allosteric site. As demonstrated in the Examples below, compounds of Formula I exhibit potent inhibition of the NS5B RdRp activity in a biochemical assay in vitro as well as inhibition of HCV replication as measured in an HCV replicon cell assay.

Definitions

It is understood that the compounds of the invention, as described herein, may be substituted with a variety of substituents or functional moieties. In general, the term "substituted," whether or not preceded by the term "optionally," and substituents contained in formulas of this invention, refer to the replacement of hydrogen radicals in a given structure with the radical of a specified substituent. When more than one position in any given structure may be substituted with more than one substituent selected from a specified group, the substituents are, unless otherwise indicated, to be understood as independent, i.e., they may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic, carbon and heteroatom substituents of organic compounds. For purposes of this invention, heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. Combinations of substituents and variables envisioned by this invention are preferably those that result in the formation of stable compounds useful as described herein, for example, in the treatment and prevention of disorders associated with HCV infection.

The term "aliphatic," as used herein, includes both saturated and unsaturated, straight chain (i.e., unbranched) or branched aliphatic hydrocarbons, which are optionally substituted with one or more functional groups. As will be appreciated by one of ordinary skill in the art, "aliphatic" is intended herein to include, but is not limited to, alkyl, alkenyl, alkynyl moieties. Thus, as used herein, the term "alkyl" includes straight and branched alkyl groups. An analogous convention applies to other generic terms such as "alkenyl," "alkynyl" and the like. Furthermore, as used herein, the terms "alkyl," "alkenyl," "alkynyl," and the like encompass both substituted and unsubstituted groups. In certain embodiments, the alkyl, alkenyl and alkynyl groups employed in the invention contain about 1-20 aliphatic carbon atoms ($C_{1-20}$). In certain other embodiments, the alkyl, alkenyl, and alkynyl groups employed in the invention contain about 1-10 aliphatic carbon atoms ($C_{1-10}$). In yet other embodiments, the alkyl, alkenyl, and alkynyl groups employed in the invention contain about 1-8 aliphatic carbon atoms ($C_{1-8}$). In still other embodiments, the alkyl, alkenyl, and alkynyl groups employed in the invention contain about 1-6 aliphatic carbon atoms ($C_{1-6}$). In yet other embodiments, the alkyl, alkenyl, and alkynyl groups employed in the invention contain about 1-4 carbon atoms ($C_{1-4}$). Aliphatic groups include, for example, for example, methyl, ethyl, n-propyl, isopropyl, allyl, n-butyl, sec-butyl, isobutyl, tert-butyl, n-pentyl, sec-pentyl, isopentyl, tert-pentyl, n-hexyl, sec-hexyl, and the like, which may bear one or more substituents. Alkenyl groups include, for example, ethenyl, propenyl, butenyl, 1-methyl-2-buten-1-yl, and the like. Alkynyl groups include, for example, ethynyl, 2-propynyl (propargyl), 1-propynyl, and the like.

The term "alkoxy," as used herein, refers to a group having the formula —OR wherein R is $C_{1-6}$alkyl or $C_{1-6}$haloalkyl. Such groups include methoxy, ethoxy, propoxy, and the like. In some embodiments, an alkoxy group may be a $C_{1-3}$alkoxy group, optionally substituted with 1-3 halogens. In some embodiments, an alkoxy group may be a $C_{1-4}$alkoxy group, optionally substituted with 1-5 halogens. When substituted with one or more halogens, alkoxy groups may be referred to a "haloalkoxy" groups.

The term "alkyl," as used herein, refers to a saturated straight chain or branched hydrocarbon. In some embodiments, alkyl groups have 1 to 10 ($C_{1-10}$), 1 to 6 ($C_{1-6}$), or 1 to 3 ($C_{1-3}$) carbon atoms. Representative saturated straight chain alkyl substituents include methyl, ethyl, n-propyl, n-butyl, n-pentyl, and n-hexyl; while saturated branched alkyl substituents include isopropyl, sec-butyl, isobutyl, tert-butyl, isopentyl, 2-methylbutyl, 3-methylbutyl, and the like.

The terms "amine" and "amino," as used herein, refer to a group having the formula —NR'R" wherein R' and R" are both hydrogen. The term "alkylamine," as used herein, refers to a group having the formula —NR'R" wherein R' is hydrogen or alkyl, and R" is alkyl. Thus, the term alkylamine includes monoalkylamine and dialkylamine.

The term "IC$_{50}$," as used herein, refers to an amount, concentration, or dosage of a particular test compound that achieves a 50% inhibition of a maximal response in an in vitro assay—such as a biochemical or enzymatic assay—that measures such response.

The term "aralkyl," as used herein refers to a group of the formula —RaRb where Ra is an alkyl group as defined above, substituted by Rb, an aryl group, as defined above, e.g., benzyl.

The term "aryl," as used herein, refers to a group of carbocylic ring system, including monocyclic, bicyclic, tricyclic, tetracyclic 3- to 14-membered carbocyclic (C$_{3-14}$) ring systems, wherein at least one of the rings is an aromatic moiety, any of which may optionally be substituted. The aryl moiety may be fully aromatic, examples of which are phenyl, naphthyl, anthracenyl, acenaphthylenyl, azulenyl, fluorenyl, indenyl, indolyl, indazolyl, triazolopyrmidinyl, and pyrenyl. The aryl group may also contain an aromatic ring in combination with a non-aromatic ring, examples of which are acenaphene, indene, and fluorene. In certain embodiments of the present invention, "aryl" refers to a mono- or bicyclic carbocyclic ring system having one or two rings satisfying the Huckel rule for aromaticity, including, but not limited to, phenyl, naphthyl, tetrahydronaphthyl, indanyl, indenyl, phenanthryl, anthracyl, and the like.

The term "cycloalkyl," as used herein, refers specifically to monocyclic or bicyclic alkyl groups having three to seven, preferably three to ten carbon atoms. Suitable cycloalkyl moieties include cyclopropyl, cyclobutyl, cyclopentyl, cyclohexyl, cycloheptyl, and the like, which may optionally be substituted.

The term "halogen," as used herein, refers to F, Cl, Br, or I.

The term "haloalkyl," as used herein, refers to an alkyl group, such as a —C$_{1-6}$alkyl group, in which one or more of the hydrogen atoms is replaced by a halogen. Such groups include chloromethyl, fluoromethyl, trifluoromethyl, and the like. In some embodiments, a haloalkyl group may be a —C$_{1-3}$alkyl group substituted with 1-3 halogens. In some embodiments, a haloalkyl group may be a —C$_{1-4}$alkyl group substituted with 1-5 halogens. The term "HCV polymerase," as used herein, refers to the NS5B polymerase of HCV.

The term "heteroaryl," as used herein, refers to a stable 3- to 15-membered aromatic ring moiety that consists of carbon atoms and from one to five heteroatoms independently selected from N, O, and S, and may optionally be substituted. In some embodiments, the heteroaryl moiety may be a monocyclic, bicyclic, tricyclic, or tetracyclic ring; and nitrogen or sulfur atoms in the ring structure may be optionally oxidized; and nitrogen atom(s) may be optionally quaternized. The heteroaryl moiety ring may be attached to the main structure at any heteroatom or carbon atom that results in the creation of a stable compound. Exemplary heteroaryl groups include pyridyl, pyrazinyl, pyrimidinyl, pyrrolyl, pyrazolyl, imidazolyl, thiazolyl, oxazolyl, isoxazolyl, thiadiazolyl, oxadiazolyl, thiophenyl, furanyl, quinolinyl, isoquinolinyl, pyrazolopyrimidinyl, furopyridinyl, and the like.

The term "heterocyclyl," as used herein, refers to a stable 3- to 15-membered aromatic or non-aromatic ring moiety that consists of carbon atoms and from one to five heteroatoms independently selected from N, O, and S, and may optionally be substituted. In some embodiments, the heterocyclic group may be a monocyclic, bicyclic, tricyclic, or tetracyclic group, which may include fused or bridged rings; and the nitrogen or sulfur atoms in the heterocyclic group may be optionally oxidized; the nitrogen atom may be optionally quaternized; and the heterocyclic group may be aromatic, or partially or fully saturated. The heterocyclic group may be attached to the main structure at any heteroatom or carbon atom that results in the creation of a stable compound. Exemplary heterocyclic groups include heteroaryl groups as described herein and non-aromatic heterocyclic groups, i.e., heterocycloalkyl groups, such as morpholinyl, piperidinyl, piperazinyl, pyranyl, pyrrolidinyl, tetrahydrofuranyl, tetrahydrothiophenyl, tetrahydropyranyl, dioxolanyl, and the like.

The term "pharmaceutically acceptable," as used herein in relation to an ingredient (such as an active ingredient, a salt thereof, or an excipient) that may be included in a pharmaceutical formulation for administration to a patient, refers to that ingredient being acceptable in the sense of being compatible with any other ingredients present in the pharmaceutical formulation and not being deleterious to the patient.

The term "preventing," as used herein, means that the compounds of the present invention are useful when administered to a patient who has not been diagnosed as possibly having the disease at the time of administration, but who would normally be expected to develop the disease or be at increased risk for the disease. Generally, the term "preventing" refers to administration of a compound of the invention prior to the onset of symptoms, particularly to patients at risk of contracting HCV infection. The compounds of the invention will slow the development of disease symptoms, delay the onset of disease, or prevent the individual from developing the disease at all.

The term "prodrug," as used herein, refers to a chemical compound that has little or no pharmacological activity per se or that has properties that are preferred for administration, but that is capable of undergoing biotransformation to a therapeutically active metabolite of interest. For example, a prodrug form of a compound of Formula I may itself have little or no inhibitory activity against HCV polymerase, but would undergo biotransformation in the body of the patient to the active form of the compound. As another example, a prodrug form of a compound of Formula I may have one or more physicochemical properties, e.g., solubility, that imparts to the compound a different pharmacokinetic or pharmacodynamic profile. Biotransformation can include hydrolysis, oxidation, photolysis, or by means of physiological or metabolic processes, e.g., by enzymatic modification. A prodrug may be thought of as including the therapeutic compound covalently linked to a promoicty, and the biotransformation process removes or modifies the promoiety to yield the therapeutic compound. Common functional groups on compounds that may be replaced with or modified to contain a promoiety include, for example, amino, carbonyl, carboxyl, hydroxyl, phosphonyl, and thiolyl groups. See, e.g., Rautio et al., *Nat Rev Drug Discov*, 2008, 7:255-270. If a parent drug contains one of these moieties, the compound may be modified using bioreversible chemistry to contain a promoiety. Alternatively, the prodrug may be prepared with the promoiety incorporated at an earlier synthetic stage, as may be desired.

The term "solvate," as used herein, refers to a complex of variable stoichiometry formed by a solute (in this invention, a compound of Formula I or a salt thereof) and a solvent. Such solvents for the purpose of the invention may not interfere with the biological activity of the solute. Examples of suitable solvents include, but are not limited to, water, methanol, ethanol and acetic acid. Preferably the solvent used is a pharmaceutically acceptable solvent. However, solvates having non-pharmaceutically acceptable solvents are within the scope of the present invention, for example, for use as intermediates in the preparation of other compounds of Formula I and their pharmaceutically acceptable salts. Most preferably the solvent used is water and the resulting solvate may also be referred to as a hydrate. As used herein and unless otherwise indicated, the term "hydrate" means a compound provided herein or a salt thereof that further includes a stoichiometric or nonstoichiometric amount of water bound by non-covalent intermolecular forces.

The term "stable," as used herein, refers to compounds that possess stability sufficient to allow their manufacture, and that maintain the integrity of the compound for a sufficient period of time to be detected and preferably for a sufficient period of time to be useful for the purposes detailed herein. For example, a compound of the invention should be sufficiently stable to permit its purification, or isolation, or identification; or should be sufficiently stable to permit formulation into a pharmaceutically acceptable dosage form.

The term "subject," as used herein, is an animal, typically a mammal, most typically a human, such as a patient. The term "host," as used herein, is a cell, such as a hepatocyte, or a human patient or other subject suspected of being, or determined to have been, infected with HCV, as determined through conventional genetic or serologic techniques.

The term "substituted," as used herein, refers to a moiety in which at least one hydrogen atom is replaced by a non-hydrogen substituent. For example if a phenyl group is said to be optionally substituted, at least one of the hydrogens in the phenyl ring is replaced with a substituent that is not hydrogen. Typically, such substituents are small moieties, such as halo, hydroxyl, $C_{1-4}$alkyl, $C_{1-4}$alkoxy, or cyano. Such substitutions generally either contribute to a desirable property for the molecule or at least do not substantially detract from the desirable properties of the molecule, and in any case should be sufficiently stable for use according to the purposes set forth herein.

The term "therapeutic amount," as used herein, refers to an amount of a compound that would be reasonably expected by the skilled medical practitioner to have a particular therapeutic effect in the patient, taking into consideration such factors as the sex, age, genetic background, body mass, body surface area, mode of administration, and the like, notwithstanding idiosynerasies of the patient's physiology. The therapeutic effect may be realized in the treatment, prevention, and/or management of a HCV infection or a condition or symptom associated with such infection, or the delay or minimization of one or more symptoms associated therewith. The term "therapeutic amount" can therefore, encompass an amount that improves overall therapy, reduces or avoids symptoms or causes of HCV infection, or enhances the therapeutic efficacy of another therapeutic agent. It is possible that a therapeutic amount of a compound may achieve different results when administered to different patients. In some cases, an amount of a compound that produces therapeutic benefit to one patient may yield little or no benefit for another patient, but is still considered a therapeutic amount. In some embodiments, a therapeutic amount of an active compound is an amount determined by the US Food and Drug Administration (or a correlative organization in another country or region) to be safe and effective in the treatment of HCV infection or another specified disease or disorder in a human patient.

It will be appreciated that reference herein to "therapy" and/or "treatment" includes, but is not limited to prevention, retardation, prophylaxis, amelioration, and/or cure of the HCV infection or consequent or associate medical symptoms, conditions, or other sequelae. It will thus be appreciated that references herein to treatment or prevention of HCV infection include treatment or prevention of chronic HCV infection, acute HCV infection, or any of the HCV-associated diseases and disorders such as liver fibrosis, hepatic steatosis, cirrhosis, cryoglobulinemia, and hepatocellular carcinoma. Accordingly, the terms "treat," "treating," and "treatment," as used herein refer to alleviating or reducing the severity of a symptom associated with HCV infection or a condition consequent to such infection. In certain embodiments, compounds of the invention will delay or slow the progression of HCV infection, or a condition consequent to such infection, thereby making it possible for the subject to enjoy a longer life span or a better quality of life.

The term "subtherapeutic amount," as used herein, refers to an amount of a compound that, if administered alone, would be expected to exhibit no therapeutic effect or no significant therapeutic effect in the patient, taking into consideration the foregoing factors. Subtherapeutic amounts of a compound of Formula I may be useful in combination therapy, in which, for example, two or more active compounds are administered to achieve a therapeutic effect.

Therapeutic or treatment effect may be measured in any manner known in the art. Therapeutic effect may be observed in asymptomatic HCV patients by way of delaying, reducing, or preventing onset or development of one or more such symptoms characteristic of HCV disease. For example, therapeutic effect may be observed through delay, reduction, or prevention of a liver pathology. As another example, therapeutic effect may be observed through reduction of viral load (such as by qPCR assessment of the number of copies of HCV RNA in a patient's blood). See, e.g., Highleyman L. and Franciscus A., "HCV Diagnostic Tools: HCV Viral Load Tests," HCSP Fact Sheet, v. 3 May 2011 [http://www.hcvadvocate.org/hepatitis/factsheets_pdf/viral-load.pdf].

The term "effective amount," as used herein, refers to an amount of a compound that, when provided to a host cell or an in vitro or ex vivo system would be expected to exhibit an overt or measurable effect in the system. For example, in an acellular or cellular assay system suitable for measuring an activity of HCV polymerase, the compounds of Formula I may inhibit or reduce such activity of HCV polymerase when provided in an effective amount. As another example, in an cellular assay system suitable for measuring replication or infectivity of HCV, the compounds of Formula I may inhibit or reduce such activity of HCV when provided in an effective amount.

Pharmaceutical Compositions and Dosage Forms

The invention provides compositions, and in particular, pharmaceutical compositions, comprising any of the compounds of Formula I (e.g., a single enantiomer, a mixture of enantiomers, or a mixture of diastereomers thereof, or a pharmaceutically acceptable salt or solvate thereof) in combination with a pharmaceutically acceptable vehicle, carrier, diluent, excipient, or a mixture of one or more of the foregoing ingredients.

While numerous embodiments of compositions according to the invention are set forth in detail below, it will be understood by the skilled person that compounds of Formula I are not limited to use in compositions specifically adapted for administration as medicaments, but that many other compositions comprising any of the compounds of Formula I may be made using conventional materials and methods. Accordingly, the invention provides compositions comprising any of the compounds of Formula I (e.g., a single enantiomer, a mixture of enantiomers, or a mixture of diastereomers thereof, or a salt or solvate thereof) in combination with at least one vehicle, carrier, diluent, excipient, or a mixture of one or more of the foregoing ingredients. For example, it is to be expected that any of the compounds of Formula I may appear in solution with a solvent that is considered not acceptable for administration to humans or other subjects. In addition, any of the compounds of Formula I may be prepared as a salt of a compound that is considered not acceptable for administration to humans or other subjects. The skilled person will understand how to prepare and interconvert such salt forms of the compounds, and such compositions comprising such compounds, by way of conventional techniques.

The amounts of various compounds of Formula I to be administered can be determined by standard procedures taking into account factors such as the compound ($IC_{50}$) potency, ($EC_{50}$) efficacy, and the biological half-life (of the compound), the age, size and weight of the patient, and the disease or disorder associated with the patient. The importance of these and other factors to be considered are known to those of ordinary skill in the art.

Amounts administered also depend on the routes of administration and the degree of oral bioavailability. For example, for compounds of Formula I with low oral bioavailability, relatively higher doses will have to be administered. Oral administration is a convenient method of administration of the compounds of Formula 1.

Suitably the pharmaceutical composition is in unit dosage form. For oral administration, for example, a tablet or capsule may be administered; for nasal application, a metered aerosol dose may be administered; for transdermal application, a topical formulation or patch may be administered; and for transmucosal delivery, a buccal patch may be administered.

Each dosage unit for oral administration may contain from 0.01 to 500 mg/Kg, for example from 0.1 to 50 mg/Kg, of a compound of Formula I- or a pharmaceutically acceptable salt thereof, calculated as the free base. The daily dosage for parenteral, nasal, oral inhalation, transmucosal, or transdermal routes may contains from 0.01 mg to 100 mg/Kg, of a compound of Formula (I). A topical formulation may contain 0.01 to 5.0% of a compound of Formula 1. The active ingredient may be administered from 1 to 4 times per day, for example once, twice or three times per day, sufficient to achieve the desired pharmaceutical activity.

The pharmaceutical compositions may be formulated in various dosage forms, including, but not limited to, the dosage forms for oral, parenteral, or topical administration. The pharmaceutical compositions may also be formulated as modified release dosage forms, including, but not limited to, delayed, extended, prolonged, sustained, pulsatile, controlled, accelerated, fast, targeted, and programmed release, and gastric retention dosage forms. These dosage forms can be prepared according to conventional methods and techniques known to those skilled in the art. See, e.g., *Remington: The Science and Practice of Pharmacy*, $21^{st}$ ed., 2005, Lippincott Williams & Wilkins; *Ansel's Pharmaceutical Dosage Forms and Drug Delivery Systems*, $9^{th}$ ed., 2010, Lippincott Williams & Wilkins.

In one aspect of the invention, the pharmaceutical compositions are provided in a dosage form for oral administration, which comprise a compound provided herein, including a single enantiomer, a mixture of enantiomers, or a mixture of diastereomers thereof, or a pharmaceutically acceptable salt, solvate; and a pharmaceutically acceptable vehicle, carrier, diluent, excipient, or a mixture thereof.

In another aspect of the invention, the pharmaceutical compositions are provided in a dosage form for parenteral administration, which comprise a compound provided herein, including a single enantiomer, a mixture of enantiomers, or a mixture of diastereomers thereof, or a pharmaceutically acceptable salt, solvate; and a pharmaceutically acceptable vehicle, carrier, diluent, excipient, or a mixture thereof.

In yet another aspect of the invention, the pharmaceutical compositions are provided in a dosage form for topical administration, which comprise a compound provided herein, including a single enantiomer, a mixture of enantiomers, or a mixture of diastereomers thereof, or a pharmaceutically acceptable salt, solvate; and a pharmaceutically acceptable vehicle, carrier, diluent, excipient, or a mixture thereof.

The pharmaceutical compositions provided herein may be provided in a unit- or multiple-dosage form. A unit-dosage form, as used herein, refers to a physically discrete unit suitable for administration to a subject, and packaged individually as is known in the art. Each unit-dose contains a predetermined quantity of the active ingredient(s) sufficient to produce the desired therapeutic effect, in association with the required pharmaceutically acceptable vehicle, carrier, diluent, excipient, or a mixture thereof. Examples of a unit-dosage form include an ampoule, syringe, and individually packaged tablet and capsule. A unit-dosage form may be administered in fractions or multiples thereof. A multiple-dosage form is a plurality of identical unit-dosage forms packaged in a single container to be administered in a segregated unit-dosage form. Examples of multiple-dosage forms include, without limitation, vials, bottles, blister-packs, and cardboard packages of tablets or capsules.

The pharmaceutical compositions provided herein may be administered at once, or multiple times at intervals of time. It is understood that the dosage and duration of treatment suitable for a particular patient may vary with the age, weight, and condition of the patient being treated, and may be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the pharmaceutical compositions provided herein.

Oral Administration

The pharmaceutical compositions provided herein may be provided in solid, semisolid, or liquid dosage forms for oral administration. As used herein, oral administration also includes buccal, lingual, and sublingual administration. Suitable oral dosage forms include, but are not limited to, tablets, capsules, pills, troches, lozenges, pastilles, cachets, pellets, medicated chewing gum, granules, bulk powders, effervescent or non-effervescent powders or granules, solutions, emulsions, suspensions, wafers, sprinkles, elixirs, and syrups.

In addition to the active ingredient(s), the pharmaceutical compositions for oral administration may contain one or more pharmaceutically acceptable carriers or excipients, including, but not limited to, binders, fillers, diluents, disintegrants, wetting agents, lubricants, glidants, coloring agents, dye-migration inhibitors, sweetening agents, and flavoring agents. Suitable pharmaceutically acceptable carriers and excipients are known and described in the art. See, e.g., R C Rowe, *Handbook of Pharmaceutical Excipients*, 6th ed., 2009, Pharmaceutical Press.

Binders or granulators impart cohesiveness to a tablet to ensure the tablet remaining intact after compression. Suitable binders or fillers include, but are not limited to, starches, such as corn starch, potato starch, and pre-gelatinized starch (e.g., STARCH 1500); gelatin; sugars, such as sucrose, glucose, dextrose, molasses, and lactose; natural and synthetic gums, such as acacia, alginic acid, alginates, extract of Irish moss, panwar gum, ghatti gum, mucilage of isabgol (psyllium) husks, polyvinylpyrrolidone (PVP), Veegum, larch arabogalactan, powdered tragacanth, and guar gum; celluloses, such as ethyl cellulose (EC), cellulose acetate, carboxymethyl cellulose (CMC), methyl cellulose, hydroxyethyl cellulose (HEC), hydroxypropyl cellulose (HPC), hydroxypropyl methyl cellulose (HPMC); microcrystalline celluloses, such as AVICEL-PH-101, AVICEL-PH-103, AVICEL RC-581, AVICEL-PH-105 (FMC Corp., Marcus Hook, Pa.); and mixtures thereof. Suitable fillers include, but are not limited to, talc, calcium carbonate, microcrystalline cellulose, powdered cellulose, dextrates, kaolin, mannitol, silicic acid, sorbitol, starch, pre-gelatinized starch, and mixtures thereof. In certain embodiments, the binder or filler is present from about 50 to about 99% by weight in the pharmaceutical compositions provided herein.

Suitable diluents include, but are not limited to, dicalcium phosphate, calcium sulfate, lactose, sorbitol, sucrose, inositol, cellulose, kaolin, mannitol, sodium chloride, dry starch, and powdered sugar. Certain diluents, such as mannitol, lactose, sorbitol, sucrose, and inositol, when present in sufficient quantity, can impart properties to some compressed tablets that permit disintegration in the mouth by chewing. Such compressed tablets can be used as chewable tablets.

Suitable disintegrants include, but are not limited to, agar; bentonite; celluloses, such as methyl cellulose and CMC; wood products; natural sponge; cation exchange resins; alginic acid; gums, such as guar gum and Veegum HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pregelatinized starch; clays; aligns; and mixtures thereof. The amount of a disintegrant in the pharmaceutical compositions provided herein varies upon the type of formulation, and is readily discernible to those of ordinary skill in the art. In certain embodiments, the pharmaceutical compositions provided herein contain from about 0.5 to about 15% or from about 1 to about 5% by weight of a disintegrant.

Suitable lubricants include, but are not limited to, calcium stearate; magnesium stearate; sodium stearyl fumarate; mineral oil; light mineral oil; glycerin; sorbitol; mannitol; glycols, such as glycerol behenate and polyethylene glycol (PEG); stearic acid; stearyl fumaric acid; sodium lauryl sulfate; talc; hydrogenated vegetable oil, including peanut oil, cottonseed oil, sunflower oil, sesame oil, olive oil, corn oil, and soybean oil; zinc stearate; ethyl oleate; ethyl laureate; agar; starch; lycopodium; silica or silica gels, such as AEROSIL® 200 (W.R. Grace Co., Baltimore, Md.) and CAB-O-SIL® (Cabot Co., Boston, Mass.); and mixtures thereof. In certain embodiments, the pharmaceutical compositions provided herein contain about 0.1 to about 5% by weight of a lubricant.

Suitable glidants include, but are not limited to, colloidal silicon dioxide, CAB-O-SIL®, and asbestos-free talc.

Suitable coloring agents include, but are not limited to, any of the approved, certified, water soluble FD&C dyes, water insoluble FD&C dyes suspended on alumina hydrate, and color lakes, and mixtures thereof. A color lake is the combination by adsorption of a water-soluble dye to a hydrous oxide of a heavy metal, resulting in an insoluble form of the dye.

Suitable flavoring agents include, but are not limited to, natural flavors extracted from plants, such as fruits, and synthetic blends of compounds which produce a pleasant taste sensation, such as peppermint and methyl salicylate.

Suitable sweetening agents include, but are not limited to, sucrose, lactose, mannitol, syrups, glycerin, and artificial sweeteners, such as saccharin and aspartame.

Suitable emulsifying agents include, but are not limited to, gelatin, acacia, tragacanth, bentonite, and surfactants, such as polyoxyethylene sorbitan monooleate (TWEEN® 20), polyoxyethylene sorbitan monooleate 80 (TWEEN® 80), and triethanolamine oleate.

Suitable suspending and dispersing agents include, but are not limited to, sodium CMC, pectin, tragacanth, Veegum, acacia, HPMC, and PVP.

Suitable preservatives include, but are not limited to, glycerin, esters of p-hydroxybenzoic acid (e.g., methyl- and propyl-paraben), benzoic add, sodium benzoate and alcohol.

Suitable wetting agents include, but are not limited to, propylene glycol monostearate, sorbitan monooleate, diethylene glycol monolaurate, and polyoxyethylene lauryl ether.

Suitable solvents include, but are not limited to, glycerin, sorbitol, ethyl alcohol, and syrup.

Suitable non-aqueous liquids utilized in emulsions include, but are not limited to, mineral oil and cottonseed oil.

Suitable organic acids include, but are not limited to, citric and tartaric acid.

Suitable sources of carbon dioxide include, but are not limited to, sodium bicarbonate and sodium carbonate.

It should be understood that a particular carrier or excipient may serve more than one function, even within the same formulation.

The pharmaceutical compositions provided herein may be provided as compressed tablets, tablet triturates, chewable lozenges, rapidly dissolving tablets, multiple compressed tablets, enteric coated tablets, sugar-coated tablets, or film-coated tablets. Enteric coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenyl salicylate, waxes, shellac, ammoniated shellac, and cellulose acetate phthalates. Sugar-coated tablets are compressed tablets surrounded by a sugar coating, which may be beneficial in covering up objectionable taste or odor and in protecting the tablets from oxidation. Film-coated tablets are compressed tablets that are covered with a thin layer or film of a water-soluble material. Film coatings include, but are not limited to, hydroxyethyl cellulose, sodium CMC, polyethylene glycol 4000, and cellulose acetate phthalate. Film coating imparts the same general characteristics as sugar coating. Multiple compressed tablets are compressed tablets made by more than one compression cycle, including layered, press-coated, and dry-coated tablets.

The tablet dosage forms may be prepared from the active ingredient in powdered, crystalline, or granular forms, alone or in combination with a pharmaceutically acceptable vehicle, carrier, diluent, or excipient, or a mixture thereof; including, e.g., a binder, disintegrant, controlled-release polymer, lubricant, diluent, and/or colorant. Flavoring and sweetening agents are especially useful in the formation of chewable tablets and lozenges.

The pharmaceutical compositions provided herein may be provided as soft or hard capsules, which can be made from, e.g., gelatin, methylcellulose, pullulan, starch, or calcium alginate. The hard gelatin capsule, also known as a dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including, but not limited to, methyl- and propyl-parabens and sorbic acid. The liquid, semisolid, and solid dosage forms provided herein may be encapsulated in a capsule using conventional methods. Suitable liquid and semisolid dosage forms include, but are not limited to, solutions and suspensions in propylene carbonate, vegetable oils, or triglycerides. The capsules may also be coated as known by those of skill in the art in order to modify or sustain dissolution of the active ingredient.

The pharmaceutical compositions provided herein may be provided in liquid and semisolid dosage forms, including, but not limited to, emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquid or solvent, emulsifying agent, and preservative. Suspensions may include a pharmaceutically acceptable suspending agent and preservative. Aqueous alcoholic solutions may include a pharmaceutically acceptable acetal, such as a di(lower alkyl) acetal of a lower alkyl aldehyde, e.g., acetaldehyde diethyl acetal; and a water-miscible solvent having one or more hydroxyl groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Other useful liquid and semisolid dosage forms include, but are not limited to, those containing an active ingredient, e.g., a compound of Formula I, and a dialkylated mono- or polyalkylene glycol, including, 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein 350, 550, and 750 refer to the approximate average molecular weight of the polyethylene glycol. These formulations may further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfite, sodium metabisulfite, thiodipropionic acid and its esters, and dithiocarbamates.

The pharmaceutical compositions provided herein for oral administration may be also provided in the form of liposomes, micelles, microspheres, or nanosystems. Micellar dosage forms can be prepared as described in U.S. Pat. No. 6,350,458.

The pharmaceutical compositions provided herein may be provided as noneffervescent or effervescent granules or powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

The pharmaceutical compositions provided herein may be formulated as immediate or modified release dosage forms, including delayed, sustained, pulsed, controlled, targeted, and programmed release forms.

The pharmaceutical compositions provided herein may be co-formulated with other active ingredients which do not impair the desired therapeutic action, or with substances that supplement the desired action.

Parenteral Administration

The pharmaceutical compositions provided herein may be administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, and subcutaneous administration.

The pharmaceutical compositions provided herein may be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science. See, e.g., *Remington: The Science and Practice of Pharmacy*, supra; *Handbook of Pharmaceutical Excipients*; supra.

The pharmaceutical compositions intended for parenteral administration may include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases. Suitable pharmaceutically acceptable carriers and excipients are known and described in the art. See, e.g., *Handbook of Pharmaceutical Excipients*, supra.

Suitable aqueous vehicles include, but are not limited to, water, saline, physiological saline or phosphate buffered saline (PBS), sodium chloride injection, Ringer's injection, isotonic dextrose injection, sterile water injection, and dextrose and lactated Ringer's injection. Non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, medium-chain triglycerides of coconut oil, and palm seed oil. Water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, N,N-dimethylacetamide, and dimethyl sulfoxide.

Suitable antimicrobial agents or preservatives include, but are not limited to, phenols, cresols, mercurials, benzyl alcohol, chlorobutanol, thimerosal, benzalkonium chloride (e.g., benzethonium chloride), methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfite and sodium metabisulfite. Suitable local anesthetics include, but are not limited to, procaine hydrochloride. Suitable suspending and dispersing agents are those as described herein, including sodium CMC, HPMC, and PVP. Suitable emulsifying agents include those described herein, including polyoxyethylene sorbitan monolaurate, polyoxyethylene sorbitan monooleate 80, and triethanolamine oleate. Suitable sequestering or chelating agents include, but are not limited to, EDTA. Suitable pH adjusting agents include, but are not limited to, sodium hydroxide, hydrochloric acid, citric acid, and lactic acid. Suitable complexing agents include, but are not limited to, cyclodextrins, including α-cyclodextrin, β-cyclodextrin, hydroxypropyl-β-cyclodextrin, sulfobutylether-β-cyclodextrin, and sulfobutylether-7-β-cyclodextrin (CAPTISOL®, CyDex, Lenexa, Kans.).

The pharmaceutical compositions provided herein may be formulated for single or multiple dosage administration. The single dosage formulations can be packaged in, e.g., an ampoule, a vial, or a syringe. In certain embodiments, the multiple dosage parenteral formulations contain an antimicrobial agent at bacteriostatic or fungistatic concentrations. In certain embodiments, the parenteral formulations provided herein are sterile, as known and practiced in the art.

In one embodiment, the pharmaceutical compositions are provided as ready-to-use sterile solutions. In another embodiment, the pharmaceutical compositions are provided as sterile dry soluble products, including lyophilized powders and hypodermic tablets, to be reconstituted with a vehicle prior to use. In yet another embodiment, the pharmaceutical compositions are provided as ready-to-use sterile suspensions. In yet another embodiment, the pharmaceutical compositions are provided as sterile dry insoluble products to be reconstituted with a vehicle prior to use. In still another embodiment, the pharmaceutical compositions are provided as ready-to-use sterile emulsions.

The pharmaceutical compositions provided herein may be formulated as immediate or modified release dosage forms, including delayed, sustained, pulsed, controlled, targeted, and programmed release forms.

The pharmaceutical compositions may be formulated as a suspension, solid, semisolid, or thixotropic liquid, for administration as an implanted depot. In one embodiment, the pharmaceutical compositions provided herein are dispersed in a solid inner matrix, which is surrounded by an outer polymeric membrane that is insoluble in body fluids but allows the active ingredient in the pharmaceutical compositions to diffuse through.

Suitable inner matrixes include polymethylmethacrylate, polybutyl-methacrylate, plasticized or unplasticized polyvinylchloride, plasticized nylon, plasticized polyethylene terephthalate, natural rubber, polyisoprene, polyisobutylene, polybutadiene, polyethylene, ethylene-vinyl acetate copolymers, silicone rubbers, polydimethylsiloxanes, silicone carbonate copolymers, hydrophilic polymers, such as hydrogels of esters of acrylic and methacrylic acid, collagen, cross-linked polyvinyl alcohol, and cross-linked partially hydrolyzed polyvinyl acetate.

Suitable outer polymeric membranes include polyethylene, polypropylene, ethylene/vinyl acetate copolymers, ethylene/propylene copolymers, ethylene/ethyl acrylate copolymers, silicone rubbers, polydimethyl siloxanes, neoprene rubber, chlorinated polyethylene, polyvinylchloride, vinyl chloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer.

Topical Administration

The pharmaceutical compositions provided herein may be administered topically to the skin, orifices, or mucosa. The topical administration, as used herein, includes (intra)dermal, conjunctival, intracorneal, intraocular, ophthalmic, auricular, transdermal, nasal, vaginal, urethral, respiratory, and rectal administration.

The pharmaceutical compositions provided herein may be formulated in any dosage forms that are suitable for topical administration for local or systemic effect, including emulsions, solutions, suspensions, creams, gels, hydrogels, ointments, dusting powders, dressings, elixirs, lotions, suspensions, tinctures, pastes, foams, films, aerosols, irrigations, sprays, suppositories, bandages, and dermal patches. The topical formulation of the pharmaceutical compositions provided herein may also comprise liposomes, micelles, microspheres, nanosystems, and mixtures thereof.

Pharmaceutically acceptable carriers and excipients suitable for use in the topical formulations provided herein include, but are not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, penetration enhancers, cryoprotectants, lyoprotectants, thickening agents, and inert gases. Suitable pharmaceutically acceptable carriers and excipients are known and described in the art. See, e.g., R C Rowe, *Handbook of Pharmaceutical Excipients*, 6$^{th}$ ed., 2009, Pharmaceutical Press.

The pharmaceutical compositions may also be administered topically by electroporation, iontophoresis, phonophoresis, sonophoresis, or nicroneedle or needle-free injection, such as POWDERJECT™ (Chiron Corp., Emeryville, Calif.), and BIOJECT™ (Bioject Medical Technologies Inc., Tualatin, Oreg.).

The pharmaceutical compositions provided herein may be provided in the form of ointments, creams, or gels. Suitable ointment vehicles include oleaginous or hydrocarbon vehicles, including lard, benzoinated lard, olive oil, cottonseed oil, and other oils; white petrolatum; emulsifiable or absorption vehicles, such as hydrophilic petrolatum, hydroxystearin sulfate, and anhydrous lanolin; water-removable vehicles, such as hydrophilic ointment; water-soluble ointment vehicles, including polyethylene glycols of varying molecular weight; and emulsion vehicles, either water-in-oil (W/O) emulsions or oil-in-water (O/W) emulsions, including cetyl alcohol, glyceryl monostearate, lanolin, and stearic acid. These vehicles are emollient but generally require addition of antioxidants and preservatives.

Suitable cream bases can be oil-in-water or water-in-oil. Cream vehicles may be water-washable, and contain an oil phase, an emulsifier, and an aqueous phase. The oil phase is also called the "internal" phase, which is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation may be a nonionic, anionic, cationic, or amphoteric surfactant.

Gels are semisolid, suspension-type systems. Single-phase gels contain organic macromolecules distributed substantially uniformly throughout a liquid carrier. Suitable gelling agents include crosslinked acrylic acid polymers, such as carbomers, carboxypolyalkylenes, CARBOPOL®; hydrophilic polymers, such as polyethylene oxides, polyoxyethylene-polyoxypropylene copolymers, and polyvinyl alcohol; cellulosic polymers, such as HPC, HEC, HPMC, hydroxypropyl methylcellulose phthalate, and methylcellulose; gums, such as tragacanth and xanthan gum; sodium alginate; and gelatin. To prepare a uniform gel, dispersing agents such as alcohol or glycerin can be added, or the gelling agent can be dispersed by trituration, mechanical mixing, and/or stirring.

The pharmaceutical compositions provided herein may be administered rectally, urethrally, vaginally, or perivaginally in the form of suppositories, pessaries, bougies, poultices or cataplasm, pastes, powders, dressings, creams, plasters, contraceptives, ointments, solutions, emulsions, suspensions, tampons, gels, foams, sprays, or enemas. These dosage forms can be manufactured using conventional processes, such as are described in *Remington: The Science and Practice of Pharmacy*, supra.

Rectal, urethral, and vaginal suppositories are solid bodies for insertion into body orifices, which are solid at ordinary temperatures but melt or soften at body temperature to release the active ingredient(s) inside the orifices. Pharmaceutically acceptable carriers utilized in rectal and vaginal suppositories include bases or vehicles, such as stiffening agents, which produce a melting point in the proximity of body temperature. Suitable vehicles include, but are not limited to, cocoa butter (theobroma oil), glycerin-gelatin, carbowax (polyoxyethylene glycol), spermaceti, paraffin, white and yellow wax, and appropriate mixtures of mono-, di- and triglycerides of fatty acids, hydrogels, such as polyvinyl alcohol, hydroxyethyl methacrylate, polyacrylic acid; and glycerinated gelatin. Combinations of the various vehicles may be used. Rectal and vaginal suppositories may further comprise antioxidants as described herein, including bisulfite and sodium metabisulfite. Rectal and vaginal suppositories may be prepared by the compressed method or molding. The typical mass of a rectal and vaginal suppository is about 2 to about 3 g.

The pharmaceutical compositions provided herein may be administered intranasally or by inhalation to the respiratory tract. The pharmaceutical compositions may be provided in the form of an aerosol or solution for delivery using a pressurized container, pump, spray, atomizer, such as an atomizer using electrohydrodynamics to produce a fine mist, or nebulizer, alone or in combination with a suitable propellant, such as 1,1,1,2-tetrafluoroethane or 1,1,1,2,3,3,3-heptafluoropropane. The pharmaceutical compositions may also be provided as a dry powder for insufflation, alone or in combination with an inert carrier such as lactose or phospholipids; or nasal drops. For intranasal use, the powder may comprise a bioadhesive agent, including chitosan or cyclodextrin.

Solutions or suspensions for use in a pressurized container, pump, spray, atomizer, or nebulizer may be formulated to contain ethanol, aqueous ethanol, or a suitable alternative agent, solvent or solvent system for dispersing, solubilizing, or extending release of the active ingredient provided herein; and/or a propellant as solvent; and/or a surfactant, such as sorbitan trioleate, oleic acid, or an oligolactic acid.

The pharmaceutical compositions provided herein may be micronized to a size suitable for delivery by inhalation, such as about 50 micrometers or less, or about 10 micrometers or less. Particles of such sizes may be prepared using a comminuting method known to those skilled in the art, such as spiral jet milling, fluid bed jet milling, supercritical fluid processing to form nanoparticles, high pressure homogenization, or spray drying.

Capsules, blisters, and cartridges for use in an inhaler or insufflator may be formulated to contain a powder mix of the pharmaceutical compositions provided herein; a suitable powder base, such as lactose or starch; and a performance modifier, such as l-leucine, mannitol, or magnesium stearate. The lactose may be anhydrous or in the form of monohydrates. Other suitable excipients or carriers include dextran, glucose, maltose, sorbitol, xylitol, fructose, sucrose, and trehalose. The pharmaceutical compositions provided herein for inhaled/intranasal administration may further comprise a suitable flavoring agent, such as menthol and levomenthol, or sweeteners, such as saccharin or saccharin sodium.

The pharmaceutical compositions provided herein for topical administration may be formulated to be immediate release or modified release, including delayed, sustained, pulsed, controlled, targeted, and programmed release.

Co-Administration and Combinations

The terms "co-administration" and "in combination with" include the administration of two or more pharmaceutically active agents (for example, a compound of Formula I and another antiviral agent or second agent) either simultaneously, concurrently, or sequentially with no specific time limits. In one embodiment, both agents are present in the cell or in the patient's body at the same time or exert their biological or therapeutic effect at the same time. In one embodiment, the two or more active agents are in the same composition or unit dosage form. In another embodiment, the two or more active agents are provided in separate compositions or unit dosage forms.

The combinations above may conveniently be presented for use in the form of a pharmaceutical formulation and, thus, pharmaceutical formulations comprising a combination as defined above together with a pharmaceutically acceptable carrier thereof represent a further aspect of the invention.

The individual components of such combinations may be administered either sequentially or simultaneously, in separate or combined pharmaceutical formulations. Appropriate doses of known active agents will be readily appreciated by those skilled in the art.

The compounds of Formula I and other individual components of such combinations may be provided in therapeutic or subtherapeutic amounts. Irrespective of whether each component in the combination is itself provided in an amount that would otherwise be considered therapeutic or subtherapeutic, and irrespective of whether the components are directed to the same or different specific therapeutic effects, a combination according to the invention is administered in an amount that a skilled practitioner would deem suitable for the treatment of HCV, as described herein. In such cases, the combination is said to be administered in a therapeutic amount. Accordingly, an amount of a compound of the invention might be considered subtherapeutic if administered alone, but would be considered to be a therapeutic amount if the combination or co-administration regimen is considered therapeutically effective. For example, an amount of a compound of Formula I may be administered in an amount that achieves a therapeutic effect, e.g., a reduction in hepatitis C viral load, in combination with one or more other active agents.

In some embodiments, a compound of Formula I may be administered in combination with one or more other antiviral agents. In some embodiments, a compound of Formula I may be administered in combination with two other antiviral agents. In some embodiments, a compound of Formula I may be administered in combination with three other antiviral agents. In some embodiments, a compound of Formula I may be administered in combination with four other antiviral agent. Such combinations are sometimes referred to as "cocktails." Some combinations of antiviral agents are being used in the clinica to ameliorate the ability of HCV to mutate to overcome the inhibitory activity of a single agent. Use of a compound of Formula 1 in such combinations can therefore impart useful therapeutic advantages.

Combinations or co-administration of the compounds of the invention with other active agents may desirably exhibit synergistic effects (i.e., the effect that is achieved when active ingredients are administered together is greater than the sum of the effects of each agent administered separately) and/or a higher barrier to drug resistance. For example, if two agents are co-administered, their combined effect may be synergistic if a therapeutic effect is achieved notwithstanding that the two agents would not be expected to yield an equivalent therapeutic effect if administered separately or together. On the contrary, antagonism of two agents may be said to exist if their combined effect is less than the sum of the effects of each agent administered separately. Synergy, drug resistance, and antagonism may be measured using any method that is generally accepted in the art, such as by way of concentration response curves for a parameter of interest. Synergy, drug resistance, or antagonism for a given combination may be determined for inhibition of HCV infection, HCV polymerase activity, a pharmacokinctic or pharmacodynamic effect, or the like.

Doses and dosing regimens of compounds of Formula I together with active second agents and combinations thereof should depend on the specific indication being treated, the age and condition of the patient, and the severity of adverse effects, and may be adjusted accordingly by those of skill in the art. Examples of doses and dosing regimens for other active moieties can be found, for example, in *Physician's Desk Reference*, and will require adaptation for use in the methods of the invention.

Accordingly, in some embodiments, there is administered to the patient a therapeutic amount of a combination comprising a compound of Formula I and at least one other active agent to a patient in need thereof. In some embodiments, the administered amount of at least one other active agent is subtherapeutic. In some embodiments, the administered amount of the at least one other agent is therapeutic. In some embodiments, the administered amount of the compound of Formula I is subtherapeutic. In other embodiments, the administered amount of the compound of Formula I is therapeutic.

The compounds of the invention may be administered as appropriate with one or more other active agents. Such active agents may be agents that have activity against HCV directly or indirectly, e.g., compounds that inhibit or reduce the replication or infectivity of HCV. Such and HCV agents include, among others, interferons, antiviral agents (e.g., ribavirin, taribavirin (viramidine), amantadine), nucleoside HCV NS5B polymerase inhibitors, non-nucleoside HCV NS5B polymerase inhibitors, HCV protease inhibitors, HCV NS5A inhibitors, HCV NS4B inhibitors, HCV NS3 helicase inhibitors, host cell entry inhibitors, and human cyclophilin inhibitors.

In some embodiments, a compound of the invention may be administered in combination with one or more interferon molecules. Such interferons include, without limitation, natural, recombinant, and modified (e.g., PEG-linked, albumin-linked) interferon molecules. Interferons include, but are not limited to, interferon alfa-2a (Roferon®), interferon alpha-2b (Intron®), interferon alfacon-1 (Infergen®), peginterferon alfa-2a (Pegasys®) or peginterferon alfa-2b (PegIntron®), recombinant alfa interferon (BLX-883; Locteron®), and albinterferon alfa 2b (Zalbin®).

In some embodiments, a compound of Formula I may be administered in combination with an interferon and ribavirin. In such cases, the compound of the invention may be said to be used to supplement the current standard of care. In some other embodiments, a compound of the invention is administered in combination with ribavirin.

In some embodiments, a compound of Formula I may be administered in combination with one or more compounds that inhibit the activity of the HCV serine protease (NS3-4A). Such protease inhibitors include, without limitation, telaprevir (Incivek™; VX-950; Vertex), boceprevir (Victrelis™; SCH503034; Merck), TMC435 (Tibotec/Medevir), danoprevir (ITMN-191/R7227; InterMune/Roche), BI 201335 (Boehringer Ingelheim), BI 12202 (Boehringer Ingelheim), vaniprevir (MK-7009; Merck), MK-5172 (Merck), ABT-450 (Abbott/Enanta); VX500 (Vertex), PHX 1766 (Phenomix), BILN2061 (Boehringer Ingelheim), GS-9256 (Gilead), GS-9451 (Gilead), BMS-650032 (Bristol-Myers Squibb), VX-985 (Vertex), ACH-1625 (Achillion), ACH-2684 (Achillion), and narlaprevir (SCH900518; Merck).

In some embodiments, a compound of Formula I may be administered in combination with one or more nucleoside inhibitors of the HCV polymerase (NS5B). Suitable NI compounds include, among others, IDX184 (Idenix), RG7128 (R-7128, RO5024048; Pharmasset/Roche), PSI-7851 (Pharmasset), PSI-938 (Pharmasset), PSI-7977 (Pharmasset), as well as phosphoramidate nucleotide analogs such as INX-189 (Inhibitex), TMC649128 (Tibotec/Medevir). Combinations of compounds of the invention other NS5B inhibitors may be used, for example, combinations with ALS-2200 or ALS-2158 (Vertex and Alios Biopharma)

In some embodiments, a compound of Formula I may be administered in combination with one or more non-nucleoside inhibitors of the HCV polymerase (NS5B). Suitable NNI compounds include, without limitation, compounds that bind to or inhibit activity through one of the four identified NNI sites on the NS5B protein. See, Powdrill et al., *Viruses,* 2010, 2:2169-95 and Appleby et al., "Viral RNA Polymerase Inhibitors," Chapter 23 in *Viral Genome Replication*, Cameron et al., eds., *Springer Science+Business Media* 2009. These compounds may be classified on the basis of the site with which they interact.

In some embodiments, a compound of Formula I may be co-administered, or provided in combination, with an NNI I inhibitor compound, an NNI II inhibitor compound, an NNI III inhibitor compound or an NNI IV inhibitor compound. Accordingly, in some embodiments, a compound of the invention may be administered in combination with one or more compounds selected from among:

NNI I compounds including, among others, JTK-109 (Japan Tobacco), BILB-1941 (Boehringer Ingelheim), MK-3281 (Merck), BI 207127 (Boehringer Ingelheim);

NNI II compounds including, among others, filibuvir (PF-868554; Pfizer), VX-759 (VCH-759; Vertex), VCH-916 (Vertex), VX-222 (VCH-222; Vertex);

NNI III compounds including, among others, GSK625433 (Glaxo SmithKline), ANA-598 (Anadys/Roche), ABT-333 (Abbott), ABT-072 (Abbott); or NNI IV compounds including, among others, HCV-796 (ViroPharma/Wyeth), tegobuvir (GS-9190; Gilead), IDX375 (Idenix).

In other embodiments, a compound of Formula I may be administered in combination with one or more other NS5B polymerase inhibitors including, among others, BMS 791325 (Bristol-Myers Squibb), R1626 (Roche), A-848837 (Abbott), and A-837093 (Abbott), as well as the compounds disclosed in International patent publications WO 02/100846 A1, WO 02/100851 A2, WO 2004/052879 A2, WO 2004/052885 A1, WO 2006/072347 A2, WO 2006/119646 A1, WO 2008/017688 A1, WO 2008/043791 A2, WO 2008/058393 A1, WO 2008/059042 A1, WO 2008/125599 A1, and WO 2009/000818 A1; U.S. Pat. Nos. 6,881,741 B2, 6,887,877 B2, and 6,936,629 B2, 7,402,608 B2, and 7,569,600 B2; and Yang et al., *Bioorg Med Chem Lett,* 2010, 20:4614-19.

In some embodiments, a compound of Formula I may be administered in combination with an active compound that inhibits another activity or function of HCV. For example, a compound of the invention may be administered in combination with one or more compounds selected from:

NS5A (regulatory protein) inhibitors, e.g., BMS-790052 (Bristol-Myers Squibb), BMS-824383 (Bristol-Myers Squibb), AZD7295 (AstraZeneca), PPI-461 (Presidio), PPI-688 (Presidio), GS-5885 (Gilead), ACH-2928 (Achillion), IDX-719 (Idenix);

NS3 (peptidase/helicase) inhibitors, e.g., BMS-650032 (Bristol-Myers Squibb);

NS4B (regulatory protein) inhibitors, e.g., clemizole (Eiger Biopharmaceuticals); Host-cell entry inhibitors, e.g., ITX5061 (iTherX); and Cyclophilin inhibitors, such as cyclophilin-A inhibitors, e.g., Debio 025 (alisporivir), SCY-635, NIM811, and other cyclosporin (ciclosporin) derivatives.

The compounds of Formula I may also be used in combination with other therapeutic agents, for example, therapeutic vaccines, antifibrotic agents, anti-inflammatory agents such as corticosteroids or NSAIDs, bronchodilators such as beta-2 adrenergic agonists and xanthines (e.g., theophylline), mucolytic agents, anti-muscarinics, anti-leukotrienes, inhibitors of cell adhesion (e.g., ICAM antagonists), anti-oxidants (e.g., N-acetylcysteine), cytokine agonists, cytokine antagonists, lung surfactants and/or antimicrobial agents. The compounds of Formula I may also be used in combination with gene replacement therapy.

While the active moieties mentioned herein as second active agents may be identified as free active moieties, salt forms (including salts with hydrogen or coordination bonds), solvates, or as non-covalent derivatives (e.g., chelates, complexes, and clathrates) of such active moieties, it is to be understood that the given representative connercial drug products are not limiting, and free active moieties, or salts or other derivative forms of the active moieties may alternatively be employed. Accordingly, reference to an active moiety should be understood to encompass not just the free active moiety but any pharmacologically acceptable salt, solvate, or other derivative form that is consistent with the specified parameters of use.

EXAMPLES

The chemistry examples, synthetic schemata, and intermediates, provided herein are intended to illustrate synthetic routes suitable for preparation of the compounds of the invention (and their intermediates), to assist in understanding the present invention. With appropriate manipulation and protection of any chemical functionality, synthesis of compounds of Formula I is accomplished by methods analogous to those described herein. Suitable protecting groups can be found, for example, in P. G. M. Wuts and T. W. Greene, *Greene's Protective Groups in Organic Synthesis,* 4th Ed., 2006, Wiley Interscience.

Methods for testing for activity of the compounds of the invention are described in the examples. The skilled persons will know of other methods for identifying compounds having activity against the NS5B polymerase. For example, McKercher et al., *Nucl Acids Res,* 2004, 32(2):422-31, describes a method for identifying NS5B inhibitor compounds.

Synthetic intermediates were analyzed LC-MS. Final products were analyzed and confirmed by LC-MS and proton NMR. The LC-MS method: the instrument was Agilent 1100 HPLC and Agilent 3200 mass spectrometer with ESI(+) detector. The analytical column used was a Synergi Hydro-RP column (00B-4375-E0; Phenomenex), and the compounds were eluted for 3 minutes (10% to 95% acetonitrile in water, containing 0.1% trifluoroacetic acid).

Example 1—3-[1-Methyl-5-(4-methyl-cyclohexyl)-1,2,3,6-tetrahydro-pyridin-4-yl]-5-phenyl-thiophene-2-carboxylic acid

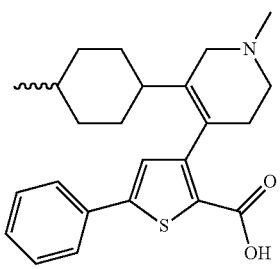

001

001 was prepared according to the following scheme:

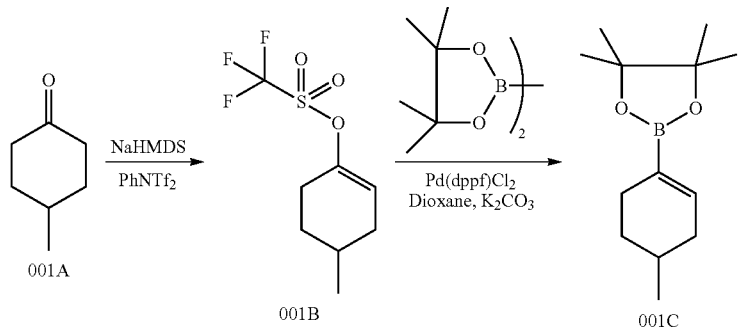

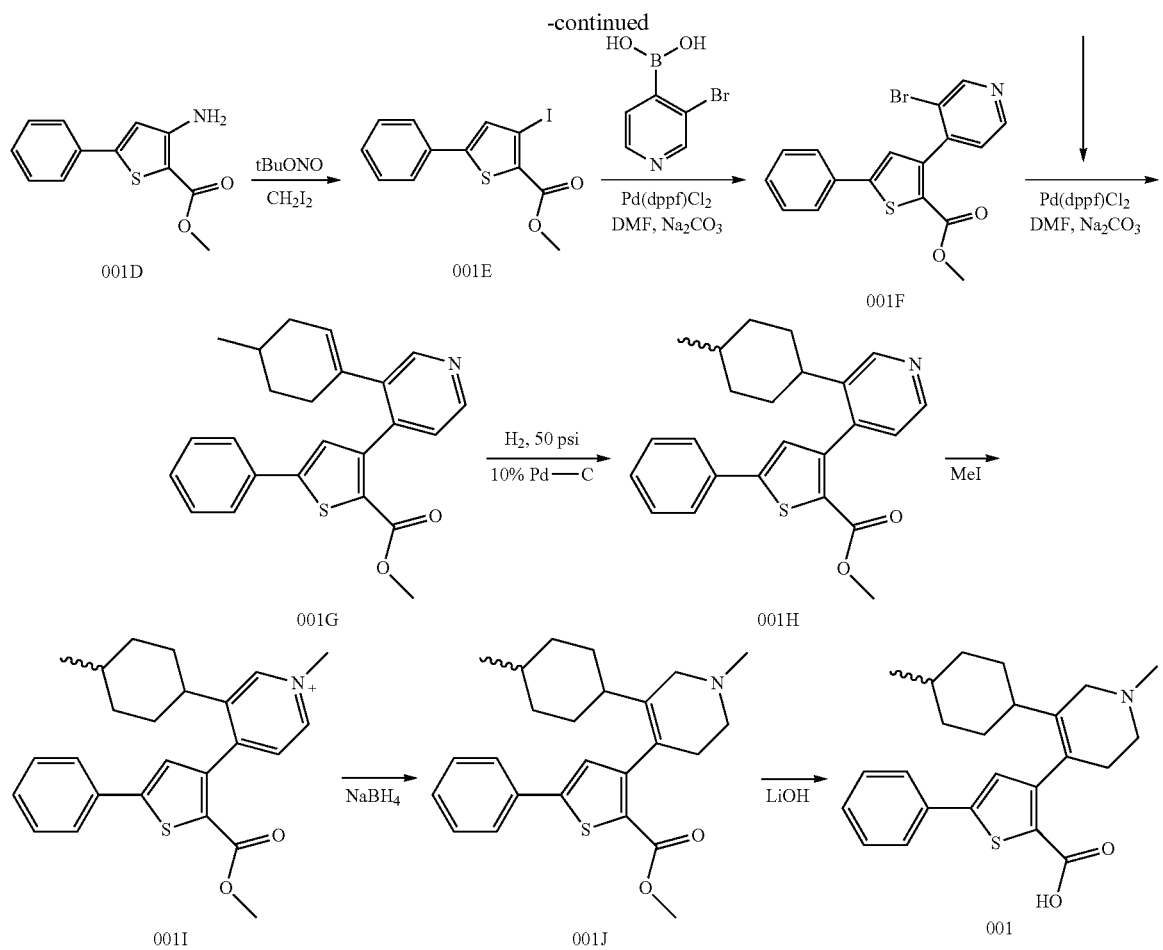

To a stirred solution of 4-cyclohexanone (2 g, 17.8 mmol) and n-phenyltrifluoromethane-sulfonimide (7.6 g, 21.36 mmol) in THF (77 mL) under $N_2$ at −78° C. was added 1 M sodium bis-trimethylsilylamide in THF (20.0 mL, 19.6 mmol). The reaction was stirred 8 hours (hr), then quenched with $H_2O$, and extracted with ether. The combined ether extract layers were dried over $MgSO_4$, filtered and purified by silica gel chromatography to give 001B as a clear oil. MS calcd: $(M+H)^+$: 245; MS found: $(M+H)^+=245$.

To a stirred solution of 001B (2.20 g, 9 mmol) in dioxane (38 mL) was added bis (pinacolato)diboron (2.74 g, 10.8 mmol), $(Pd(dppf)Cl_2$ (0.197 g, 0.27 mmol), 1,1'-bis(diphenylphosphino)ferrocene (0.150 g, 0.27 mmol), and AcOK (potassium acetate; 2.64 g, 27 mmol). The mixture was degassed by evacuating the reaction flask under vacuum followed by $N_2$ back-fill (3×). Under $N_2$, the reaction was then heated to 90° C. and stirred overnight (approx. 16 hr). The reaction was cooled to room temperature (RT) and diluted with $H_2O$. The mixture was extracted with ethyl acetate (EtOAc) (3×). The combined organic layers were washed with brine, dried over $MgSO_4$, filtered, and then purified by silica gel chromatography to give compound 001C as a clear oil. MS calcd: $(M+H)^+$: 209. MS found: $(M+H)^+=209$.

To a 50° C. solution of diiodomethane (9 g, 34 mmol) in $CH_3CN$ (30 mL) were added sequentially tert-butyl nitrite (1.75 g, 17 mmol) followed by methyl 3-amino-5-phenyl-thiophene-2-carboxylate (001D; 2.64 g, 11.3 mmol). The reaction was stirred for 1.5 hr and then poured into a solution of sodium bisulfite (20 g in 50 mL $H_2O$) and stirred for 20 minutes (min). The resulting mixture was extracted with EtOAc and concentrated in vacuo. Silica gel column purification (0-5% EtOAc in hexane) gave 001E as yellow solid. MS calcd: $(M+H)^+=345$. MS found: $(M+H)^+=345$.

N,N'-dimethyl formamide (DMF) (10 mL) and $H_2O$ (2 mL) were added to a mixture of 3-bromopyridine-4-boronic acid (0.535 g, 2.65 mmol), compound 001E (0.61 g, 1.77 mmol), $Pd(dppf)Cl_2$ (0.065 g, 0.089 mmol), and sodium carbonate ($Na_2CO_3$; 0.563 g, 5.31 mmol) under nitrogen ($N_2$) and stirred at 88° C. for 3 hr. The reaction was cooled to RT, and to it was added ice-water and EtOAc. The layers were separated and the aqueous layer was back-extracted with EtOAc (2×). The combined organic layers were then washed with brine, dried over anhydrous $Na_2SO_4$, filtered over Celite®, and concentrated under reduced pressure. The product was purified by flash chromatography (silica gel) eluting with 0-5% methanol (MeOH) in $CH_2Cl_2$ to give 001F as an off-white solid. MS calcd: $(M+H)^+=375$. MS found: $(M+H)^+=375$.

DMF (10 mL) and $H_2O$ (2 mL) were added to a mixture of 001C (0.31 g, 1.4 mmol), 001F (0.340 g, 0.91 mmol), $Pd(dppf)Cl_2$ (0.033 g, 0.0455 mmol), and $Na_2CO_3$ (0.3 g, 2.8 mmol) under $N_2$ and stirred at 88° C. for 3 hr. The reaction was cooled to RT, and to it was added ice-water and EtOAc. The layers were separated and the aqueous layer was back-extracted with EtOAc (2×). The combined organic layers were washed with brine, dried over anhydrous Na$_2$SO$_4$, filtered over Celite®, and concentrated under reduced pressure. The residue was purified by flash chromatography (silica gel) eluting with 0-5% MeOH in CH$_2$Cl$_2$ to give compound 001G as a solid. MS calcd: (M+H)$^+$=390. MS found: (M+H)$^+$=390.

001G (100 mg, 0.257 mmol) was dissolved in MeOH (15 mL), and 10% Pd/C (20 mg) was added as the catalyst. Hydrogenation under 50 psi H$_2$ was run overnight. Filtration and concentration gave 001H. MS calcd: (M+H)$^+$=392. MS found: (M+H)$^+$=392.

Methyl iodide (0.08 mL, 1.278 mmol) was added to a solution of 001H (100 mg, 0.256 mmol) in 5 mL of acetonitrile (ACN) and the mixture was stirred for 3 hr at 80° C. The reaction mixture was cooled to RT and concentrated in vacuo. The crude 001I was used directly in the next step. MS calcd: (M)$^+$=406. MS found: (M)$^+$=406.

Sodium borohydride (42 mg, 1.1 mmol) was added to a solution of 001I (111 mg, 0.275 mmol) in MeOH (6 mL) at RT with constant stirring. The reaction mixture was stirred overnight at 80° C. The reaction mixture was quenched with water (20 mL) and extracted with EtOAc (3×20 mL). The organic layers were combined, dried over anhydrous Na$_2$SO$_4$, and concentrated to obtain the product as brown oil, which was purified by column chromatography(silica gel, 0-10% MeOH in CH$_2$Cl$_2$) to yield the 001J. MS calcd: (M+H)$^+$=410. MS found: (M+H)$^+$=410.

001J (50 mg) was dissolved in tetrahydrofuran (THF; 2 mL) and ethanol (EtOH; 1 mL). Lithium hydroxide solution (LiOH; 2 M, 0.5 mL) was then added. The reaction was stirred at RT for 16 hr, and then diluted with EtOAc. The organic layer was washed with water and concentrated. The final product was precipitated out in hexane and washed more with hexane. The powder of compound 001 was obtained with lyophilization. MS calcd: (M+H)$^+$=396. MS found: (M+H)$^+$=396.

Example 2—5-Iodo-3-[1-methyl-5-(4-methyl-cyclohexyl)-1,2,3,6-tetrahydro-pyridin-4-yl]-thiophene-2-carboxylic acid

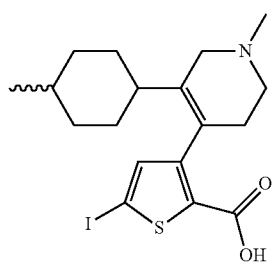

002

002 was prepared according to the following scheme:

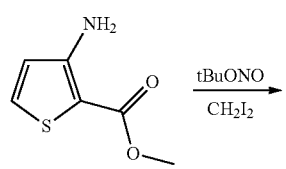

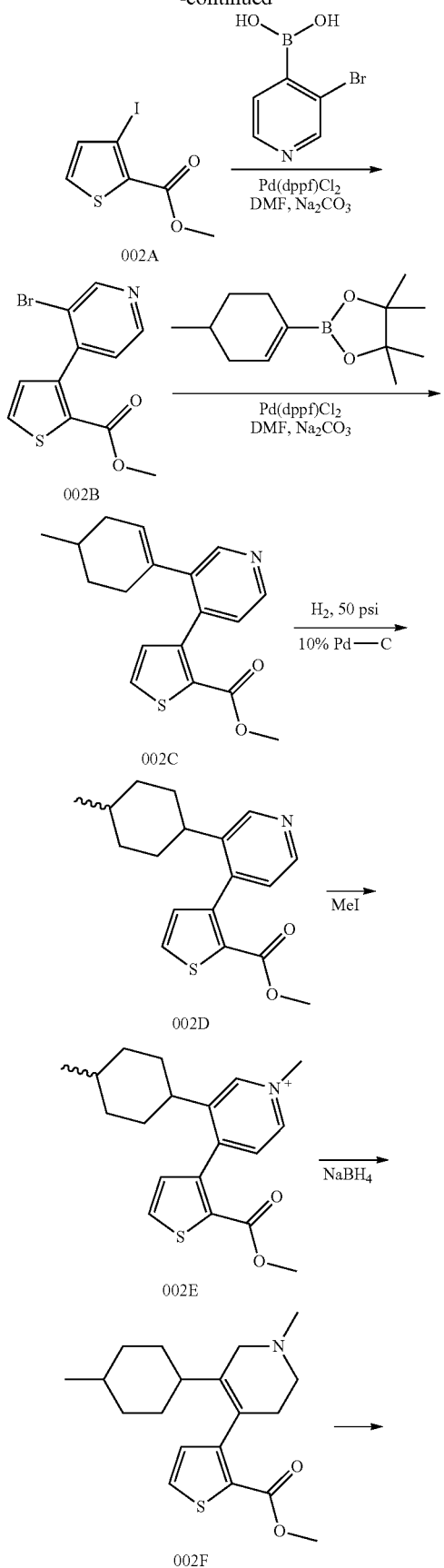

-continued

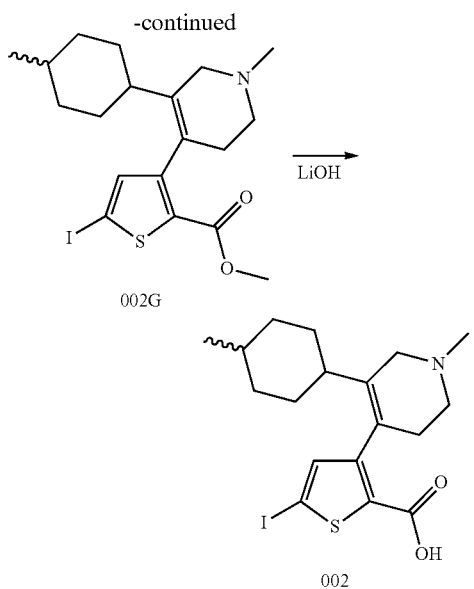

To a 50° C. solution of diiodomethane (9 g, 34 mmol) in CH₃CN (30 mL) were added, sequentially, tert-butyl nitrite (1.75 g, 17 mmol) followed by methyl 3-amino-2-thiophenecarboxylate (1.77 g, 11.3 mmol). The reaction was stirred for 1.5 hr and then poured into a solution of sodium bisulfite (20 g in 50 mL H₂O) and stirred for 20 min. The resulting mixture was extracted with EtOAc and concentrated in vacuo. Silica gel column separation (0-5% EtOAc in hexane) gave compound 002A as light yellow solid. MS calcd: (M+H)⁺: 269. MS found: (M+H)⁺=269.

DMF (10 mL) and H₂O (2 mL) were added to a mixture of 3-bromopyridine-4-boronic acid (0.535 g, 2.65 mmol), 002A (0.47 g, 1.77 mmol), Pd(dppf)Cl₂ (0.065 g, 0.089 mmol), and Na₂CO₃ (0.563 g, 5.31 mmol) under N₂ and the mixtures was stirred at 88° C. for 3 hr. The reaction was cooled to RT, and to it was added ice-water and EtOAc. The organic layer was washed with water (3×) and the combined aqueous layers were back-extracted with EtOAc (2×). The combined organic layers were washed with brine, dried over anhydrous Na₂SO₄, and concentrated under reduced pressure. The product was purified by flash chromatography (silica gel), eluting with 0-5% MeOH in CH₂Cl₂ to give 002B as an off-white solid. MS calcd: (M+H)⁺: 299. MS found: (M+H)⁺=299.

DMF (10 mL) and H₂O (2 mL) were added to a mixture of 4-methyl-cyclohexenyl-boronic ester (0.31 g, 1.4 mmol), 002B (0.27 g, 0.91 mmol), Pd(dppf)Cl₂ (0.033 g, 0.0455 mmol), and Na₂CO₃ (0.3 g, 2.8 mmol) under N₂, and the mixture was stirred at 92° C. for 4 hr. The reaction was cooled to RT, and to it was added ice-water and EtOAc. The organic layer was washed with water (3×) and the combined aqueous layers were back-extracted with EtOAc (2×). The combined organic layers were washed with brine, dried over anhydrous Na₂SO₄, and concentrated under reduced pressure. The product was purified by flash chromatography (silica gel), eluting with 0-5% McOH in CH₂Cl₂ to give 002C as a solid. MS calcd: (M+H)⁺=314. MS found: (M+H)⁺=314.

102C (80.4 mg, 0.257 mmol) was dissolved in MeOH (15 mL), and 10% Pd/C (15 mg) was added as the catalyst. Hydrogenation under 50 psi H₂ was run overnight. Filtration and concentration gave compound 102D. MS calcd: (M+H)⁺=316. MS found: (M+H)⁺=316.

Methyl iodide (0.08 mL, 1.278 mmol) was added to a solution of (80.6 mg, 0.256 mmol) of compound 102D in 5 mL of ACN, and the mixture was stirred for 3 hr at 80° C. The reaction mixture was cooled to RT and concentrated in vacuo. The crude 102E was used directly in the next step. MS calcd: (M)⁺=330. MS found: (M)⁺=330.

Sodium borohydride (42 mg, 1.1 mmol) was added to a solution of 002E (90.75 mg, 0.275 mmol) in MeOH (6 mL) at RT with constant stirring. The reaction mixture was stirred overnight at 80° C. The reaction mixture was quenched with water (20 mL) and extracted with EtOAc (3×20 mL). The organic layers were combined, dried over anhydrous Na₂SO₄, and concentrated to obtain the compound as brown oil, which was purified by column chromatography (silica gel, 0-10% McOH in CH₂Cl₂) to yield 002F. MS calcd: (M+H)⁺=334. MS found: (M+H)⁺=334.

A solution of 002F (1 g, 3 mmol) in dry THF (10 mL) was added dropwise at −77° C. under N₂ to 2 M lithium diisopropylamide (LDA) in THF/heptane/ethylbenzene (3 mL) maintaining an internal temperature <−70° C. The stirring was continued at −77° C. for 2.5 hr. A solution of iodine (2.3 g) in dry THF (5 mL) was added dropwise to the stirred reaction mixture maintaining an internal temperature <−70° C. After stirring under N₂ at −77° C. for 1.5 hr, the reaction mixture was quenched by addition of saturated NH₄Cl solution and warmed to 0° C. The mixture was diluted with 5% sodium thiosulfate solution, then the organic phase was separated and the aqueous phase was extracted with EtOAc. The combined organic phases were dried (Na₂SO₄), filtered, and evaporated. The product was dried to give 002G. MS calcd: (M+H)⁺=460. MS found: (M+H)⁺=460.

002G (50 mg) was dissolved in THF (2 mL) and EtOH (1 mL). LiOH (2 M, 0.5 mL) was then added. The reaction was stirred at RT for 16 hr, and then diluted with EtOAc. The organic layer was washed with water and concentrated. The final product was precipitated in hexane and washed more with hexane. The powder of compound 002 was obtained after lyophilization. MS calcd: (M+H)⁺=446. MS found: (M+H)⁺=446.

Example 3—5-(3,3-Dimethyl-but-1-ynyl)-3-[1-methyl-5-(4-methyl-cyclohexyl)-1,2,3,6-tetrahydro-pyridin-4-yl]-thiophene-2-carboxylic acid

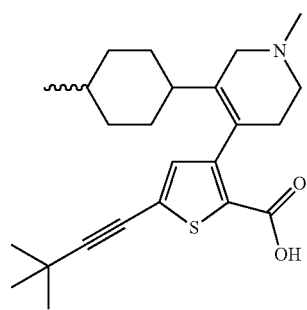

To a 25 mL round bottom flask under N₂, 002G (1 eq.), copper iodide (0.15 eq.) and Pd(dppf)Cl₂ (0.05 eq.) were added. DMF, triethylamine (TEA; 4 eq.), and 3,3-dimethylbut-1-yne (3 eq.) were added and the reaction mixture stirred at 60° C. for 2 hr under $N_2$. The reaction mixture was filtered over Celite® and washed with EtOAc. The solution was diluted with water and extracted (2×) with EtOAc. The organic phases were combined and washed (with water (2×). The organic layer was separated, dried ($Na_2SO_4$), evaporated, and purified by column chromatography to give compound 003A. MS calcd: $(M+H)^+=414$. MS found: $(M+H)^+=414$.

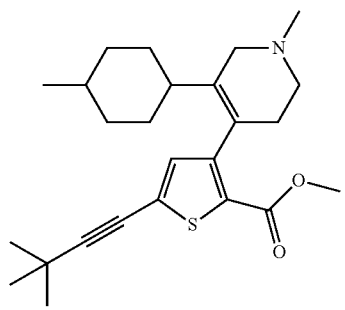

003A 003A (50 mg) was dissolved in THF (2 mL) and EtOH (1 mL). LiOH (2 M, 0.5 mL) was then added. The reaction was stirred at RT for 16 hr, and then diluted with EtOAc. The organic layer was washed with water and concentrated. The final product was precipitated out in hexane and washed more with hexane. The powder of 003 was obtained after lyophilization. MS calcd: $(M+H)^+=400$. MS found: $(M+H)^+=400$.

Example 4—5-(4-Amino-phenyl)-3-[1-methyl-5-(4-methyl-cyclohexyl)-1,2,3,6-tetrahydro-pyridin-4-yl]-thiophene-2-carboxylic acid

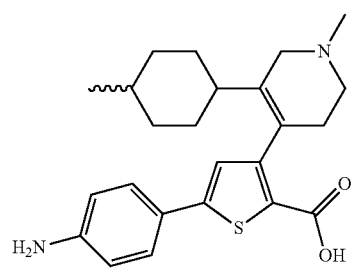

004

DMF (10 mL) and $H_2O$ (2 mL) were added to a mixture of [4-({[(1,1-dimethylethyl)oxy]-carbonyl}amino)phenyl] boronic acid (0.33 g, 1.4 mmol), 002G (0.42 g, 0.91 mmol), Pd(dppf)$Cl_2$ (0.033 g, 0.0455 mmol), and $Na_2CO_3$ (0.3 g, 2.8 mmol) under $N_2$, and the mixture was stirred at 92° C. for 4 hr. The reaction was cooled to RT, and to it was added ice-water and EtOAc. The organic layer was washed with water (3×) and the combined aqueous layers were back-extracted with EtOAc (2×). The combined organic layers were washed with brine, dried over anhydrous $Na_2SO_4$, and concentrated under reduced pressure. The product was purified by flash chromatography (silica gel), eluting with 0-5% MeOH in $CH_2Cl_2$ to give 004A as an oil. MS calcd: $(M+H)^+=525$. MS found: $(M+H)^+=525$.

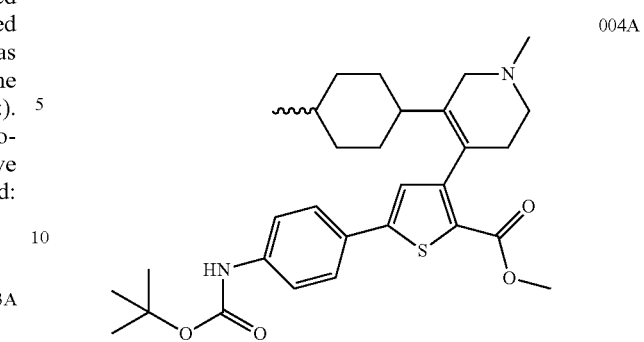

004A 004A (0.19 g) was stirred in dichloromethane (DCM; 3 mL) and trifluoroacetic acid (TFA; 1 mL) at RT under $N_2$ for 1 hr. The reaction was evaporated in vacuo and the residue partitioned between sodium bicarbonate solution and DCM. The organic phase was evaporated and dried in vacuo to give 004B. MS calcd: $(M+H)^+=425$. MS found: $(M+H)^+=425$.

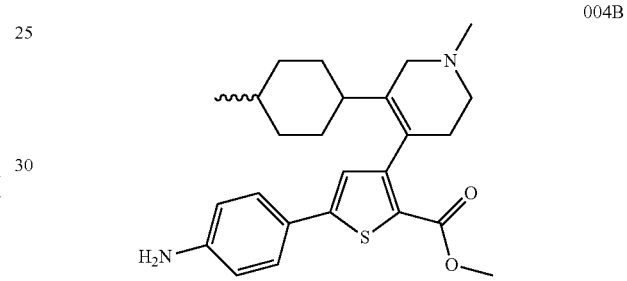

004B 004B (50 mg) was dissolved in THF (2 mL) and EtOH (1 mL). LiOH (2 M, 0.5 mL) was then added. The reaction was stirred at RT for 16 hr, and then diluted with EtOAc. The organic layer was washed with water and concentrated. The final product was precipitated out in hexane and washed more with hexane. The powder of 004 was obtained with lyophilization. MS calcd: $(M+H)^+=411$. MS found: $(M+H)^+=411$.

Example 5—3-[1-Methyl-5-(4-methyl-cyclohexyl)-1,2,3,6-tetrahydro-pyridin-4-yl]-5-(4-pyrazolo[1,5-a]pyrimidin-2-yl-phenyl)-thiophene-2-carboxylic acid

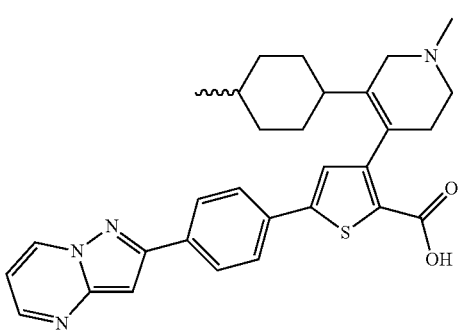

005

A solution of 3-(4-bromophenyl)-1H-pyrazol-5-amine (5.00 g) in acetic acid (80 mL) was treated with 1,1,3,3- tetramethoxypropane (4.13 g) and the mixture heated at 110° C. for 1.5 hr. On cooling to RT, the precipitated solid was isolated by filtration, washed with water (3×10 mL) and dried in vacuo at 40° C. The residue was recrystallized from acetic acid and dried in vacuo at 40° C. to give 005A. MS calcd: (M+H)$^+$: 274/276. MS found: (M+H)$^+$=274/276.

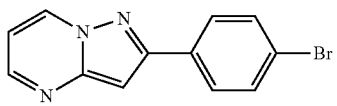

005A

A mixture of compound 005A (5 g), bis(pinacolato)diboron (6.7 g), AcOK (5.4 g) and Pd(dppf)Cl$_2$ (1 g) in dry 1,4-dioxane (20 mL) was heated to 100° C. under N$_2$ for 15 hr. The solvent was evaporated and the residue partitioned between water (10 mL) and DCM (30 mL). The aqueous phase was extracted further with DCM (20 mL) and the combined organic layers were evaporated. The residue was purified by SPE chromatography, eluting with cyclohexane/EtOAc (3:1) to give 005B. MS calcd: (M+H)$^+$=322. MS found: (M+H)$^+$=322.

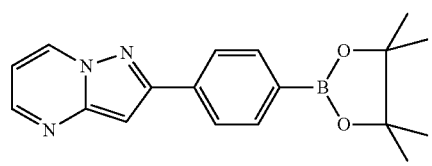

005B

DMF (10 mL) and H$_2$O (2 mL) were added to a mixture of [4-(4,4,5,5-tetramethyl-1,3,2-dioxaborolan-2-yl)phenyl]pyrazolo[1,5-a]pyrimidine (0.45 g, 1.4 mmol), 002 (0.4 g, 0.91 mmol), Pd(dppf)Cl$_2$ (0.033 g, 0.0455 mmol), and Na$_2$CO$_3$ (0.3 g, 2.8 mmol) under N$_2$, and stirred at 92° C. for 4 hr. The reaction was cooled to RT, and to it was added ice-water and EtOAc. The organic layer was washed with water (3×) and the combined aqueous layers were back-extracted with EtOAc (2×). The combined organic layers were washed with brine, dried over anhydrous Na$_2$SO$_4$, and concentrated under reduced pressure. The product was purified by flash chromatography (silica gel) to give 005. MS calcd: (M+H)$^+$=513. MS found: (M+H)$^+$=513.

Example 6—3-[1-Cyclopropylmethyl-5-(4-methyl-cyclohexyl)-1,2,3,6-tetrahydro-pyridin-4-yl]-5-phenyl-thiophene-2-carboxylic acid

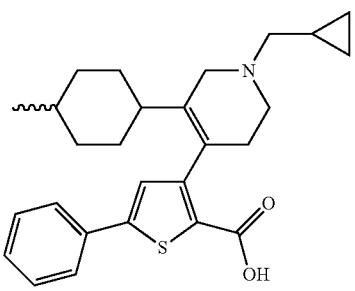

006

006 was prepared by the same method as 001, using cyclopropyl-methyl bromide instead of methyl iodide. MS calcd: (M+H)$^+$=436. MS found: (M+H)$^+$=436.

Example 8—3-[1-(3-Hydroxy-propyl-5-(4-methyl-cyclohexyl)-1,2,3,6-tetrahydro-pyridin-4-yl]-5-phenyl-thiophene-2-carboxylic acid

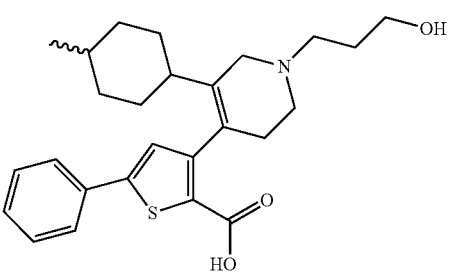

008

008 was prepared by the same method as 001, using tert-butyl dimethylsilyl 3-iodopropyl ether instead of methyl iodide. MS calcd: (M+H)$^+$=440. MS found: (M+H)$^+$=440.

Example 9—3-[1-Isopropyl-5-(4-methyl-cyclohexyl)-1,2,3,6-tetrahydro-pyridin-4-yl]-5-phenyl-thiophene-2-carboxylic acid

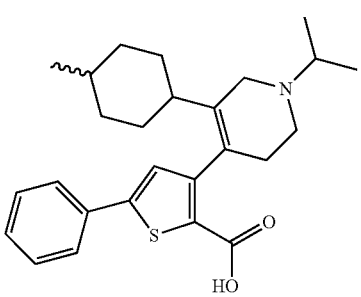

009

009 was prepared by the same method as 001, using isopropyl iodide instead of methyl iodide. MS calcd: (M+H)$^+$=424. MS found: (M+H)$^+$=424.

Example 11—5-(3-Hydroxy-3-methyl-but-1-ynyl)-3-[1-methyl-5-(4-methyl-cyclohexyl)-1,2,3,6-tetrahydro-pyridin-4-yl]-thiophene-2-carboxylic acid

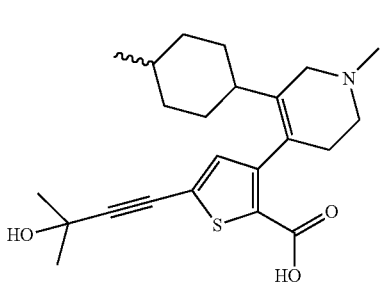

011

011 was prepared by the same method as 003, using 2-methyl-3-butyn-2-ol instead of 3,3-dimethyl-but-1-yne. MS calcd: (M+H)$^+$=402. MS found: (M+H)$^+$=402.

Example 12—5-(4-tert-Butoxycarbonylamino-phenyl)-3-[1-methyl-5-(4-methyl-cyclohexyl)-1,2,3,6-tetrahydro-pyridin-4-yl]-thiophene-2-carboxylic acid

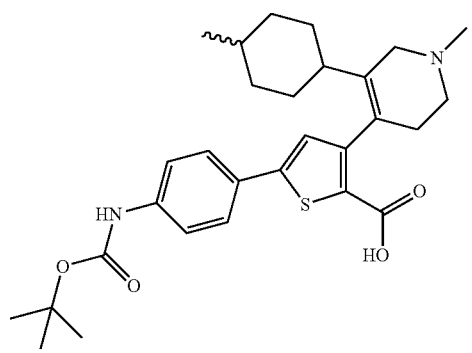

012

004A (50 mg) was dissolved in THF (2 mL) and EtOH (1 mL). LiOH (2 M, 0.5 mL) was then added. The reaction was stirred at RT for 16 hr, and then diluted with EtOAc. The organic layer was washed with water and concentrated. The final product was precipitated out in hexane and washed more with hexane. The powder of 012 was obtained with lyophilization. MS calcd: $(M+H)^+=511$. MS found: $(M+H)^+=511$.

Example 13—3-[1-Methyl-5-(4-methyl-cyclohexyl)-1,2,3,6-tetrahydro-pyridin-4-yl]-5-{4-[(thiazole-4-carbonyl)-amino]-phenyl}-thiophene-2-carboxylic acid

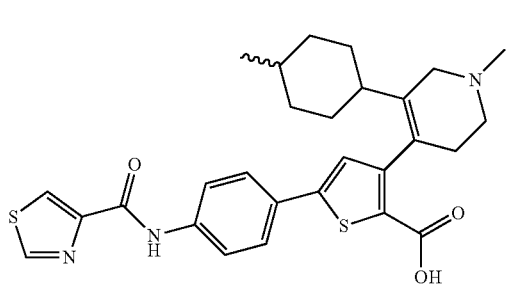

013

1,3-Thiazole-4-carboxylic acid (100 mg) was dissolved in DMF (3 mL). 2-(7-aza-1H-benzotriazole-1-yl)-1,1,3,3-tetramethyluronium hexafluorophosphate (HATU; 325 mg) and diisopropylethylamine (DIPEA; 0.35 mL) were added and the reaction mixture was stirred at RT for 15 min. Compound 004B (161 mg, 0.38 mmol) was added and the reaction mixture was stirred at RT for 1 hr. The reaction mixture was evaporated in vacuo and the residue was dissolved in DCM. This was washed with NaHCO₃ solution (2×) followed by 2 N HCl (2×). The DCM was separated and concentrated to obtain the compound as a brown oil, which was purified by column chromatography to give 013A. MS calcd: $(M+H)^+=536$. MS found: $(M+H)^+=536$.

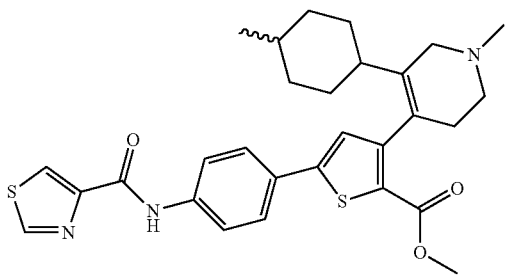

013A 013A (50 mg) was dissolved in THF (2 mL) and EtOH (1 mL). LiOH (2 M, 0.5 mL) was then added. The reaction was stirred at RT for 16 hr, and then diluted with EtOAc. The organic layer was washed with water and concentrated. The final product was precipitated out in hexane and washed more with hexane. The powder of 013 was obtained with lyophilization. MS calcd: $(M+H)^+=521$. MS found: $(M+H)^+=521$.

Example 14—5-(3,3-Dimethyl-but-1-ynyl)-3-[1-ethyl-5-(4-methyl-cyclohexyl)-1,2,3,6-tetrahydro-pyridin-4-yl]-thiophene-2-carboxylic acid

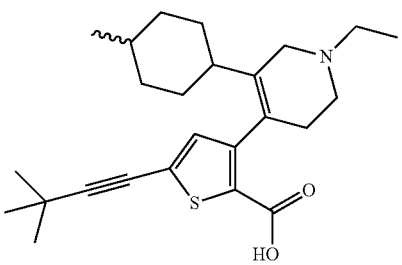

014

014 was prepared according to the following scheme.

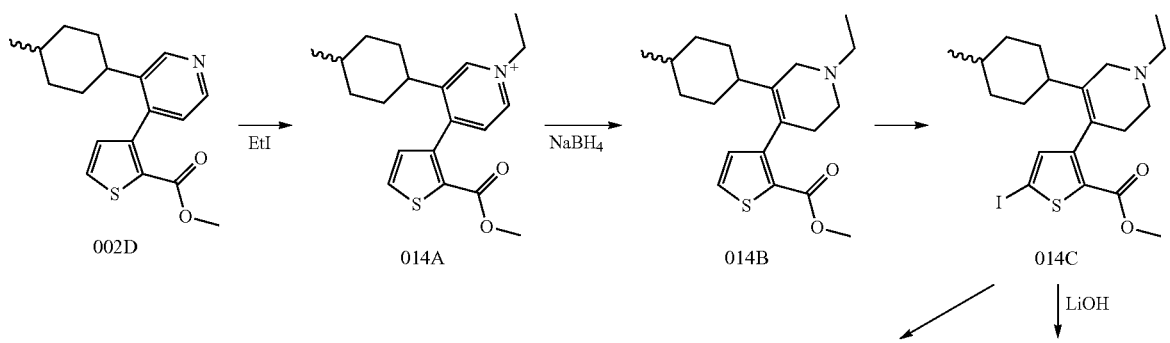

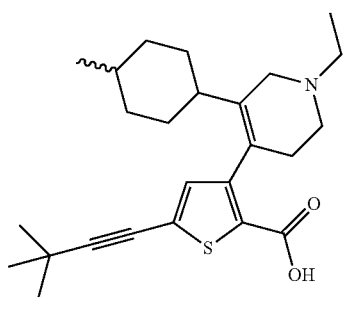

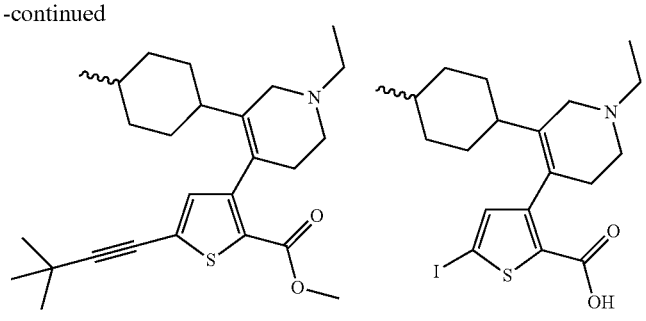

15

Ethyl iodide (0.08 mL, 1.278 mmol) was added to a solution of (80.6 mg, 0.256 mmol) of 002D in 5 mL of ACN and the mixture was stirred for 3 hr at 80° C. The reaction mixture was cooled to RT and concentrated in vacuo. The crude 014A was used directly in the next step. MS calcd: for $M^+=345$. MS found: $M^+=345$.

Sodium borohydride (42 mg, 1.1 mmol) was added to a solution of 014A (90.75 mg, 0.275 mmol) in MeOH (6 mL) at RT with constant stirring. The reaction mixture was stirred overnight at 80° C. The reaction mixture was quenched with water (20 mL) and extracted with EtOAc (3×20 mL). The organic layers were combined, dried over anhydrous $Na_2SO_4$, and concentrated to obtain the compound as brown oil, which was purified by column chromatography (silica gel, 0-10% MeOH in $CH_2Cl_2$) to yield 014B. MS calcd: $(M+H)^+=348$. MS found: $(M+H)^+=348$.

A solution of 014B (1 g, 3 mmol) in dry THF (10 mL) was added dropwise at −77° C. under $N_2$ to 2 M LDA in THF/heptane/ethylbenzene (3 mL), while maintaining an internal temperature <−70° C. The stirring continued at −77° C. for 2.5 hr. A solution of iodine (2.3 g) in dry THF (5 mL) was added dropwise to the stirred reaction mixture while maintaining an internal temperature <−70° C. After stirring under $N_2$ at −77° C. for 1.5 hr, the reaction mixture was quenched by addition of saturated $NH_4Cl$ solution and warmed to 0° C. The mixture was diluted with 5% sodium thiosulfate solution, then the organic phase was separated and the aqueous phase was extracted with EtOAc. The combined organic phases were dried ($Na_2SO_4$), filtered and evaporated. The product was dried to give 014C. MS calcd: $(M+H)^+=474$. MS found: $(M+H)^+=474$.

To a 25 mL round bottom flask under $N_2$, 014C (1 eq.), copper iodide (0.15 eq.) and $Pd(dppf)Cl_2$ (0.05 eq.) are added. DMF, TEA (4 eq.), and 3,3-dimethyl-but-1-yne (3 eq.) were added and the reaction mixture was stirred at 60° C. for 2 hr under a $N_2$ atmosphere. The reaction mixture was filtered on Celite® and washed with EtOAc. The filtrate was diluted with water, and extracted twice with EtOAc. The organic phases were combined and washed twice with water. The organic layer was separated, dried ($Na_2SO_4$), evaporated, and purified by column chromatography to give 014D. MS calcd: $(M+H)^+=428$. MS found: $(M+H)^+=428$.

Compound 014D (50 mg) was dissolved in THF (2 mL) and EtOH (1 mL). LiOH (2 M, 0.5 mL) was then added. The reaction was stirred at RT for 16 hr, and then diluted with EtOAc. The organic layer was washed with water and concentrated. The final product was precipitated out in hexane and washed more with hexane. The powder of 014 was obtained with lyophilization. MS calcd: $(M+H)^+=414$. MS found: $(M+H)^+=414$.

Example 15—3-[1-Ethyl-5-(4-methyl-cyclohexyl)-1,2,3,6-tetrahydro-pyridin-4-yl]-5-(4-pyrazolo[1,5-a]pyrimidin-2-yl-phenyl)-thiophene-2-carboxylic acid

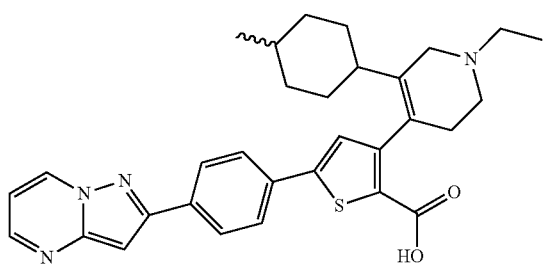

014C (50 mg) was dissolved in THF (2 mL) and EtOH (1 mL). LiOH (2 M, 0.5 mL) was then added. The reaction was stirred at RT for 16 hr, and then diluted with EtOAc. The organic layer was washed with water and concentrated. The final product was precipitated out in hexane and washed more with hexane. The powder of 014E was obtained with lyophilization. MS calcd: $(M+H)^+=460$. MS found: $(M+H)^+=460$.

015 was then prepared by the same method as 005, using intermediate 014E instead of 002. MS calcd: $(M+H)^+=526$. MS found: $(M+H)^+=526$.

Example 16—5-Cyclohexylethynyl-3-[1-ethyl-5-(4-methyl-cyclohexyl)-1,2,3,6-tetrahydro-pyridin-4-yl]-thiophene-2-carboxylic acid

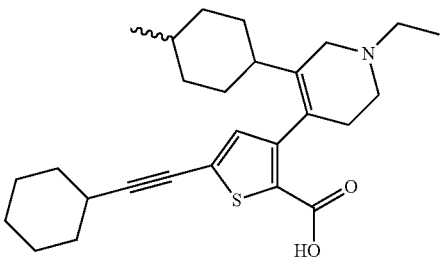

016 was prepared by the same method as 014, using cyclohexylacetylene instead 3,3-dimethyl-but-1-yne. MS calcd: $(M+H)^+=440$. MS found: $(M+H)^+=440$.

Example 18—5-(4-Acetylamino-phenyl)-3-[1-ethyl-5-(4-methyl-cyclohexyl)-1,2,3,6-tetrahydro-pyridin-4-yl]-thiophene-2-carboxylic acid

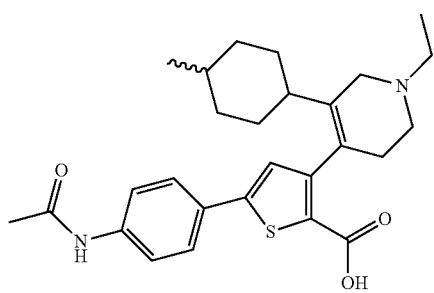

018

DMF (10 mL) and H₂O (2 mL) were added to a mixture of [4-({[(1,1-dimethylethyl)oxy]carbonyl}amino)phenyl]boronic acid (0.33 g, 1.4 mmol), 014C (0.43 g, 0.91 mmol), Pd(dppf)Cl₂ (0.033 g, 0.0455 mmol) and Na₂CO₃ (0.3 g, 2.8 mmol) under N₂, and stirred at 92° C. for 4 hr. The reaction was cooled to RT, and to it was added ice-water and EtOAc. The organic layer was washed with water (3×) and the combined aqueous layers were back-extracted with EtOAc (2×). The combined organic layers were washed with brine, dried over anhydrous Na₂SO₄, and concentrated under reduced pressure. The product was purified by flash chromatography (silica gel), eluting with 0-5% MeOH in CH₂Cl₂ to give 018A. MS calcd: (M+H)⁺=539. MS found: (M+H)⁺=539.

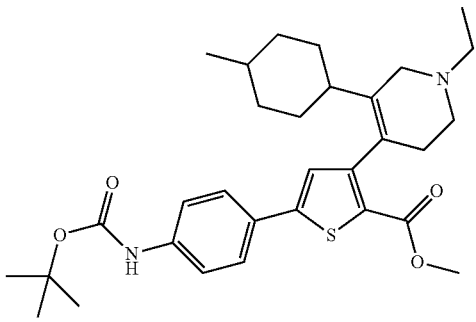

018A 018A (0.19 g) was stirred in DCM (3 mL) and TFA (1 mL) at RT under N₂ for 1 hr. The reaction was evaporated in vacuo and the residue partitioned between NaHCO₃ solution and DCM. The organic phase was evaporated and dried in vacuo to give 018B. MS calcd: for (C₂₄H₃₄N₂O₃S+H)⁺=439. MS found: (M+H)⁺=439.

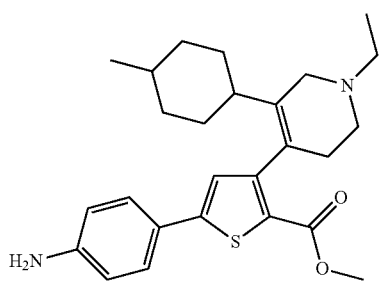

018B

Acetyl chloride (9.6 mg, 0.12 mmol) was added at 0-15° C. to a solution of TEA (40 mg, 0.3 mmol) and 018B (23.4 mg. 0.053 mmol) in DCM (3 mL). After 20 min the mixture was warmed rapidly to RT. After being stirred 30 min, DCM (5 mL) and 2N NaOH (1 mL) was added, and the organic layer was separated and washed with water. The organic layers were separated, dried and concentrated to give a brown oil. Purification by silica gel column chromatography gave 018C. MS calcd: (M+H)⁺=481. MS found: (M+H)⁺=481.

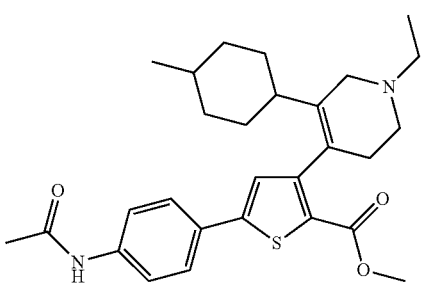

018C 018C (20 mg) was dissolved in THF (2 mL) and EtOH (1 mL). LiOH (2 M, 0.5 mL) was then added. The reaction was stirred at RT for 16 hr, and then diluted with EtOAc. The organic layer was washed with water and concentrated. The final product was precipitated out in hexane and washed more with hexane. The powder of 018 was obtained with lyophilization. MS calcd: (M+H)⁺=467. MS found: (M+H)⁺=467.

Example 19—3-[1-Ethyl-5-(4-methyl-cyclohexyl)-1,2,3,6-tetrahydro-pyridin-4-yl]-5-{4-[(thiazole-4-carbonyl)-amino]-phenyl}-thiophene-2-carboxylic acid

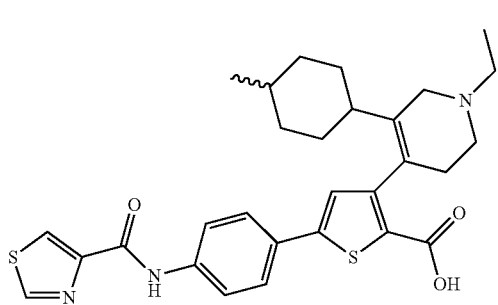

019

019 was prepared by the same method as 013, using 018B instead of 004B. MS calcd: (M+H)⁺=535. MS found: (M+H)⁺=535.

Example 20—5-(4-Benzoylamino-phenyl)-3-[1-ethyl-5-(4-methyl-cyclohexyl)-1,2,3,6-tetrahydro-pyridin-4-yl]-thiophene-2-carboxylic acid

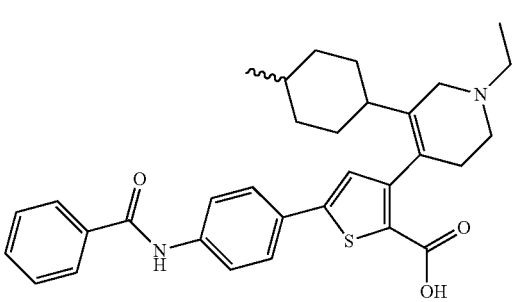

020

020 was prepared by the same method as 018, using benzoyl chloride instead of acetyl chloride. MS calcd: (M+H)⁺=529. MS found: (M+H)⁺=529.

Example 21—5-(3-Amino-3-methyl-but-1-ynyl)-3-[1-ethyl-5-(4-methyl-cyclohexyl)-1,2,3,6-tetrahydro-pyridin-4-yl]-thiophene-2-carboxylic acid

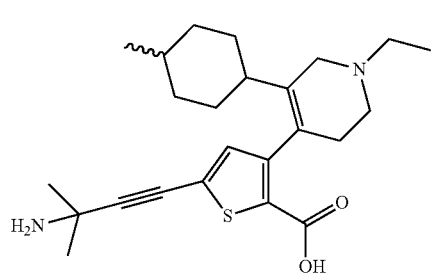

To a 25 mL round bottom flask under $N_2$, 014C (1 eq.), copper iodide (0.15 eq.) and Pd(dppf)Cl, (0.05 eq.) were added. DMF, TEA (4 eq.), and 1,1-dimethylpropargylamine (3 eq.) were added, and the reaction mixture was stirred at 60° C. for 2 hr under a $N_2$ atmosphere. The reaction mixture was filtered over Celite® and washed with EtOAc. The filtrate was diluted with water and extracted twice with EtOAc. The organic phase were combined and washed twice with water. The organic layer was separated, dried ($Na_2SO_4$), evaporated, and purified by column chromatography to give intermediate 021A. MS calcd: (M+H)⁺=429. MS found: (M+H)⁺=429.

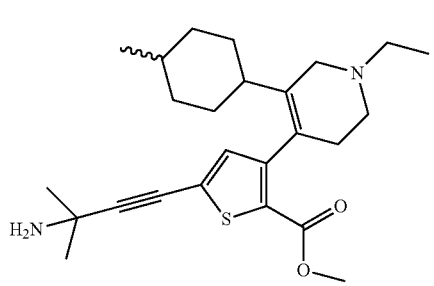

021A (25 mg) was dissolved in THF (2 mL) and EtOH (1 mL). LiOH (2 M, 0.5 mL) was then added. The reaction was stirred at RT for 16 hr, and then diluted with EtOAc. The organic layer was washed with water and concentrated. The final product was precipitated out in hexane and washed more with hexane. The powder of 021 was obtained with lyophilization. MS calcd: (M+H)⁺=415. MS found: (M+H)⁺=415.

Example 22—3-[1-Ethyl-5-(4-methyl-cyclohexyl)-1,2,3,6-tetrahydro-pyridin-4-yl]-5-{3-methyl-3-[(thiazole-4-carbonyl)-amino]-but-1-ynyl}-thiophene-2-carboxylic acid

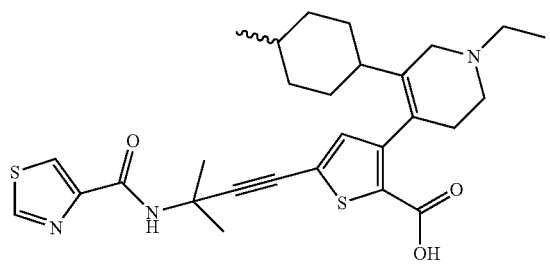

022 was prepared by the same method as 013, using 021A instead of 004B. MS calcd: (M+H)⁺=526. MS found: (M+H)⁺=526.

Example 23—5-(3-Dimethylamino-3-methyl-but-1-ynyl)-3-[1-ethyl-5-(4-methyl-cyclohexyl)-1,2,3,6-tetrahydro-pyridin-4-yl]-thiophene-2-carboxylic acid

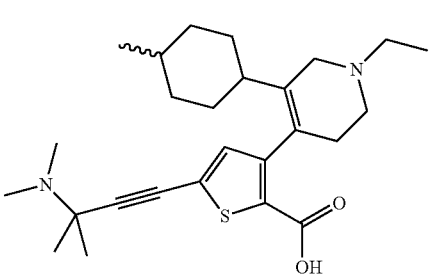

021A (40 mg, 0.093 mmol), formaldehyde (14 mg, 0.45 mmol), and sodium triacetoxyborohydride (0.21 g, 1 mmol) were mixed in 1,2-dichloroethane (DCE; 5 mL). The reaction was stirred at RT overnight. The reaction was quenched with saturated aqueous $NaHCO_3$, and the product was extracted with EtOAc (20 mL). The EtOAc extract was dried ($MgSO_4$), and the solvent was evaporated. Separation by chromatography gave 023A as a yellow semisolid. MS calcd: (M+H)⁺=457. MS found: (M+H)⁺=457.

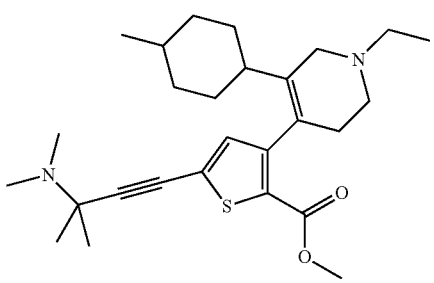

023A (25 mg) was dissolved in THF (2 mL) and EtOH (1 mL). LiOH (2 M, 0.5 mL) was then added. The reaction was stirred at RT for 16 hr, and then diluted with EtOAc. The organic layer was washed with water and concentrated. The final product was precipitated out in hexane and washed more with hexane. The powder of 023 was obtained with lyophilization. MS calcd: (M+H)⁺=443. MS found: (M+H)⁺=443.

Example 24—5-(3-Acetylamino-phenyl)-3-[1-ethyl-5-(4-methyl-cyclohexyl)-1,2,3,6-tetrahydro-pyridin-4-yl]-thiophene-2-carboxylic acid

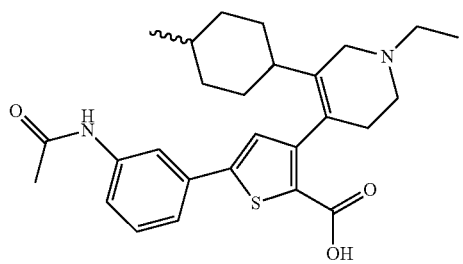

DMF (10 mL) and H$_2$O (2 mL) were added to a mixture of [3-({[(1,1-dimethylethyl)oxy]-carbonyl}amino)phenyl] boronic acid (0.33 g, 1.4 mnol), 014C (0.43 g, 0.91 mmol), Pd(dppf)Cl$_2$ (0.033 g, 0.0455 mmol), and Na$_2$CO$_3$ (0.3 g, 2.8 mmol) under N$_2$, and stirred at 92° C. for 4 hr. The reaction was cooled to RT, and to it was added ice-water and EtOAc. The organic layer was washed with water (3×) and the combined aqueous layers were back-extracted with EtOAc (2×). The combined organic layers were washed with brine, dried over anhydrous Na$_2$SO$_4$, and concentrated under reduced pressure. The product was purified by flash chromatography (silica gel), eluting with 0-5% MeOH in CH$_2$Cl$_2$ to give 024A. MS calcd: (M+H)$^+$=539 MS found: (M+H)$^+$=539.

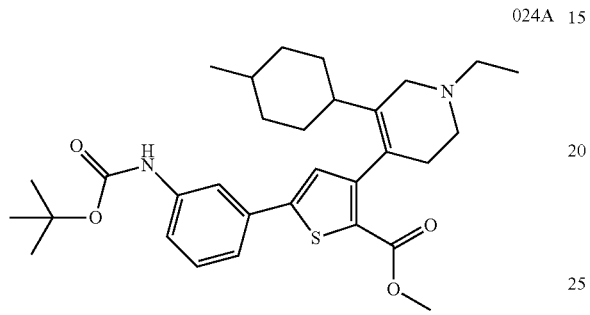

024A 024A (0.19 g) was stirred in DCM (3 mL) and TFA (1 mL) at RT under N$_2$ for 1 hr. The reaction was evaporated in vacuo and the residue partitioned between saturated sodium bicarbonate solution and DCM. The organic phase was evaporated and dried in vacuo to give 024B. MS calcd: (M+H)$^+$=439. MS found: (M+H)$^+$=439.

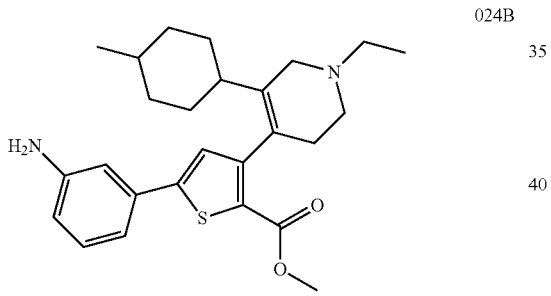

024B

Acetyl chloride (9.6 mg, 0.12 mmol) was added at 0-15° C. to a solution of TEA (40 mg, 0.3 mmol) and 024B (23.4 mg. 0.053 mmol) in DCM (3 mL). After 20 min the mixture was warmed rapidly to RT. After being stirred 30 min, DCM (5 mL) and 2 N NaOH (1 mL) was added, and the organic layer was separated and washed with water. The organic layers were separated, dried and concentrated, giving a brown oil. Separation by column chromatography gave 024C. MS calcd: (M+H)$^+$=481. MS found: (M+H)$^+$=481.

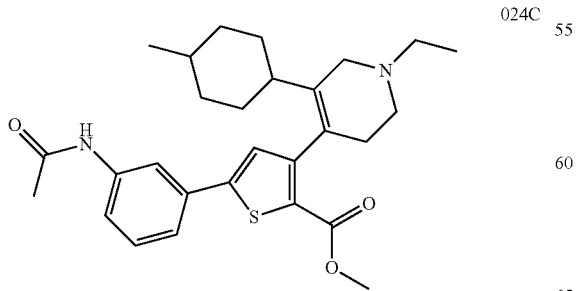

024C 024C (24 mg) was dissolved in THF (2 mL) and EtOH (1 mL). LiOH (2 M, 0.5 mL) was then added. The reaction was stirred at RT for 16 hr, and then diluted with EtOAc. The organic layer was washed with water and concentrated. The final product was precipitated out in hexane and washed more with hexane. The powder of 024 was obtained with lyophilization. MS calcd: (M+H)$^+$=467. MS found: (M+H)$^+$=467.

Example 25—3-[1-Ethyl-5-(4-methyl-cyclohexyl)-1,2,3,6-tetrahydro-pyridin-4-yl]-5-{3-[(thiazole-4-carbonyl)-amino]-phenyl}-thiophene-2-carboxylic acid

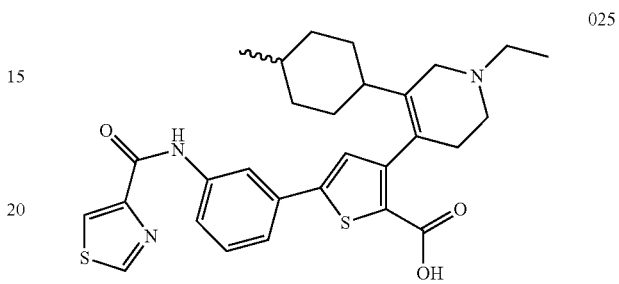

025

025 was prepared by the same method as 019, using 024B instead of 018B. MS calcd: (M+H)$^+$=536. MS found: (M+H)$^+$=536.

Example 26—5-(3-Amino-phenyl)-3-[1-ethyl-5-(4-methyl-cyclohexyl)-1,2,3,6-tetrahydro-pyridin-4-yl]-thiophene-2-carboxylic acid

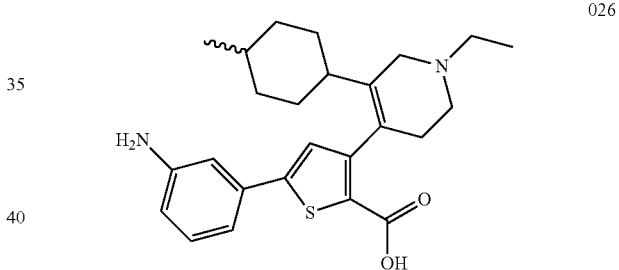

026

024B (24 mg) was dissolved in THF (2 mL) and EtOH (1 mL). LiOH (2 M, 0.5 mL) was then added. The reaction was stirred at RT for 16 hr, and then diluted with EtOAc. The organic layer was washed with water and concentrated. The final product was precipitated out in hexane and washed more with hexane. The powder of 026 was obtained with lyophilization. MS calcd: (M+H)$^+$=425. MS found: (M+H)$^+$=425.

Example 30—3-[1-Ethyl-5-(4-methyl-cyclohexyl)-1,2,3,6-tetrahydro-pyridin-4-yl]-5-(3-methyl-hex-1-ynyl)-thiophene-2-carboxylic acid

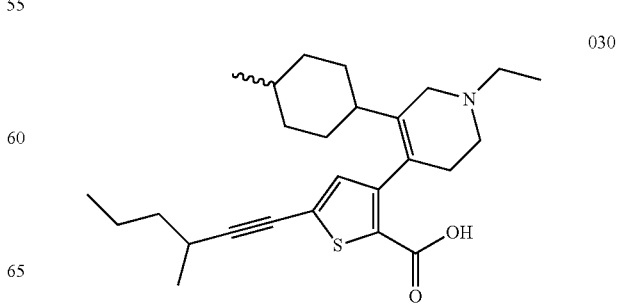

030

030 was prepared by the same method as 014, using 3-methyl-1-hexyne instead of 3,3-dimethyl-but-1-yne. MS calcd: (M+H)⁺=428. MS found: (M+H)⁺=428.

Example 31—5-Cyclopentylethynyl-3-[1-ethyl-5-(4-methyl-cyclohexyl)-1,2,3,6-tetrahydro-pyridin-4-yl]-thiophene-2-carboxylic acid

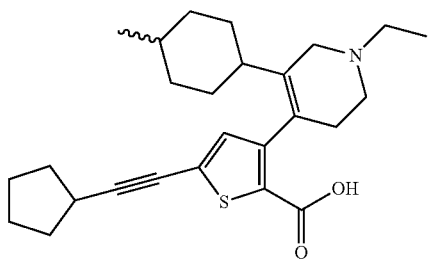

031

031 was prepared by the same method as 014, using cyclopentylacetylene instead of 3,3-dimethyl-but-1-yne. MS calcd: (M+H)⁺=426. MS found: (M+H)⁺=426.

Example 33—5-(3,3-Diethoxy-prop-1-ynyl)-3-[1-ethyl-5-(4-methyl-cyclohexyl)-1,2,3,6-tetrahydro-pyridin-4-yl]-thiophene-2-carboxylic acid

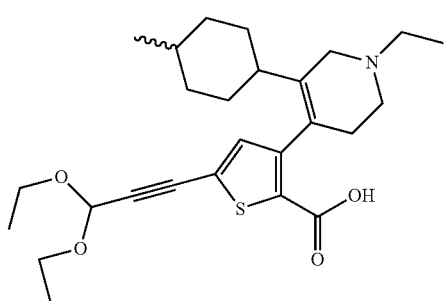

033

033 was prepared by the same method as 014, using propargylaldehyde diethyl acetal instead of 3,3-dimethyl-but-1-yne. MS calcd: (M+H)⁺=460. MS found: (M+H)⁺=460.

Example 35—5-(4-Carboxy-phenyl)-3-[1-ethyl-5-(4-methyl-cyclohexyl)-1,2,3,6-tetrahydro-pyridin-4-yl]-thiophene-2-carboxylic acid

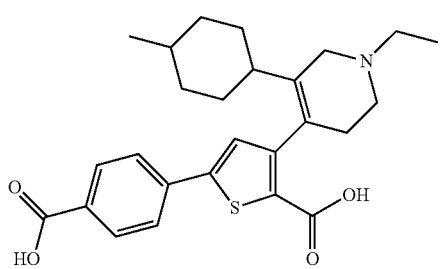

035

DMF (10 mL) and water (2 mL) were added to a mixture of 4-carboxyphenylboronic acid (0.23 g, 1.4 mmol), 014C (0.43 g, 0.91 mmol), Pd(dppf)Cl₂ (0.033 g, 0.0455 mmol), and Na₂CO₃ (0.3 g, 2.8 mmol) under N₂, and stirred at 92° C. for 4 hr. The reaction was cooled to RT, and to it was added ice-water and EtOAc. The organic layer was washed with water (3×) and the combined aqueous layers were back-extracted with EtOAc (2×). The combined organic layers were washed with brine, dried over anhydrous Na₂SO₄, and concentrated under reduced pressure. The product was purified by flash chromatography (silica gel), eluting with 0-5% MeOH in CH₂Cl₂ to give 035A. MS calcd: (M+H)⁺=468. MS found: (M+H)⁺=468.

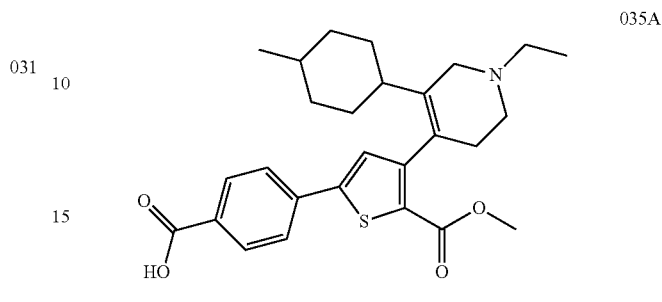

035A 035A (25 mg) was dissolved in THF (2 mL) and EtOH (1 mL). LiOH (2 M, 0.5 mL) was then added. The reaction was stirred at RT for 16 hr, and then diluted with EtOAc. The organic layer was washed with water and concentrated. The final product was precipitated out in hexane and washed more with hexane. The powder of 035 was obtained with lyophilization. MS calcd: (M+H)⁺=454. MS found: (M+H)⁺=454.

Example 36—3-[5-(4-Methyl-cyclohexyl)-1-(toluene-4-sulfonyl)-1,2,3,6-tetrahydro-pyridin-4-yl]-5-phenyl-thiophene-2-carboxylic acid

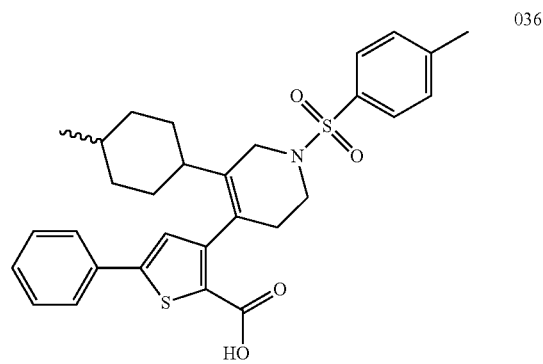 [SMILES: Cc1ccc(S(=O)(=O)N2CCC(c3cc(-c4ccccc4)sc3C(=O)O)=C(C3CCC(C)CC3)C2)cc1]

036

To a solution of 004B (25 mg, 0.058 mmol) and TEA (0.022 mL, 0.174 mmol) in CH₂Cl₂ (6 mL) cooled by an ice-water bath was added p-toluenesulfonyl chloride (22 mg, 0.115 mmol). The reaction was allowed to warm to RT overnight. The reaction mixture was concentrated and purified by preparative thin layer chromatography (prep-TLC, 50% EtOAc in hexane) to yield 036A (21 mg, 66%).

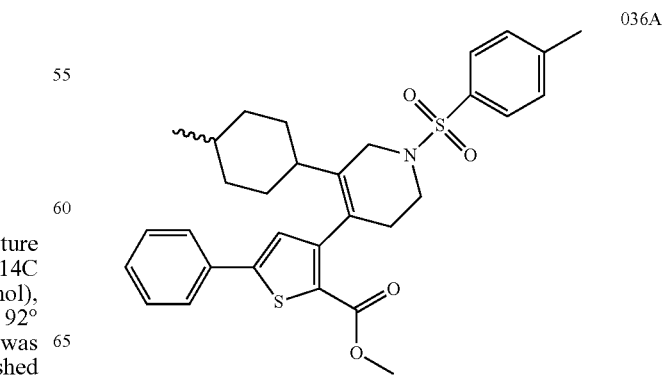

036A 036A (21 mg) was dissolved in THF (2 mL) and EtOH (1 mL). LiOH solution (2 M, 0.5 mL) was then added. The reaction was stirred at RT for 16 hr. The reaction mixture was acidified with 1 M HCl to pH 4-5 and concentrated to remove the organic solvent, then extracted with EtOAc (3×10 mL). The combined organic layers were washed with 10% citric acid aq, water, brine, then dried over MgSO$_4$ and concentrated. The residue was then purified by prep-TLC to give 036. MS calcd: (M+H)$^+$=536. MS found: (M+H)$^+$=536.

Example 37—4-(2-Carboxy-5-phenyl-thiophen-3-yl)-5-(4-methyl-cyclohexyl)-3,6-dihydro-2H-pyridine-1-carboxylic acid tert-butyl ester

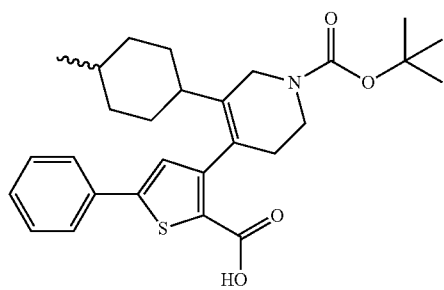

037 was prepared by the same method as 036, using di-tert-butyl dicarbonate instead of p-toluenesulfonyl chloride. MS calcd: (M+H)$^+$=482. MS found: (M+H)$^+$=482.

Example 39—3-[1-Methanesulfonyl-5-(4-methyl-cyclohexyl)-1,2,3,6-tetrahydro-pyridin-4-yl]-5-phenyl-thiophene-2-carboxylic acid

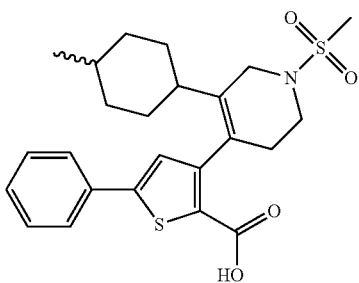

039 was prepared by the same method as 036, using methanesulfonyl chloride instead of p-toluenesulfonyl chloride. MS calcd: (M+H)$^+$=460. MS found: (M+H)$^+$=460.

Example 40—3-[5-(4-Methyl-cyclohexyl)-1,2,3,6-tetrahydro-pyridin-4-yl]-5-phenyl-thiophene-2-carboxylic acid

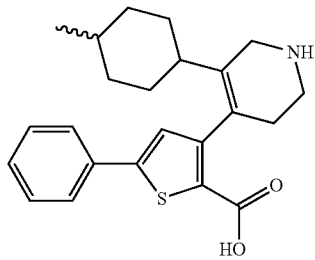

040A was prepared by the same method as 001J, using benzyl bromide instead of methyl iodide. MS calcd: (M+H)$^+$=486. MS found: (M+H)$^+$=486.

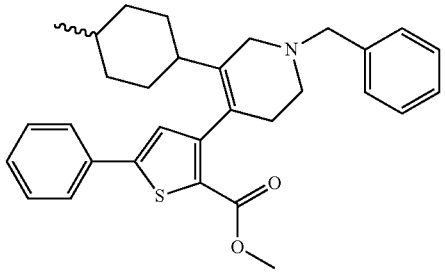

A solution of the product from 040A (81 mg, 0.17 mmol) in 1,2-dichoroethane (5 mL) was treated with 1-choroethylchoroformate (49 μL, 0.51 mmol) and the mixture heated to reflux for 4 hr. Methanol (2 mL) was carefully added to the mixture and heating continued for 2 hr. The mixture was allowed to cool to RT and concentrated to give 040B as an oil (66 mg, 99%). The crude 040B was used without further purification.

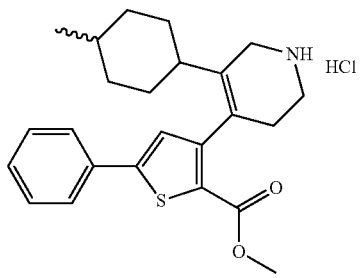

040B (20 mg) was dissolved in THF (2 mL) and EtOH (1 mL). LiOH (2 M, 0.5 mL) was then added. The reaction was stirred at RT for 16 hr. The reaction mixture was acidified with 1 M HCl to pH 4-5 and concentrated to remove organic solvent then extracted with EtOAc (3×10 mL). The combined organic layers was washed with brine, dried over MgSO$_4$, and concentrated to obtain the crude product, which was then purified by prep-TLC to give 040. MS calcd: (M+H)$^+$=382. MS found: (M+H)$^+$=382.

Example 40X—Methyl 3-(5-(4-methylcyclohexyl)-1,2,3,6-tetrahydropyridin-4-yl)-5-phenylthiophene-2-carboxylate

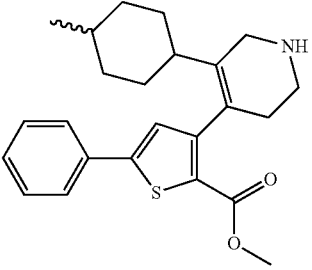

001H (240 mg, 0.61 mmol) was dissolved in ACN (5 mL) and treated with benzyl bromide (0.11 mL, 0.90 mmol). The resultant reaction mixture was stirred for 3 hr at 80° C., cooled to RT, and concentrated in vacuo. The crude reaction product was carried to the next step without purification. The intermediate was dissolved in MeOH (10 mL) and treated with sodium borohydride (0.80 g, 2.2 mmol) under constant stirring. The reaction mixture was stirred overnight at 80° C., quenched with water (20 mL), and extracted with EtOAc (3×20 mL). The combined organic layer was dried under anhydrous Na$_2$SO$_4$ and concentrated to obtain the compound as a brown oil. Purification by flash chromatography (silica gel, 0-5% MeOH in methylene chloride) afforded the intermediate compound (210 mg, yield 77%). The intermediate compound (210 mg, 0.432 mmol) was dissolved in DCE (5 mL) and treated with 1-chloroethylchloroformate (70 μL, 0.60 mmol). The resultant mixture was stirred under reflux for 4 hr. MeOH (2 mL) was added to the reaction mixture in small portions and the heating was continued for an additional 2 hr. The mixture was allowed to cool to RT and concentrated to afford crude 040X (180 ing) as an oil, which was used in additional chemistry without purification. MS calcd: (M+H)$^+$=396. MS found: (M+H)$^+$=396.

Example 41—3-[1-Methyl-4-(4-methyl-cyclohexyl)-1,2,5,6-tetrahydro-pyridin-3-yl]-5-phenyl-thiophene-2-carboxylic acid

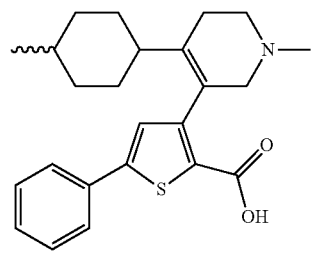

041

To a stirred solution of 001E (2.41 g, 9 mmol) in dioxane (38 mL) was added bis (pinacolato)diboron (2.74 g, 10.8 mmol), Pd(dppf)Cl$_2$ (0.197 g, 0.27 mmol), dppf (0.150 g, 0.27 mmol), and AcOK (2.64 g, 27 mmol). The mixture was degassed by evacuating the reaction flask under vacuum followed by N$_2$ back-fill (3×). Under N$_2$, the reaction was then heated to 90° C. and stirred overnight (approx. 16 hr). The reaction was cooled to RT and diluted with H$_2$O. The mixture was extracted with EtOAc (3×). The combined organic layers were washed with brine, dried over MgSO$_4$, filtered, and then purified by silica gel chromatography to give 041A as a solid. MS calcd: (M+H)$^+$: 263. MS found: (M+H)$^+$=263.

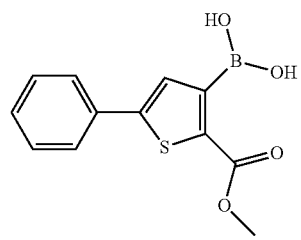

041A

DMF (5 mL) and H$_2$O (1 mL) were added to a mixture of 3-bromopyridine-4-boronic acid (0.27 g, 1.3 mmol), 001B (0.31 g, 1.3 mmol), Pd(dppf)Cl$_2$ (0.048 g, 0.065 mmol) and Na$_2$CO$_3$ (0.41 g, 3.9 mmol) under N$_2$ and stirred at 90° C. for 4 hr. The reaction was cooled to RT, and to it was added ice-water and EtOAc. The layers were separated and the organic layer was washed with water (3×) and the combined aqueous layers were back-extracted with EtOAc (2×). The combined organic layers were then washed with brine, dried over anhydrous Na$_2$SO$_4$, and concentrated under reduced pressure. The product was purified by flash chromatography (silica gel) eluting with 0-5% MeOH in CH$_2$Cl$_2$ to give 041B as an off-white solid. MS calcd: (M+H)$^+$: 253. MS found: (M+H)$^+$=253.

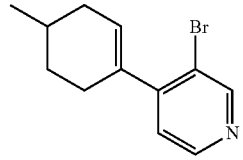

041B

DMF (5 mL) and H$_2$O (1 mL) were added to a mixture of 041A (0.26 g, 1.0 mmol), compound 041B (0.28 g, 1.1 mmol), Pd(dppf)Cl$_2$ (0.037 g, 0.05 mmol) and Na$_2$CO$_3$ (0.41 g, 3.9 mmol) under N$_2$, and stirred at 90° C. for 4 hr. The reaction was cooled to RT, and to it was added ice-water and EtOAc. The layers were separated and the organic layer was washed with water (3×) and the combined aqueous layers were back-extracted with EtOAc (2×). The combined organic layers were then washed with brine, dried over anhydrous Na$_2$SO$_4$, and concentrated under reduced pressure. The product was purified by flash chromatography (silica gel) eluting with 0-5% MeOH in CH$_2$Cl$_2$ to give compound 041C as an off-white solid. MS calcd: (M+H)$^+$: 290. MS found: (M+H)$^+$=390.

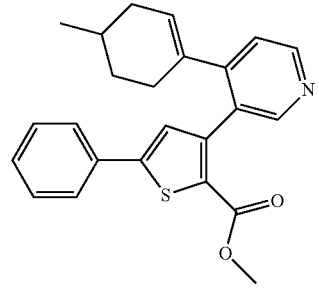

41C 041C (100 mg, 0.257 mmol) was dissolved in MeOH (15 mL), and 10% Pd/C (20 mg) was added as the catalyst. Hydrogenation under 50 psi H$_2$ was run overnight. Filtration and concentration gave 041D. MS calcd: (M+H)$^+$=392. MS found: (M+H)$^+$=392.

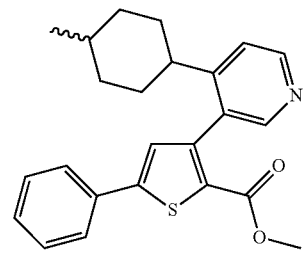

041D

Methyl iodide (0.08 mL, 1.278 mmol) was added to a solution of 041D (99 mg, 0.25 mmol) in ACN (5 mL), and the mixture was stirred for 3 hr at 80° C. The reaction mixture was cooled to RT and concentrated in vacuo. The crude 041E was used directly in the next step. MS calcd: (M)⁺=406. MS found: (M)⁺=406.

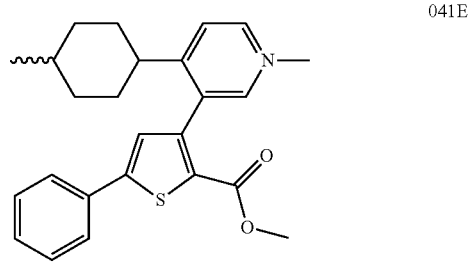

041E

Sodium borohydride (42 mg, 1.1 mmol) was added to a solution of 041E (110 mg, 0.27 mmol) in MeOH (6 mL) at RT with constant stirring. The reaction mixture was stirred overnight at 80° C. The reaction mixture was quenched with water (20 mL) and extracted with EtOAc (3×20 mL). The organic layers were combined, dried over anhydrous Na₂SO₄, and concentrated to obtain the product as brown oil, which was purified by column chromatography (silica gel, 0-10% MeOH in CH₂Cl₂) to yield 041F. MS calcd: (M+H)⁺=410. MS found: (M+H)⁺=410.

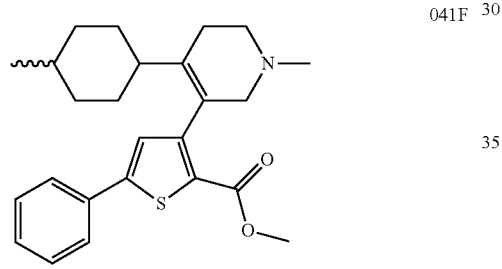

041F 041F (50 mg) was dissolved in THF (2 mL) and EtOH (1 mL). LiOH (2 M, 0.5 mL) was then added. The reaction was stirred at RT for 16 hr, then diluted with EtOAc. The organic layer was washed with water and concentrated. The final product was precipitated out in hexane and washed more with hexane. The powder of 041 was obtained with lyophilization. MS calcd: (M+H)⁺=396. MS found: (M+H)⁺=396.

Example 42—3-[1-Methyl-5-(4-methyl-cyclohexyl)-1,2,3,6-tetrahydro-pyridin-4-yl]-5-{4-[(pyridine-2-carbonyl)-amino]-phenyl}-thiophene-2-carboxylic acid

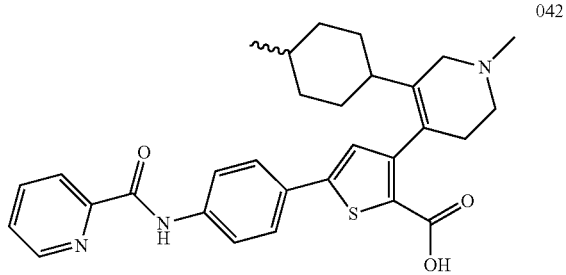 [SMILES: CC1CCC(C2=C(c3cc(-c4ccc(NC(=O)c5ccccn5)cc4)sc3C(=O)O)CCN(C)C2)CC1]

042

042 was prepared by the same method as 013, using 2-pyridinecarboxylic acid instead of 1,3-thiazole-4-carboxylic acid. MS calcd: (M+H)⁺=516. MS found: (M+H)⁺=516.

Example 43—3-[1-Benzyl-5-(4-methyl-cyclohexyl)-1,2,3,6-tetrahydro-pyridin-4-yl]-5-phenyl-thiophene-2-carboxylic acid

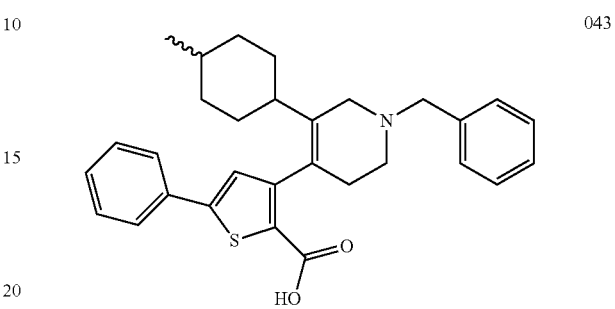

043

043 was prepared by the same method as 001, using benzyl bromide instead of methyl iodide. MS calcd: (M+H)⁺=472. MS found: (M+H)⁺=472.

Example 45—3-[5-(4-Methyl-cyclohexyl)-1-(pyrazine-2-carbonyl)-1,2,3,6-tetrahydro-pyridin-4-yl]-5-phenyl-thiophene-2-carboxylic acid

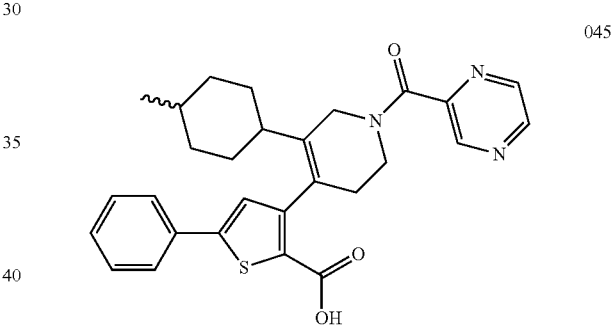

045

045 was prepared by the same method as 071, using pyrazine-2-carbonyl chloride instead of acetyl chloride. MS calcd: (M+H)⁺=489. MS found: (M+H)⁺=489.

Example 46—5-(3,3-Dimethyl-but-1-ynyl)-3-[1-methyl-5-(4-methyl-cyclohexyl)-1,2,3,6-tetrahydro-pyridin-4-yl]-thiophene-2-carboxylic acid

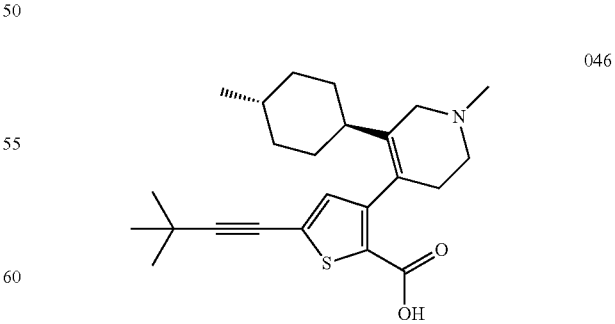

046

046 was prepared by the same method as 003. The pure trans-1-methyl isomer was isolated by preparative thin layer chromatography via repeated migration with 3% MeOH in dichloromethane. MS calcd: (M+H)⁺=400. MS found: (M+H)⁺=400.

Example 47—3-[1-Methyl-5-(4-methyl-cyclohexyl)-1,2,3,6-tetrahydro-pyridin-4-yl]-5-{4-[(thiazole-4-carbonyl)-amino]-phenyl}-thiophene-2-carboxylic acid

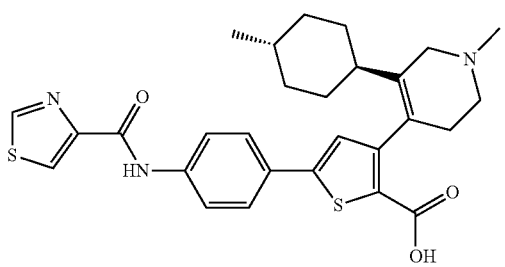

047

047 was prepared by the same method as 013. The pure trans-1-methyl isomer was isolated by preparative thin layer chromatography via repeated migration with 3% MeOH in dichloromethane. MS calcd: (M+H)$^+$=522. MS found: (M+H)$^+$=522.

Example 48—3-[1-Ethyl-5-(4-methyl-cyclohexyl)-1,2,3,6-tetrahydro-pyridin-4-yl]-5-{4-[(2-methyl-thiazole-4-carbonyl)-amino]-phenyl}-thiophene-2-carboxylic acid

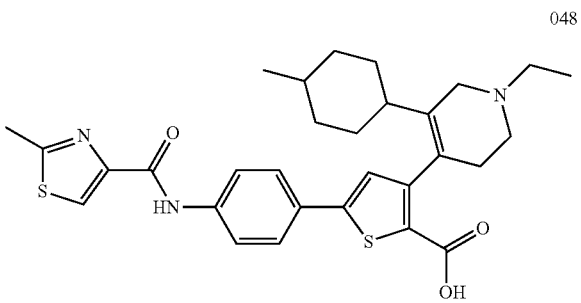 [SMILES: CCN1CCC(c2cc(-c3ccc(NC(=O)c4csc(C)n4)cc3)sc2C(=O)O)=C(C2CCC(C)CC2)C1]

048

048 was prepared by the same method as compound 019, using 2-methyl-1,3-thiazole-4-carboxylic acid instead of 1,3-thiazole-4-carboxylic acid. MS calcd: (M+H)$^+$=550. MS found: (M+H)$^+$=550.

Example 50—3-[1-Ethyl-5-(4-methyl-cyclohexyl)-1,2,3,6-tetrahydro-pyridin-4-yl]-5-{4-[(thiazole-5-carbonyl)-amino]-phenyl}-thiophene-2-carboxylic acid

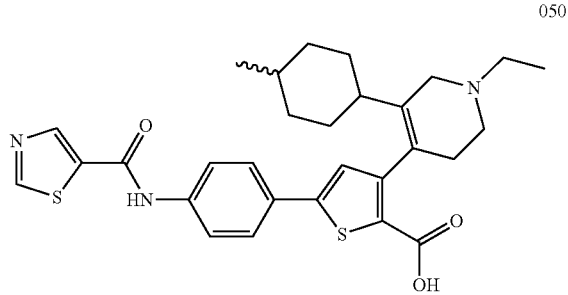 [SMILES: CCN1CCC(c2cc(-c3ccc(NC(=O)c4cncs4)cc3)sc2C(=O)O)=C(C2CCC(C)CC2)C1]

050

050 was prepared by the same method as 019, using 1,3-thiazole-5-carboxylic acid instead of 1,3-thiazole-4-carboxylic acid. MS calcd: (M+H)$^+$=536. MS found: (M+H)$^+$=536.

Example 51—5-{4-[(1,5-Dimethyl-1H-pyrazole-3-carbonyl)-amino]-phenyl}-3-[1-ethyl-5-(4-methyl-cyclohexyl)-1,2,3,6-tetrahydro-pyridin-4-yl]-thiophene-2-carboxylic acid

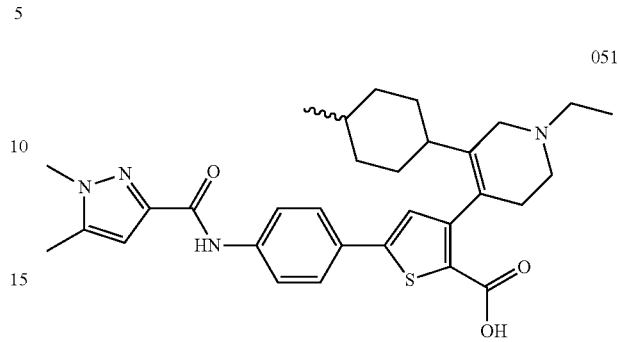

051

051 was prepared by the same method as 019, using 1,5-dimethyl-1H-pyrazole-3-carboxylic acid instead of 1,3-thiazole-4-carboxylic acid. MS calcd: (M+H)$^+$=547. MS found: (M+H)$^+$=547.

Example 53—3-[1-Ethyl-5-(4-methyl-cyclohexyl)-1,2,3,6-tetrahydro-pyridin-4-yl]-5-{4-[(5-methyl-isoxazole-3-carbonyl)-amino]-phenyl}-thiophene-2-carboxylic acid

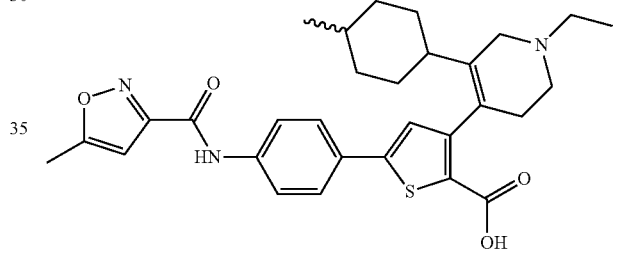

053

053 was prepared by the same method as 019, using 5-methylisoxazole-3-carboxylic acid instead of 1,3-thiazole-4-carboxylic acid. MS calcd: (M+H)$^+$=534. MS found: (M+H)$^+$=534.

Example 59—5-{3-Fluoro-4-[(thiazole-4-carbonyl)-amino]-phenyl}-3-[1-methyl-5-(4-methyl-cyclohexyl)-1,2,3,6-tetrahydro-pyridin-4-yl]-thiophene-2-carboxylic acid

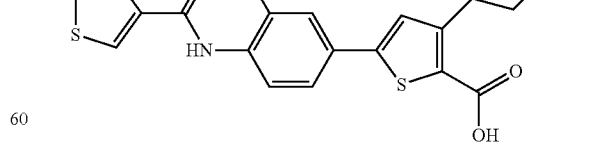

059

DMF (10 mL) and H$_2$O (2 mL) were added to a mixture of 4-amino-3-fluorophenylboronic acid (0.26 g, 1.4 mmol), 002G (0.42 g, 0.91 mmol), Pd(dppf)Cl$_2$ (0.033 g, 0.0455 mmol), and Na$_2$CO$_3$ (0.3 g, 2.8 mmol) under N$_2$. The mixture was stirred at 92° C. for 4 hr. The reaction was cooled to RT, and to it was added ice-water (5 mL) and EtOAc (50 mL). The organic layer was washed with water (2×10 mL) and the combined aqueous layers were back-extracted with EtOAc (10 mL). The combined organic layers were washed with brine, dried over anhydrous Na₂SO₄, and concentrated under reduced pressure. The product was purified by flash chromatography (silica gel), eluting with 0-5% MeOH in CH₂Cl₂ to give 059A as an oil. MS calcd: (M+H)⁺=443. MS found: (M+H)⁺=443.

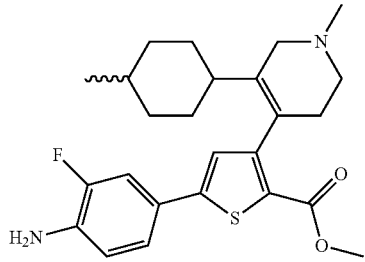

059A 1,3-Thiazole-4-carboxylic acid (100 mg) was dissolved in DMF (3 mL). To it were added HATU (325 mg) and DIPEA (0.35 mL) and the reaction mixture was stirred at RT for 15 min. Compound 059A (168 mg, 0.38 mmol) was added and the reaction mixture was stirred at RT for 4 hr. The reaction mixture was evaporated in vacuo and the residue was dissolved in DCM (50 mL). This was washed with sodium bicarbonate solution (2×10 mL) followed by brine. The organic layer was concentrated and purified by column chromatography with 0-5% MeOH in DCM as eluent to give pure 059B. MS calcd: (M+H)⁺=554. MS found: (M+H)⁺=554.

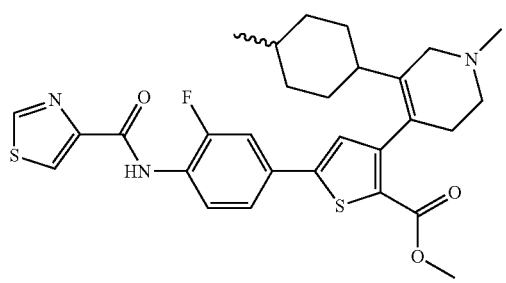

059B 059B (50 mg) was dissolved in THF (2 mL) and EtOH (1 mL). LiOH (2 M, 0.5 mL) was then added. The reaction was stirred at RT for 16 hr, and then diluted with EtOAc. The organic layer was washed with water and concentrated. The final product was precipitated out in hexane and washed once with hexane. The powder of 059 was obtained with lyophilization. MS calcd: (M+H)⁺=540. MS found: (M+H)⁺=540.

Example 60—5-{2-Fluoro-4-[(thiazole-4-carbonyl)-amino]-phenyl}-3-[1-methyl-5-(4-methyl-cyclohexyl)-1,2,3,6-tetrahydro-pyridin-4-yl]-thiophene-2-carboxylic acid

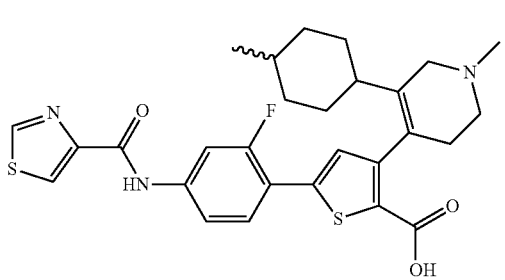

060

060 was prepared by the same method as 059, using 4-amino-2-fluorophenylboronic acid pinacol ester instead of 4-amino-3-fluorophenylboronic acid. MS calcd: (M+H)⁺=540. MS found: (M+H)⁺=540.

Example 62—3-[1-Ethyl-5-(4-methyl-cyclohexyl)-1,2,3,6-tetrahydro-pyridin-4-yl]-5-[4-(pyridin-2-ylcarbamoyl)-phenyl]-thiophene-2-carboxylic acid

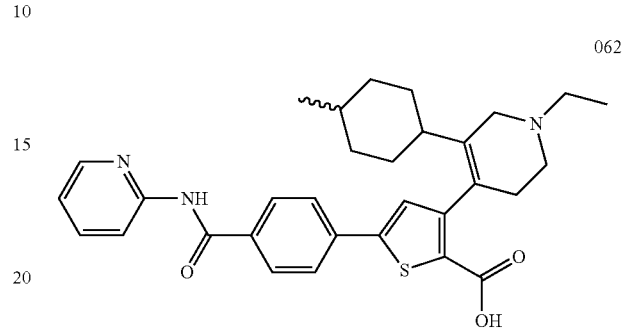

062

062 was prepared according to the following scheme:

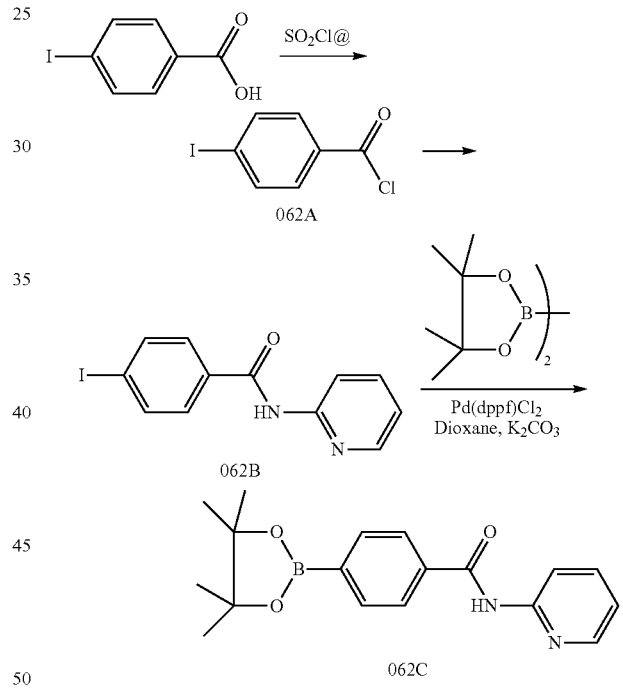

To solid 4-iodobenzoic acid (5 mmol) was slowly added thionyl chloride (10 mL). The reaction was refluxed for 4 hr, and the reaction mixture was then concentrated to dryness to give compound 062A.

Crude 062A was dissolved in 1,2-dichloroethane (20 mL), and to it was added 2-aminopyiridine (5 mmol), TEA (2 mL), and DMAP (10 mg). The mixture was reluxed for 24 hr, and then concentrated. The crude product was then purified by column chromatography, using 0-100% EtOAc in DCM to give 062B.

Compound 062C was prepared by the same method as 005B, using 062B instead of 005A.

062 was prepared by the same method as 005, using intermediates 062C and 014E instead of 005B and 002. MS calcd: (M+H)⁺=530. MS found: (M+H)⁺=530.

Example 63—3-[5-(2-Cyclopentyl-ethyl)-1-methyl-1,2,3,6-tetrahydro-pyridin-4-yl]-5-phenyl-thiophene-2-carboxylic acid

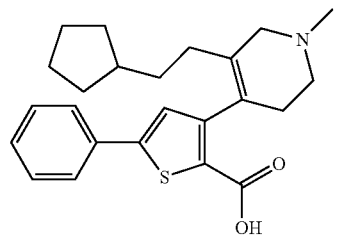

To a 25 mL round bottom flask were added 001F (187 mg, 0.5 mmol), copper iodide (0.15 eq.) and Pd(dppf)Cl$_2$ (0.05 eq.), DMF (5 mL), TEA (4 eq.), and cyclopentylacetylene (3 eq.). The reaction mixture was stirred at 60° C. for 2 hr under a N$_2$ atmosphere. The reaction mixture was filtered through Celite® and washed with EtOAc. The filtrate was diluted with water, and extracted twice with EtOAc. The organic phases were combined and washed twice with water. The organic layer was separated, dried (Na$_2$SO$_4$), evaporated, and purified by column chromatography to give 063A. MS calcd: (M+H)$^+$=388. MS found: (M+H)$^+$=388.

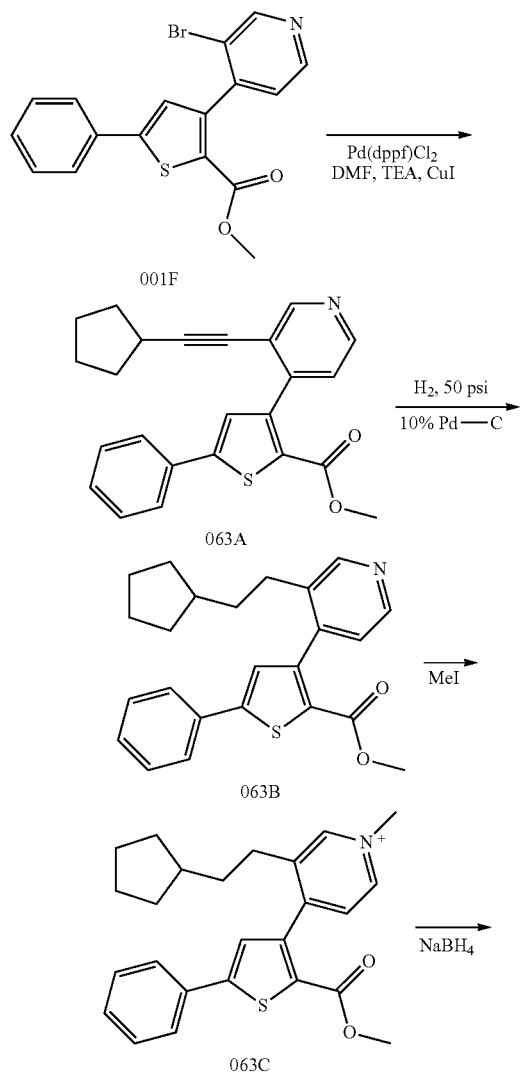

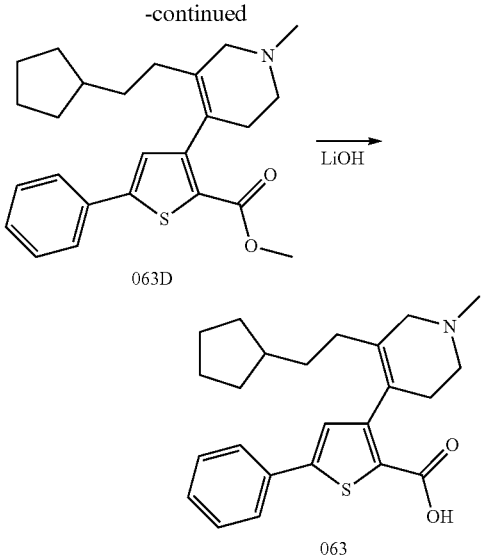

Compound 063A (100 mg, 0.257 mmol) was dissolved in MeOH (15 mL), and 10% Pd/C (20 mg) was added as the catalyst. Hydrogenation under 50 psi H$_2$ was run overnight. Filtration and concentration gave 063B. MS calcd: (M+H)$^+$=392. MS found: (M+H)$^+$=392.

Methyl iodide (0.08 mL, 1.278 mmol) was added to a solution of 063B (100 mg, 0.256 mmol) in 5 mL of ACN and the mixture was stirred for 3 hr at 80° C. The reaction mixture was cooled to RT and concentrated in vacuo. The crude 063C was used in the next step. MS calcd: (M)$^+$=406. MS found: (M)$^+$=406.

Sodium borohydride (42 mg, 1.1 mmol) was added to a solution of 063C (111 mg, 0.275 mmol) in MeOH (6 mL) at RT with constant stirring. The reaction mixture was stirred overnight at 80° C. The reaction mixture was quenched with water (20 mL) and extracted with EtOAc (3×20 ml). The organic layers were combined, dried over anhydrous Na$_2$SO$_4$, and concentrated to obtain the product as brown oil, which was purified by column chromatography (silica gel, 0-10% MeOH in CH$_2$Cl$_2$) to yield the 063D. MS calcd: (M+H)$^+$=410. MS found: (M+H)$^+$=410.

063D (50 mg) was dissolved in tetrahydrofuran (THF; 2 mL) and EtOH (1 mL). LiOH (2 M, 0.5 mL) was then added. The reaction was stirred at RT for 16 hr, and then diluted with EtOAc. The organic layer was washed with water and concentrated. The final product was precipitated out in hexane and washed once more with hexane. The powder of 063 was obtained with lyophilization. MS calcd: (M+H)$^+$=396. MS found: (M+H)$^+$=396.

Example 64—3-[1-Methyl-5-(4-trifluoromethyl-cyclohexyl)-1,2,3,6-tetrahydro-pyridin-4-yl]-5-phenyl-thiophene-2-carboxylic acid

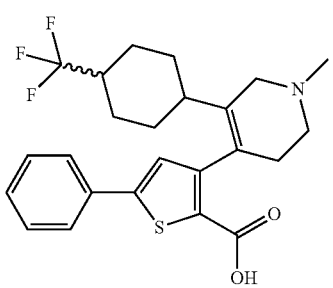

064 was prepared by the same method as 001, using 4-(trifluoromethyl)cyclohexan-1-one instead of 4-methylcyclohexanone. MS calcd: (M+H)+=450. MS found: (M+H)+=450.

Example 65—5-(3,3-Dimethyl-but-1-ynyl)-3-[4-(4-methyl-cyclohexyl)-1-(tetrahydro-pyran-4-ylmethyl)-1,2,5,6-tetrahydro-pyridin-3-yl]-thiophene-2-carboxylic acid

065

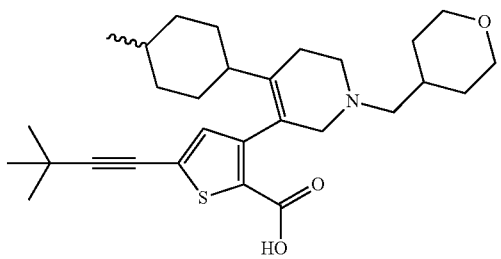

065 was prepared by the same method as 117 (see below), using 4-formyltetrahydropyran instead of tetrahydrofuran-3-carboxaldehyde. MS calcd: (M+H)+=484. MS found: (M+H)+=484.

Example 67—3-[1-Methyl-5-(4-methyl-cyclohexyl)-1,2,3,6-tetrahydro-pyridin-4-yl]-5-{4-[methyl-(thiazole-4-carbonyl)-amino]-phenyl}-thiophene-2-carboxylic acid

067

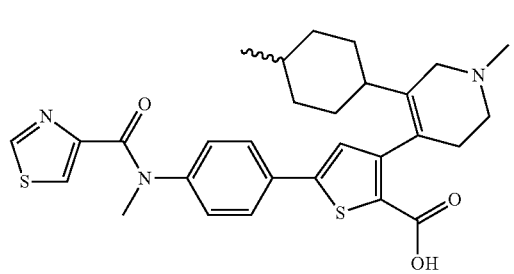

067 was prepared by the same method as 059, using 4-(aminomethyl)benzeneboronic acid instead of 4-amino-3-fluorophenylboronic acid. MS calcd: (M+H)+=536. MS found: (M+H)+=536.

Example 68—5-(3,3-Dimethyl-but-1-ynyl)-3-[1-methyl-5-(4-methyl-cyclohex-1-enyl)-1,2,3,6-tetrahydro-pyridin-4-yl]-thiophene-2-carboxylic acid

068

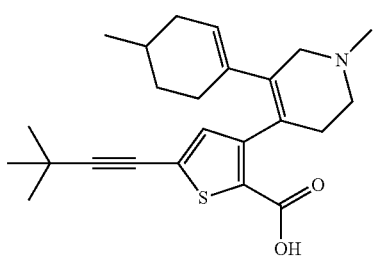

Methyl iodide (0.08 mL, 1.278 mmol) was added to a solution of 002C (80 mg, 0.256 mmol) in 5 mL of ACN and the mixture was stirred for 3 hr at 80° C. The reaction mixture was cooled to RT and concentrated in vacuo. The crude 068A was used directly in the next step. MS calcd: (M)+=328. MS found: (M)+=328.

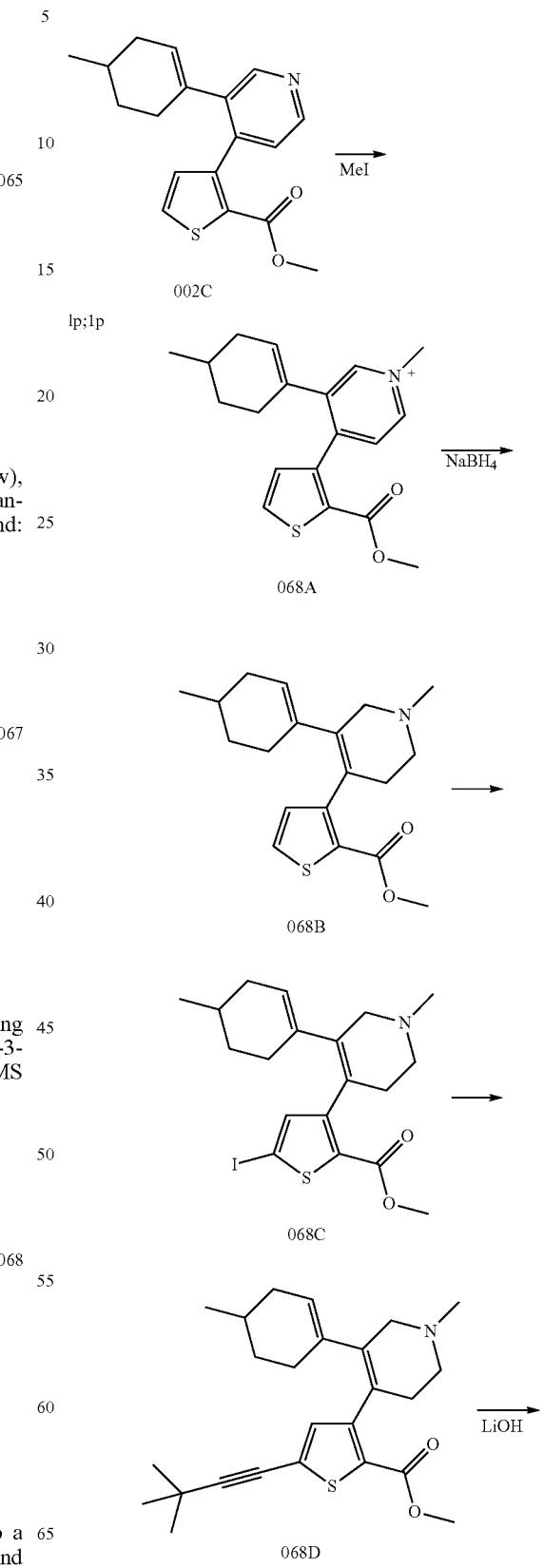

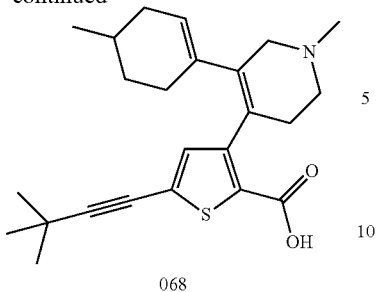

068

Sodium borohydride (42 mg, 1.1 mmol) was added to a solution of 068A (90 mg, 0.275 mmol) in MeOH (6 mL) at RT with constant stirring. The reaction mixture was stirred overnight at 80° C. The reaction was quenched with water (20 mL) and extracted with EtOAc (3×20 mL). The organic layers were combined, dried over anhydrous Na$_2$SO$_4$, and concentrated to obtain the product as brown oil, which was purified by column chromatography (silica gel, 0-10% MeOH in CH$_2$Cl$_2$) to yield 068B. MS calcd: (M+H)$^+$=332. MS found: (M+H)$^+$=332.

A solution of 068B (496 mg, 1.5 mmol) in dry THF (10 mL) was added dropwise at −77° C. under N$_2$ to 2 M LDA in THF/heptane/ethylbenzene (1.5 mL) maintaining an internal temperature <−70° C. The stirring was continued at −77° C. for 2.5 hr. A solution of iodine (1.6 g) in dry THF (2 mL) was added dropwise to the stirred reaction mixture maintaining an internal temperature <−70° C. After stirring under N$_2$ at −77° C. for 1.5 hr, the reaction was quenched by addition of saturated NH$_4$Cl solution and warmed to 0° C. The mixture was diluted with 5% sodium thiosulfate solution, then the organic phase was separated and the aqueous phase was extracted with EtOAc. The combined organic phases were dried (Na$_2$SO$_4$), filtered, and evaporated. The product was dried to give 068C. MS calcd: (M+H)$^+$=458. MS found: (M+H)$^+$=458.

To a 25 mL round bottom flask under N$_2$, 068C (1 eq.), copper iodide (0.15 eq.) and Pd(dppf)Cl$_2$ (0.05 eq.) were added. DMF, TEA (4 eq.), and 3,3-dimethyl-but-1-yne (3 eq.) were added and the reaction mixture stirred at 60° C. for 2 hr under N$_2$. The reaction mixture was filtered over Celite® and washed with EtOAc. The solution was diluted with water and extracted (2×) with EtOAc. The organic phases were combined and washed with water (2×). The organic layer was separated, dried (Na$_2$SO$_4$), evaporated, and purified by column chromatography to give 068D. MS calcd: (M+H)$^+$=412. MS found: (M+H)$^+$=412.

068D (20 mg) was dissolved in THF (2 mL) and EtOH (1 mL). LiOH (2 M, 0.5 mL) was then added. The reaction was stirred at RT for 16 hr, and then diluted with EtOAc. The organic layer was washed with water and concentrated. The final product was precipitated in hexane and washed more with hexane. The powder of 068 was obtained after lyophilization. MS calcd: (M+H)$^+$=398. MS found: (M+H)$^+$=398.

Example 69—3-[1-Methyl-5-(4-methyl-cyclohex-1-enyl)-1,2,3,6-tetrahydro-pyridin-4-yl]-5-{4-[(thiazole-2-carbonyl)-amino]-phenyl}-thiophene-2-carboxylic acid

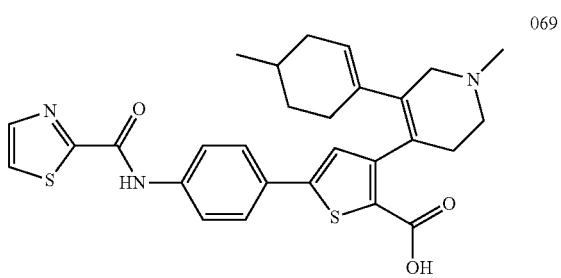 [SMILES: CC1CC=C(C2=C(c3cc(-c4ccc(NC(=O)c5nccs5)cc4)sc3C(=O)O)CCN(C)C2)CC1]

069

069 was prepared by the same method as 013, using intermediate 068C instead of 002G. MS calcd: (M+H)$^+$=520. MS found: (M+H)$^+$=520.

Example 76—3-[5-(4-Methyl-cyclohexyl)-1-(3-phenyl-propanoyl)-1,2,3,6-tetrahydropyridin-4-yl]-5-phenyl-thiophene-2-carboxylic acid

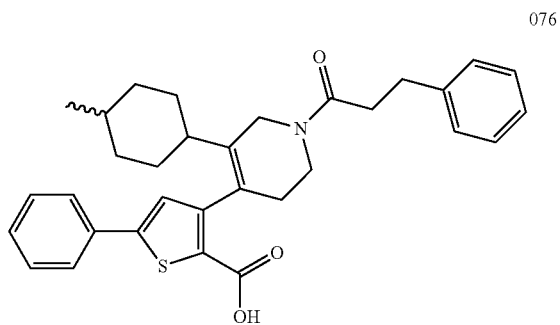 [SMILES: CC1CCC(C2=C(c3cc(-c4ccccc4)sc3C(=O)O)CCN(C(=O)CCc3ccccc3)C2)CC1]

076

076 was prepared by the same method as 071, using 3-phenylpropanoyl chloride instead of acetyl chloride. MS calcd: (M+H)$^+$=514. MS found: (M+H)$^+$=514.

Example 77—3-[1-Butyryl-5-(4-methyl-cyclohexyl)-1,2,3,6-tetrahydro-pyridin-4-yl]-5-phenyl-thiophene-2-carboxylic acid

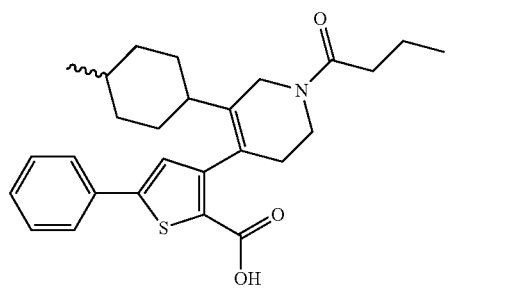

077

077 was prepared by the same method as 071, using butyryl chloride instead of acetyl chloride. MS calcd: (M+H)⁺=452. MS found: (M+H)⁺=452.

Example 80—3-[5-(4-Methyl-cyclohexyl)-1-(4-phenyl-butyl)-1,2,3,6-tetrahydro-pyridin-4-yl]-5-phenyl-thiophene-2-carboxylic acid

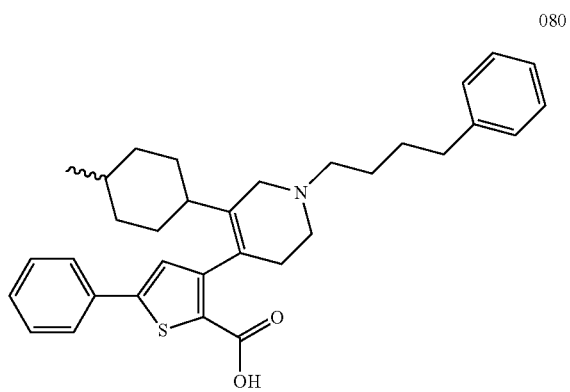 [SMILES: CC1CCC(C2=C(c3cc(-c4ccccc4)sc3C(=O)O)CCN(CCCCc3ccccc3)C2)CC1]

080 was prepared by the same method as 001, using 5-bromo-4-phenylbutane instead of methyl iodide. The hydrolysis reaction was conducted as described for 071. MS calcd: (M+H)⁺=514. MS found: (M+H)⁺=514.

Example 81—3-[1-(2-Hydroxy-ethyl)-5-(4-methyl-cyclohexyl)-1,2,3,6-tetrahydro-pyridin-4-yl]-5-phenyl-thiophene-2-carboxylic acid

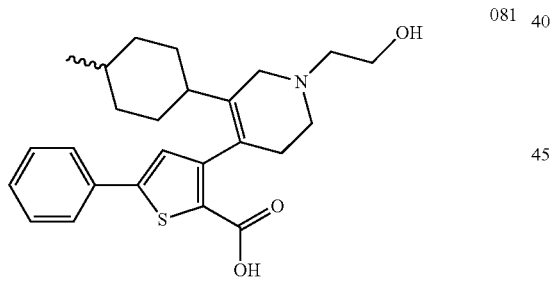

001H was dissolved in ACN (5 mL) and treated with ethyl bromoacetate (0.025 mL, 0.27 mmol). The resultant mixture was stirred at 80° C. over 12 hr, followed by cooling to RT, and concentrating in vacuo. The crude product was dissolved in MeOH (10 mL) and treated with sodium borohydride (0.80 g, 2.2 mmol) under constant stirring. The reaction mixture was continued to stir at 80° C. overnight, quenched with water (20 mL), and extracted into EtOAc (3×20 mL). The combined organic layers were dried over anhydrous Na₂SO₄, and concentrated to obtain a crude intermediate methyl ester as a brown oil. The ester intermediate was purified by flash chromatography (silica gel, 0-5% MeOH in methylene chloride) to yield pure methyl ester. The hydrolysis of the ester was conducted according to the procedure described for 171 to afford 081. MS calcd: (M+H)⁺=426. MS found: (M+H)⁺=426.

Example 83—3-[1-(2-Carboxy-ethyl)-5-(4-methyl-cyclohexyl)-1,2,3,6-tetrahydro-pyridin-4-yl]-5-phenyl-thiophene-2-carboxylic acid

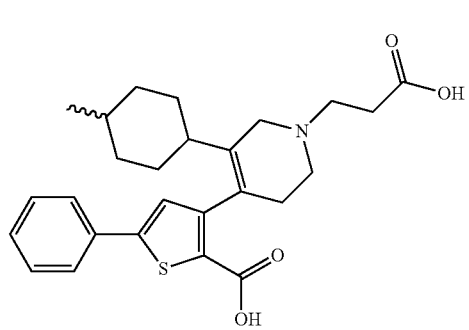

083 was prepared by the same method as 001, using ethyl-3-bromopropionate instead of methyl iodide. The hydrolysis reaction was conducted as described for 071. MS calcd: (M+H)⁺=454. MS found: (M+H)⁺=454.

Example 84—3-[1-Carbamoyl-5-(4-methyl-cyclohexyl)-1,2,3,6-tetrahydro-pyridin-4-yl]-5-phenyl-thiophene-2-carboxylic acid

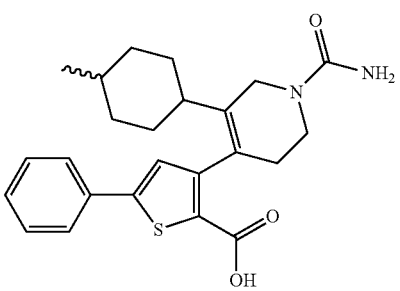

084 was prepared by the same method as 071, using TMS-isocyanate instead of acetyl chloride. MS calcd: (M+H)⁺: 425. MS found: (M+H)⁺=425.

Example 85—3-[1-Ethylcarbamoyl-5-(4-methyl-cyclohexyl)-1,2,3,6-tetrahydro-pyridin-4-yl]-5-phenyl-thiophene-2-carboxylic acid

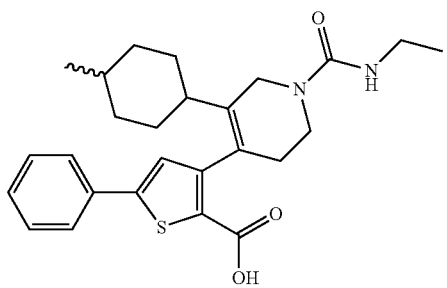

085 was prepared by the same method as 071, using ethyl isocyanate instead of acetyl chloride. MS calcd: (M+H)⁺=453. MS found: (M+H)⁺=453.

Example 86—3-[1-(4-Chloro-benzyl)-5-(4-methyl-cyclohexyl)-1,2,3,6-tetrahydro-pyridin-4-yl]-5-phenyl-thiophene-2-carboxylic acid

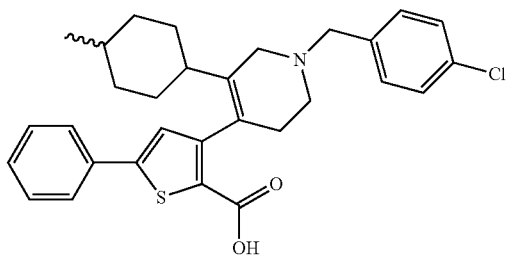

086

086 was prepared by the same method as 071, using p-chloro-benzylbromide instead of acetyl chloride. MS calcd: (M+H)⁺=506. MS found: (M+H)⁺=506.

Example 87—3-[5-(4-Methyl-cyclohexyl)-1-pyridin-2-ylmethyl-1,2,3,6-tetrahydro-pyridin-4-yl]-5-phenyl-thiophene-2-carboxylic acid

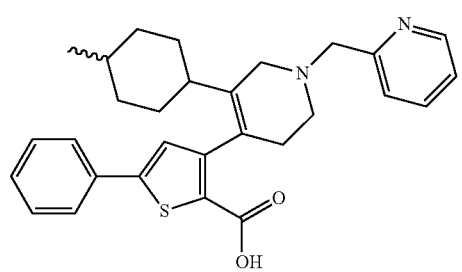

087

A solution of 40X (20 mg, 0.05 mmol) was dissolved in methylene chloride (6 mL), cooled to 0° C., and treated with pyridine-1-carboxaldehyde (6.27 mg, 0.055 mmol), TEA (0.007 mL, 0.05 mmol), and sodium triacetoxyborohydride (20 mg, 0.10 mmol). The resultant reaction mixture was warmed to RT, and stirred overnight. The reaction mixture was concentrated and purified by prep-TLC (silica gel, 50% EtOAc in hexane) to afford an intermediate methyl ester. Hydrolysis was conducted as described according to procedure for 071. MS calcd: (M+H)⁺=473. MS found: (M+H)⁺=473.

Example 88—3-[1-(5,7-Dimethyl-[1,2,4]triazolo[1,5-a]pyrimidin-2-ylmethyl)-5-(4-methyl-cyclohexyl)-1,2,3,6-tetrahydro-pyridin-4-yl]-5-phenyl-thiophene-2-carboxylic acid 088 was prepared by the same method as 087, using 88e from the scheme set forth below instead of pyridine-1-carboxaldehyde. MS calcd: (M+H)⁺=542. MS found: (M+H)⁺=542.

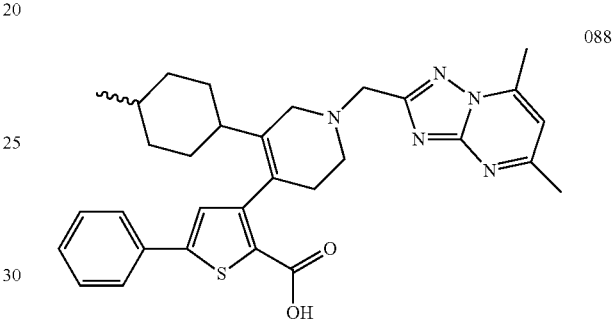

088

A mixture of glycolic acid (26.2 g, 345 mmol) and water (10 mL) was treated with aminoguanidine bicarbonate (23.5 g, 172 mmol) in small portions over a period of 0.1 hr. The resultant mixture was gently heated to maintain an internal temp of 25° C. during the addition. The mixture was then treated with slow addition of conc. nitric acid (1.0 mL), followed by heating to an internal temperature of 104-108° C. over 22 hr. The heating was then discontinued and the solution allowed to cool with stirring. The resultant slurry was cooled down 10° C., stirred over 2 hr, filtered, and rinsed with EtOH. The solids were dried overnight in a vacuum to provide the product 88a as a glycolic acid salt (29.5 g, 85%). MS calcd: (M+H)⁺=115. MS found: (M+H)⁺=115.

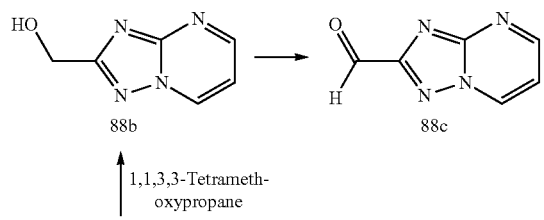

88b → 88c

↑ 1,1,3,3-Tetramethoxypropane

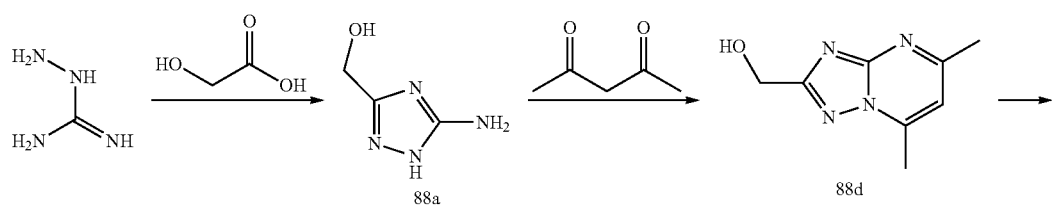

88a → 88d

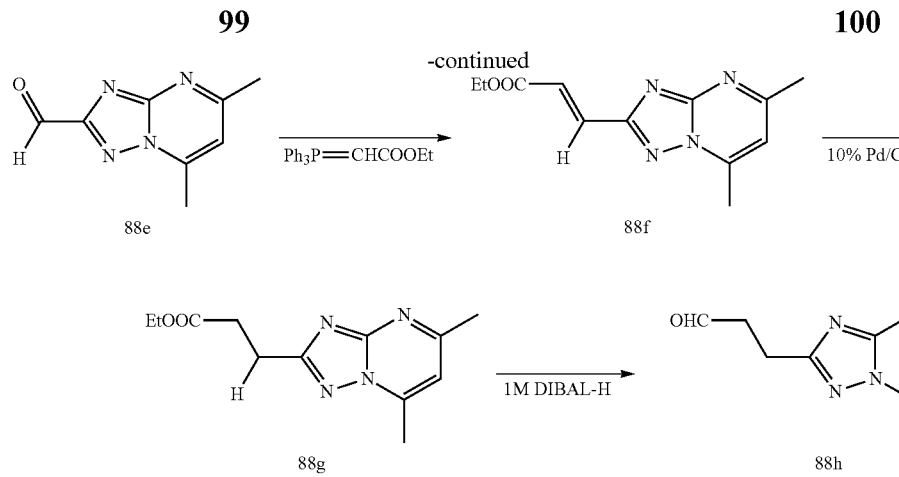

A 100 mL flask was charged with glycolate salt of 88a (25.0 g, 130 mmol), 1,1,3,3-tetramethoxypropane (26.0 g, 200 mmol), acetic acid (100 mL), and EtOH (20 mL). The resultant mixture was heated to a reflux over 1 hr, cooled to RT, diluted with DCM (250 mL) and treated with Celite (2.5 g). The mixture then stirred for 1 hr, filtered through a Buchner funnel packed with Celite, and rinsed with EtOH. The resultant solution was distilled to 5 vols, then cooled to 0° C. over 2 hr. The slurry was filtered and the cake was rinsed with cool EtOH. The solids were dried to provide the product 88b (6.1 g, 46%). MS calcd: $(M+H)^+=151$. MS found: $(M+H)^+=151$.

Compound 88b (1.50 g, 10.0 mmol) was dissolved in $CH_2Cl_2$ (50 mL), and the resultant solution was treated with iodobenzene diacetate (3.54 g, 11 mmol), followed by the addition of (2,2,6,6-tetramethylpiperidin-1-yl)oxyl (TEMPO; 230 mg, 0.015 mmol). The resultant mixture was warmed to RT and stirred. MTBE (50 mL) was slowly charged to the reactor, causing the product to precipitate, and the slurry was stirred for 0.5 hr. The reaction mixture was filtered, washed twice with 1:1DCM/MTBE, and dried in a vacuum overnight to yield the product 88c (1.38 g, 89%). MS calcd: $(M+H)^+=149$. MS found: $(M+H)^+=149$.

88a glycolic acid salt (10.0 g, 52.6 mmol) was dissolved in EtOH (120 mL), and the resultant solution was treated with pentane-2,4-dione (6 mL, 57.8 mmol) and acetic acid (1.0 mL). The mixture was heated to reflux for 1 hr, then cooled to RT, and diluted with DCM (25 mL), followed by addition of Celite (2.5 g). After stirring for 1 hr, the mixture was filtered through a Buchner funnel packed with Celite and rinsed with EtOH. The solution was distilled to 5 vols, then cooled to 0° C. for 1-2 hr. The slurry was filtered and the cake was rinsed with cool EtOH. The solids were dried to provide the product 88d (13.0 g, 82%). MS calcd: $(M+H)^+=179$. MS found: $(M+H)^+=179$.

A 50 mL reactor was sequentially charged with $CH_2Cl_2$ (10 mL), 88d (6.80 g, 38 mmol), and iodobenzene diacetate (13.5 g, 42 mmol). Upon dissolution of the iodobenzene diacetate, TEMPO (437 mg, 2.8 mmol) was added in a single portion, and the resultant mixture was warmed to RT. The reaction was stirred for a short time and treated with MTBE (10 mL). The precipitated product was stirred for an additional 0.5 hr. The reaction mixture was filtered, washed twice with 1:1 DCM:MTBE, and dried in a vacuum overnight to yield the product 88e (5.5 g, 79%). MS calcd: $(M+H)^+=177$. MS found: $(M+H)^+=177$.

Compound 88e (1.30 g, 7.5 mmol) was dissolved in THF (75 mL) and the resultant solution was treated with (ethoxycarbonyl methylene) triphenylphosphorane (2.60 g, 15 mmol). The reaction mixture was stirred for 3 hr. The solvent was evaporated in vacuo and the crude product purified by column chromatography over silica (DCM, 5% MeOH) to give the product 88f. MS calcd: $(M+H)^+=247$. MS found: $(M+H)^+=247$.

Compound 88f (200 mg, 0.257 mmol) was dissolved in MeOH (50 mL) and the resultant mixture was treated with 10% Pd/C (50 mg). Hydrogenation under 50 psi $H_2$ was run for 48 hr, followed by filtration and concentration to give the product 88g (200 mg, 99%). MS calcd: $(M+H)^+=249$. MS found: $(M+H)^+=249$.

Compound 88g (0.246 g, 1 mmol) was dissolved in THF (75 mL), and the resultant solution cooled to −78° C. and treated with 1 M diisobutylaluminum hydride (DIBAL-H) in hexane (1.0 mL, 1.0 mmol). The reaction mixture was stirred at −78° C. for 3 hr, quenched with saturated citric acid (20 mL), and extracted with EtOAc (3×20 mL). The organic layers were combined, dried over anhydrous $Na_2SO_4$, and concentrated to obtain a crude product as a brown oil. Purification by column chromatography afforded the product 88h. MS calcd: $(M+H)^+=205$. MS found: $(M+H)^+=205$.

Example 89—3-[5-(4-Methyl-cyclohexyl)-1-pyridin-3-ylmethyl-1,2,3,6-tetrahydro-pyridin-4-yl]-5-phenyl-thiophene-2-carboxylic acid

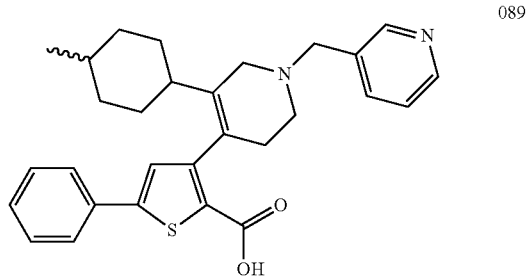 [SMILES: CC1CCC(C2=C(c3cc(-c4ccccc4)sc3C(=O)O)CCN(Cc3cccnc3)C2)CC1]

089

089 was prepared by the same method as 087, using pyridine-2-carboxaldehyde instead of pyridine-1-carboxaldehyde. MS calcd: $(M+H)^+=473$. MS found: $(M+H)^+=473$.

Example 91—3-[1-[3-(5,7-Dimethyl-[1,2,4]triazolo[1,5-a]pyrimidin-2-yl)-propyl]-5-(4-methyl-cyclohexyl)-1,2,3,6-tetrahydro-pyridin-4-yl]-5-phenyl-thiophene-2-carboxylic acid

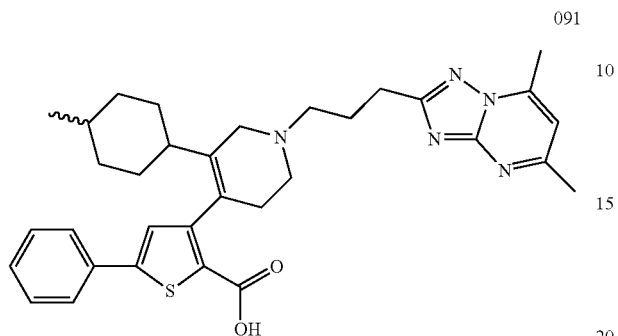

091 was prepared by the same method as 087, using 88h instead of pyridine-1-carboxaldehyde. MS calcd: (M+H)$^+$: 570. MS found: (M+H)$^+$=570.

Example 92—3-[5-(4-Methyl-cyclohexyl)-1-[1,2,4]triazolo[1,5-a]pyrimidin-2-ylmethyl-1,2,3,6-tetrahydro-pyridin-4-yl]-5-phenyl-thiophene-2-carboxylic acid

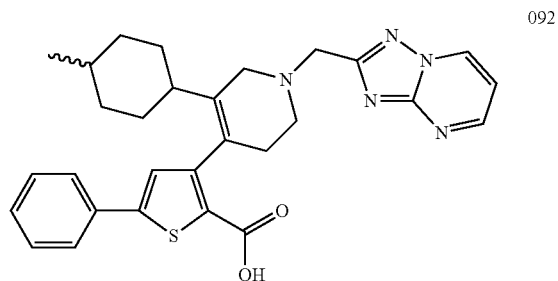 [SMILES: CC1CCC(C2=C(c3cc(-c4ccccc4)sc3C(=O)O)CCN(Cc3nc4ncccn4n3)C2)CC1]

The glycolate salt of 88a (25.0 g, 130 mmol), was dissolved in EtOH (20 mL) and treated with 1,1,3,3-tetramethoxypropane (26.0 g, 200 mmol), followed by acetic acid (100 mL). The resultant mixture was heated to a slight reflux over 1 hr, and the resulting solution was cooled to RT, then diluted with methylene chloride (250 mL) and treated with Celite (2.5 g). The resultant mixture was stirred for 1 hr, filtered through a Buchner funnel packed with Celite, and rinsed with EtOH. The solution was distilled to 5 vols, then cooled to 0° C. for 1-2 hr. The slurry was filtered and the cake was rinsed with cool EtOH. The solids were dried to provide an intermediate alcohol. This alcohol (60 mg, 0.4 mmol) was dissolved in methylene chloride (10 mL) and treated with iodobenzene diacetate (142 mg, 44 mmol). Upon dissolution of iodobenzene diacetate, the resultant mixture was treated with TEMPO (9 mg, 0.06 mmol) by a single charge, and the resultant mixture was allowed to warm to RT. MTBE (10 mL) was slowly added to the reaction mixture, and the resultant slurry stirred for 0.5 hr, then filtered, washed twice with 1:1 dichloromethane/MTBE, and dried in a vacuum overnight to yield the desired intermediate aldehyde 88c (54 mg, 91%). The final was prepared according to a procedure described for 087, using 88c instead of pyridine-1-carboxaldehyde. MS calcd: (M+H)$^+$=514. MS found: (M+H)$^+$=514.

Example 93—3-[5-(4-Methyl-cyclohexyl)-1-(2-pyridin-4-yl-acetyl)-1,2,3,6-tetrahydro-pyridin-4-yl]-5-phenyl-thiophene-2-carboxylic acid

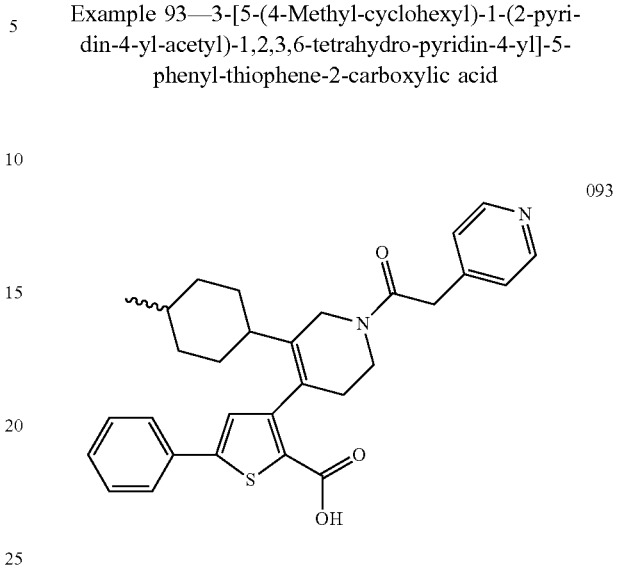

4-Pyridylacetic acid hydrochloride (12 mg, 0.05 mmol) was dissolved in methylene chloride (6 mL), cooled to 0° C., and treated with TEA (0.021 mL, 0.15 mmol) and isobutyl chloroformate (0.008 mL, 0.06 mmol). To the resultant mixture was added 40X (20 mg, 0.05 mmol) over 1 hr with constant stirring. The mixture was stirred overnight, concentrated and purified by prep-TLC (silica gel, 50% EtOAc in hexane) to afford an intermediate methyl ester. Hydrolysis was conducted as described for 071. MS calcd: (M+H)$^+$=501. MS found: (M+H)$^+$=501.

Example 95—3-[5-(4-Methyl-cyclohexyl)-1-(1-methyl-1H-indol-3-ylmethyl)-1,2,3,6-tetrahydro-pyridin-4-yl]-5-phenyl-thiophene-2-carboxylic acid

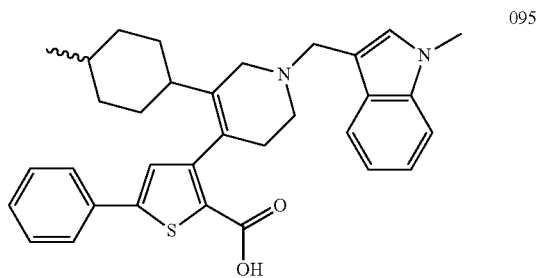 [SMILES: CC1CCC(C2=C(c3cc(-c4ccccc4)sc3C(=O)O)CCN(Cc3cn(C)c4ccccc34)C2)CC1]

40X (10 mg, 0.025 mmol) was dissolved in methylene chloride (3 mL), cooled to 0° C., and treated with 1-methylindole-3-carboxaldehyde (5 mg, 0.03 mmol), TEA (0.007 mL, 0.05 mmol), and sodium triacetoxyborohydride (10 mg, 0.05 mmol). The resultant reaction mixture was warmed to RT, and stirred overnight. The reaction mixture was concentrated and purified by prep-TLC (silica gel, 50% EtOAc in hexane) to afford an intermediate methyl ester. The hydrolysis reaction was conducted as described for 071. MS calcd: (M+H)$^+$: 525. MS found: (M+H)$^+$=525.

Example 96—3-[5-(4-Methyl-cyclohexyl)-1-(2-naphthalen-2-yl-acetyl)-1,2,3,6-tetrahydro-pyridin-4-yl]-5-phenyl-thiophene-2-carboxylic acid

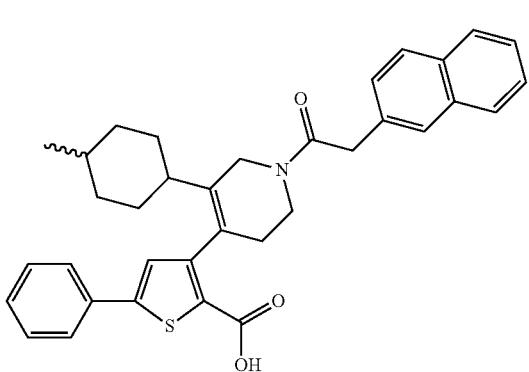

096

096 was prepared by the same method as 095, using 2-naphthalene acetic acid instead of 1-methylindole-3-carboxaldehyde. MS calcd: $(M+H)^+=550$. MS found: $(M+H)^+=550$.

Example 98—3-[5-(4-Methyl-cyclohexyl)-1-(1-methyl-1H-indole-3-carbonyl)-1,2,3,6-tetrahydro-pyridin-4-yl]-5-phenyl-thiophene-2-carboxylic acid

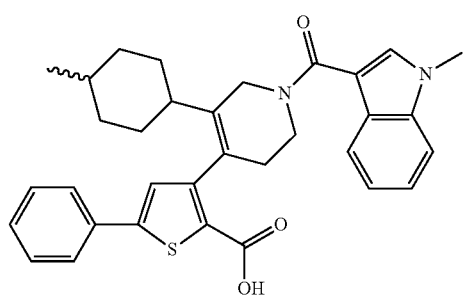

098

098 was prepared by the same method as 093, using 1-methylindole-3-carboxylic acid instead of 4-pyridylacetic acid. MS calcd: $(M+H)^+=539$. MS found: $(M+H)^+=539$.

Example 100—3-[1-Methyl-5-(4-methyl-cyclohexyl)-1,2,3,6-tetrahydro-pyridin-4-yl]-5-{4-[(thiazole-4-carbonyl)-amino]-phenyl}-thiophene-2-carboxylic acid ethyl ester

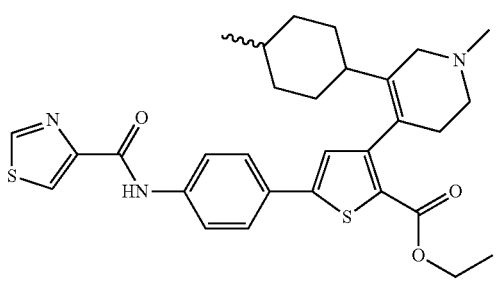

100

A solution of 013 (20 mg, 0.038 mmol) in DCM (4 mL) was treated with EtOH (50 mg), EDC (15 mg, 0.8 mmol) and dimethylaminopyridine (DMAP; 97 mg, 0.8 mmol). The reaction was stirred at RT for 10 hr. DCM and NaHCO$_3$ (aq) were added and the organic layer was washed with water and brine, dried, and evaporated to a residue that was purified by silica gel column chromatography using CH$_2$Cl$_2$:MeOH as eluent to provide pure 100. MS calcd: $(M+H)^+=550$. MS found: $(M+H)^+=550$.

Example 101—3-[1-Methyl-5-(4-methyl-cyclohexyl)-1,2,3,6-tetrahydro-pyridin-4-yl]-5-{4-[(thiazole-4-carbonyl)-amino]-phenyl}-thiophene-2-carboxylic acid 2,2-dimethyl-propionyloxymethyl ester

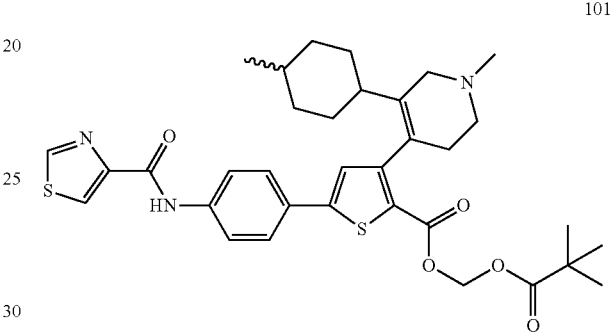

101

To a solution of 013 (16 mg, 0.03 mmol, 1 equiv) in dry DMF (2 mL) under N$_2$ atmosphere were added cesium carbonate (29 mg, 0.09 mmol, 3 eq.) and pivaloyloxymethyl chloride (0.013 mL, 0.09 mmol, 3 equiv). The suspension was stirred at RT for 3 hr. The reaction mixture was concentrated and the resulting residue was purified by column chromatography to yield pure 101. MS calcd: $(M+H)^+=636$. MS found: $(M+H)^+=636$.

Example 102—3-[1-Methyl-5-(4-methyl-cyclohexyl)-1,2,3,6-tetrahydro-pyridin-4-yl]-5-{4-[(thiazole-4-carbonyl)-amino]-phenyl}-thiophene-2-carboxylic acid acetoxymethyl ester

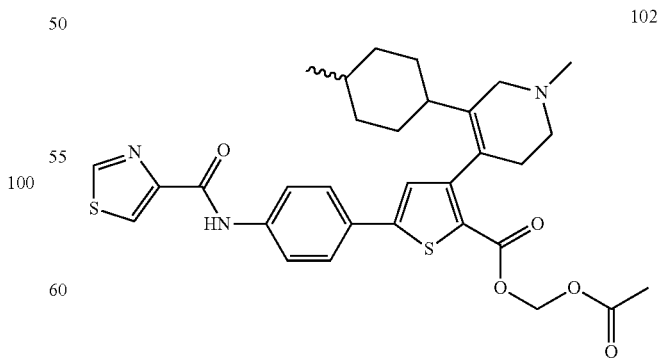

102

102 was prepared by the same method as 101, using bromomethyl acetate instead of pivaloyloxymethyl chloride. MS calcd: $(M+H)^+=594$. MS found: $(M+H)^+=594$.

Example 103—3-[1-Methyl-5-(4-methyl-cyclohexyl)-1,2,3,6-tetrahydro-pyridin-4-yl]-5-{4-[(thiazole-4-carbonyl)-amino]-phenyl}-thiophene-2-carboxylic acid 2-dimethylamino-ethyl ester

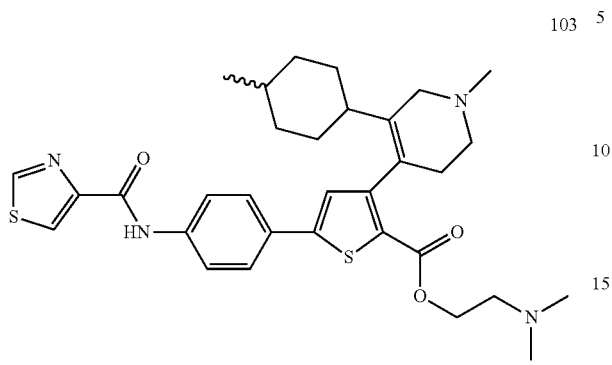

103

To a solution of 002 (89 mg, 0.2 mmol) in DMF (3.0 ML) were added HATU (76 mg, 0.2 mmol), 2-dimethylaminoethanol (0.37 mmol), and DMAP (0.15 mmol). The reaction mixture was stirred, at RT for 2 hr, and concentrated under reduced pressure. To the residue was added water, and this was extracted with EtOAc. The organic phase was dried over anhydrous Na$_2$SO$_4$ and evaporated under reduced pressure. The crude product was purified by chromatography on a silica gel column to give 103A.

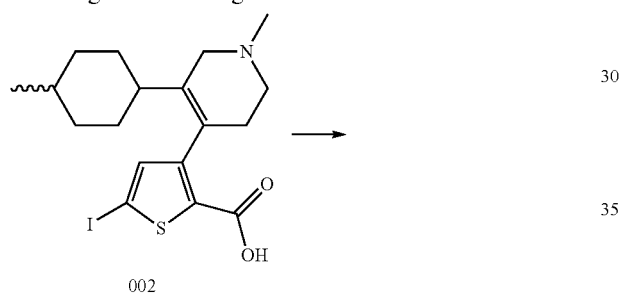

002

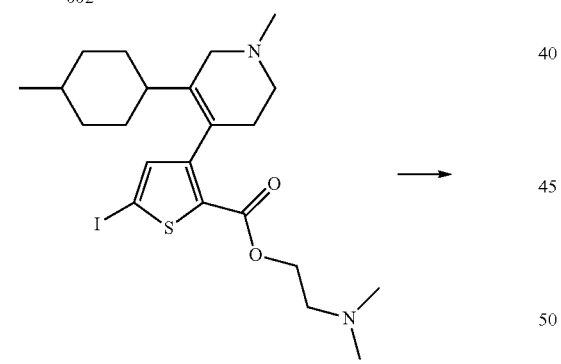

103A

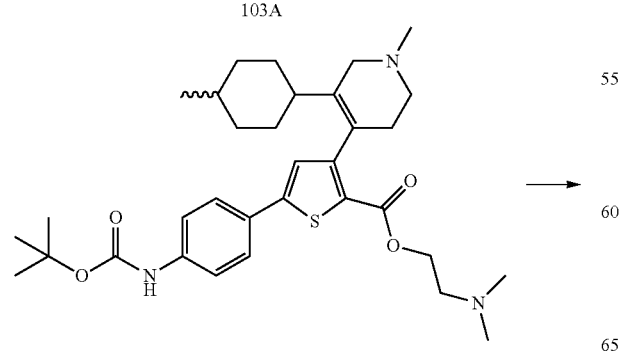

103B

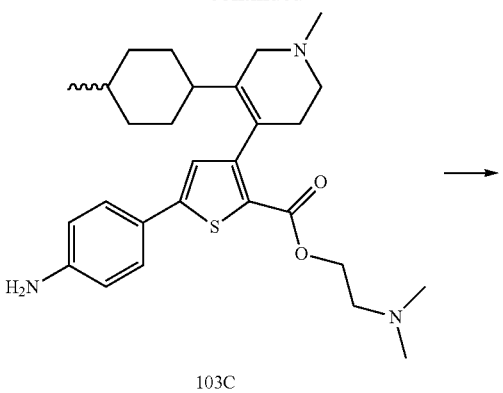

103C

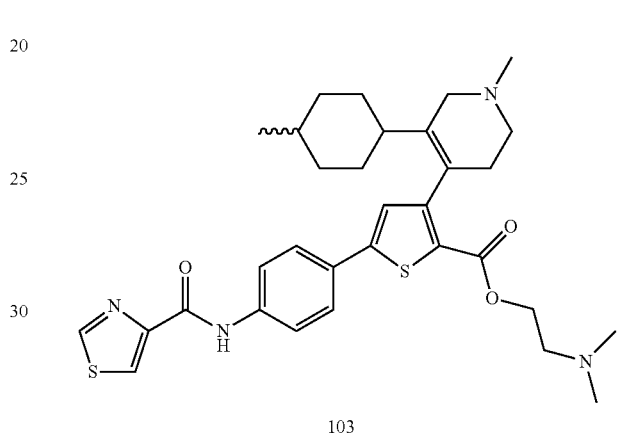

103

103 was prepared by the same method as 013A, using 103A instead of 002G. MS calcd: (M+H)$^+$=593. MS found: (M+H)$^+$=593.

Example 104—3-[1-Methyl-5-(4-methyl-cyclohexyl)-1,2,3,6-tetrahydro-pyridin-4-yl]-5-{4-[(thiazole-4-carbonyl)-amino]-phenyl}-thiophene-2-carboxylic acid 1-ethoxycarbonyloxy-ethyl ester

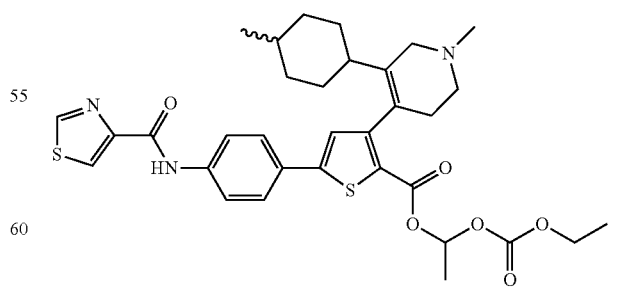

104

104 was prepared by the same method as 101, using 1-chloroethyl ethyl carbonate instead of pivaloyloxymethyl chloride. MS calcd: (M+H)$^+$=638. MS found: (M+H)$^+$=638.

Example 108—3-[1-Methyl-5-(4-methyl-cyclohexyl)-1,2,3,6-tetrahydro-pyridin-4-yl]-5-{4-[(thiazole-4-carbonyl)-amino]-phenyl}-thiophene-2-carboxylic acid 5-methyl-2-oxo-[1,3]dioxol-4-ylmethyl ester

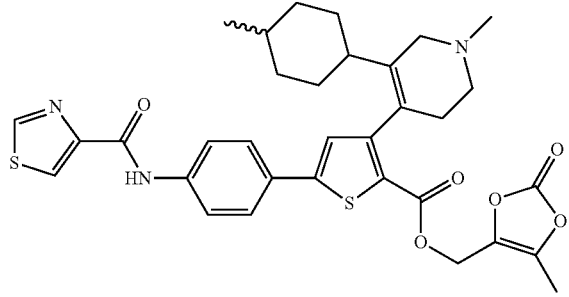

108

108 was prepared by the same method as 101, using 4-chloromethyl-5-methyl-1,3-dioxol-2-one instead of pivaloyloxymethyl chloride. MS calcd: (M+H)⁺=634. MS found: (M+H)⁺=634.

Example 109—3-[1-Methyl-5-(4-methyl-cyclohex-1-enyl)-1,2,3,6-tetrahydro-pyridin-4-yl]-5-phenyl-thiophene-2-carboxylic acid

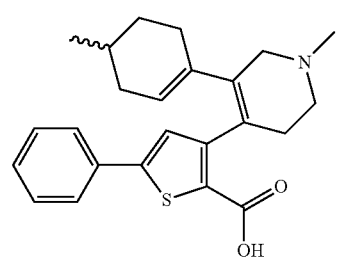

109

109A was prepared by the same method as 001I, using 001G instead of 001H.

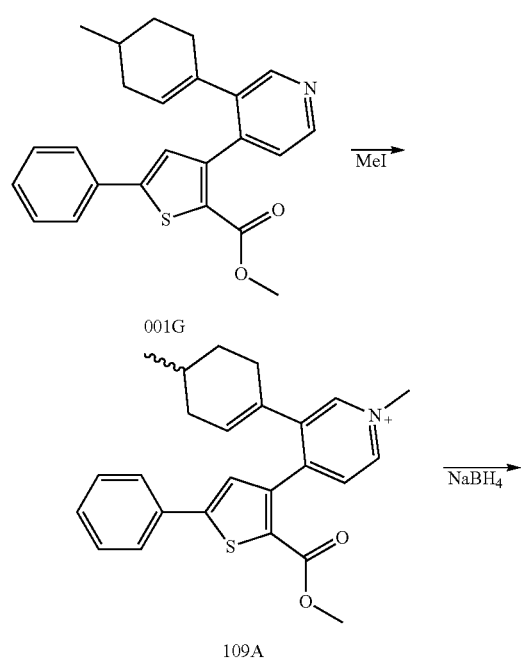

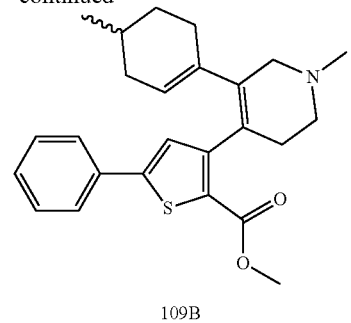

109B 109B was prepared by the same method as 001J, using 109A instead of 001I.

109 was then prepared by the same method as 001, using 109B instead of 001J. MS calcd: (M+H)⁺=394. MS found: (M+H)⁺=394.

Example 110—3-[5-(4-Methyl-cyclohexyl)-1-(4-phenyl-propyl)-1,2,3,6-tetrahydro-pyridin-4-yl]-5-phenyl-thiophene-2-carboxylic acid

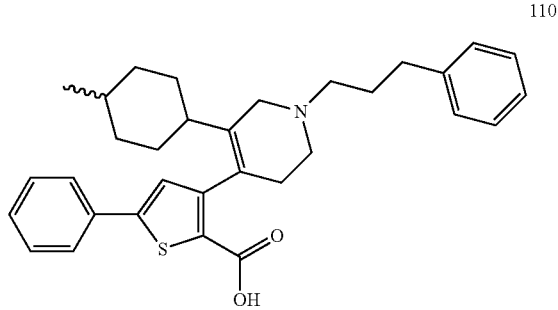 [SMILES: CC1CCC(C2=C(c3cc(-c4ccccc4)sc3C(=O)O)CCN(CCCc3ccccc3)C2)CC1]

110

110 was prepared by the same method as 001, using 3-bromo-1-phenylpropane instead of methyl iodide. The hydrolysis reaction was conducted as described for 071.

Example 111—5-(3,3-Dimethyl-but-1-ynyl)-3-[4-(4-methyl-cyclohexyl)-1,2,5,6-tetrahydro-pyridin-3-yl]-thiophene-2-carboxylic acid

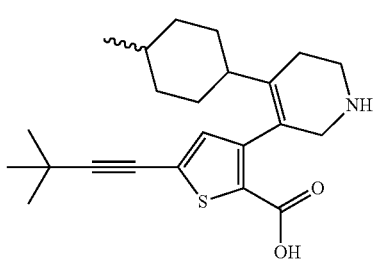

111

To a mixture of 3-bromopyridine-4-boronic acid (10 mmol) and 001B (20 mmol) in DMF (50 mL) and water (15 mL) were added Pd(dppf)Cl₂ (0.5 mmol), and Na₂CO₃ (30 mmol) under N₂ and the resulting mixture was stirred at 80° C. until LCMS showed total consumption of 3-bromopyridine-4-boronic acid (3 hr under these condition). The reaction was cooled to RT, and to it was added water (30 mL) and EtOAc (100 mL). The layers were separated and the aqueous layer is back-extracted with EtOAc (50 mL). The combined organic layers were washed with water (2×30 mL) brine (30 mL), dried over anhydrous Na₂SO₄, filtered over Celite®, and concentrated under reduced pressure. The residue was purified by flash chromatography (silica gel) eluting with 0-50% EtOAc in hexanes to give 111A.

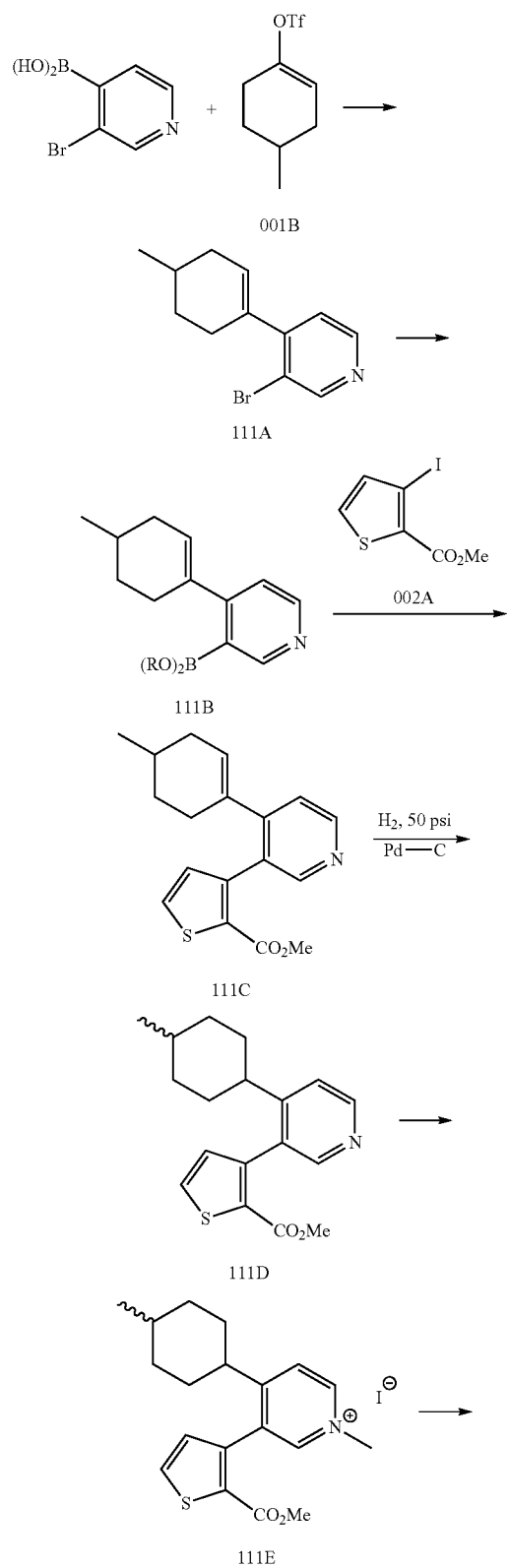

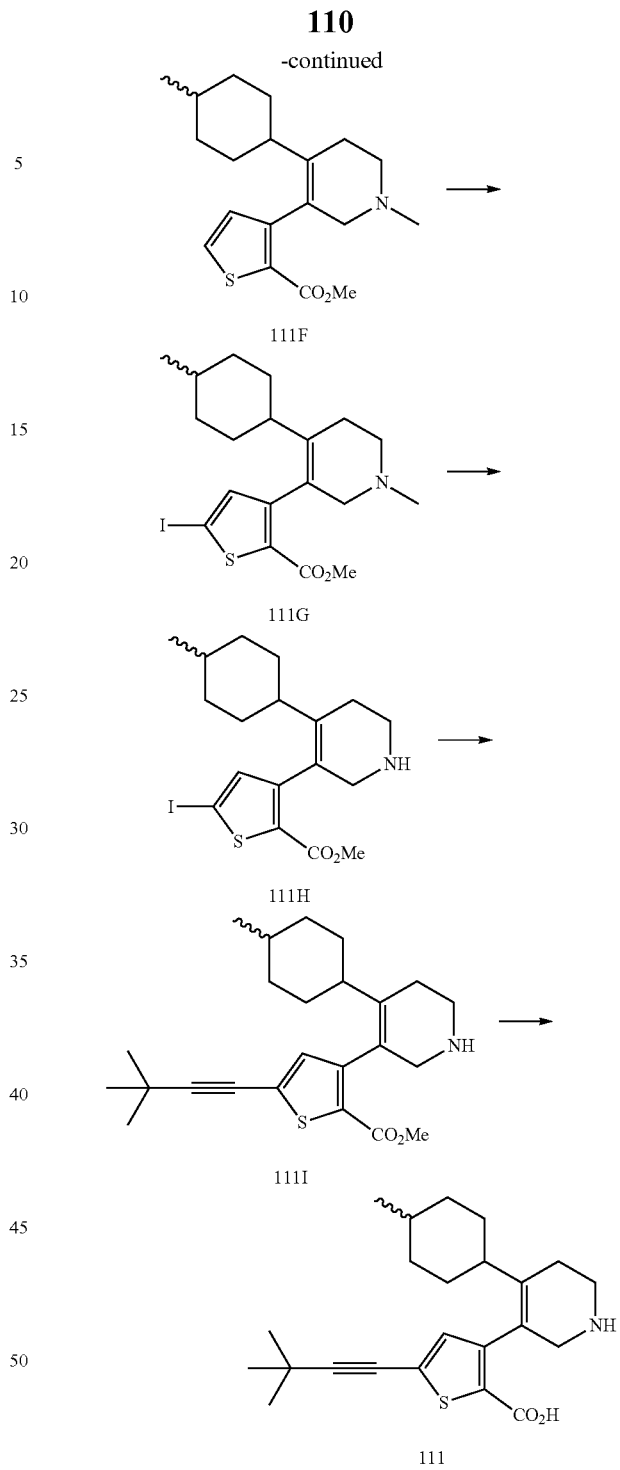

To solution of 111A (10 mmol) in THF (50 mL) at −78° C. was added n-BuLi (12 mmol). After stirring for 30 min, triisopropyl borate (15 mmol) was added to the reaction mixture. The reaction was allowed to warm to RT over 2 hr, and to it was added saturated aqueous NaH₂PO₄ (10 mL). The resulting mixture was stirred at RT for 30 min, and then diluted with EtOAc (50 mL). The organic layer was separated, and the aqueous layer was extracted with EtOAc (50 mL). The combined organic layers were washed with brine (30 mL), dried over Na₂SO₄, filtered, and concentrated to give 111B, which was used without further purification.

To a mixture of 002A (10 mmol) and 111B (10 mmol) in DMF (50 mL) and water (15 mL) were added Pd(dppf)Cl₂

(0.5 mmol), and Na$_2$CO$_3$ (30 mmol) under N$_2$ and the resulting mixture was stirred at 80° C. for 2 hr. The reaction was cooled to RT, and to it was added water (30 mL) and EtOAc (50 mL). The layers were separated and the aqueous layer is back-extracted with EtOAc (50 mL). The combined organic layers were washed with water (2×20 mL), brine (20 mL), dried over anhydrous Na$_2$SO$_4$, filtered over Celite®, and concentrated under reduced pressure. The residue was purified by flash chromatography (silica gel) eluting with 0-50% EtOAc in hexanes to give 111C.

A mixture of 111C (10 mmol) and Pd—C(10%, wet, 200 mg) in MeOH (50 mL) was hydrogenated with a Parr Shaker under 50 psi H$_2$ for 15 hr. The mixture was filtered through Celite®, and concentrated to give 111D.

Methyl iodide (20 mmol) was added to a solution of 111D (5 mmol) in 20 mL of ACN and the mixture was stirred for 3 hr at 80° C. The reaction mixture was cooled to RT and concentrated to give crude 111E. Crude 111E (5 mmol) was dissolved in MeOH (20 mL) at RT, and to it was added NaBH$_4$ (10 mmol). The reaction was monitored by LCMS, and more NaBH$_4$ (3 mmol each time) was added to the reaction in 1-hour intervals until 111E was totally consumed. The reaction mixture was quenched with water (20 mL) and extracted with EtOAc (3×50 mL). The organic layers were combined, dried over anhydrous Na$_2$SO$_4$, and concentrated to obtain the product as brown oil, which was purified by column chromatography (silica gel, 0-10% MeOH in CH$_2$Cl$_2$) to yield 111F.

To a solution of 111F (3 mmol) in THF (10 mL) at −78° C. under N$_2$ was added dropwise 2.0 M LDA in THF/heptane/ethylbenzene (3 mL). The stirring was continued at −78° C. for 2.5 hr. A solution of iodine (2.3 g) in dry THF (5 mL) was added dropwise to the reaction mixture. After stirring at −78° C. for 1.5 hr, the reaction mixture was quenched with saturated NH$_4$Cl solution and warmed to 0° C. The mixture was diluted with 5% Na$_2$S$_2$O$_3$ solution, then the organic phase was separated and the aqueous phase was extracted with EtOAc (50 mL). The combined organic phases were dried (Na$_2$SO$_4$), filtered, and evaporated. The residue was purified by column chromatography (silica gel, 0-10% MeOH in CH$_2$Cl$_2$) to give 111G.

111G (3.0 mmol) in DCE (15 mL) was treated with 1-chloroethylchloroformate (3.6 mmol), and the mixture was stirred under reflux for 4 hr. MeOH (2 mL) was then added to the reaction mixture in small portions and the heating was continued for an additional 2 hr. The mixture was allowed to cool to RT and concentrated to afford a crude 111H, which was used without purification.

To a mixture of 111H (0.1 mmol), copper iodide (0.02 mmol) and Pd(dppf)Cl$_2$ (0.01 mmol) under N$_2$ were added DMF (2 mL), TEA (0.5 mL), and 3,3-dimethyl-but-1-yne (0.5 mmol). The reaction mixture was stirred at 60° C. for 2 hr under N$_2$, then filtered over Celite® and rinsed with EtOAc. The solution was diluted with water (20 mL) and extracted (2×30 mL) with EtOAc. The organic phases were combined, washed with water (2×15 mL), dried (Na$_2$SO$_4$), evaporated, and purified by column chromatography (0-15%) MeOH in DCM to give 111I.

111I (30 mg) was dissolved in THF (2 mL) and EtOH (1 mL). LiOH (2 M, 0.5 mL) was then added. The reaction was stirred at RT for 16 hr, and then to it were added saturated NaH$_2$PO$_4$ (3 mL), water (3 mL), and EtOAc (30 mL). The organic layer was separated, washed with water (5 mL), dried with Na$_2$SO$_4$, and concentrated to give 111. MS calcd: (M+H)$^+$=386. MS found: (M+H)$^+$=386.

Example 112—5-(3,3-Dimethyl-but-1-ynyl)-3-[1-methyl-4-(4-methyl-cyclohexyl)-1,2,5,6-tetrahydro-pyridin-3-yl]-thiophene-2-carboxylic acid

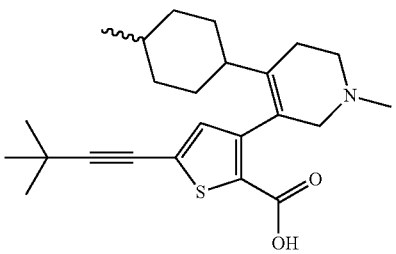

112

112 was prepared by the same method as 003, using 111G instead of 002G. MS calcd: (M+H)$^+$=400. MS found: (M+H)$^+$=400.

Example 113—5-(3,3-Dimethyl-but-1-ynyl)-3-[1-(2-hydroxy-ethyl)-4-(4-methyl-cyclohexyl)-1,2,5,6-tetrahydro-pyridin-3-yl]-thiophene-2-carboxylicacid

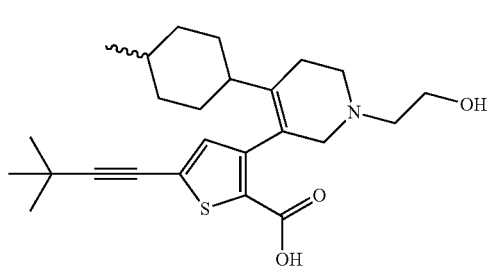

113

To a solution of 111I (50 mg) in DCE (2 mL) was added (tert-butyldimethylsilyloxy)-acetaldehyde, activated molecule sieves 4A powder (100 mg), and sodium triacetoxyborohydride (100 mg). After the reaction was stirred at RT for 2 hr, the reaction mixture was filtered through Celite®, and rinsed with THF (5 mL). The filtrate was treated with tetrabutylanmmonium fluoride (20 mg) and KF (100 mg, powder). After the mixture was stirred at RT overnight, it was filtered through Celite®, rinsed with DCM/MeOH (5:1), and concentrated. Purification and subsequent hydrolysis of the intermediate ester, and extraction to recover the resulting acid were conducted generally as described for 112, to give 113. MS calcd: (M+H)$^+$=430. MS found: (M+H)$^+$=430.

Example 114—5-(3,3-Dimethyl-but-1-ynyl)-3-[1-(3-hydroxy-propyl)-4-(4-methyl-cyclohexyl)-1,2,5,6-tetrahydro-pyridin-3-yl]-thiophene-2-carboxylic acid

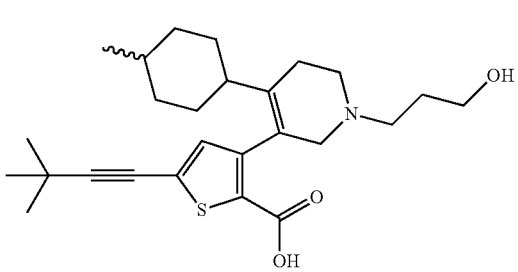

114

114 is prepared by the same method as 117, using 3-(tert-butyldimethylsilyloxy)-1-propanal instead of tetrahydrofuran-3-carboxaldehyde. MS calcd: (M+H)$^+$=444. MS found: (M+H)$^+$=444.

Example 116—5-(3,3-Dimethyl-but-1-ynyl)-3-[4-(4-methyl-cyclohexyl)-1-(tetrahydro-furan-3-yl)-1,2,5,6-tetrahydro-pyridin-3-yl]-thiophene-2-carboxylic acid

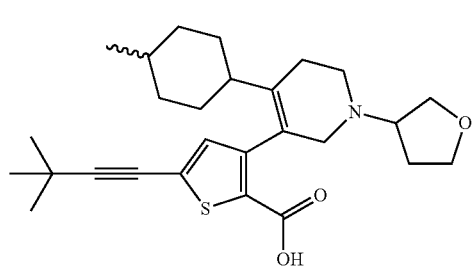

116

To a solution of 111I (50 mg) in DCE (2 mL) is added dihydrofuran-3(2H)-one (100 mg), activated molecule sieves 4A powder (100 mg), and sodium triacetoxyborohydride (100 mg). The reaction is stirred at RT for 15 hr, the mixture is filtered through Celite®, rinsed with EtOAc (20 mL), and concentrated. Purification and subsequent hydrolysis of the intermediate ester, and extraction to recover the resulting acid, are conducted generally as described for 112, to give 116.

Example 117—5-(3,3-Dimethyl-but-1-ynyl)-3-[4-(4-methyl-cyclohexyl)-1-(tetrahydro-furan-3-ylmethyl)-1,2,5,6-tetrahydro-pyridin-3-yl]-thiophene-2-carboxylic acid

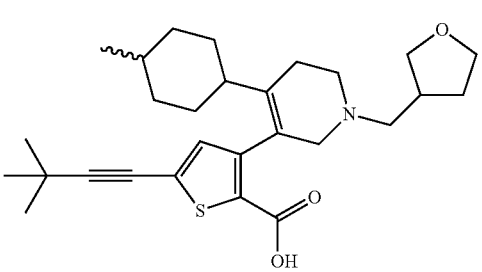

117

To a solution of 111H (50 mg) in DCE (2 mL) were added tetrahydrofuran-3-carboxaldehyde (100 mg), and sodium triacetoxyborohydride (100 mg). The reaction was stirred at RT for 15 hr, and the mixture was filtered through Celite®, rinsed with EtOAc (20 mL), and concentrated to give 117A.

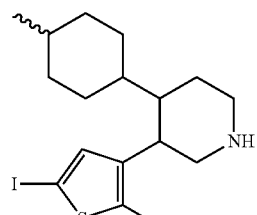

111H

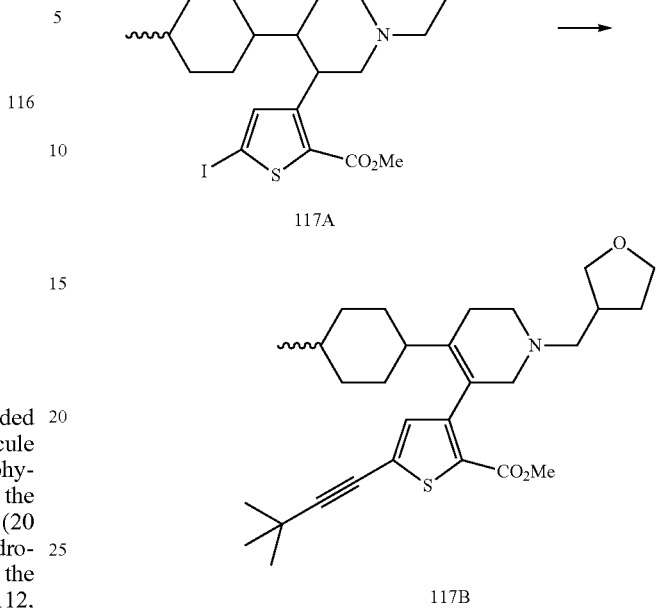

117A

117B

To a mixture of 117A (0.1 mmol), copper iodide (0.02 mmol) and Pd(dppf)Cl$_2$ (0.01 mmol) under N$_2$ were added DMF (2 mL), TEA (0.5 mL), and 3,3-dimethyl-but-1-yne (0.5 mmol). The reaction mixture was stirred at 60° C. for 2 hr under N$_2$. The reaction mixture was filtered over Celite® and rinsed with EtOAc. The solution was diluted with water (20 mL) and extracted (2×30 mL) with EtOAc. The organic phases were combined, washed with water (2×15 mL), dried (Na$_2$SO$_4$), evaporated, and purified by column chromatography (0-15%) MeOH in DCM to give 117B.

117B (30 mg) was dissolved in THF (2 mL), water (1 mL), and MeOH (1 mL). LiOH (2 M, 0.5 mL) was then added. The reaction was stirred at RT for 5 hr, and then water (1 mL), and EtOAc (3 mL) were added. The organic layer was separated, concentrated, and lyophilized to give 117. MS calcd: (M+H)$^+$=470. MS found: (M+H)$^+$=470.

Example 119—5-(3,3-Dimethyl-but-1-ynyl)-3-[4-(4-methyl-cyclohexyl)-1-(tetrahydro-furan-3-carbonyl)-1,2,5,6-tetrahydro-pyridin-3-yl]-thiophene-2-carboxylic acid

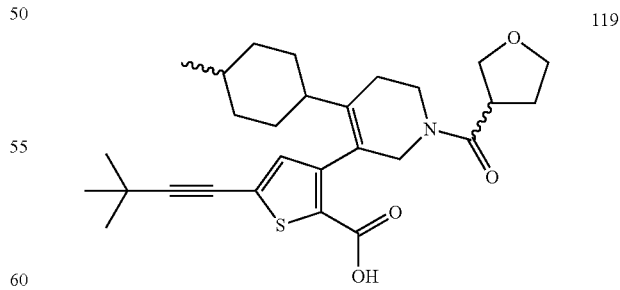

119

To a solution of 111I (50 mg) in DCM (2 mL) is added tetrahydrofuran-3-carboxylic acid (0.2 mmol), 1-ethyl-3-(3-dimethylaminopropyl)carbodiimide (EDCI; 0.3 mmol), TEA (0.05 mL) and DMAP (5 mg). The reaction is stirred at RT for 15 hr, and the mixture is diluted with EtOAc (205 mL), washed with water (2×10 mL) and brine (10 mL), dried over MgSO$_4$, and concentrated. Purification and subsequent hydrolysis of the intermediate ester, and extraction to recover the resulting acid are conducted generally as described for 112, to give 119.

Example 120—5-(3,3-Dimethyl-but-1-ynyl)-3-[1-(3-hydroxy-cyclopentanecarbonyl)-4-(4-methyl-cyclohexyl)-1,2,5,6-tetrahydro-pyridin-3-yl]-thiophene-2-carboxylic acid

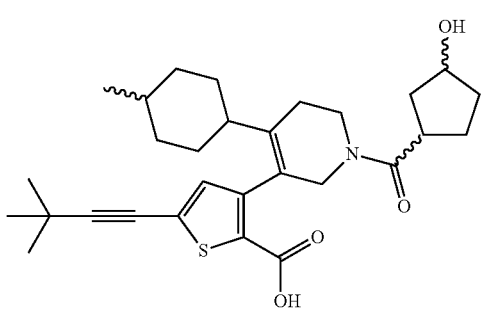

120

To a solution of 111I (50 mL) in DCM (2 mL) is added 3-oxo-1-cyclopentanecarboxylic acid (0.2 mmol), EDCI (0.3 mmol), TEA (0.05 mL) and DMAP (5 mg). After the reaction is stirred at RT for 15 hr, the reaction mixture is diluted with MeOH (1 mL). NaBH₄ (1 mmol) is added, and the mixture stirred until the reduction of ketone is complete (about 30 min). The mixture is diluted with acetone (1 mL) and EtOAc (40 mL), washed with water (2×10 mL) and brine (10 mL), dried over MgSO₄, and concentrated. Purification and subsequent hydrolysis of the intermediate ester, and extraction to recover the resulting acid, are conducted generally as described for 112, to give 120.

Example 121—5-(3,3-Dimethyl-but-1-ynyl)-3-[4-(4-methyl-cyclohexyl)-1-(tetrahydro-furan-3-sulfonyl)-1,2,5,6-tetrahydro-pyridin-3-yl]-thiophene-2-carboxylic acid

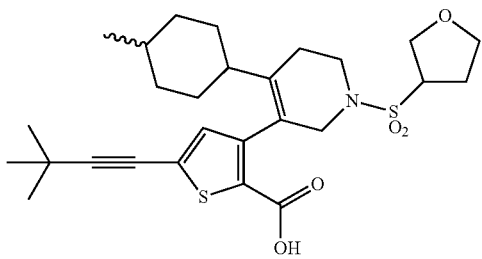

121

To a solution of 111I (50 mg) in DCM (2 mL) is added tetrahydrofuran-3-sulfonyl chloride (0.2 mmol) and TEA (0.5 mmol). The mixture is stirred for 1 hr, and then treated with aqueous Na₂CO₃ (1 M, 0.5 mL). After stirring is continued for 10 min, the mixture is diluted with EtOAc (40 mL), washed with water (2×10 mL) and brine (10 mL), dried over MgSO₄, and concentrated. Purification and subsequent hydrolysis of the intermediate ester, and extraction to recover the resulting acid are conducted generally as described for 112, to give 121.

Example 122—3-[4-(4-Methyl-cyclohexyl)-1-(tetrahydro-furan-3-carbonyl)-1,2,5,6-tetrahydro-pyridin-3-yl]-5-{4-[(thiazole-4-carbonyl)-amino]-phenyl}-thiophene-2-carboxylic acid

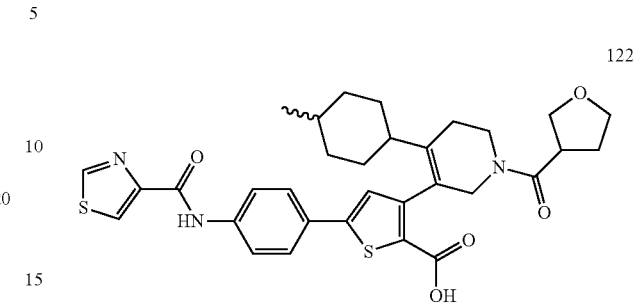

122

To a solution of 111H (50 mg) in DCM (2 mL) is added tetrahydrofuran-3-carboxylic acid (0.2 mmol), EDCI (0.3 mmol), TEA (0.05 mL) and DMAP (5 mg). The reaction is stirred at RT for 15 hr, the mixture is diluted with EtOAc (50 mL), washed with water (2×10 mL) and brine (10 mL), dried over MgSO₄, and concentrated. The residue is purified by column chromatography with 0-10% MeOH in DCM to give the ester 122A.

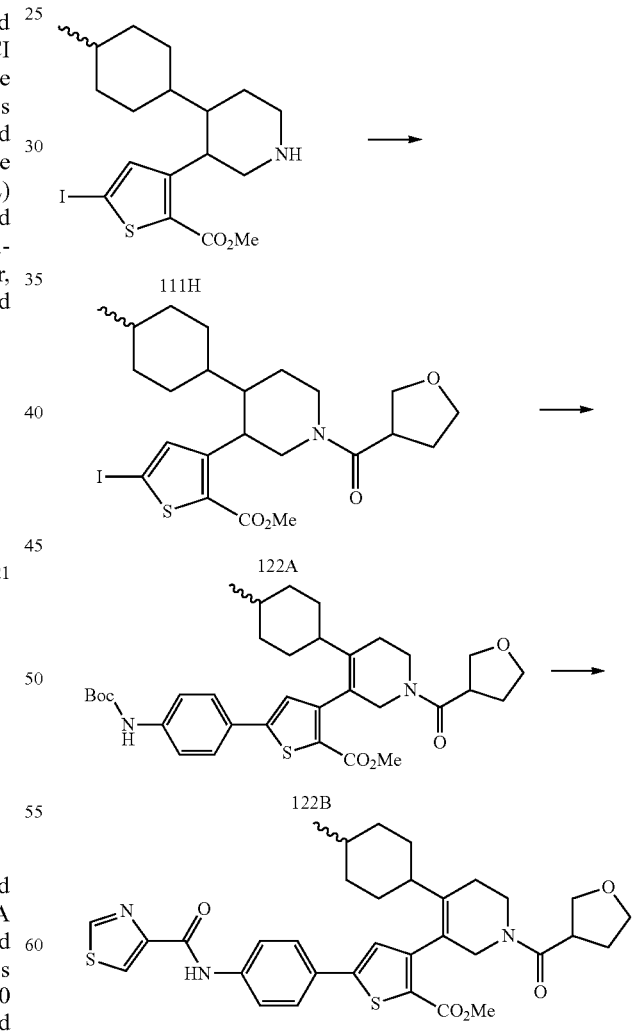

A mixture of 122A, [4-({[(1,1-dimethylethyl)oxy]carbonyl}amino)phenyl]boronic acid (0.2 mmol), Pd(dppf)

Cl$_2$ (0.01 mmol), and Na$_2$CO$_3$ (0.3 mmol) in DMF (2 mL) and H$_2$O (0.5 mL) under N$_2$ is stirred at 92° C. for 4 hr. The reaction is diluted with EtOAc (50 mL), washed with water (2×10 mL) and brine (10 ml), dried over anhydrous Na$_2$SO$_4$, and concentrated under reduced pressure. The residue is purified by flash chromatography (silica gel), eluting with 0-5% MeOH in CH$_2$Cl$_2$ to give 122B.

122B is stirred in DCM (3 mL) and trifluoroacetic acid (TFA, 1 mL) at RT under N$_2$ for 1 hr. The reaction is evaporated in vacuo. The residue is dissolved in DMF (2 mL), and to it is added HATU (0.2 mmol), TEA (0.5 mmol), and 1,3-thiazole-4-carboxylic acid (0.2 mmol). After the reaction is stirred at RT for 15 hr, the mixture is diluted with EtOAc (50 mL), washed with water (2×10 mL) and brine (10 mL), dried over MgSO$_4$, and concentrated. The residue is purified by column chromatography with 0-10% MeOH in DCM to give ester 122C. Purification and subsequent hydrolysis of 122C, and extraction to recover the resulting acid, are conducted generally as described for 112, to give 122.

Example 123—3-[4-(4-Methyl-cyclohexyl)-1-(tetrahydro-furan-3-carbonyl)-1,2,5,6-tetrahydro-pyridin-3-yl]-5-(4-pyrazolo[1,5-a]pyrimidin-2-yl-phenyl)-thiophene-2-carboxylic acid

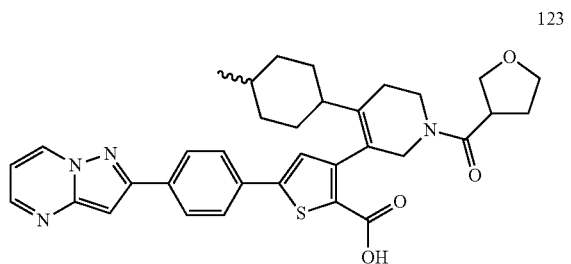 [SMILES: CC1CCC(C2=C(c3cc(-c4ccc(-c5cc6ncccn6n5)cc4)sc3C(=O)O)CN(C(=O)C3CCOC3)CC2)CC1]

123

123A is prepared by the same method as 122B, using 005B instead of [4-({[(1,1-dimethylethyl)oxy]carbonyl}amino)phenyl]boronic acid in the reaction with 122A. Hydrolysis of the methyl ester intermediate, and extraction to recover the resulting acid, are conducted generally as described for 112, to give 123.

Example 124—5-(3,3-Dimethyl-but-1-ynyl)-3-[1-(2-fluoro-ethyl)-4-(4-methyl-cyclohexyl)-1,2,5,6-tetrahydro-pyridin-3-yl]-thiophene-2-carboxylic acid

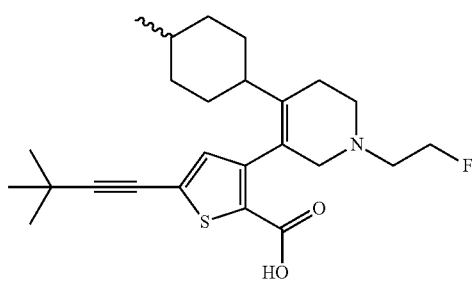

124

124 was prepared by the same method as 117, using 1-bromo-2-fluoroethane with DIEA instead of tetrahydrofuran-3-carboxaldehyde. MS calcd: (M+H)$^+$=432. MS found: (M+H)$^+$=432.

Example 125—3-[1-Methyl-5-(4-methyl-cyclohexyl)-1,2,3,6-tetrahydro-pyridin-4-yl]-5-{4-[(thiazole-4-carbonyl)-amino]-phenyl}-thiophene-2-carboxylic acid phenyl ester

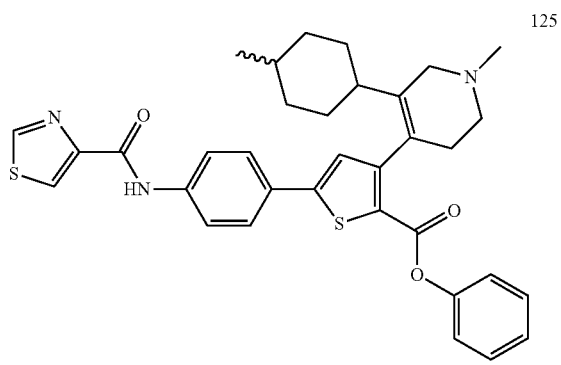 [SMILES: CC1CCC(C2=C(c3cc(-c4ccc(NC(=O)c5cscn5)cc4)sc3C(=O)Oc3ccccc3)CCN(C)C2)CC1]

125

125 was prepared by the same method as 100, using phenol instead of EtOH. MS calcd: (M+H)$^+$=598. MS found: (M+H)$^+$=598.

Example 126—3-[1-Methyl-5-(4-methyl-cyclohexyl)-1,2,3,6-tetrahydro-pyridin-4-yl]-5-{4-[(thiazole-4-carbonyl)-amino]-phenyl}-thiophene-2-carboxylic acid cyclohexyloxycarbonyl-oxymethyl ester

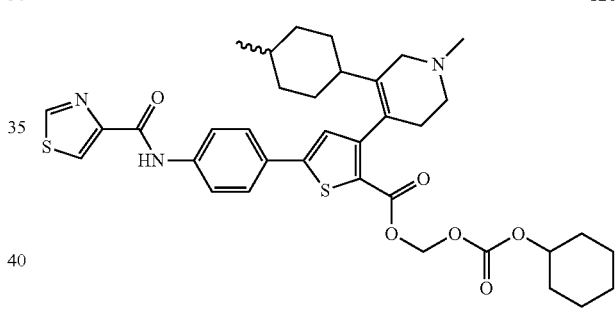

126

126 was prepared by the same method as 101, using 1-chloromethyl cyclohexyl carbonate instead of pivaloyloxymethyl chloride. MS calcd: (M+H)$^+$=678. MS found: (M+H)$^+$=678.

Example 127—5-(3,3-Dimethyl-but-1-ynyl)-3-[5-(4-methyl-cyclohexyl)-1-pyridin-2-ylmethyl-1,2,3,6-tetrahydro-pyridin-4-yl]-thiophene-2-carboxylic acid

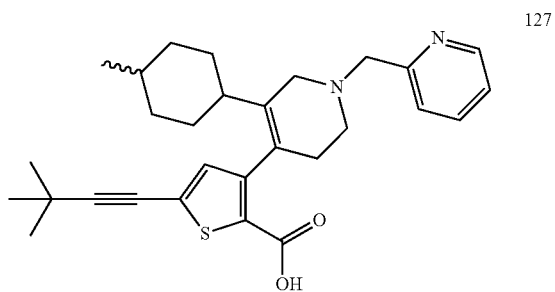 [SMILES: CC1CCC(C2=C(c3cc(C#CC(C)(C)C)sc3C(=O)O)CCN(Cc3ccccn3)C2)CC1]

127

Intermediate 002G (0.29 g, 0.623 mmol) was dissolved in dichloroethane (10 mL) and was treated with 1-chloroethyl chloroformate (0.086 mL, 0.795 mmol), followed by DIPEA (0.138 mL, 0.795 mmol) with stirring under argon. After 20 hr, the reaction mixture was evaporated under reduced pressure and the resulting brown foam was dissolved in MeOH (20 mL), and heated to reflux with stirring. After 1 hr, the reaction mixture was evaporated under reduced pressure and the brown oily product 127A was directly used in the next step.

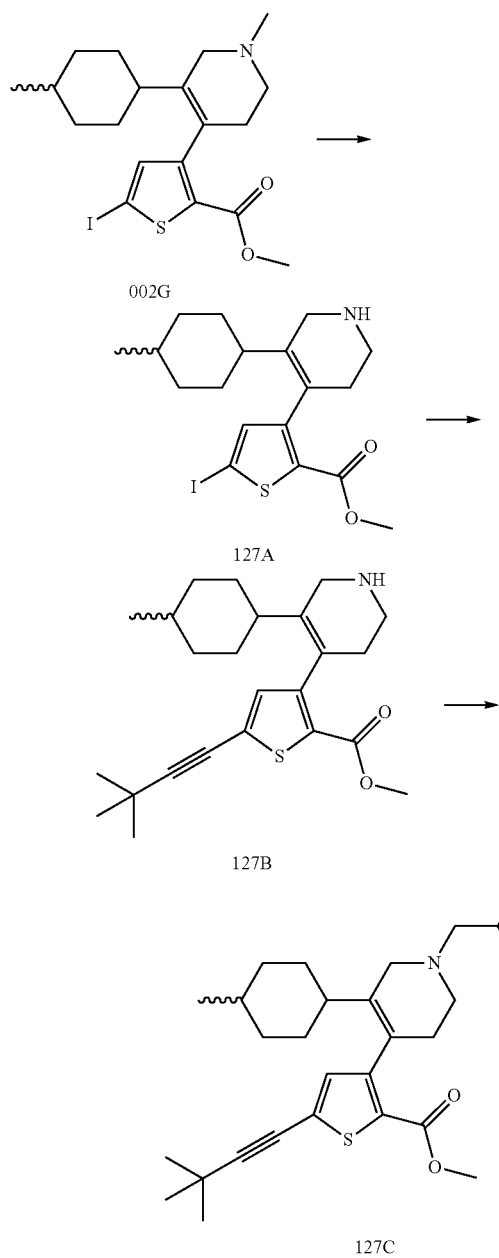

To a mixture of 127A (0.05 mmol), copper iodide (0.01 mmol) and Pd(dppf)Cl$_2$ (0.005 mmol) under N$_2$ were added DMF (2 mL), TEA (0.5 mL), and 3,3-dimethyl-but-1-yne (0.3 mmol). The reaction mixture was stirred at 60° C. for 2 hr under N$_2$. The reaction mixture was filtered over Celite® and rinsed with EtOAc. The solution was diluted with water (20 mL) and extracted (2×30 mL) with EtOAc. The organic phases were combined, washed with water (2×15 mL), dried (Na$_2$SO$_4$), evaporated, and purified by column chromatography (0-15%) MeOH in DCM to give 127B.

127B (20 mg, 0.04 mmol) was dissolved in dichloroethane (3 mL), and treated with 2-pyridinecarboxaldehyde (12.3 mg, 0.11 mmol), TEA (0.02 mL, 0.15 mmol), and sodium triacetoxyborohydride (30 mg, 0.15 mmol). The reaction was stirred overnight at RT. The reaction mixture was concentrated and purified by prep-TLC (silica gel, 50% EtOAc in hexane) to give an intermediate methyl ester 127C.

127C (20 mg) was dissolved in THF (2 mL) and EtOH (1 mL). LiOH (2 M, 0.5 mL) was then added. The reaction was stirred at RT for 16 hr, and then diluted with EtOAc. The organic layer was washed with water and concentrated. The final product was precipitated in hexane and washed more with hexane. The powder of 127 was obtained after lyophilization. MS calcd: (M+H)$^+$=477. MS found: (M+H)$^+$=477.

Example 128—5-(3,3-Dimethyl-but-1-ynyl)-3-[1-(5,7-dimethyl-[1,2,4]triazolo[1,5-a]pyrimidin-2-ylmethyl)-5-(4-methyl-cyclohexyl)-1,2,3,6-tetrahydro-pyridin-4-yl]-thiophene-2-carboxylic acid

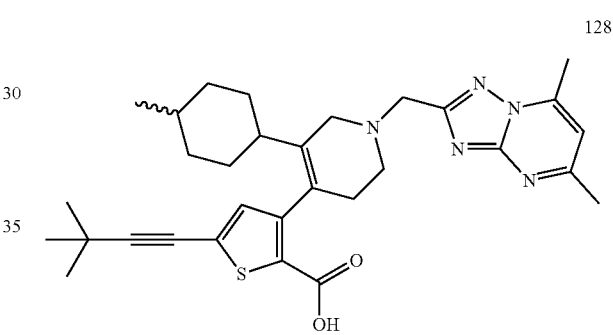

128 was prepared by the same method as 127, using 88e instead of 2-pyridinecarboxaldehyde. MS calcd: (M+H)$^+$=546. MS found: (M+H)$^+$=546.

Example 130—3-[1-(5,7-Dimethyl-[1,2,4]triazolo[1,5-a]pyrimidin-2-ylmethyl)-5-(4-methyl-cyclohexyl)-1,2,3,6-tetrahydro-pyridin-4-yl]-5-{4-[(thiazole-4-carbonyl)-amino]-phenyl}-thiophene-2-carboxylic acid

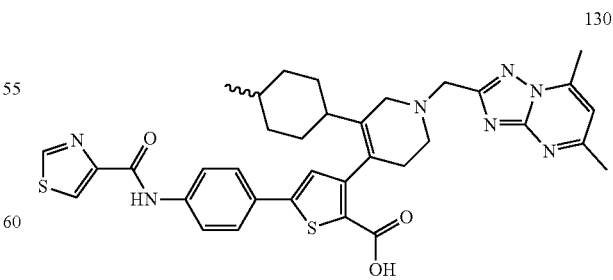

A solution of 127A (20 mg, 0.045 mmol) was dissolved in dichloroethane (3 mL), and treated with 88e (19.4 mg, 0.11 mmol), TEA (0.02 mL, 0.15 mmol), and sodium triacetoxyborohydride (30 mg, 0.15 mmol). The reaction was stirred overnight at RT. The reaction mixture was concentrated and purified by prep-TLC (silica gel, 50% EtOAc in hexane) to give an intermediate 130A.

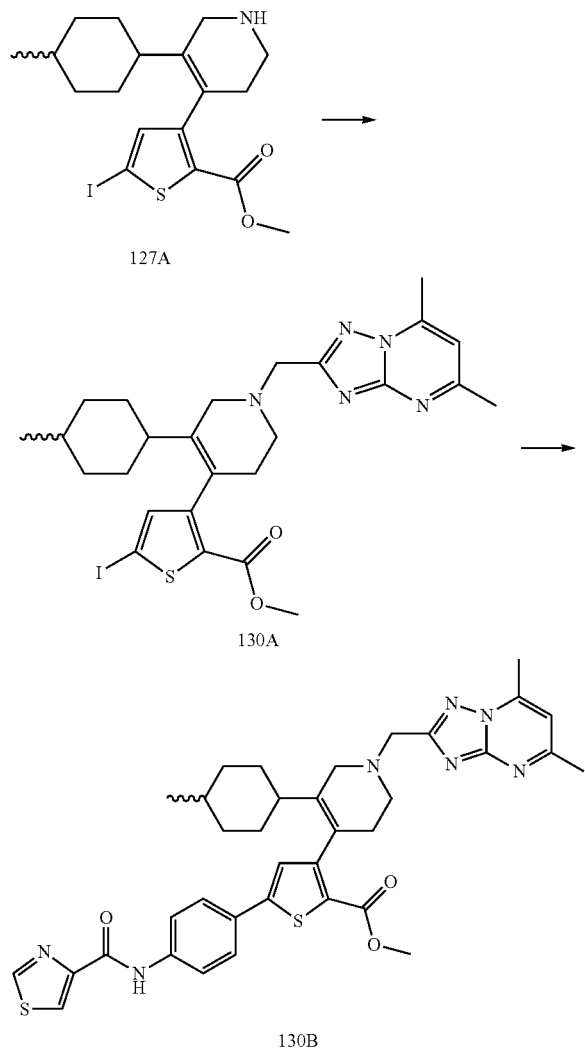

130 was then prepared by the same method as 013, using 130A instead of 002G to give 130B, followed by hydrolysis to give the acid. MS calcd: (M+H)⁺=668. MS found: (M+H)⁺=668.

Example 131—3-[5-(4-Methyl-cyclohexyl)-1-pyridin-2-ylmethyl-1,2,3,6-tetrahydro-pyridin-4-yl]-5-{4-[(thiazole-4-carbonyl)-amino]-phenyl}-thiophene-2-carboxylic acid

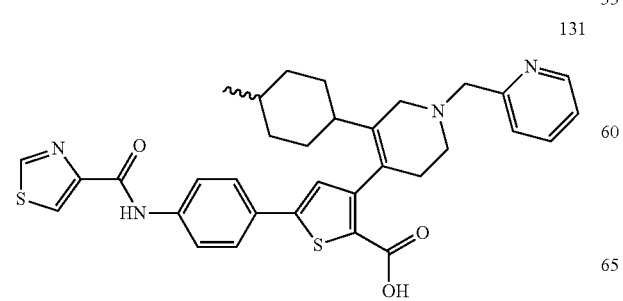

131 was prepared by the same method as 130, using 2-pyridinecarbox-aldehyde instead of 88e. MS calcd: (M+H)⁺=599. MS found: (M+H)⁺=599.

Example 132—5-[4-(7-Amino-pyrazolo[1,5-a]pyrimidin-2-yl)-phenyl]-3-[1-methyl-5-(4-methyl-cyclohexyl)-1,2,3,6-tetrahydro-pyridin-4-yl]-thiophene-2-carboxylic acid, hydrochloride salt

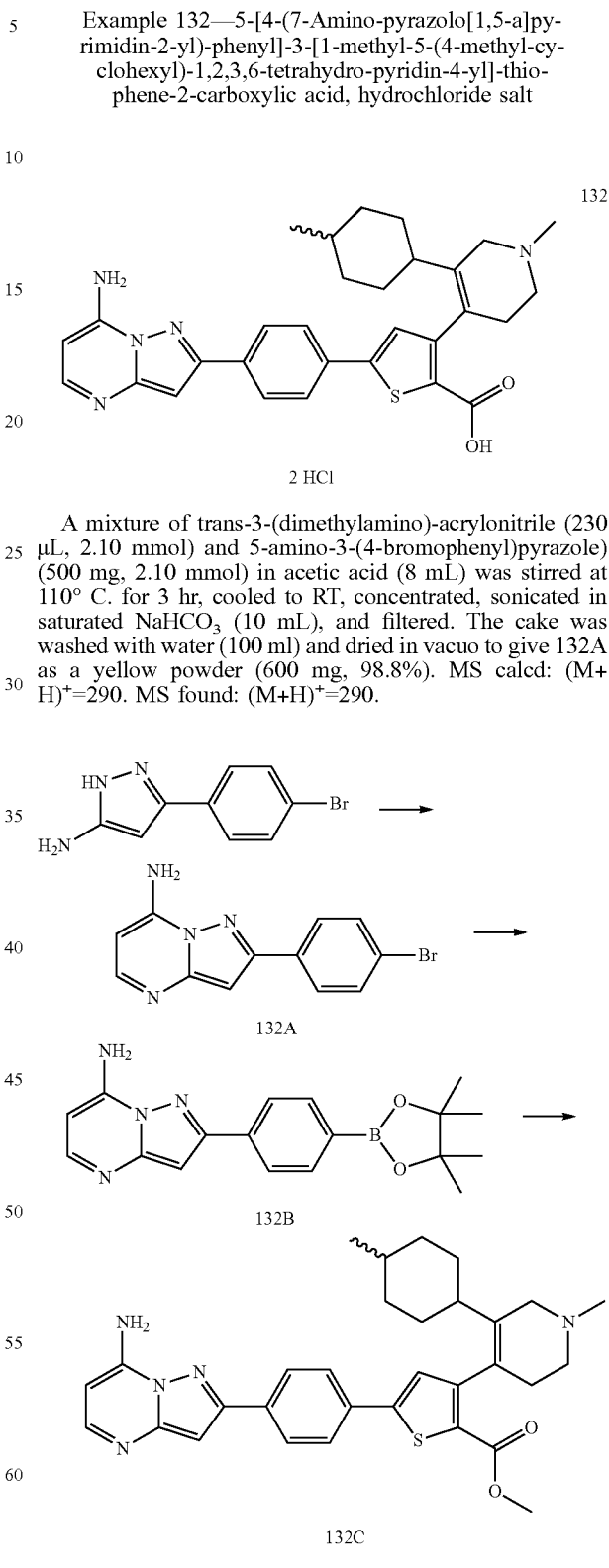

A mixture of trans-3-(dimethylamino)-acrylonitrile (230 µL, 2.10 mmol) and 5-amino-3-(4-bromophenyl)pyrazole) (500 mg, 2.10 mmol) in acetic acid (8 mL) was stirred at 110° C. for 3 hr, cooled to RT, concentrated, sonicated in saturated NaHCO₃ (10 mL), and filtered. The cake was washed with water (100 ml) and dried in vacuo to give 132A as a yellow powder (600 mg, 98.8%). MS calcd: (M+H)⁺=290. MS found: (M+H)⁺=290.

132B was prepared by the same method as 005B, using 132A instead of 005A. MS calcd: (M+H)⁺=337. MS found: (M+H)⁺=337.

132C was prepared by the same method as 129B, using 132B instead of 4-bromophenylboronic acid. MS calcd: (M+H)⁺=542. MS found: (M+H)⁺=542.

132 was then prepared by the same method as 129, using 132C instead of 129C. MS calcd: (M+H)⁺=528. MS found: (M+H)⁺=528.

Example 133—5-(3,3-Dimethyl-but-1-ynyl)-3-[5-(4-methyl-cyclohexyl)-1-pyridin-4-ylmethyl-1,2,3,6-tetrahydro-pyridin-4-yl]-thiophene-2-carboxylic acid

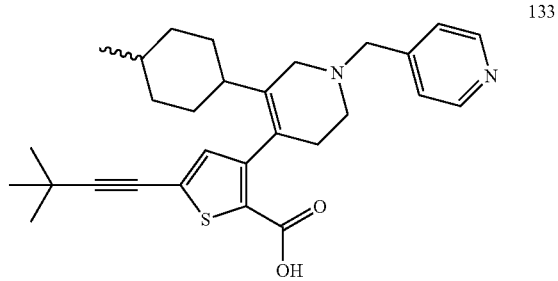 [SMILES: CC1CCC(C2=C(c3cc(C#CC(C)(C)C)sc3C(=O)O)CCN(Cc3ccncc3)C2)CC1]

133

Compound 133 was prepared by the same method as 127, using 4-pyridinecarboxaldehyde instead of 2-pyridinecarboxaldehyde. MS calcd: (M+H)⁺=477. MS found: (M+H)⁺=477.

Example 134—5-Cyclopropylethynyl-3-[5-(4-methyl-cyclohexyl)-1-pyridin-2-ylmethyl-1,2,3,6-tetrahydro-pyridin-4-yl]-thiophene-2-carboxylic acid

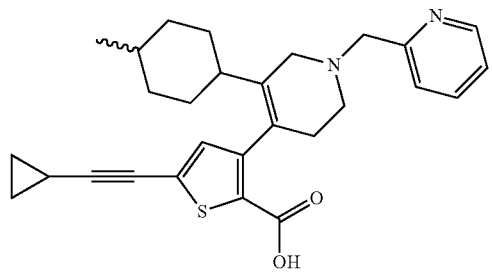

134

Compound 134 was prepared by the same method as 127, using cyclopropylacetylene instead of 3,3-dimethyl-1-butyne. MS calcd: (M+H)⁺=461. MS found: (M+H)⁺=461.

Example 135—5-[4-(3a,7a-Dihydro-furo[3,2-b]pyridin-2-yl)-phenyl]-3-[1-methyl-5-(4-methyl-cyclohexyl)-1,2,3,6-tetrahydro-pyridin-4-yl]-thiophene-2-carboxylic acid

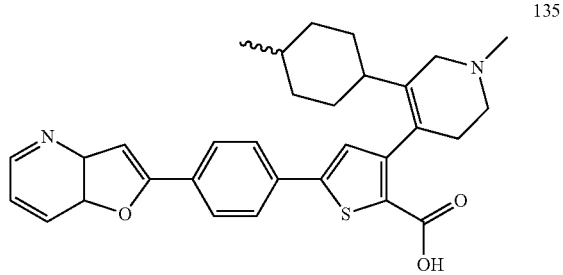 [SMILES: CC1CCC(C2=C(c3cc(-c4ccc(C5=CC6N=CC=CC6O5)cc4)sc3C(=O)O)CCN(C)C2)CC1]

135

135A was prepared by the same method as 129A, using 4-bromophenylacetylene instead of trimethylsilylacetylene and 2-iodo-3-hydroxypyridine instead of 4-bromothiazole and heating at 90° C. MS calcd: (M+H)⁺=275. MS found: (M+H)⁺=275.

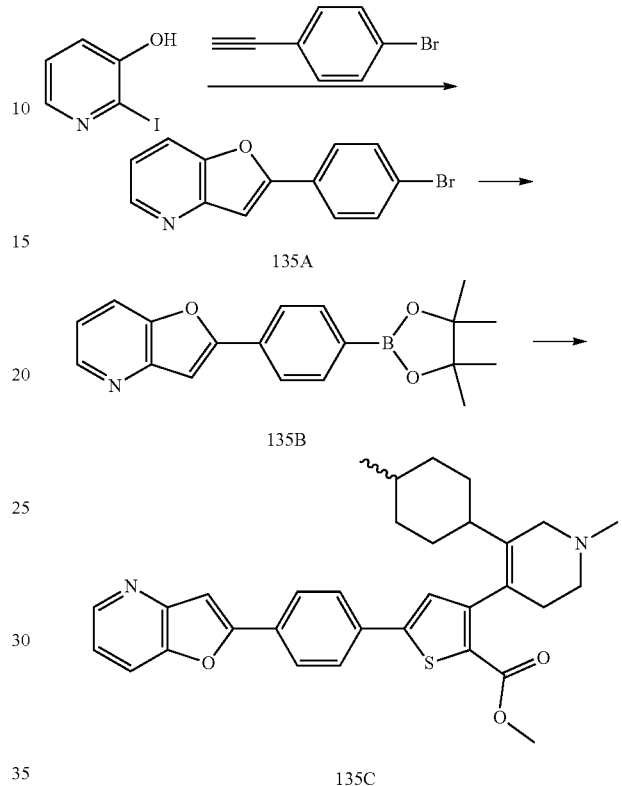

135B was prepared by the same method as 005B, using 135A instead of 005A. MS calcd: (M+H)⁺=322. MS found: (M+H)⁺=322.

135C was prepared by the same method as 129B, using 135B instead of 4-bromophenylboronic acid. MS calcd: (M+H)⁺=527. MS found: (M+H)⁺=527.

135 was then prepared by the same method as 129, using 135C instead of 129C. MS calcd: (M+H)⁺=513. MS found: (M+H)⁺=513.

Example 136—3-[1-(5-Chloro-1-methyl-3-trifluoromethyl-1H-pyrazol-4-ylmethyl)-5-(4-methyl-cyclohexyl)-1,2,3,6-tetrahydro-pyridin-4-yl]-5-(3,3-dimethyl-but-1-ynyl)-thiophene-2-carboxylic acid

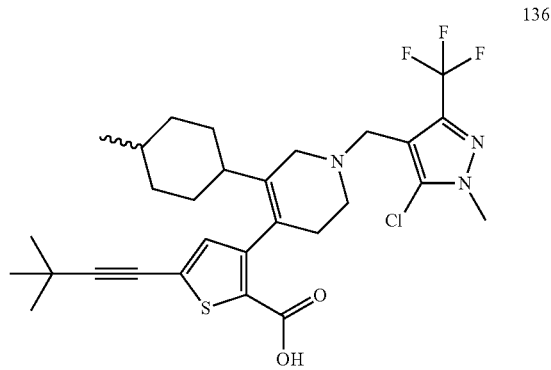 [SMILES: CC1CCC(C2=C(c3cc(C#CC(C)(C)C)sc3C(=O)O)CCN(Cc3c(C(F)(F)F)nn(C)c3Cl)C2)CC1]

136

136 was prepared by the same method as 127, using 5-chloro-1-methyl-3-(trifluoromethyl)-1H-pyrazole-4-carbaldehyde instead of 2-pyridinecarboxaldehyde. MS calcd: (M+H)⁺=597. MS found: (M+H)⁺=597.

Example 137—5-(3,3-Dimethyl-but-1-ynyl)-3-[1-(2-methoxy-ethyl)-4-(4-methyl-cyclohexyl)-1,2,5,6-tetrahydro-pyridin-3-yl-]-thiophene-2-carboxylic acid

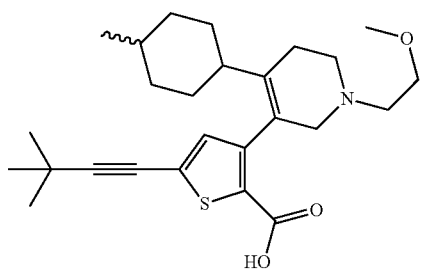

137

137 was prepared by the same method as 117, using 2-bromoethyl methyl ether with DIEA instead of tetrahydrofuran-3-carboxaldehyde. MS calcd: (M+H)⁺=444. MS found: (M+H)⁺=444.

Example 138—5-Cyclopropylethynyl-3-[1-(2-hydroxy-ethyl)-5-(4-methyl-cyclohexyl)-1,2,3,6-tetrahydro-pyridin-4-yl]-thiophene-2-carboxylic acid

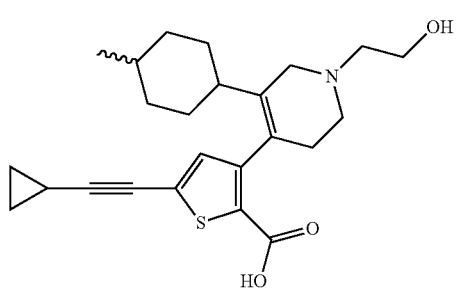

138

138A was prepared by the same method as 127B, using cyclopropylacetylene instead of tert-butylacetylene.

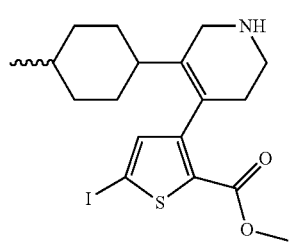

127A

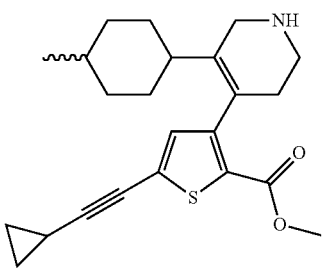

138A

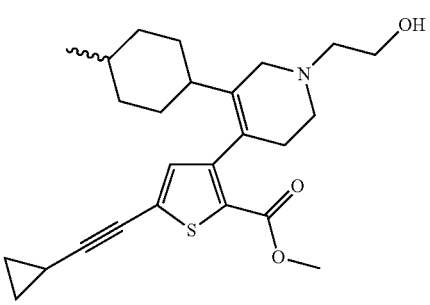

138B

To a solution of 138A (50 mg) in DCE (2 ml) was added (tert-butyldimethylsilyloxy)-acetaldehyde, activated molecule sieves 4A powder (100 mg), and sodium triacetoxyborohydride (100 mg). After the reaction was stirred at RT for 2 hr, the reaction mixture was filtered through Celite®, and rinsed with THF (5 mL). The filtrate was treated with tetrabutylammonium fluoride (20 mg) and KF (100 mg, powder). After the mixture was stirred at RT overnight, it was filtered through Celite®, rinsed with DCM/MeOH (5/1), and concentrated. The crude product was purified with preparative TLC, developing with 10% MeOH in DCM to give 138B.

138 was then prepared by the same method as 001, using 138B instead of 001J. MS calcd: (M+H)⁺=414. MS found: (M+H)⁺=414.

Example 139—5-[4-(3-Methyl-3H-imidazo[4,5-b]pyridin-2-yl)-phenyl]-3-[1-methyl-5-(4-methyl-cyclohexyl)-1,2,3,6-tetrahydro-pyridin-4-yl]-thiophene-2-carboxylic acid

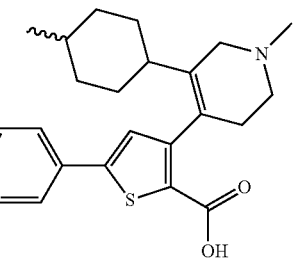

139

139A was prepared by the same method as 137A, using 2,3-diaminopyridine and 4-iodobenzoic acid instead of 4-bromo-1,2-diaminobenzene and thiazole-4-carboxylic acid. MS calcd: (M+H)⁺=322. MS found: (M+H)⁺=322.

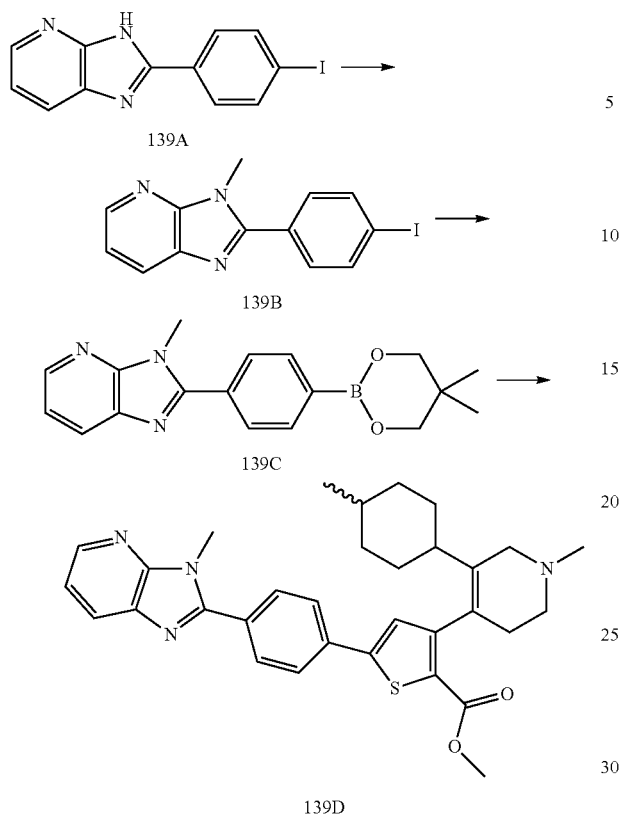

139B was prepared by the same method as 137B, using 139A instead of 137A. MS calcd: $(M+H)^+=336$. MS found: $(M+H)^+=336$.

139C was prepared by the same method as 005B, using bis(neopentyl glycolato) diboron and 139B instead of bis (pinacolato) diboron and 005A. MS calcd: $(M+H)^+=322$. MS found: $(M+H)^+=322$.

139D was prepared by the same method as 129B, using 139C instead of 4-bromophenylboronic acid. MS calcd: $(M+H)^+=541$. MS found: $(M+H)^+=541$.

139 was then prepared by the same method as 129, using 139D instead of 129C. MS calcd: $(M+H)^+=527$. MS found: $(M+H)^+=527$.

Example 140—5-[4-(3H-Imidazo[4,5-b]pyridin-2-yl)-phenyl]-3-[1-methyl-5-(4-methyl-cyclohexyl)-1,2,3,6-tetrahydro-pyridin-4-yl]-thiophene-2-carboxylic acid

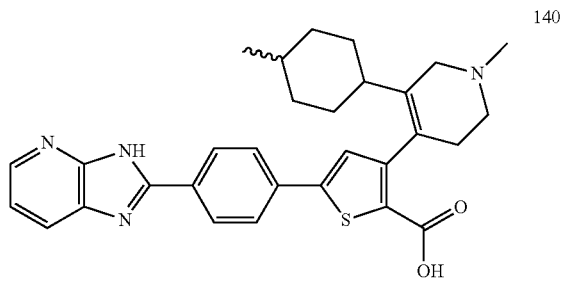 [SMILES: CC1CCC(C2=C(c3cc(-c4ccc(-c5nc6cccnc6[nH]5)cc4)sc3C(=O)O)CCN(C)C2)CC1]

140A was prepared by the same method as 137B, using 139A and 2-(trimethylsilyl)ethoxymethyl chloride instead of iodomethane. MS calcd: $(M+H)^+=452$. MS found: $(M+H)^+=452$.

140B was prepared by the same method as 005B, using bis(neopentyl glycolato) diboron and 140A instead of bis (pinacolato) diboron and 005A. MS calcd: $(M+H)^+=438$. MS found: $(M+H)^+=438$.

140C was prepared by the same method as 129B, using 140B instead of 4-bromophenylboronic acid. MS calcd: $(M+H)^+=657$. MS found: $(M+H)^+=657$.

140 was then prepared by the same method as 138, using 140C instead of 138C to give 140. MS calcd: $(M+H)^+=513$. MS found: $(M+H)^+=513$.

Example 141—3-[5-(4-Methyl-cyclohexyl)-1-pyridin-2-ylmethyl-1,2,3,6-tetrahydro-pyridin-4-yl]-5-(4-pyrazolo[1,5-a]pyrimidin-2-yl-phenyl)-thiophene-2-carboxylic acid

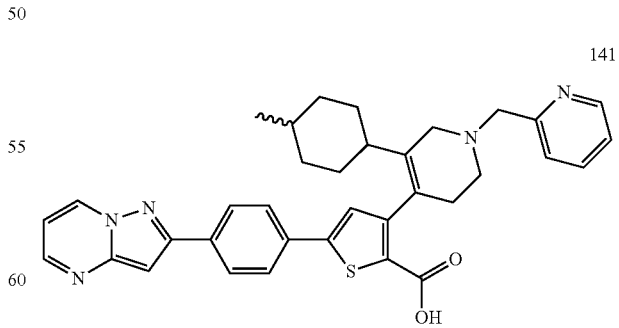

A solution of 127A (20 mg, 0.045 mmol) was dissolved in dichloroethane (3 mL), and treated with 2-pyridinecarboxaldehyde (12.3 mg, 0.11 mmol), TEA (0.02 mL, 0.15 mmol), and sodium triacetoxyborohydride (30 mg, 0.15 mmol). The reaction was stirred overnight at RT. The reaction mixture was concentrated and purified by prep-TLC (silica gel, 50% EtOAc in hexane) to give an intermediate methyl ester 141A.

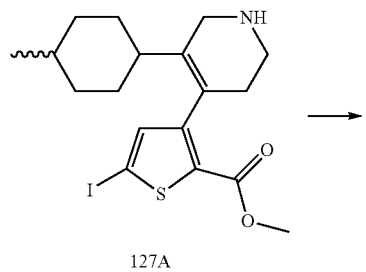

127A

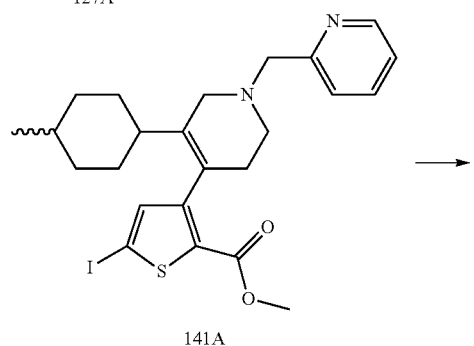

141A

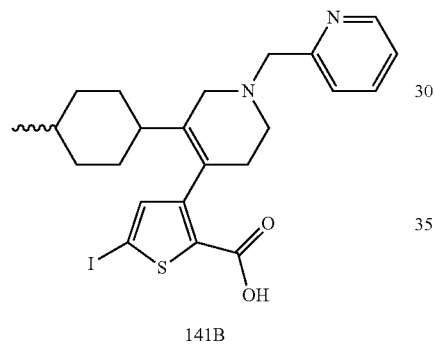

141B 141A (20 mg) was dissolved in THF (2 mL) and EtOH (1 mL). LiOH (2 M, 0.5 mL) was then added. The reaction was stirred at RT for 16 hr, and then diluted with EtOAc. The organic layer was washed with water and concentrated to give 141B.

141 was prepared by the same method as 005, using 005B reacted with 141B instead of 102. MS calcd: $(M+H)^+=590$. MS found: $(M+H)^+=590$.

Example 142—5-(3,3-Dimethyl-but-1-ynyl)-3-[1-(1,3-dimethyl-1H-pyrazol-4-ylmethyl)-5-(4-methyl-cyclohexyl)-1,2,3,6-tetrahydro-pyridin-4-yl]-thiophene-2-carboxylic acid

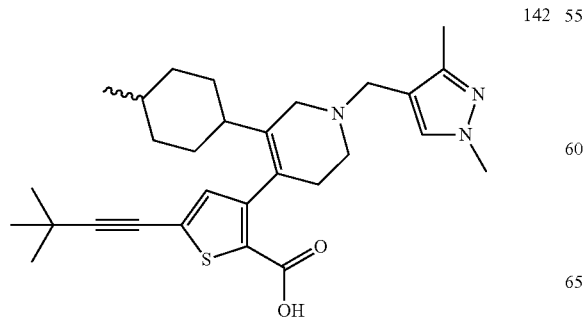

142

142 was prepared by the same method as 127, using 1,3-dimethyl-1H-pyrazole-4-carbaldehyde instead of 2-pyridinecarboxaldehyde. MS calcd: $(M+H)^+=494$. MS found: $(M+H)^+=494$.

Example 143—3-[5-(4-Methyl-cyclohexyl)-1-quinolin-2-ylmethyl-1,2,3,6-tetrahydro-pyridin-4-yl]-5-phenyl-thiophene-2-carboxylic acid

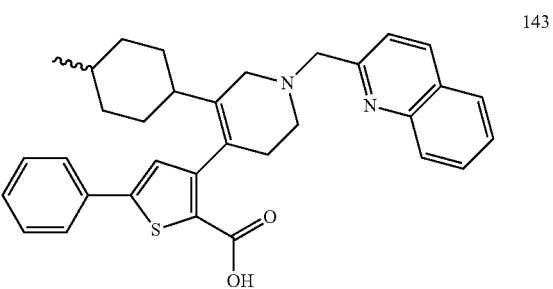 [SMILES: CC1CCC(C2=C(c3cc(-c4ccccc4)sc3C(=O)O)CCN(Cc3ccc4ccccc4n3)C2)CC1]

143

143 is prepared by the same method as 087, using quinoline-2-carboxaldehyde instead of pyridine-1-carboxaldehyde. MS calcd: $(M+H)^+=523$. MS found: $(M+H)^+=523$.

Example 144—3-[1-(2-Bromo-pyridin-4-ylmethyl)-5-(4-methyl-cyclohexyl)-1,2,3,6-tetrahydro-pyridin-4-yl]-5-phenyl-thiophene-2-carboxylic acid

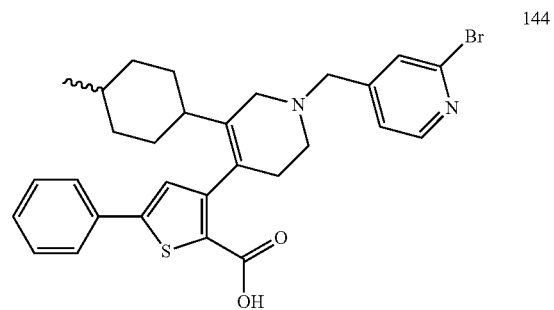 [SMILES: CC1CCC(C2=C(c3cc(-c4ccccc4)sc3C(=O)O)CCN(Cc3ccnc(Br)c3)C2)CC1]

144

144 was prepared by the same method as 087, using 2-bromo-isonicotinaldehyde instead of pyridine-1-carboxaldehyde. MS calcd: $(M+H)^+=552$. MS found: $(M+H)^+=552$.

Example 145—3-[5-(4-Methyl-cyclohexyl)-1-(2-thiophen-2-yl-pyridin-4-ylmethyl)-1,2,3,6-tetrahydro-pyridin-4-yl]-5-phenyl-thiophene-2-carboxylic acid

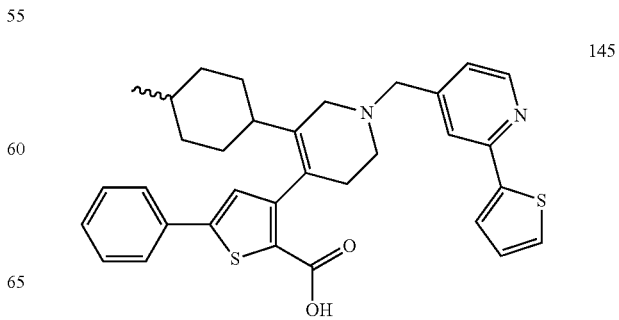

145

145 was prepared by the same method as 087, using 2-(thiophen-2-yl)isonicotinaldehyde instead of pyridine-1-carboxaldehyde. MS calcd: (M+H)⁺=556. MS found: (M+H)⁺=556.

Example 146—3-[1-(3,5-Dichloro-pyridin-4-ylmethyl)-5-(4-methyl-cyclohexyl)-1,2,3,6-tetrahydro-pyridin-4-yl]-5-phenyl-thiophene-2-carboxylic acid

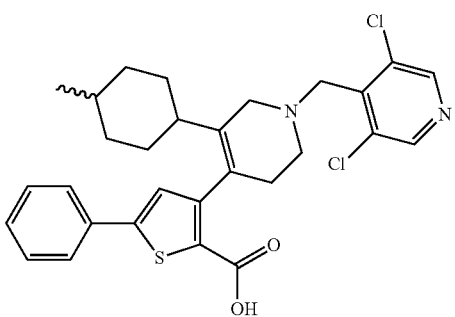

146 was prepared by the same method as 087, using 3,5-dichloroisonicotinaldehyde instead of pyridine-1-carboxaldehyde. MS calcd: (M+H)⁺=542. MS found: (M+H)⁺=542.

Example 147—3-[1-[2-(4-Fluoro-phenyl)-pyridin-4-ylmethyl]-5-(4-methyl-cyclohexyl)-1,2,3,6-tetrahydro-pyridin-4-yl]-5-phenyl-thiophene-2-carboxylic acid

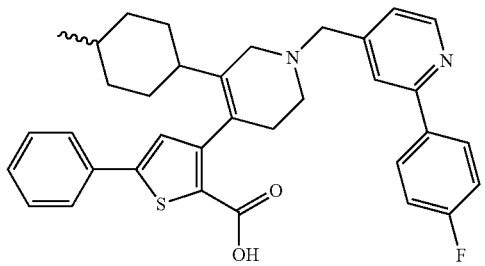

147 was prepared by the same method as 087, using 2-(4-fluorophenyl)-isonicotinaldehyde instead of pyridine-1-carboxaldehyde. MS calcd: (M+H)⁺=567. MS found: (M+H)⁺=567.

Example 151—3-[1-(5,7-Diisopropyl-[1,2,4]triazolo[1,5-a]pyrimidin-2-ylmethyl)-5-(4-methyl-cyclohexyl)-1,2,3,6-tetrahydro-pyridin-4-yl]-5-phenyl-thiophene-2-carboxylic acid

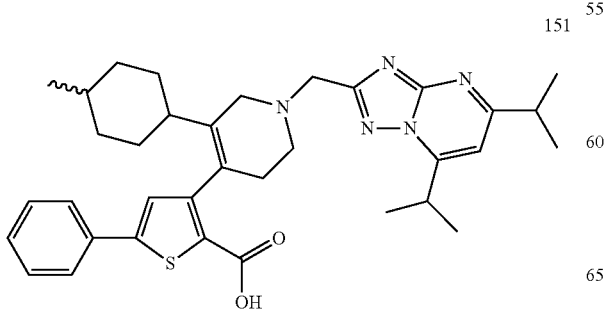

151 was prepared by the same method as 088 using 2,6-dimethylheptane-3,5-dione instead of pentane-2,4-dione. MS calcd: (M+H)⁺=598. MS found: (M+H)⁺=598.

Example 152—3-[1-(2-Benzoimidazol-1-yl-acetyl)-5-(4-methyl-cyclohexyl)-1,2,3,6-tetrahydro-pyridin-4-yl]-5-phenyl-thiophene-2-carboxylic acid

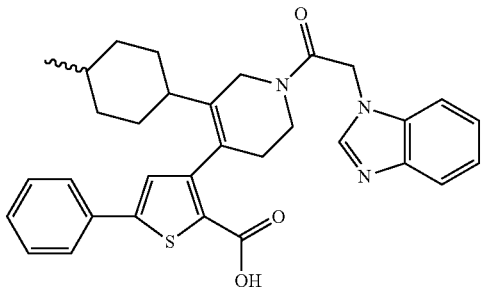

152 was prepared by the same method as 093, using 2-(1H-benzo[d]imidazol-1-yl)acetic acid (prepared by reacting benzimidazole with bromoacetic acid ester, followed by hydrolysis of the ester) instead of 4-pyridylacetic acid hydrochloride. MS calcd: (M+H)⁺=540. MS found: (M+H)⁺=540.

Example 153—3-[5-(4-Methyl-cyclohexyl)-1-(2-[1,2,4]triazolo[1,5-a]pyridin-2-yl-acetyl)-1,2,3,6-tetrahydro-pyridin-4-yl]-5-phenyl-thiophene-2-carboxylic acid

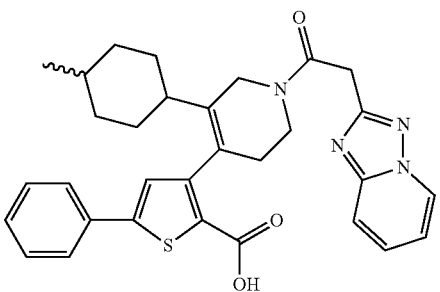

153 was prepared by the same method as 093, using 2-([1,2,4]triazolo[1,5-a]pyridin-2-yl)acetic acid instead of 4-pyridylacetic acid hydrochloride. MS calcd: (M+H)⁺=541. MS found: (M+H)⁺=541.

Example 154—3-[5-(4-Methyl-cyclohexyl)-1-(6-trifluoromethyl-pyridine-3-carbonyl)-1,2,3,6-tetrahydro-pyridin-4-yl]-5-phenyl-thiophene-2-carboxylic acid

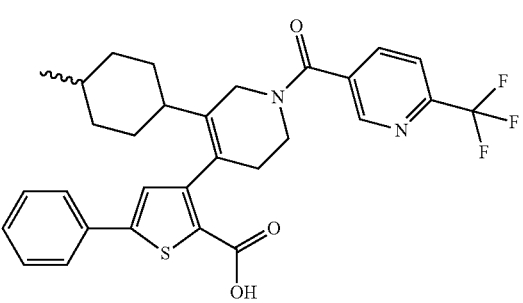

154 was prepared by the same method as 093, using 6-(trifluoromethyl)nicotinic acid instead of 4-pyridylacetic acid hydrochloride. MS calcd: (M+H)⁺=555. MS found: (M+H)⁺=555.

Example 155—3-[1-(3-Amino-pyrazine-2-carbonyl)-5-(4-methyl-cyclohexyl)-1,2,3,6-tetrahydro-pyridin-4-yl]-5-phenyl-thiophene-2-carboxylic acid

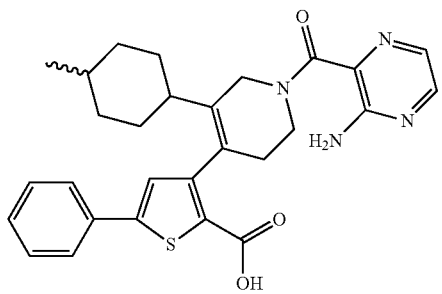

155

155 was prepared by the same method as 093, using 3-aminopyrazine-2-carboxylic acid instead of 4-pyridylacetic acid hydrochloride. MS calcd: (M+H)⁺=503. MS found: (M+H)⁺=503.

Example 156—3-[5-(4-Methyl-cyclohexyl)-1-(3-methyl-3H-imidazole-4-carbonyl)-1,2,3,6-tetrahydro-pyridin-4-yl]-5-phenyl-thiophene-2-carboxylic acid

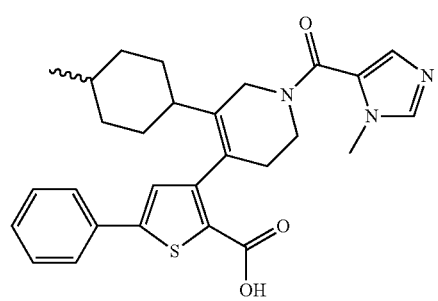

156

156 was prepared by the same method as 093, using 1-methyl-1H-imidazole-5-carboxylic acid instead of 4-pyridylacetic acid hydrochloride. MS calcd: (M+H)⁺=490. MS found: (M+H)⁺=490.

Example 158—3-[1-Methyl-5-(4-methyl-cyclohexyl)-1,2,3,6-tetrahydro-pyridin-4-yl]-5-[4-(2-thiazol-4-yl-vinyl)-phenyl]-thiophene-2-carboxylic acid

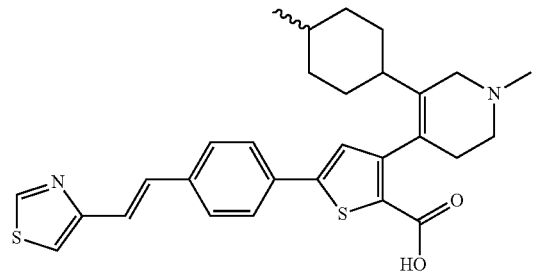

158

A mixture of 4-bromobenzyl bromide (1.00 g, 4.00 mmol) and triphenylphosphine (1.70 g, 6.00 mmol) in toluene (10 mL) was stirred at 80° C. overnight. The reaction mixture was concentrated, followed by sonication in hexane, filtration, and a subsequent hexane wash gave a white solid, which was dried in vacuo. This white solid (906 mg, 1.77 mmol) was dissolved in THF (10 mL), cooled to 0° C., and lithium hexamethyl disilazide (1 M) in THF (1.95 mL, 1.95 mmol) was added. After 0.5 hr, thiazole-4-carboxaldehyde (200 mg, 1.77 mmol) was added, the ice bath was removed, and the mixture stirred for 0.5 hr. The reaction mixture was quenched by the addition of water, extracted with EtOAc (2×30 mL), the organic layer was washed with brine, dried over MgSO₄, concentrated and filtered through a silica plug using 30%-100% EtOAc/hexane to give 158A as a clear oil. MS calcd: (M+H)⁺=267. MS found: (M+H)⁺=267.

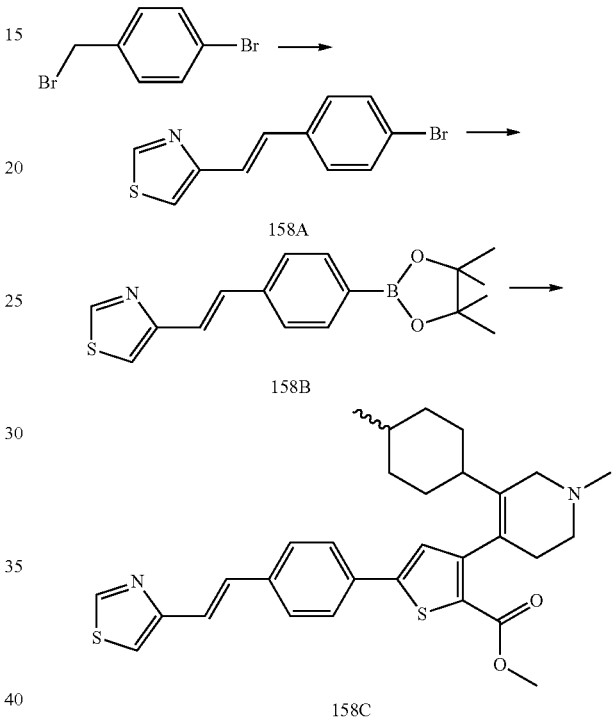

158B was prepared by the same method as 005B, using 158A instead of 005A. MS calcd: (M+H)⁺=314. MS found: (M+H)⁺=314.

158C was prepared by the same method as 129B, using 158B instead of 4-bromophenylboronic acid. MS calcd: (M+H)⁺=519. MS found: (M+H)⁺=519.

158 was then prepared by the same method as 129, using 158C instead of 129C. MS calcd: (M+H)⁺=505. MS found: (M+H)⁺=505.

Example 159—3-[5-(4-Methyl-cyclohexyl)-1,2,3,6-tetrahydro-pyridin-4-yl]-5-{4-[(thiazole-4-carbonyl)-amino]-phenyl}-thiophene-2-carboxylic acid

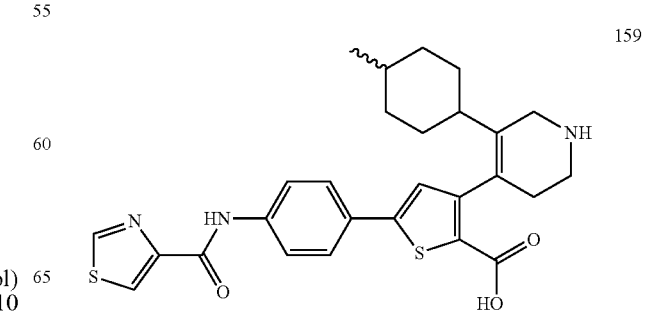

159

Thiazole-4-carboxylic acid (1.42 g, 11 mmol) in DCM (20 mL) was treated with oxallyl chloride (8 mL, 2 M solution in DCM), followed by 2 drops of DMF. After 1 hr at RT, solvent was evaporated, and the residue was redissolved in DCM (20 mL). To the solution was added 4-(4,4,5,5-tetramethyl-1,3,2-dioxaborolan-2-yl)benzenamine (2.20 g, 10 mmol) and TEA (2 mL). After 30 min at RT, the reaction mixture was diluted with ether (100 mL), washed with water, sodium bicarbonate, and brine. The organic layer was dried over anhydrous MgSO$_4$, filtered and concentrated to give 159A, which was used without further purification.

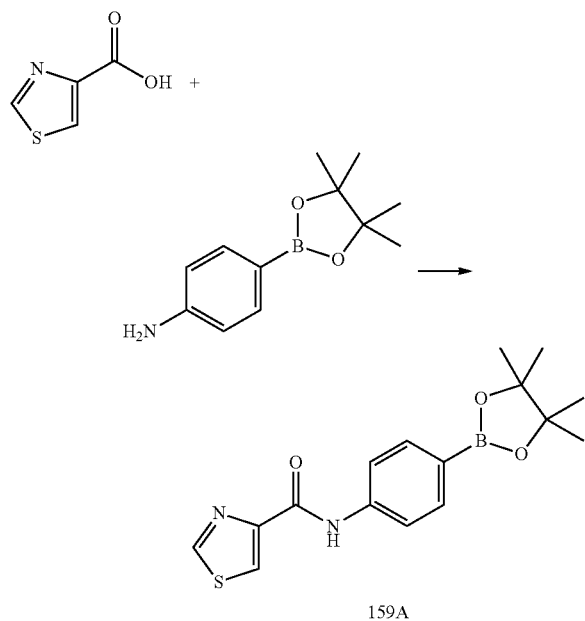

159A 159 was then prepared by the same method as 005, using 159A and 127A instead of 005B and 002. The coupling product was further hydrolyzed with LiOH to give 159. MS calcd: (M+H)$^+$=508. MS found: (M+H)$^+$=508.

Example 160—5-{2,5-Difluoro-4-[(thiazole-4-carbonyl)-amino]-phenyl}-3-[1-methyl-5-(4-methyl-cyclohexyl)-1,2,3,6-tetrahydro-pyridin-4-yl]-thiophene-2-carboxylic acid

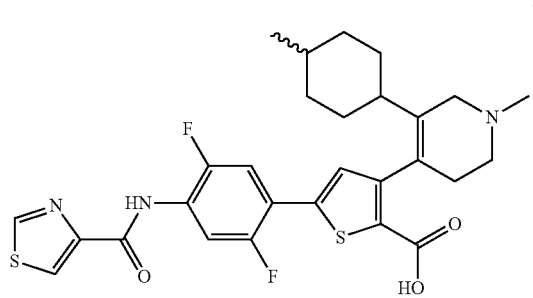

160

160 was prepared by the same method as 059, using 4-amino-2,5-difluorophenylboronic acid pinacol ester instead of 4-amino-3-fluorophenylboronic acid. MS calcd: (M+H)$^+$=558. MS found: (M+H)$^+$=558.

Example 161—5-[4-(5,7-Dimethyl-pyrazolo[1,5-a]pyrimidin-2-yl)-phenyl]-3-[1-methyl-5-(4-methyl-cyclohexyl)-1,2,3,6-tetrahydro-pyridin-4-yl]-thiophene-2-carboxylic acid

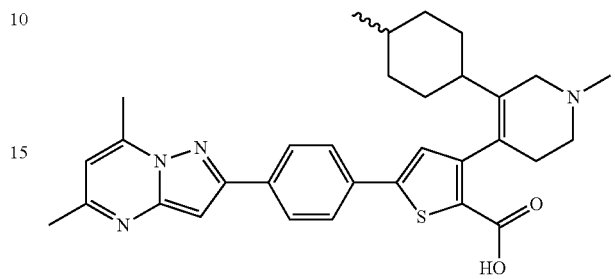

161

A mixture of acetylacetone (126 mg, 1.26 mmol) and 5-amino-3-(4-bromophenyl)pyrazole (300 mg, 1.26 mmol) in EtOH was refluxed overnight, concentrated and used for the preparation of 161B without further purification. MS calcd: (M+H)$^+$=303. MS found: (M+H)$^+$=303.

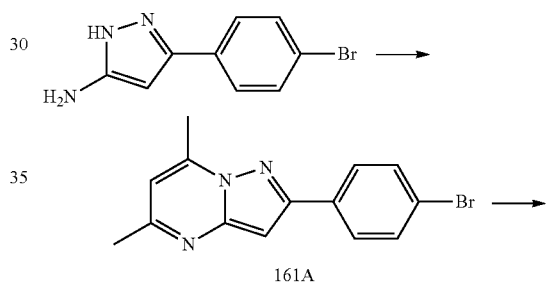

161A

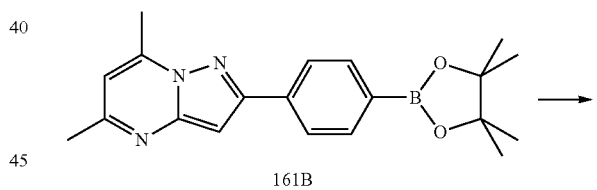

161B

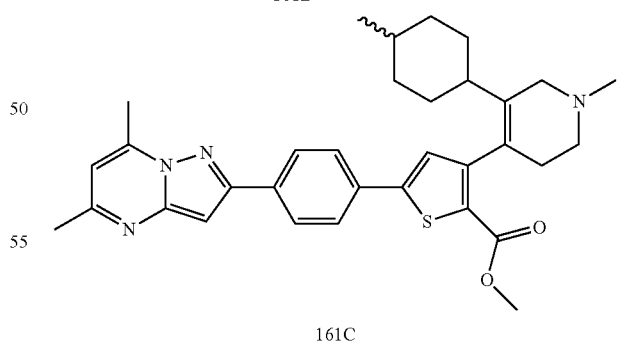

161C 161B was prepared by the same method as 005B, using 161A instead of 005A. MS calcd: (M+H)$^+$=350. MS found: (M+H)$^+$=350.

161C was prepared by the same method as 129B, using 161B instead of 4-bromophenylboronic acid. MS calcd: (M+H)$^+$=555. MS found: (M+H)$^+$=555.

161 was prepared by the same method as 129, using 161C instead of 129C. MS calcd: (M+H)$^+$=541. MS found: (M+H)$^+$=541.

Example 162—3-[1-Methyl-5-(4-methyl-cyclohexyl)-1,2,3,6-tetrahydro-pyridin-4-yl]-5-[4-(7-methyl-pyrazolo[1,5-a]pyrimidin-2-yl)-phenyl]-thiophene-2-carboxylic acid

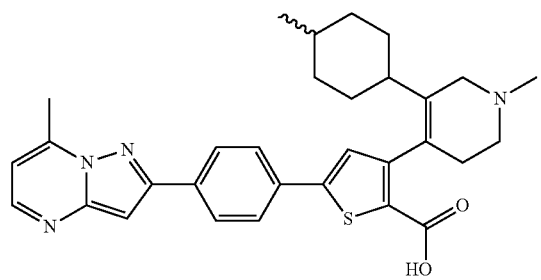

162

162 was prepared by the same method as 161, using trans 4-methoxy-3-buten-2-one instead of acetylacetone to give the title compound. MS calcd: (M+H)$^+$=527. MS found: (M+H)$^+$=527.

Example 163—3-[1-Methyl-5-(4-methyl-cyclohexyl)-1,2,3,6-tetrahydro-pyridin-4-yl]-5-[4-(6-methyl-pyrazolo[15-a]pyrimidin-2-yl)-phenyl]-thiophene-2-carboxylic acid

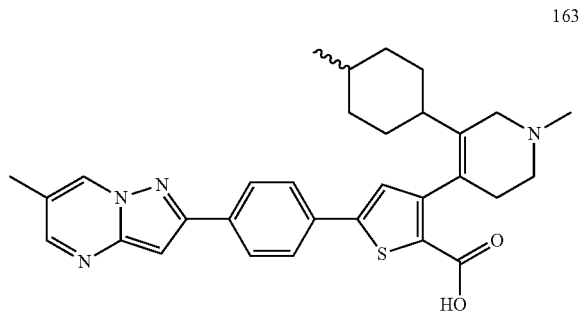

163

163A was prepared by the same method as 132A, using 3-ethoxymethacrolein instead of trans-3-(dimethylamino)-acrylonitrile. MS calcd: (M+H)$^+$=289. MS found: (M+H)$^+$=289.

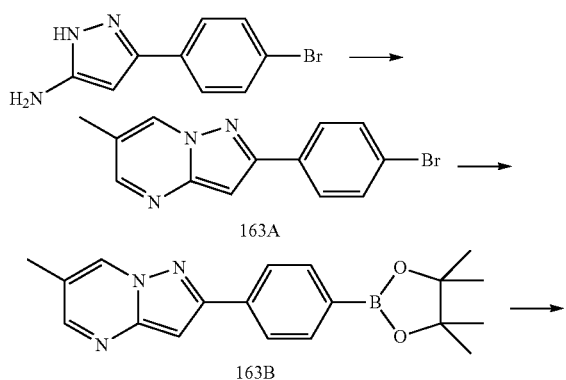

163A

163B

-continued

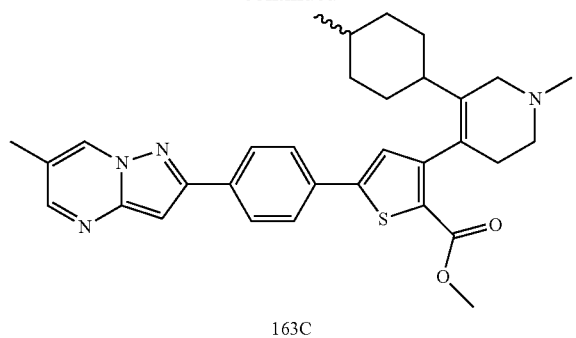

163C 163B was prepared by the same method as 005B, using 163A instead of 005A. MS calcd: (M+H)$^+$=336. MS found: (M+H)$^+$=336.

163C was prepared by the same method as 129B, using 163B instead of 4-bromophenylboronic acid. MS calcd: (M+H)$^+$=541. MS found: (M+H)$^+$=541.

163 was then prepared by the same method as 129, using 163C instead of 129C. MS calcd: (M+H)$^+$=527. MS found: (M+H)$^+$=527.

Example 164—5-(4-Imidazol[1,2-b]pyridazin-2-yl-phenyl)-3-[1-methyl-5-(4-methyl-cyclohexyl)-1,2,3, 6-tetrahydro-pyridin-4-yl]-thiophene-2-carboxylic acid

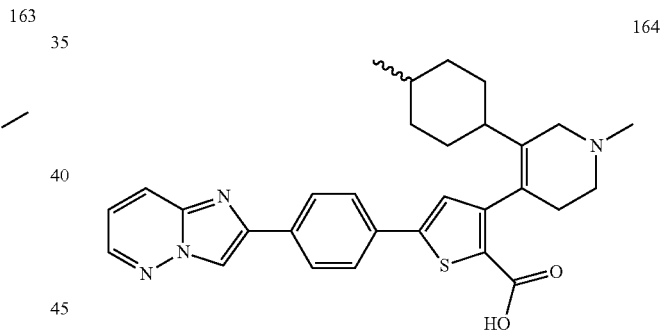

164

A mixture of 3-aminopyridazine (100 mg, 1.05 mmol), 2,4'-dibromoacetophenone (146 mg, 0.53 mmol) and NaHCO$_3$ (133 mg, 1.58 mmol) in EtOH (3 mL) was refluxed for 4 h. The reaction mixture was concentrated, diluted in EtOAc, washed with water, brine, dried over MgSO$_4$, concentrated and used for the preparation of 164B without further purification. MS calcd: (M+H)$^+$=275. MS found: (M+H)$^+$=275.

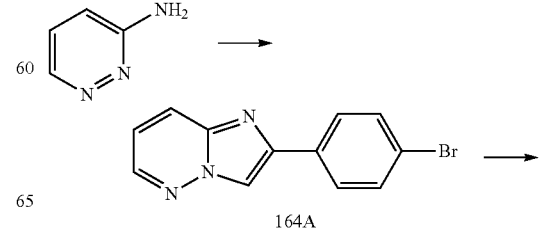

164A

-continued

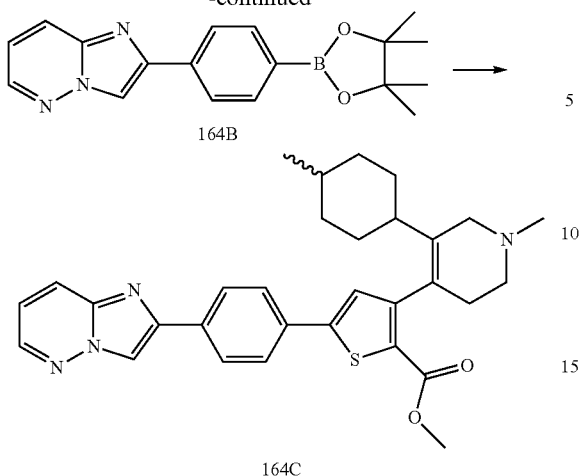

164B was prepared by the same method as 005B, using 164A instead of 005A. MS calcd: $(M+H)^+=322$. MS found: $(M+H)^+=322$.

164C was prepared by the same method as 129B, using 164B instead of 4-bromophenylboronic acid. MS calcd: $(M+H)^+=527$. MS found: $(M+H)^+=527$.

164 was then prepared by the same method as 129, using 164C instead of 129C. MS calcd: $(M+H)^+=513$. MS found: $(M+H)^+=513$.

Example 165—3-[1-Methyl-5-(4-methyl-cyclohexyl)-1,2,3,6-tetrahydro-pyridin-4-yl]-5-(4-pyrazolo[4,3-b]pyridin-2-yl-phenyl)-thiophene-2-carboxylic acid

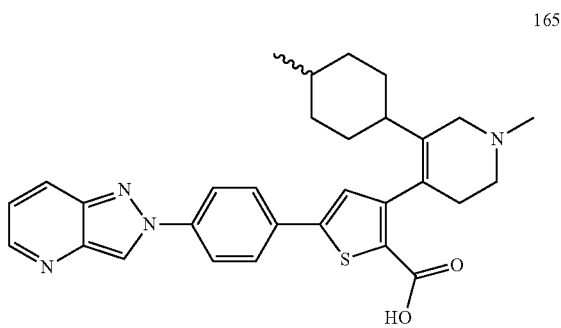 [SMILES: CC1CCC(C2=C(c3cc(-c4ccc(-n5cc6ncccc6n5)cc4)sc3C(=O)O)CCN(C)C2)CC1]

165A was prepared by the same method as 129B. MS calcd: $(M+H)^+=489$. MS found: $(M+H)^+=489$.

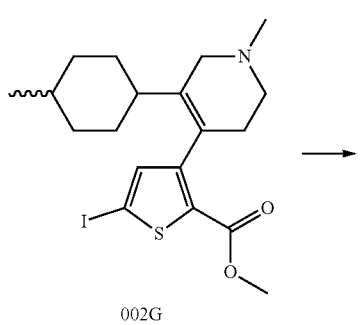

-continued

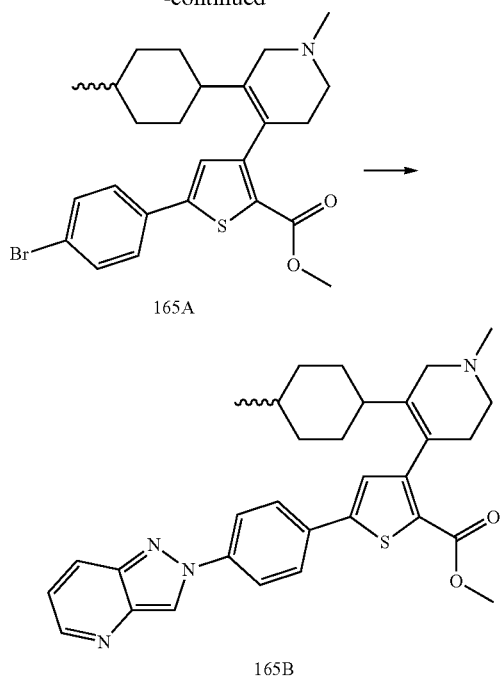

A mixture of 165A (75 mg, 0.15 mmol), pyrazolo[4,3-b]pyridine (110 mg, 0.92 mmol), $K_3PO_4$ (54.3 mg, 0.26 mmol), Cu(I)I (2.4 mg, 0.01 mmol), and trans-N,N'-dimethylcyclohexane-1,2-diamine (6 μL, 0.04 mmol) in toluene (2 mL) was heated and stirred at 120° C. for 48 hr. The reaction mixture was diluted in EtOAc, washed with water, brine, dried over $MgSO_4$, concentrated and purified by prep-TLC using 3:7:1 EtOAc/DCM/MeOH (v/v) to afford 165B. MS calcd: $(M+H)^+=527$. MS found: $(M+H)^+=527$.

165 was then prepared by the same method as 129, using 165B instead of 129C. MS calcd: $(M+H)^+=513$. MS found: $(M+H)^+=513$.

Example 166—5-{3,5-Difluoro-4-[(thiazole-4-carbonyl)-amino]-phenyl}-3-[1-methyl-5-(4-methylcyclohexyl)-1,2,3,6-tetrahydro-pyridin-4-yl]-thiophene-2-carboxylic acid

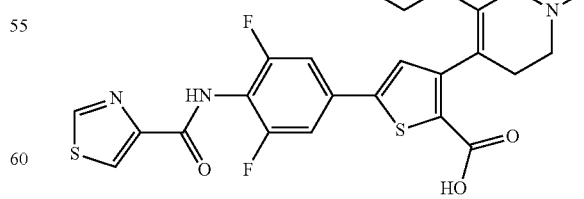

166 was prepared by the same method as 059, using 4-amino-3,5-difluorophenylboronic acid pinacol ester instead of 4-amino-3-fluorophenylboronic acid. MS calcd: $(M+H)^+=558$. MS found: $(M+H)^+=558$.

Example 167—3-[1-Methyl-4-(4-methyl-cyclo-hexyl)-1,2,5,6-tetrahydro-pyridin-3-yl]-5-{4-[(thiaz-ole-4-carbonyl)-amino]-phenyl}-thiophene-2-carboxylic acid

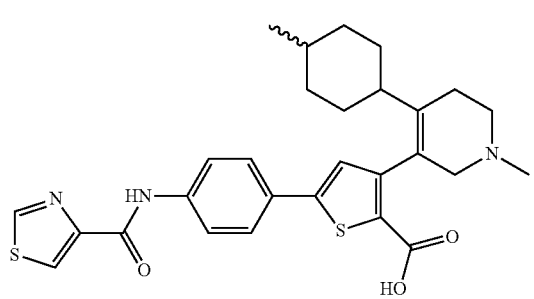

167

167 was prepared by the same method as 013, using 111G instead of 002G. MS calcd: (M+H)⁺=522. MS found: (M+H)⁺=522.

Example 168—5-(3,3-Dimethyl-but-1-ynyl)-3-[1-(2-hydroxy-ethyl)-5-(4-methyl-cyclohexyl)-1,2,3,6-tetrahydro-pyridin-4-yl]-thiophene-2-carboxylic acid

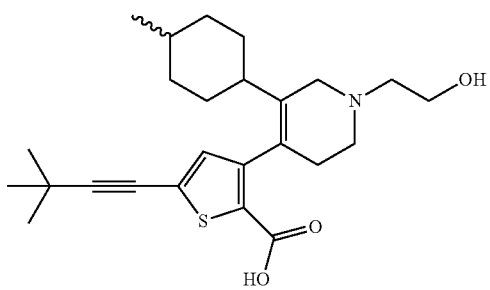

168

168 was prepared by the same method as 117, using 2-(tert-butyldimethylsilyloxy)-acetaldehyde instead of tetrahydrofuran-3-carboxaldehyde. MS calcd: (M+H)⁺=430. MS found: (M+H)⁺=430.

Example 169—3-[1-Methyl-4-(4-methyl-cyclo-hexyl)-1,2,5,6-tetrahydro-pyridin-3-yl]-5-(4-pyra-zolo[1,5-a]pyrimidin-2-yl-phenyl)-thiophene-2-car-boxylic acid

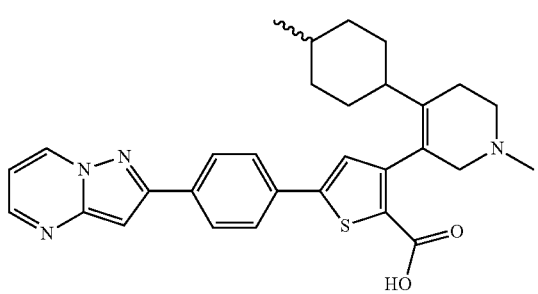

169

169A was prepared by treatment of 111G (100 mg) with LiOH (saturated solution, 0.3 mL) in THF (3 mL). After the reaction mixture was stirred overnight, to the mixture was added phorphoric acid (5 M in water, 0.2 mL), and the reaction mixture was diluted with EtOAc (10 mL). The layers were separated, and the aqueous layer was extracted with EtOAc (10 mL). Combined organic layers were washed with brine (5 mL), dried over anhydrous Na₂SO₄, filtered, and concentrated. The crude 169A was used without further purification.

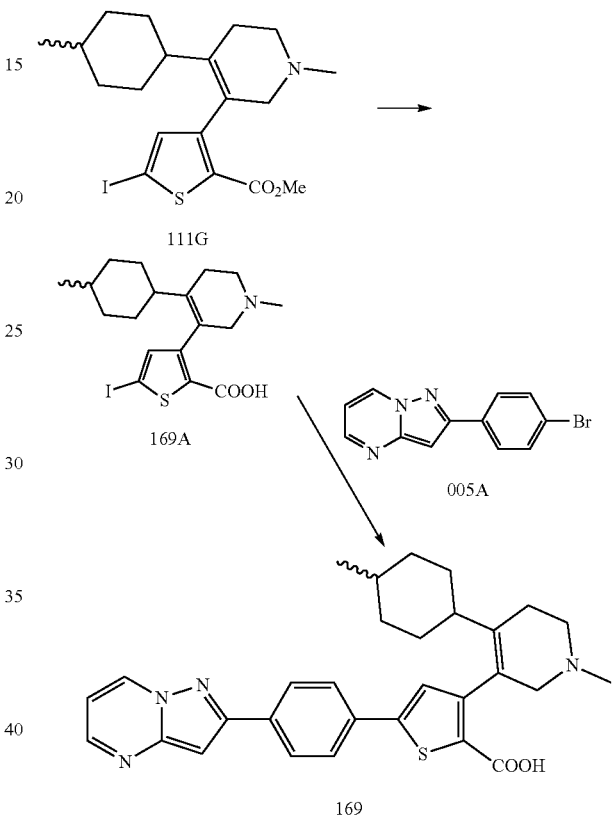

169 was then prepared by the same method as 005, using 169A instead of 002. MS calcd: (M+H)⁺=513. MS found: (M+H)⁺=513.

Example 170—5-(3,3-Dimethyl-but-1-ynyl)-3-[1-(2-hydroxy-acetyl)-4-(4-methyl-cyclohexyl)-1,2,5,6-tetrahydro-pyridin-3-yl]-thiophene-2-carboxylic acid

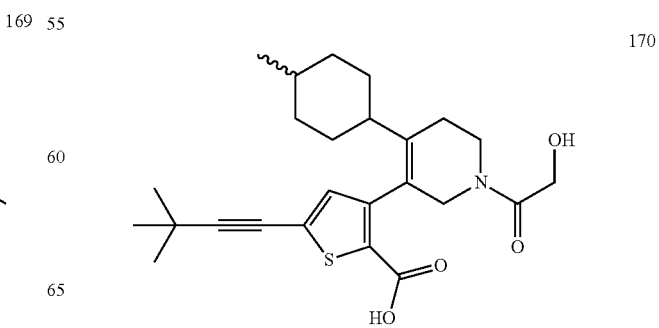

170

Acetoxyacetic acid (12 mg) was dissolved in DMF (3 mL). To the solution were added HATU (38 mg) DIPEA (0.1 mL), and 111H (20 mg). The reaction mixture was stirred at RT for 55 min. The reaction was then diluted with EtOAc (30 mL), washed with water (2×10 mL), dried over anhydrous MgSO₄, and purified by column (eluted with 10-100% EtOAc/hexanes) to give compound 170A.

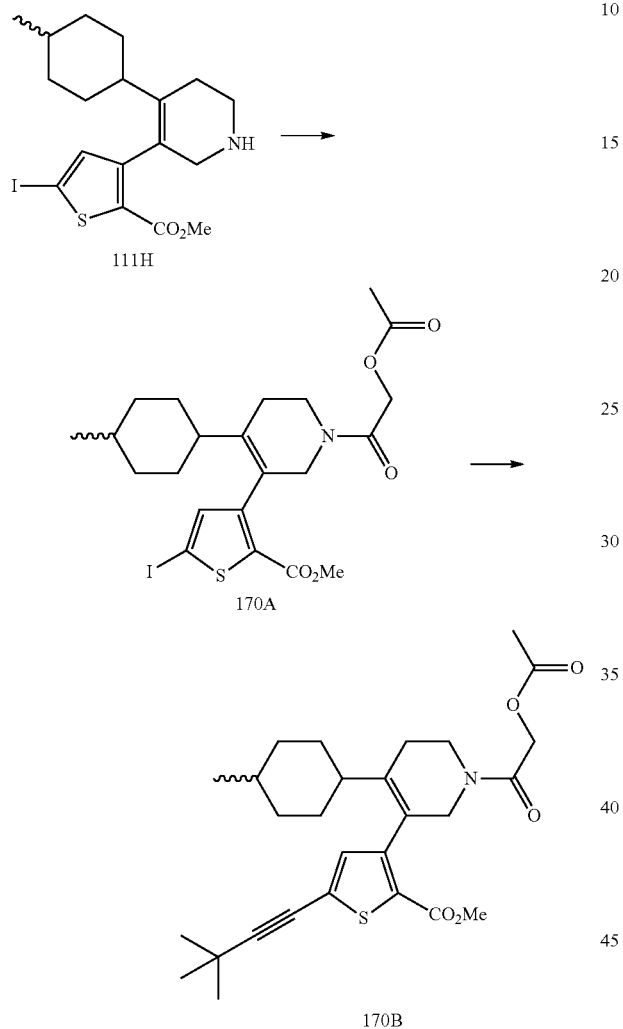

Compound 170A was treated with copper iodide (0.15 eq.) TEA (4 eq.), 3,3-dimethyl-but-1-yne (3 eq.), and Pd(dppf)Cl₂ (0.05 eq.) in DMF (2 mL). The reaction mixture was stirred at 60° C. for 2 hr under N₂. The reaction mixture was filtered on Celite® and washed with EtOAc. The filtrate was diluted with water, and extracted twice with EtOAc. The organic phases were combined and washed twice with water. The organic layer was separated, dried (Na₂SO₄), evaporated, and purified by column chromatography to give 170B.

Hydrolysis of 170B was performed using LiOH in THF (2 mL) and EtOH (1 mL). The reaction was stirred at RT for 6 hr, and then diluted with EtOAc. The organic layer was washed with water and concentrated. The final product was precipitated out in hexane and washed more with hexane. The powder of 170 was obtained with lyophilization. MS calcd: (M+H)⁺=444. MS found: (M+H)⁺=444.

Example 171—5-Iodo-3-[4-(4-methyl-cyclohexyl)-1,2,5,6-tetrahydro-pyridin-3-yl]-thiophene-2-carboxylic acid

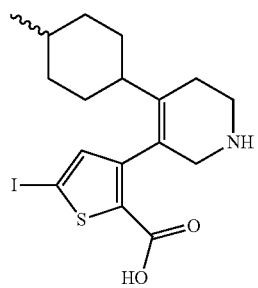

111H (20 mg) was hydrolyzed with LiOH (30 mg) in solvent of THF, MeOH, and water (2:1:1) for 2 hr. Extraction of the mixture with EtOAc, washing with water, and concentration gave pure product 171. MS calcd: (M+H)⁺=432. MS found: (M+H)⁺=432.

Example 172—5-(1-Methyl-cyclopropylethynyl)-3-[1-methyl-5-(4-methyl-cyclohexyl)-1,2,3,6-tetrahydro-pyridin-4-yl]-thiophene-2-carboxylic acid

172

1.6 M BuLi in hexane (9.04 mL, 14.46 mmol) was slowly added to a solution of (cyclopropylethynyl)trimethylsilane (1.00 g, 7.23 mmol) in ethyl ether (10 mL). The reaction mixture was stirred at RT overnight, cooled to −78° C., dimethyl sulfate (0.89 mL, 9.40 mmol) was added, and the reaction mixture warmed to RT over the course of 1.5 hr. sat. NH₄Cl was added and the reaction mixture was extracted with ethyl ether. The organic layer was washed with water, brine, dried over MgSO₄, and concentrated to afford 172A, which was used for the preparation of 172B without further purification.

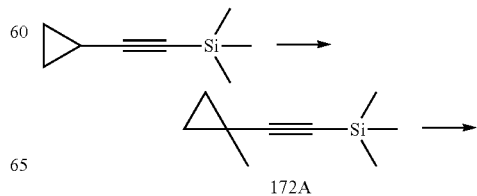

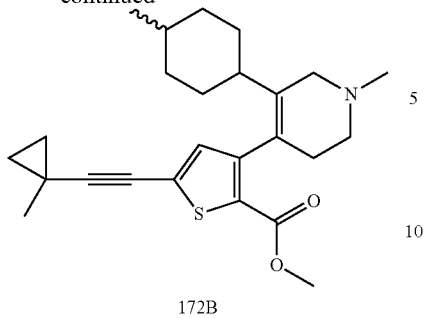

172B

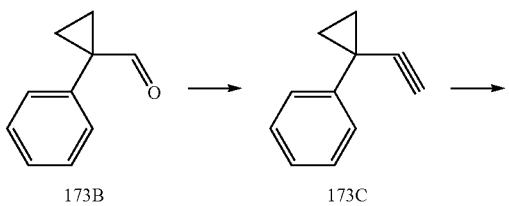

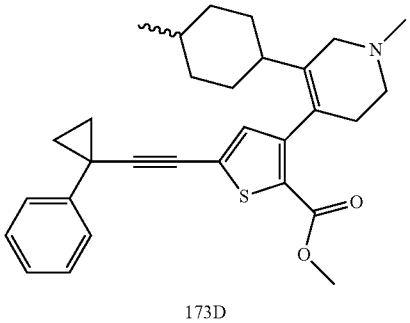

173D

A mixture of 172A (50 mg, 0.33 mmol), 068C (50 mg, 0.11 mmol), Pd(dppf)Cl$_2$ (8 mg, 0.01 mmol), KF (19 mg, 0.33 mmol), Cu(I)I (4 mg, 0.02 mmol), and benzyltrimethylammonium chloride (2 mg, 0.01 mmol) in DMF:TEA (1 mL, 1:1, v/v) was stirred at 90° C. for 1 hr. The reaction mixture was concentrated and purified by prep-TLC using 10% MeOH/DCM to afford 172B. MS calcd: (M+H)$^+$=412. MS found: (M+H)$^+$=412.

172 was prepared by the same method as 129, using 172B instead of 129C. MS calcd: (M+H)$^+$=398. MS found: (M+H)$^+$=398.

Example 173—3-[1-Methyl-5-(4-methyl-cyclohexyl)-1,2,3,6-tetrahydro-pyridin-4-yl]-5-(1-phenyl-cyclopropylethynyl)-thiophene-2-carboxylic acid

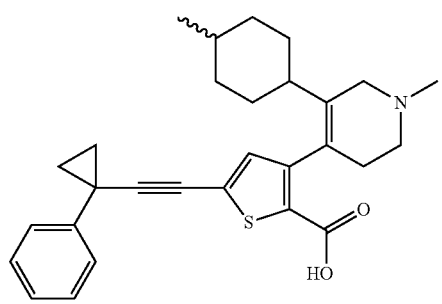

173

To a solution of 1-phenyl-1-cyclopropanecarboxylic acid (1.18 g, 5.0 mmol) in anhydrous ether (10 mL) at 0° C. was added slowly lithium aluminum hydride solution in THF (1.0 M, 6.0 mL)). The reaction was then stirred at RT for 2 hr. To the reaction mixture was then added water (0.24 mL), 15% aqueous NaOH (0.24 mL), and water (0.72 mL) while stirring. The mixture was stirred for 20 min at RT, filtered and concentrated to give the crude 173A, which was used for the next step without purification.

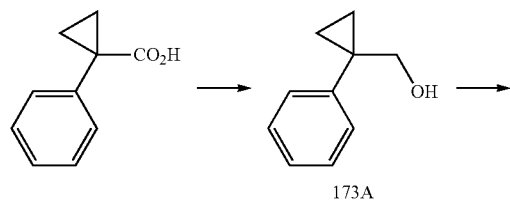

173A

To a suspension of 173A and molecular sieves (powdered, activated, 4A) in DCM was added PCC (10 mmol). After stirring for 12 hr at RT, the reaction was filtered through silica gel, and concentrated to give crude aldehyde 173B, which was used for the next step without purification.

To a solution of 173B and potassium carbonate (30 mmol) in MeOH (30 mL) was added dimethyl (diazomethyl)phosphonate (11 mmol). The reaction was stirred at RT for 3 hr, and was then filtered through Celite. The filtrate was concentrated, and dissolved in 5% DCM/hexane, and the solution was filtered through silica gel, rinsed with 10% DCM/hexanes. The filtrate was concentrated to give 173C.

173D was prepared by the same method as 003A, using 173C instead of tert-butylacetylene. MS calcd: (M+H)$^+$=474. MS found: (M+H)$^+$=474.

173 was then prepared by the same method as 129, using 173D instead of 129C. MS calcd: (M+H)$^+$=460. MS found: (M+H)$^+$=460.

Example 174—5-(1-Benzyl-cyclopropylethynyl)-3-[1-methyl-5-(4-methyl-cyclohexyl)-1,2,3,6-tetrahydro-pyridin-4-yl]-thiophene-2-carboxylicacid

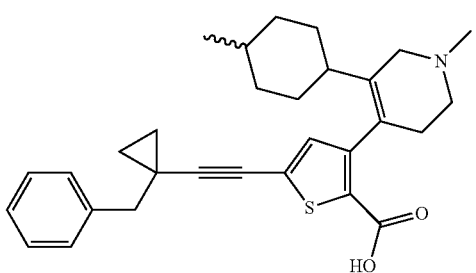

174

174 was prepared by the same method as 172, using benzyl bromide instead of dimethyl sulfate in the first step. MS calcd: (M+H)$^+$=474. MS found: (M+H)$^+$=474.

Example 176—5-Cyclopentylethynyl-3-[1-methyl-4-(4-methyl-cyclohexyl)-1,2,5,6-tetrahydro-pyridin-3-yl]-thiophene-2-carboxylic acid

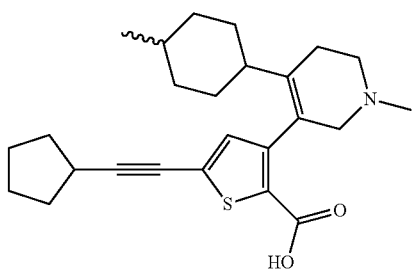
176

176 was prepared by the same method as 031, using 111G instead of 014C. MS calcd: $(M+H)^+=412$. MS found: $(M+H)^+=412$.

Example 177—5-(3-Methyl-hex-1-ynyl)-3-[1-methyl-4-(4-methyl-cyclohexyl)-1,2,5,6-tetrahydro-pyridin-3-yl]-thiophene-2-carboxylic acid

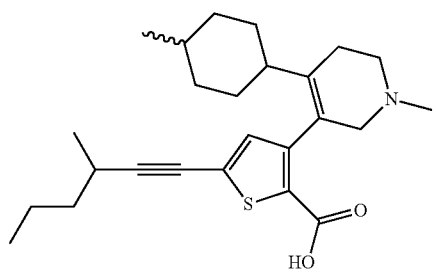
177

177 was prepared by the same method as 030, using 111G instead of 014C. MS calcd: $(M+H)^+=414$. MS found: $(M+H)^+=414$.

Example 178—5-(3-methyl-4-(thiazole-4-carboxamido)phenyl)-3-(1-methyl-5-(4-methylcyclohexyl)-1,2,3,6-tetrahydropyridin-4-yl)thiophene-2-carboxylic acid

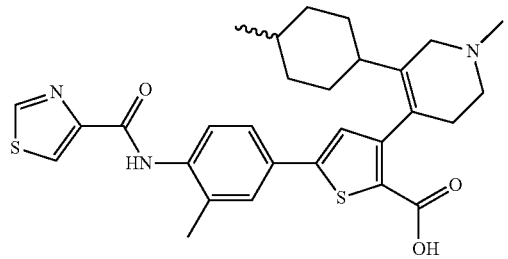
178

178A was prepared by the same method as 002G, using triisopropyl borate instead of iodine. MS calcd: $(M+H)^+=379$. MS found: $(M+H)^+=379$.

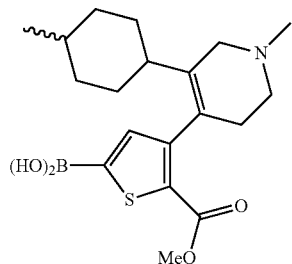
178A 178B was prepared by the same method as 004A, using 4-bromo-2-methylaniline and 178A instead of 002G and [4-({[(1,1-dimethylethyl)oxy]-carbonyl}amino)phenyl]boronic acid. MS calcd: $(M+H)^+=440$. MS found: $(M+H)^+=440$.

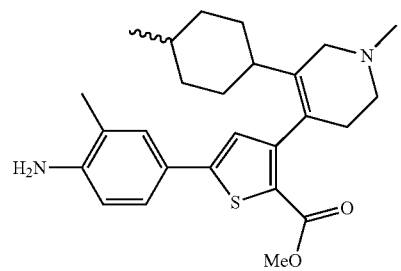
178B 178C was prepared by the same method as 013A, using 178B instead of 004B. MS calcd: $(M+H)^+=551$. MS found: $(M+H)^+=551$.

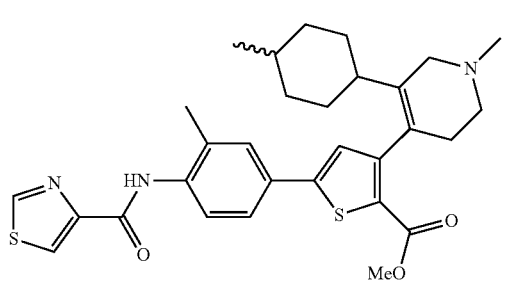
178C 178 was then prepared by the same method as 129, using 178C instead of 129C. MS calcd: $(M+H)^+=537$. MS found: $(M+H)^+=537$.

Example 179—5-(3-methoxy-4-(thiazole-4-carboxamido)phenyl)-3-(1-methyl-5-(4-methylcyclohexyl)-1,2,3,6-tetrahydropyridin-4-yl)thiophene-2-carboxylic acid

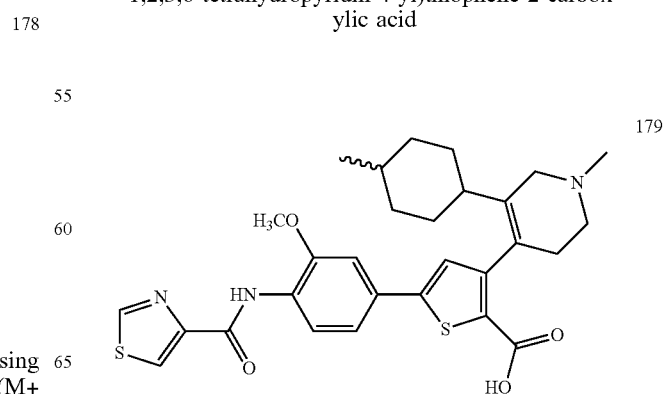
179

179A was prepared by the same method as 004A, using 4-bromo-2-methoxyaniline and 178A instead of 002G and [4-({[(1,1-dimethylethyl)oxy]-carbonyl}amino)phenyl]boronic acid. MS calcd: (M+H)$^+$=456. MS found: (M+H)$^+$=456.

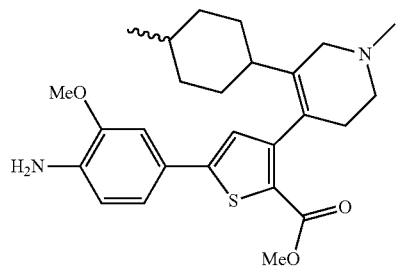

179A 179B was prepared by the same method as 013A, using 179A instead of 004B. MS calcd: (M+H)$^+$=567. MS found: (M+H)$^+$=567.

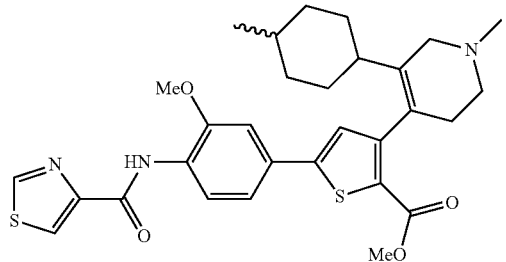

179B 179 was prepared by the same method as 000, using 179B instead of 001J. MS calcd: (M+H)$^+$=553. MS found: (M+H)$^+$=553.

Example 180—5-(3-cyano-4-(thiazole-4-carboxamido)phenyl)-3-(1-methyl-5-(4-methylcyclohexyl)-1,2,3,6-tetrahydropyridin-4-yl)thiophene-2-carboxylic acid

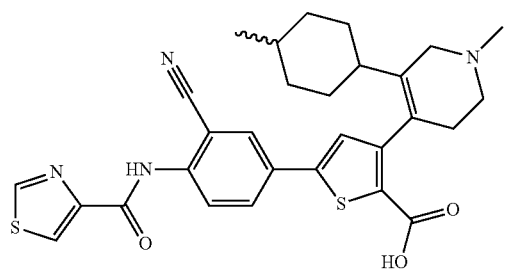

180

180A was prepared by the same method as 004A, using 2-amino-5-bromobenzonitrile and 178A instead of 002G and [4-({[(1,1-dimethylethyl)oxy]-carbonyl}amino)phenyl]boronic acid. MS calcd: (M+H)$^+$=451. MS found: (M+H)$^+$=451.

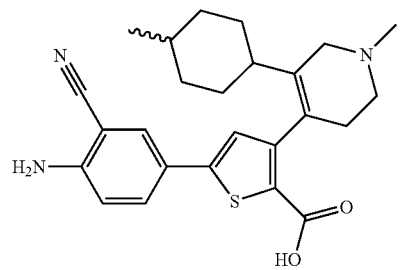

180A 180B was prepared by the same method as 013A, using 180A instead of 004B. MS calcd: (M+H)$^+$=562. MS found: (M+H)$^+$=562.

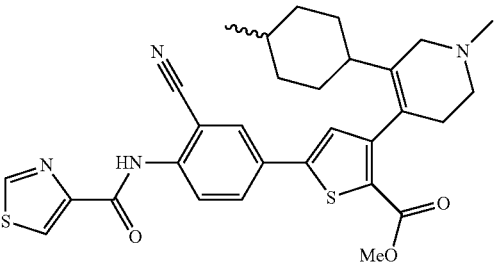

180B 180 was prepared by the same method as 129, using 180B instead of 129C. MS calcd: (M+H)$^+$=548. MS found: (M+H)$^+$=548.

Example 181—5-(3-ethyl-4-(thiazole-4-carboxamido)phenyl)-3-(1-methyl-5-(4-methylcyclohexyl)-1,2,3,6-tetrahydropyridin-4-yl)thiophene-2-carboxylic acid

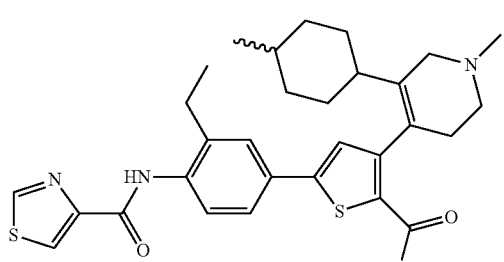

181

181A was prepared by the same method as 005B, using 4-bromo-2-ethyl aniline instead of 005A. MS calcd: (M+H)$^+$=248. MS found: (M+H)$^+$=248.

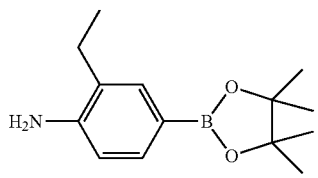

181A 181B was prepared by the same method as 004A, using 181A instead of [4-({[(1,1-dimethylethyl)oxy]-carbonyl}amino)phenyl]boronic acid. MS calcd: (M+H)$^+$=453. MS found: (M+H)$^+$=453.

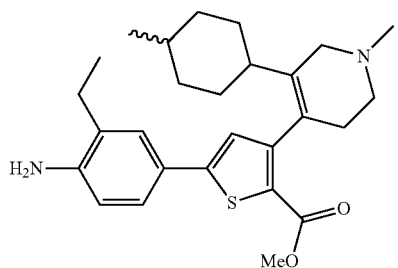

181C was prepared by the same method as 013A, using 181B instead of 004B. MS calcd: (M+H)$^+$=565. MS found: (M+H)$^+$=565.

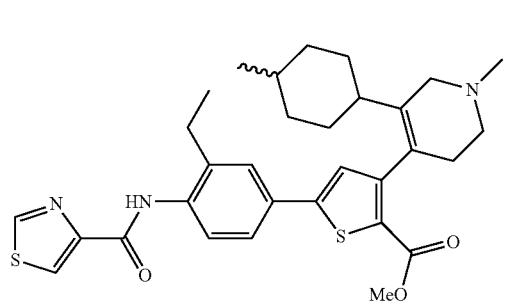

181 was prepared by the same method as 129, using 181C instead of 129C. MS calcd: (M+H)$^+$=551. MS found: (M+H)$^+$=551.

Example 182—5-(3-chloro-4-(thiazole-4-carboxamido)phenyl)-3-(1-methyl-5-(4-methylcyclohexyl)-1,2,3,6-tetrahydropyridin-4-yl)thiophene-2-carboxylic acid

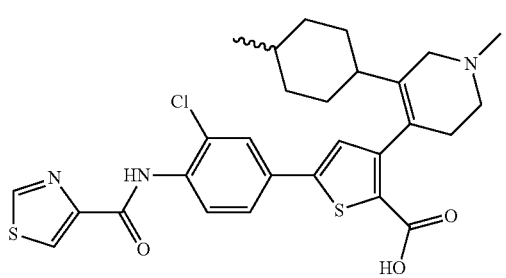

182A was prepared by the same method as 062B, reacting 4-bromo-2-chloroaniline with thiazole-4-carboxylic acid instead of 4-iodobenzoic acid. MS calcd: (M+H)$^+$=319. MS found: (M+H)$^+$=319.

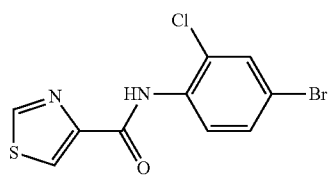

182B was prepared by the same method as 005B, using 182A instead of 005A. MS calcd: (M+H)$^+$=366. MS found: (M+H)$^+$=366.

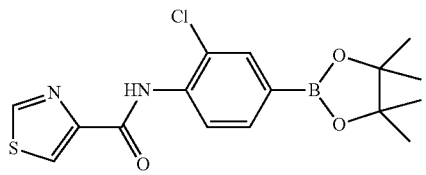

182 was prepared by the same method as 005, using 182B instead of 005B. MS calcd: (M+H)$^+$=557. MS found: (M+H)$^+$=557.

Example 183—3-(1-methyl-5-(4-methylcyclohexyl)-1,2,3,6-tetrahydropyridin-4-yl)-5-(4-(thiazole-4-carboxamido)-3-(trifluoromethyl)phenyl)thiophene-2-carboxylic acid

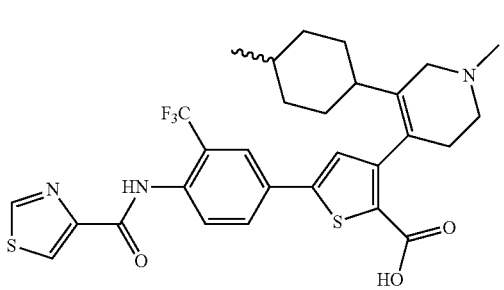

183A was prepared by the same method as 013A, using 2-amino-5-bromobenzotriflouride instead of 004B. MS calcd: (M+H)$^+$=352. MS found; (M+H)$^+$=352.

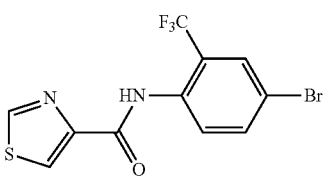

183B was prepared by the same method as 005B, using 183A instead of 005A. MS calcd: (M+H)$^+$=399. MS found: (M+H)$^+$=399.

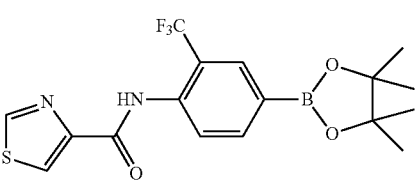

183 was prepared by the same method as 005, using 183B instead of 005B. MS calcd: (M+H)$^+$=591. MS found: (M+H)$^+$=591.

Example 184—5-(4-(5-methoxypyrazolo[1,5-a]pyrimidin-2-yl)phenyl)-3-(1-methyl-5-(4-methylcyclohexyl)-1,2,3,6-tetrahydropyridin-4-yl)thiophene-2-carboxylic acid

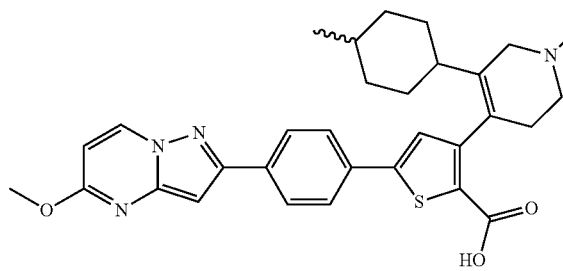
184

A mixture of 3-(4-bromophenyl)-1H-pyrazol-5-amine (714 mg, 3.00 mmol), ethyl 3-ethoxyacrylate (649 mg, 4.50 mmol) and Cs$_2$CO$_3$ (1.47 g, 4.50 mmol) in DMF (20 mL) was heated at 110° C. for 5 hr, cooled to RT, AcOH (10 mL) was added, stirred for 1 hr, sonicated in a mixture of H$_2$O and EtOAc, followed by filtration. The cake was washed with H$_2$O and dried in vacuo overnight. The yellow solid 184A was dissolved in DMF (20 mL) and NaH (60% dispersion in mineral oil, 360 mg, 9.00 mmol) was added in portions. After stirring at RT for 15 min, iodomethane (374 μL, 6.00 mmol) was added and stirring continued for 5 hr. The reaction was quenched with saturated NH$_4$Cl, extracted with EtOAc:MeOH (5:1, v/v), the organic layer was washed with brine, dried over MgSO$_4$, concentrated and column chromatography using 0-5% MeOH/DCM afforded 184B (minor product) and 185A (major product). MS calcd: (M+H)$^+$=305. MS found: (M+H)$^+$=305.

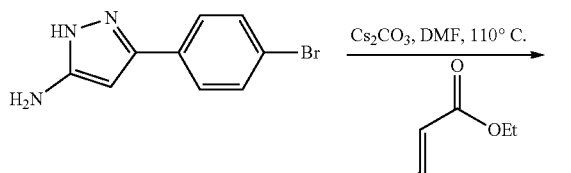

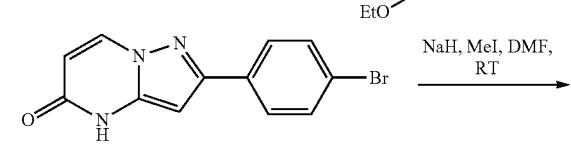
184A

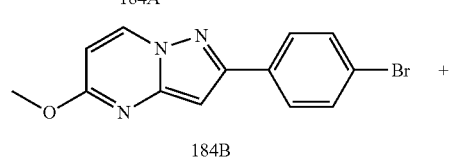
184B

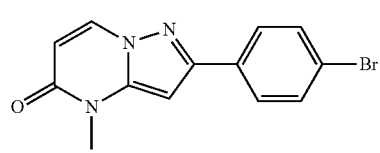
185A 184C was prepared by the same method as 005B, using 184B instead of 005A. MS calcd (M+H)$^+$: 352. MS found (M+H)$^+$:352.

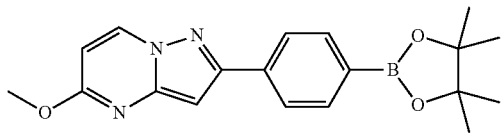
184C 184 was prepared by the same method as 005, using 184C instead of 005B. MS calcd (M+H)$^+$: 544. MS found (M+H)$^+$: 544.

Example 185—3-(1-methyl-5-(4-methylcyclohexyl)-1,2,3,6-tetrahydropyridin-4-yl)-5-(4-(4-methyl-5-oxo-4,5-dihydropyrazolo[1,5-a]pyrimidin-2-yl)phenyl)thiophene-2-carboxylic acid

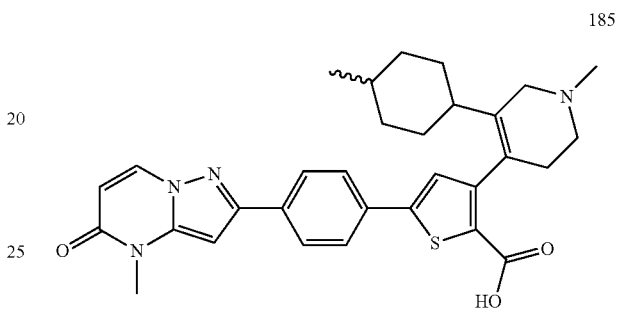
185

185A was prepared along with 184B. MS calcd: (M+H)$^+$=305. MS found: (M+H)$^+$=305.

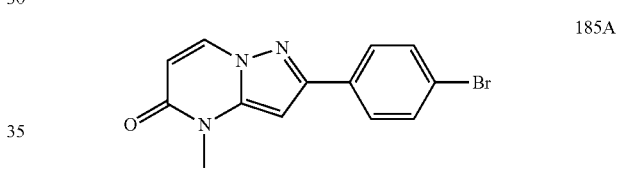
185A 185B was prepared by the same method as 005B, using 185A instead of 005A. MS calcd: (M+H)$^+$=352. MS found: (M+H)$^+$=352.

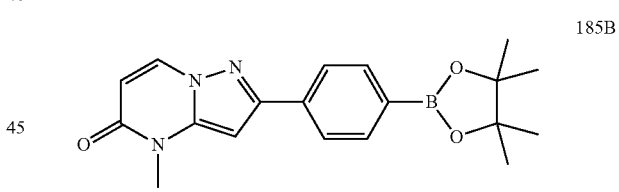
185B 185 was prepared by the same method as 005, using 185B instead of 005B. MS calcd: (M+H)$^+$=544. MS found: (M+H)$^+$=544.

Example 186—3-(1-((1-methyl-1H-pyrazol-4-yl)methyl)-5-(4-methylcyclohexyl)-1,2,3,6-tetrahydropyridin-4-yl)-5-(4-(thiazole-4-carboxamido)phenyl)thiophene-2-carboxylic acid

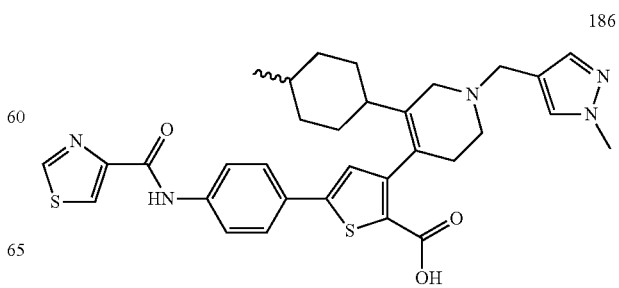
186

186 was prepared by the same method as 130, using 1-methyl-1H-pyrazole-4-carbaldehyde instead of 88e. MS calcd: (M+H)⁺=602. MS found: (M+H)⁺=602.

Example 187—5-(3-methyl-4-(pyrazolo[1,5-a]pyrimidin-2-yl)phenyl)-3-(1-methyl-5-(4-methylcyclohexyl)-1,2,3,6-tetrahydropyridin-4-yl)thiophene-2-carboxylic acid

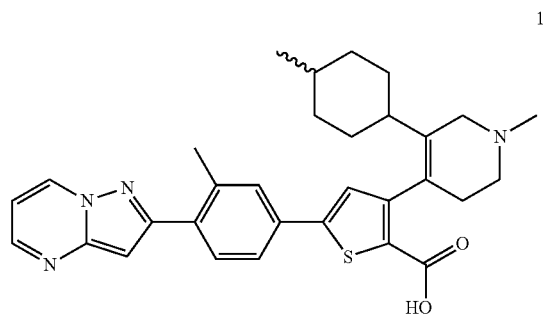

187 was prepared according to the following scheme:

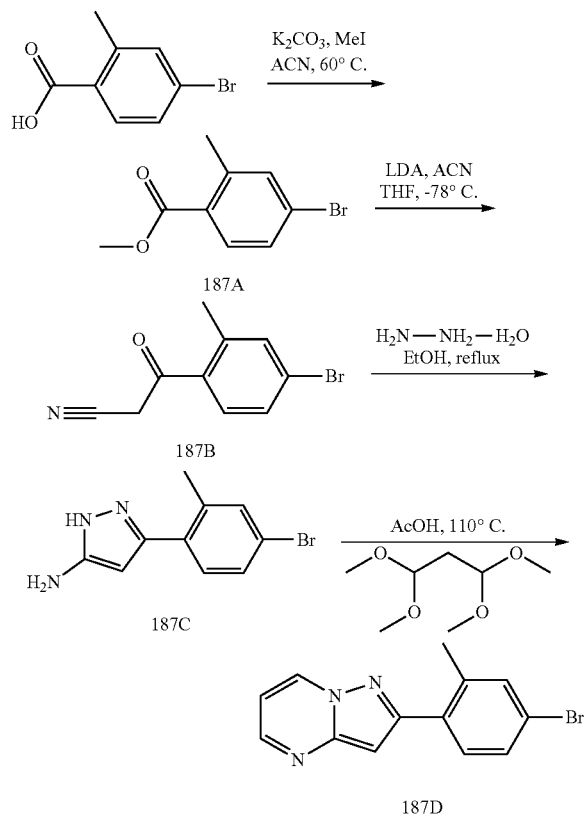

A mixture of 4-bromo-2-methylbenzoic acid (2.15 g, 10 mmol), K₂CO₃ (4.14 g, 30 mmol) and iodomethane (1.87 mL, 30 mmol) in ACN (50 mL) was heated at 60° C. for 3 hr, concentrated, diluted in DCM and filtered through silica plug to afford 187A. Anhydrous ACN (2.05 mL, 39.3 mmol) was added dropwise at −78° C. under N₂ to 2 M lithium diisopropylamide (LDA) in THF/heptane/ethylbenzene (20 mL, 40 mmol) and the stirring at −78° C. for 0.5 hr. A solution of 187A (3 g, 13.10 mmol) in dry THF (6 mL) was added dropwise, stirred at 78° C. for 2.5 hr, quenched with sat. NH₄Cl, extracted with EtOAc:MeOH (5:1, v/v), the organic layer was washed with brine, dried over MgSO₄, and concentrated to afforded 187B, which was mixed together with hydrazine monohydrate and refluxed in EtOH overnight. The mixture was concentrated, followed by column chromatography using 0-10% MeOH/DCM to afford 187C and 187D was prepared by the same method as 005A, using 187C instead of 3-(4-bromophenyl)-1H-pyrazol-5-amine. MS calcd: (M+H)⁺: 289. MS found: (M+H)⁺=289.

187E was prepared by the same method as 005B, using 187D instead of 005A. MS calcd: (M+H)⁺=336. MS found: (M+H)⁺=336.

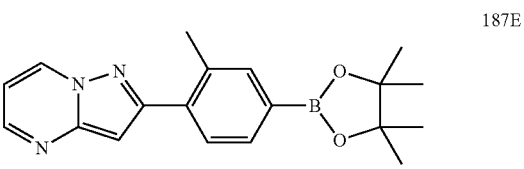 [SMILES: Cc1cc(B2OC(C)(C)C(C)(C)O2)ccc1-c1cc2ncccn2n1]

187 was prepared by the same method as 005, using 187E instead of 005B. MS calcd: (M+H)⁺=528. MS found: (M+H)⁺=528.

Example 188—3-(1-(2-hydroxyethyl)-4-(4-methylcyclohexyl)-1,2,5,6-tetrahydropyridin-3-yl)-5-(4-(thiazole-4-carboxamido)phenyl)thiophene-2-carboxylic acid

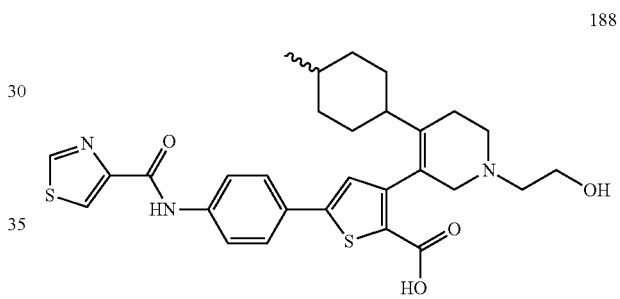

Example 188 was prepared according to the following scheme:

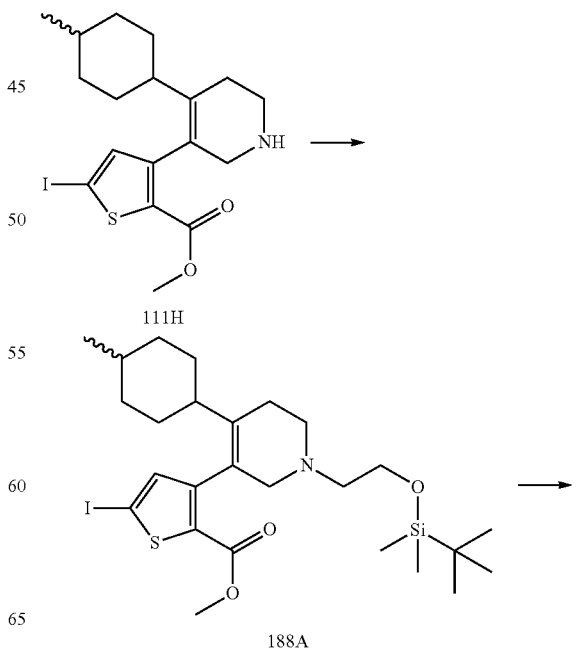

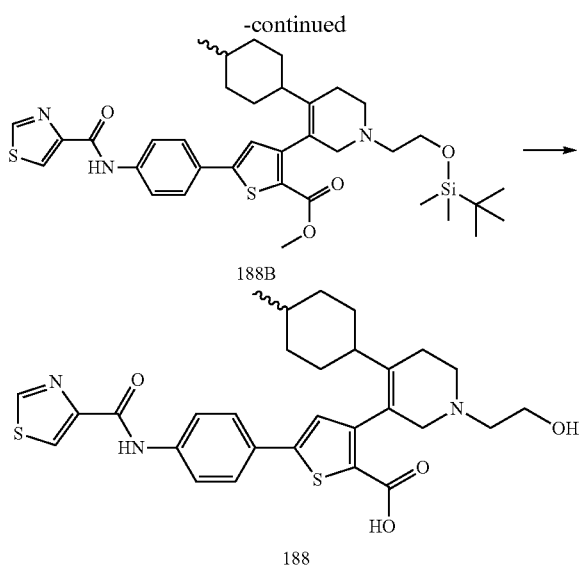

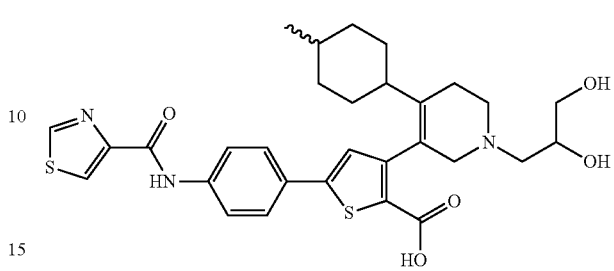

To a solution of 111H (50 mg) in DCE (2 mL) were added (tert-butyldimethylsilyloxy)-acetaldehyde (100 mg), and sodium triacetoxyborohydride (100 mg). The reaction was stirred at RT for 15 hr, and the mixture was filtered through Celite®, rinsed with EtOAc (20 mL), and concentrated to give 188A.

To a mixture of 188A (0.1 mmol), and Pd(dppf)Cl$_2$ (0.003 mmol) under N$_2$ was added DMF (2 mL), water (0.5 mL), Na$_2$CO$_3$ (0.3 mmol), and 159A (0.12 mmol). The coupling reaction was run at 88° C. for 2 hrs. The solution was diluted with water (20 mL) and extracted (2×30 mL) with EtOAc. The organic phases were combined, washed with water (2×15 mL), dried (Na$_2$SO$_4$), evaporated, and purified by column chromatography (0-15%) MeOH in DCM to give 188B.

188B (30 mg) was dissolved in THF (2 mL), water (1 mL), and MeOH (1 mL). LiOH (2 M, 0.5 mL) was then added. The reaction was stirred at RT for 5 hr, and then water (1 mL) and EtOAc (3 mL) were added. The organic layer was separated, concentrated, and lyophilized to give 188. MS calcd: (M+H)$^+$=552. MS found: (M+H)$^+$=552.

Example 189—3-(1-((2,2-dimethyl-1,3-dioxolan-4-yl)methyl)-4-(4-methylcyclohexyl)-1,2,5,6-tetrahydropyridin-3-yl)-5-(4-(thiazole-4-carboxamido)phenyl)thiophene-2-carboxylic acid

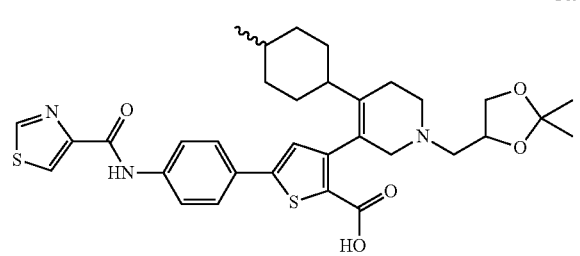

189 was prepared by the same method as 188, using (R)-(+)-2,2-dimethyl-1,3-dioxolane-4-carboxaldehyde instead of (tert-butyldimethylsilyloxy)-acetaldehyde. MS calcd: (M+H)$^+$=622. MS found: (M+H)$^+$=622.

Example 190—3-(1-(2,3-dihydroxypropyl)-4-(4-methylcyclohexyl)-1,2,5,6-tetrahydropyridin-3-yl)-5-(4-(thiazole-4-carboxamido)phenyl)thiophene-2-carboxylic acid

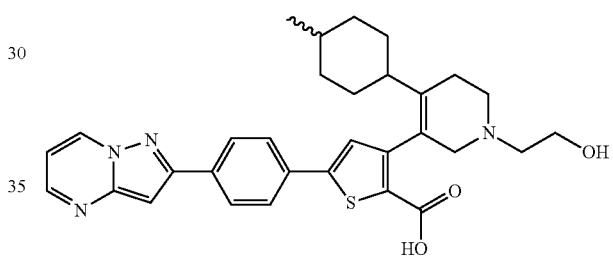

190 was prepared by the hydrolysis of 189, using 6 M HCl and MeOH (1:3 v:v) at RT for 2 hr. Upon completion, the mixture was extracted with EtOAc and washed with NaHCO$_3$, and brine. Concentration and lyophilization gave 190 as an off-white powder. MS calcd: (M+H)$^+$=582. MS found: (M+H)$^+$=582.

Example 191—3-(1-(2-hydroxyethyl)-4-(4-methylcyclohexyl)-1,2,5,6-tetrahydropyridin-3-yl)-5-(4-(pyrazolo[1,5-a]pyrimidin-2-yl)phenyl)thiophene-2-carboxylic acid

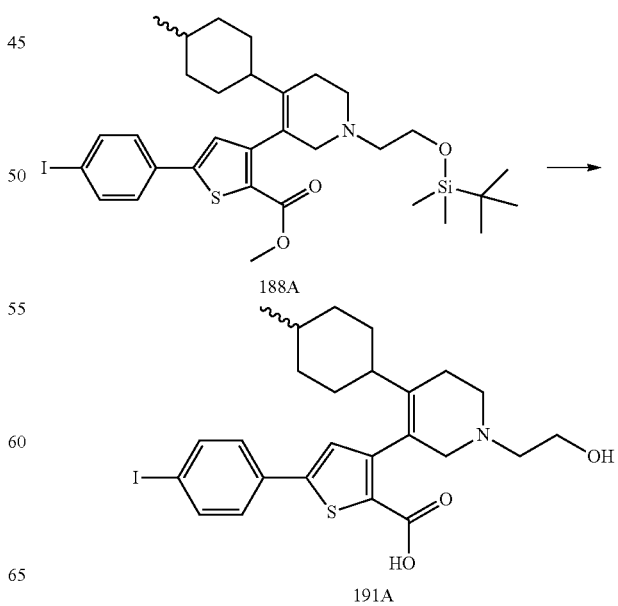

188A (60 mg) was dissolved in THF (2 mL), water (1 mL), and MeOH (1 mL). LiOH (2 M, 0.5 mL) was then added. The reaction was stirred at RT for 5 hr, and then water (1 mL) and EtOAc (3 mL) were added. The organic layer was separated, and concentrated to give 191A.

To a mixture of 191A (0.1 mmol), and Pd(dppf)Cl₂ (0.003 mmol) under N₂ were added DMF (2 mL), water (0.5 mL), Na₂CO₃ (0.3 mmol), and 005B (0.12 mmol). The coupling reaction was run at 88° C. for 4 hr. The solution was diluted with water (20 mL) and extracted (2×30 mL) with EtOAc. The organic phases were combined, dried over Na₂SO₄, evaporated, and purified by column chromatography (0-15%) MeOH in DCM to give 191. MS calcd: (M+H)⁺=543. MS found: (M+H)⁺=543.

Example 192—3-(1-(2,3-dihydroxypropyl)-4-(4-methylcyclohexyl)-1,2,5,6-tetrahydropyridin-3-yl)-5-(4-(pyrazolo[1,5-a]pyrimidin-2-yl)phenyl)thiophene-2-carboxylic acid

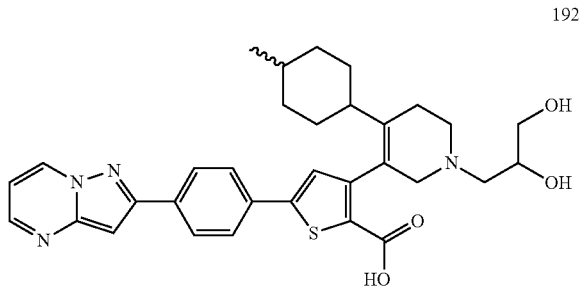 [SMILES: CC1CCC(C2=C(c3cc(-c4ccc(-c5cc6ncccn6n5)cc4)sc3C(=O)O)CN(CC(O)CO)CC2)CC1]

192

To a solution of 111H (60 mg) in DCE (2 mL) were added (R)-(+)-2,2-dimethyl-1,3-dioxolane-4-carboxaldehyde (100 mg), and sodium triacetoxyborohydride (100 mg). The reaction was stirred at RT for 15 hr, and the mixture was filtered through Celite®, rinsed with EtOAc (20 mL), and concentrated to give 189A.

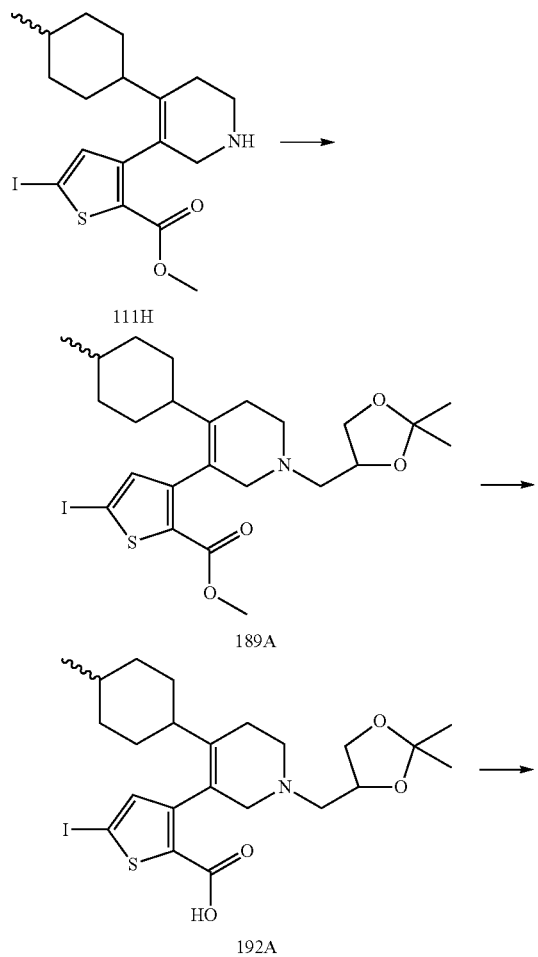

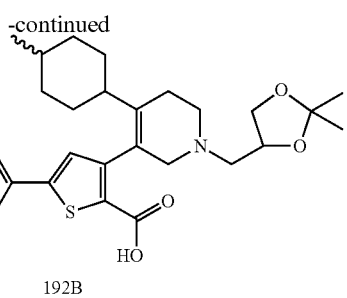

192B 189A (60 mg) was dissolved in THF (2 mL), water (1 mL), and MeOH (1 mL). LiOH (2 M, 0.5 mL) was then added. The reaction was stirred at RT for 5 hr, and then water (1 mL) and EtOAc (3 mL) were added. The organic layer was separated, concentrated, and lyophilized to give 192A.

To a mixture of 192A (0.1 mmol), and Pd(dppf)Cl₂ (0.003 mmol) under N₂ were added DMF (2 mL), water (0.5 mL), Na₂CO₃ (0.3 mmol), and 005B (0.12 mmol). The coupling reaction was run at 88° C. for 2 hrs. The solution was diluted with water (20 mL) and extracted (2×30 mL) with EtOAc. The organic phases were combined, washed with water (2×15 mL), dried (Na₂SO₄), evaporated, and purified by column chromatography (0-15%) MeOH in DCM to give 192B.

Hydrolysis of 192B was carried out by using 6 M HCl and MeOH (1:3 in volume) at RT for 2 hr. The reaction mixture was extracted with EtOAc and washed with NaHCO₃, and brine. Concentration and lyophilization gave 192 as an off-white powder. MS calcd: (M+H)⁺=573. MS found: (M+H)⁺=573.

Example 193—3-(1-((1-methyl-1H-pyrazol-4-yl)methyl)-4-(4-methylcyclohexyl)-1,2,5,6-tetrahydropyridin-3-yl)-5-(4-(thiazole-4-carboxamido)phenyl)thiophene-2-carboxylic acid

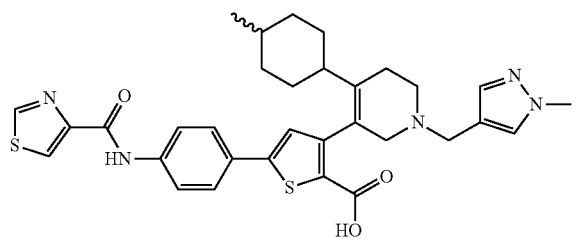

193

193 was prepared by the same method as 188, using 1-methyl-1H-pyrazole-4-carbaldehyde instead of (tert-butyldimethylsilyloxy)-acetaldehyde. MS calcd: (M+H)⁺=602. MS found: (M+H)⁺=602.

Example 194—3-(1-((1-methyl-1H-pyrazol-4-yl)methyl)-4-(4-methylcyclohexyl)-1,2,5,6-tetrahydropyridin-3-yl)-5-(4-(pyrazolo[1,5-a]pyrimidin-2-yl)phenyl)thiophene-2-carboxylic acid

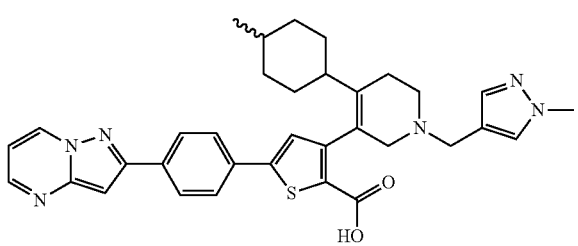

194

194 was prepared by the same method as 191, using 1-methyl-1H-pyrazole-4-carbaldehyde instead (tert-butyldimethylsilyloxy)-acetaldehyde. MS calcd: (M+H)⁺=593. MS found: (M+H)⁺=593.

Example 195—3-(1-((1,3-dimethyl-1H-pyrazol-4-yl)methyl)-4-(4-methylcyclohexyl)-1,2,5,6-tetrahydropyridin-3-yl)-5-(4-(thiazole-4-carboxamido)phenyl)thiophene-2-carboxylic acid (tert-butyldimethylsilyloxy)-acetaldehyde at the first step. MS calcd: (M+H)⁺=616. MS found: (M+H)⁺=616.

Example 196—3-(1-methyl-4-(4-methylcyclohexyl)-1,2,5,6-tetrahydropyridin-3-yl)-5-(3-methyl-4-(thiazole-4-carboxamido)phenyl)thiophene-2-carboxylic acid

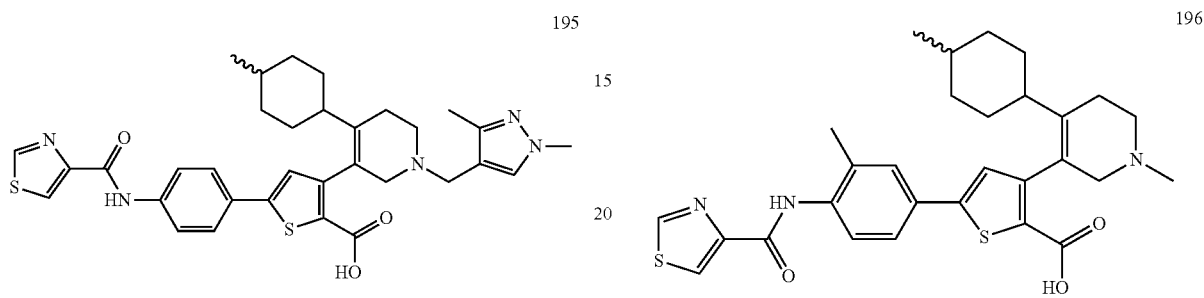

195 was prepared by the same method as 188, using 1,3-dimethyl-1H-pyrazole-4-carboxaldehyde instead of 196 was prepared according to the scheme shown below.

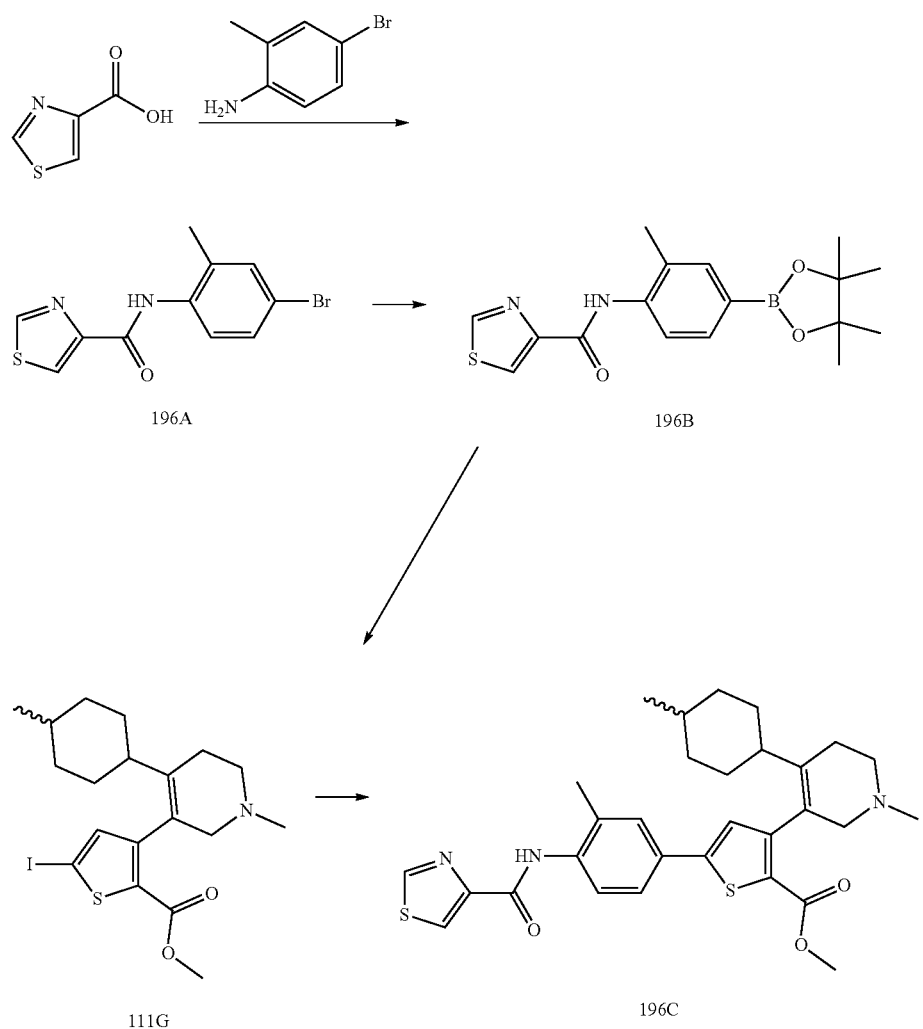

Thiazole-4-carboxylic acid (1.42 g, 11 mmol) in DCM (20 mL) was treated with oxallyl chloride (8 mL, 2 M solution in DCM), followed by 2 drops of DMF. After 1 hr at RT, solvent was evaporated, and the residue was redissolved in DCM (20 mL). To the solution was added 4-bromo-2-methylaniline (1.86 g, 10 mmol) and TEA (2 mL). After 30 min at RT, the reaction mixture was diluted with ether (100 mL), washed with water, sodium bicarbonate, and brine. The organic layer was dried over anhydrous $MgSO_4$, filtered, concentrated and purified to give 196A.

A mixture of 196A (1 g), bis(pinacolato)diboron (1.5 g), AcOK (1.1 g) and $Pd(dppf)Cl_2$ (0.1 g) in dry 1,4-dioxane (20 mL) was heated to 100° C. under $N_2$ for 15 hr. The solvent was evaporated and the residue partitioned between water (10 mL) and DCM (30 mL). The aqueous phase was extracted further with DCM (20 mL) and the combined organic layers were evaporated. The residue was purified by SPE chromatography, eluting with cyclohexane/EtOAc (3:1) to give 196B. MS calcd: $(M+H)^+=345$. MS found: $(M+H)^+=345$.

To a mixture of 111G (0.1 mmol), and $Pd(dppf)Cl_2$ (0.003 mmol) under $N_2$, were added DMF (2 mL), water (0.5 mL), $Na_2CO_3$ (0.3 mmol), and 196B (0.12 mmol). The coupling reaction was run at 88° C. for 2 hr. The solution was diluted with water (20 mL) and extracted (2×30 mL) with EtOAc. The organic phases were combined, washed with water (2×15 mL), dried ($Na_2SO_4$), evaporated, and purified by column chromatography (0-15%) MeOH in DCM to give 196C.

196C (30 mg) was dissolved in THF (2 mL), water (1 mL), and MeOH (1 mL). LiOH (2 M, 0.5 mL) was then added. The reaction was stirred at RT for 5 hr, and then water (1 mL) and EtOAc (3 mL) were added. The organic layer was separated, concentrated, and lyophilized to give 196. MS calcd: $(M+H)^+=536$. MS found: $(M+H)^+=536$.

Example 197—3-(1-(2-hydroxyethyl)-4-(4-methylcyclohexyl)-1,2,5,6-tetrahydropyridin-3-yl)-5-(3-methyl-4-(thiazole-4-carboxamido)phenyl)thiophene-2-carboxylic acid

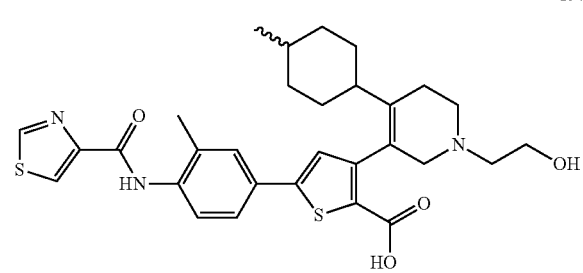

197

197 was prepared by the same method as 196, using 188A instead of 111G. MS calcd: $(M+H)^+=566$. MS found: $(M+H)^+=566$.

Example 198—5-(3-fluoro-4-(thiazole-4-carboxamido)phenyl)-3-(1-methyl-4-(4-methylcyclohexyl)-1,2,5,6-tetrahydropyridin-3-yl)thiophene-2-carboxylic acid

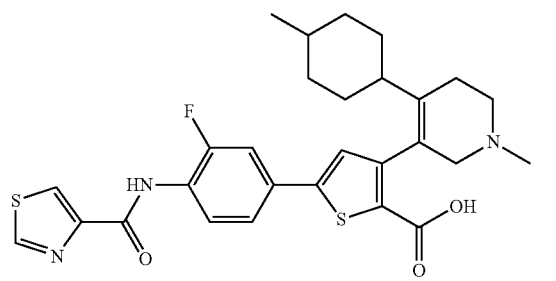

198

198 was prepared by the same method as 059, using 111G instead of 002G. MS calcd: $(M+H)^+=540$. MS found: $(M+H)^+=540$.

Example 199—3-(1-((1-methyl-1H-pyrazol-4-yl)methyl)-4-(4-methylcyclohexyl)-1,2,5,6-tetrahydropyridin-3-yl)-5-(3-methyl-4-(thiazole-4-carboxamido)phenyl)thiophene-2-carboxylic acid

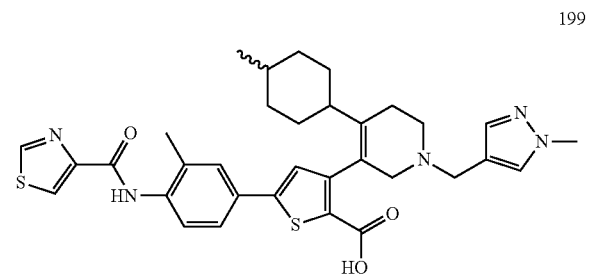 [SMILES: Cc1cc(-c2cc(C3=C(C4CCC(C)CC4)CCN(Cc4cnn(C)c4)C3)c(C(=O)O)s2)ccc1NC(=O)c1cscn1]

199

199 was prepared by the same method as 188, using 1-methyl-1H-pyrazole-4-carbaldehyde and 196B instead (tert-butyldimethylsilyloxy)-acetaldehyde. MS calcd: $(M+H)^+=616$. MS found: $(M+H)^+=616$.

Example 200—3-(4-(4,4-difluorocyclohexyl)-1-methyl-1,2,5,6-tetrahydropyridin-3-yl)-5-(4-(thiazole-4-carboxamido)phenyl)thiophene-2-carboxylic acid

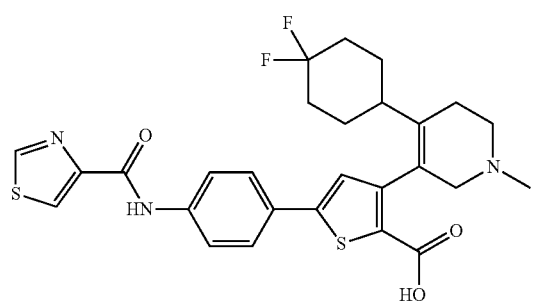

200

200 was prepared according to the following scheme:

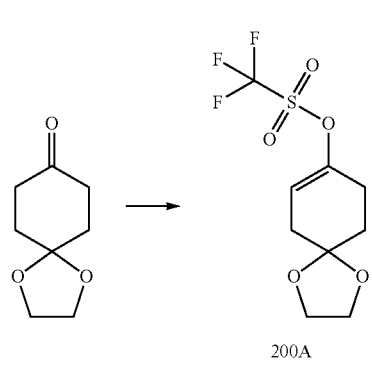
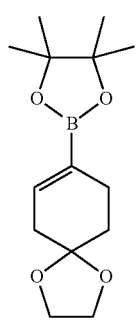
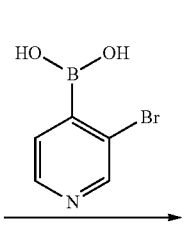
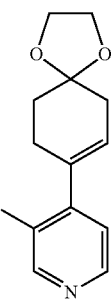
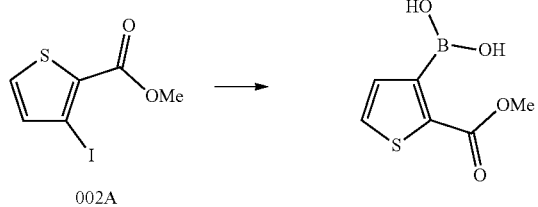
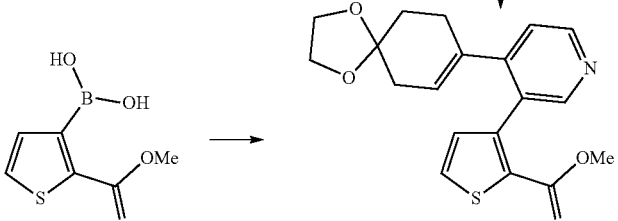
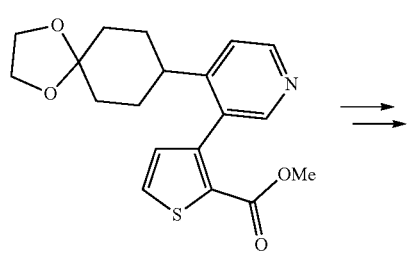
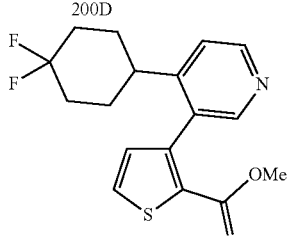
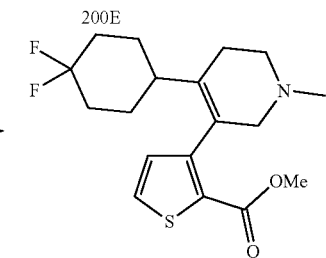
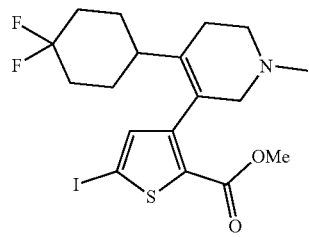
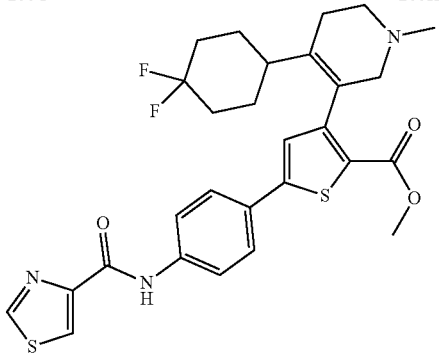
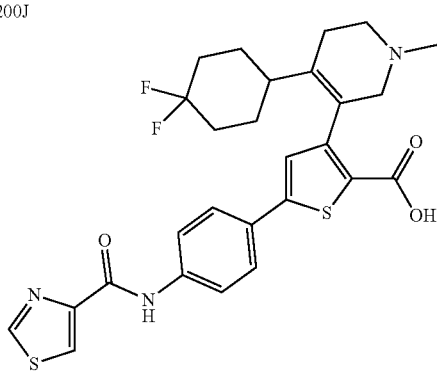

To a stirred solution of 1,4-cyclohexanedione monoethylene acetal (2.7 g, 17.8 mmol) and n-phenyltrifluoromethane-sulfonimide (7.6 g, 21.36 mmol) in THF (77 mL) under $N_2$ at −78° C., was added 1 M sodium bis-trimethylsilylamide in THF (20.0 mL, 19.6 mmol). The reaction was stirred 8 hr, then quenched with $H_2O$, and extracted with ether. The combined ether extract layers were dried over $MgSO_4$, filtered and purified by silica gel chromatography to give 200A as a colorless oil.

To a stirred solution of 200A (2.59 g, 9 mmol) in dioxane (38 mL) was added his (pinacolato)diboron (2.74 g, 10.8 mmol), [1,1'-bis(diphenylphosphino)ferrocene]dichloropalladium(II) (Pd(dppf)Cl$_2$; 0.197 g, 0.27 mmol), 1,1'-bis(diphenylphosphino)ferrocene (0.150 g, 0.27 mmol), and AcOK (2.64 g, 27 mmol). The mixture was degassed by evacuating the reaction flask under vacuum followed by $N_2$ back-fill (3×). Under $N_2$, the reaction was then heated to 90° C. and stirred overnight (approx. 16 hr). The reaction was cooled to RT and diluted with $H_2O$. The mixture was extracted with EtOAc (3×). The combined organic layers were washed with brine, dried over $MgSO_4$, filtered, and then purified by silica gel chromatography to give 200B as clear oil.

DMF (10 mL) and $H_2O$ (2 mL) were added to a mixture of 3-bromopyridine-4-boronic acid (0.3 g, 1.5 mmol), 200B (0.61 g, 1.77 mmol), Pd(dppf)Cl$_2$ (0.065 g, 0.089 mmol), and $Na_2CO_3$ (0.563 g, 5.31 mmol) under $N_2$ and stirred at 88° C. for 3 hr. The reaction was cooled to RT, and to it was added ice-water and EtOAc. The layers were separated and the aqueous layer was back-extracted with EtOAc (2×). The combined organic layers were then washed with brine, dried over anhydrous $Na_2SO_4$, filtered over Celite®, and concentrated under reduced pressure. The product was purified by flash chromatography (silica gel) eluting with 0-5% methanol (MeOH) in $CH_2Cl_2$ to give 200C as an off-white solid.

To a stirred solution of 002A (2.41 g, 9 mmol) in dioxane (38 mL) was added bis (pinacolato)diboron (2.74 g, 10.8 mmol), Pd(dppf)Cl$_2$ (0.197 g, 0.27 mmol), dppf (0.150 g, 0.27 mmol), and AcOK (2.64 g, 27 mmol). The mixture was degassed by evacuating the reaction flask under vacuum followed by $N_2$ back-fill (3×). Under $N_2$, the reaction was then heated to 90° C. and stirred overnight (approx. 16 hr). The reaction was cooled to RT and diluted with $H_2O$. The mixture was extracted with EtOAc (3×). The combined organic layers were washed with brine, dried over $MgSO_4$, filtered, and then purified by silica gel chromatography to give 200D as a solid.

DMF (10 mL) and $H_2O$ (2 mL) were added to a mixture of 200C (0.41 g, 1.4 mmol), 200D (0.20 g, 1 mmol), Pd(dppf)Cl$_2$ (0.033 g, 0.0455 mmol), and $Na_2CO_3$ (0.3 g, 2.8 mmol) under Nz and stirred at 88° C. for 3 hr. The reaction was cooled to RT, and to it was added ice-water and EtOAc. The layers were separated and the aqueous layer was back-extracted with EtOAc (2×). The combined organic layers were washed with brine, dried over anhydrous $Na_2SO_4$, filtered over Celite®, and concentrated under reduced pressure. The residue was purified by flash chromatography (silica gel) eluting with 0-5% MeOH in $CH_2Cl_2$ to give 200E as a solid.

200E (110 mg, 0.31 mmol) was dissolved in MeOH (15 mL), and 10% Pd/C (20 mg) was added as the catalyst. Hydrogenation under 50 psi $H_2$ was run overnight. Filtration and concentration gave 200F.

A solution of 200F (100 mg, 0.3 mmol, 1.0 equiv.) was treated with 6M HCl in MeOH at 60.deg. C. and then concentrated to dryness. The crude oil was again dissolved in $CH_2Cl_2$ (5 mL) and was treated at 0° C. with DAST (1.2 mmol). After being stirred at 0° C. for 30 min and at 25° C. for 48 hr, the reaction mixture was diluted ($CH_2Cl_2$), washed (1× saturated aqueous $NaHCO_3$, and 1× brine), dried ($Na_2SO_4$), and concentrated under reduced pressure. Flash chromatography of the residue (SiO$_2$, 10percent EtOAc/Hexanes) provided 200G as a yellow solid.

Methyl iodide (0.08 mL, 1.278 mmol) was added to a solution of 200G (60 mg, 0.17 mmol) in ACN (5 mL) and the mixture was stirred for 3 hr at 80° C. The reaction mixture was cooled to RT and concentrated in vacuo. The crude intermediate 200G1 was used directly in the next step.

Sodium borohydride (42 mg, 1.1 mmol) was added to a solution of 200G1 (60 mg, 0.175 mmol) in MeOH (6 mL) at RT with constant stirring. The reaction mixture was stirred overnight at 80° C. The reaction mixture was quenched with water (20 mL) and extracted with EtOAc (3×20 mL). The organic layers were combined, dried over anhydrous $Na_2SO_4$, and concentrated to obtain 200H as yellow oil.

A solution of 200H (50 mg, 0.14 mmol) in dry THF (4 mL) was added at −77° C. under $N_2$ to 2 M lithium diisopropylamide (LDA) in THF/heptane/ethylbenzene (0.01 mL) maintaining an internal temperature <−70° C. The stirring was continued at −77° C. for 2.5 hr. A solution of iodine (23 mg) was added to the stirred reaction mixture maintaining an internal temperature <−70° C. After stirring under $N_2$ at −77° C. for 1.5 hr, the reaction mixture was quenched by addition of saturated $NH_4Cl$ solution and warmed to 0° C. The mixture was diluted with 5% sodium thiosulfate solution, then the organic phase was separated and the aqueous phase was extracted with EtOAc. The combined organic phases were dried ($Na_2SO_4$), filtered, and evaporated. The product was dried to give 200I.

To a mixture of 200I (0.1 mmol), and Pd(dppf)Cl$_2$ (0.003 mmol) under $N_2$ were added DMF (2 mL), water (0.5 mL), $Na_2CO_3$ (0.3 mmol), and 159A (0.12 mmol). The coupling reaction was run at 88° C. for 2 hrs. The solution was diluted with water (2 mL) and extracted (2×3 mL) with EtOAc. The organic phases were combined, washed with water (2×1.5 mL), dried ($Na_2SO_4$), evaporated, and purified by column chromatography (0-5%) MeOH in DCM to give 200J.

200J (20 mg) was dissolved in THF (2 mL) and EtOH (1 mL). LiOH (2 M, 0.5 mL) was then added. The reaction was stirred at RT for 16 hr, and then diluted with EtOAc. The organic layer was washed with water and concentrated. The final product was precipitated in hexane and washed more with hexane. The powder of 200 was obtained after lyophilization. MS calcd: (M+H)$^+$=544. MS found: (M+H)$^+$=544.

Example 201—3-(5-(2,4-dichlorophenyl)-1-methyl-1,2,3,6-tetrahydropyridin-4-yl)-5-(4-(thiazole-4-carboxamido)phenyl)thiophene-2-carboxylic acid

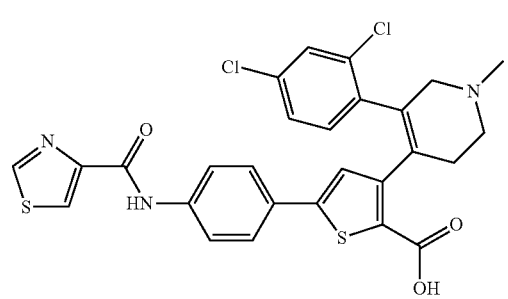
201

201 was prepared according to the following scheme.

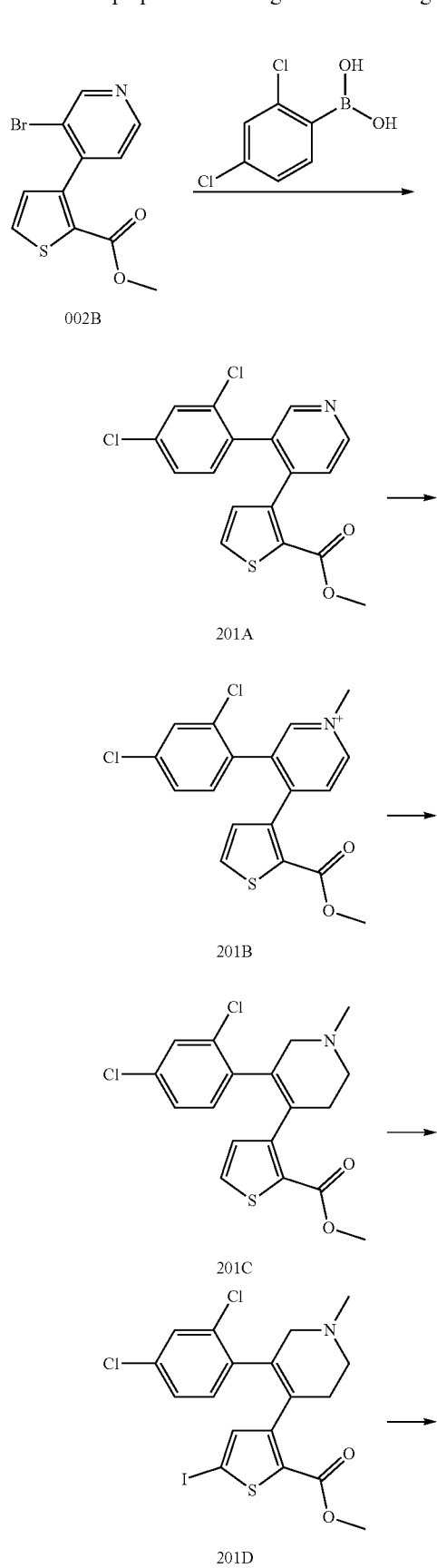

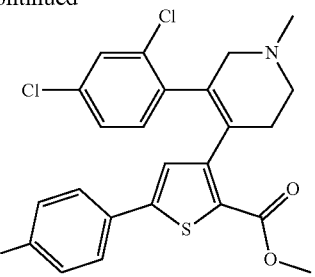

DMF (10 mL) and H$_2$O (2 mL) were added to a mixture of 2,4-dichlorophenylboronic acid (0.26 g, 1.4 mmol), 002B (0.27 g, 0.91 mmol), Pd(dppf)Cl$_2$ (0.033 g, 0.0455 mmol), and Na$_2$CO$_3$ (0.3 g, 2.8 mmol) under N$_2$, and the mixture was stirred at 92° C. for 4 hr. The reaction was cooled to RT, and to it was added ice-water and EtOAc. The organic layer was washed with water (3×) and the combined aqueous layers were back-extracted with EtOAc (2×). The combined organic layers were washed with brine, dried over anhydrous Na$_2$SO$_4$, and concentrated under reduced pressure. The product was purified by flash chromatography (silica gel), eluting with 0-5% MeOH in CH$_2$Cl$_2$ to give 201A as a solid. MS calcd: (M+H)$^+$=365. MS found: (M+H)$^+$=365.

Methyl iodide (0.04 mL, 1.278 mmol) was added to a solution of (93 mg, 0.256 mmol) of 201A in 5 mL of ACN, and the mixture was stirred for 3 hr at 80° C. The reaction mixture was cooled to RT and concentrated in vacuo. The crude 201B was used directly in the next step.

Sodium borohydride (42 mg, 1.1 mmol) was added to a solution of 201B (110 mg, 0.275 mmol) in MeOH (6 mL) at RT with constant stirring. The reaction mixture was stirred overnight at 80° C. The reaction mixture was quenched with water (20 mL) and extracted with EtOAc (3×20 mL). The organic layers were combined, dried over anhydrous Na$_2$SO$_4$, and concentrated to obtain the compound as brown oil, which was purified by column chromatography (silica gel, 0-10% MeOH in CH$_2$Cl$_2$) to yield 201C.

A solution of 201C (1 g, 3 mmol) in dry THF (10 mL) was added dropwise at −77° C. under N$_2$ to 2 M lithium diisopropylamide (LDA) in THF/heptane/ethylbenzene (3 mL) maintaining an internal temperature <−70° C. The stirring was continued at −77° C. for 2.5 hr. A solution of iodine (2.3 g) in dry THF (5 mL) was added dropwise to the stirred reaction mixture maintaining an internal temperature <−70° C. After stirring under N$_2$ at −77° C. for 1.5 hr, the reaction mixture was quenched by addition of saturated NH$_4$Cl solution and warmed to 0° C. The mixture was diluted with 5% sodium thiosulfate solution, then the organic phase was separated and the aqueous phase was extracted with EtOAc. The combined organic phases were dried (Na$_2$SO$_4$), filtered, and evaporated. The product was dried to give 201D.

To a mixture of 201D (0.1 mmol), and Pd(dppf)Cl$_2$ (0.003 mmol) under N$_2$ were added DMF (2 mL), water (0.5 mL), Na$_2$CO$_3$ (0.3 mmol), and 159A (0.12 mmol). The coupling reaction was run at 88° C. for 2 hrs. The solution was diluted with water (20 mL) and extracted (2×30 mL) with EtOAc. The organic phases were combined, washed with water (2×15 mL), dried (Na$_2$SO$_4$), evaporated, and purified by column chromatography (0-15%) MeOH in DCM to give 201E.

201E (30 mg) was dissolved in THF (2 mL) and EtOH (1 mL). LiOH (2 M, 0.5 mL) was then added. The reaction was stirred at RT for 16 hr, and then diluted with EtOAc. The organic layer was washed with water and concentrated. The final product was precipitated in hexane and washed more with hexane. The powder of 201 was obtained after lyophilization. MS calcd: (M+H)$^+$=571. MS found: (M+H)$^+$=571.

Example 202—3-(1-methyl-5-(p-tolyl)-1,2,3,6-tetrahydropyridin-4-yl)-5-(4-(thiazole-4-carboxamido)phenyl)thiophene-2-carboxylic acid

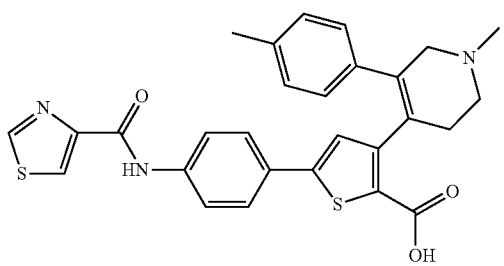

202 was prepared by the same method as 201, using p-tolylboronic acid instead of 2,4-dichlorophenylboronic acid. MS calcd: (M+H)$^+$=516. MS found: (M+H)$^+$=516.

Example 203—5-(6-aminopyridin-3-yl)-3-(1-methyl-5-(4-methylcyclohexyl)-1,2,3,6-tetrahydropyridin-4-yl)thiophene-2-carboxylic acid

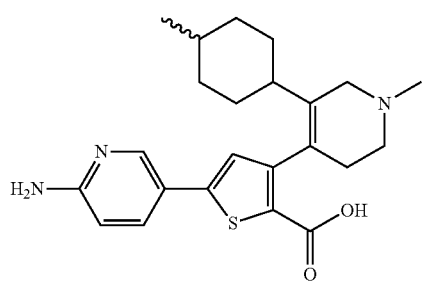

DMF (10 mL) and water (2 mL) were added to a mixture of 4-carboxyphenylboronic acid (0.23 g, 1.4 mmol), 002G (0.43 g, 0.9 mmol), Pd(dppf)Cl$_2$ (0.033 g, 0.0455 mmol), and Na$_2$CO$_3$ (0.3 g, 2.8 mmol) under N$_2$, and stirred at 92° C. for 4 hr. The reaction was cooled to RT, and to it was added ice-water and EtOAc. The organic layer was washed with water (3×) and the combined aqueous layers were back-extracted with EtOAc (2×). The combined organic layers were washed with brine, dried over anhydrous Na$_2$SO$_4$, and concentrated under reduced pressure. The product was purified by flash chromatography (silica gel), eluting with 0-5% MeOH in CH$_2$Cl$_2$ to give 203A. MS calcd: (M+H)$^+$=468. MS found: (M+H)$^+$=468.

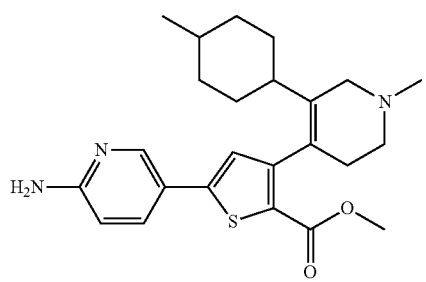

203A (25 mg) was dissolved in THF (2 mL) and EtOH (1 mL). LiOH (2 M, 0.5 mL) was then added. The reaction was stirred at RT for 16 hr, and then diluted with EtOAc. The organic layer was washed with water and concentrated. The final product was precipitated out in hexane and washed more with hexane. The powder of 203 was obtained with lyophilization. MS calcd: (M+H)$^+$=412. MS found: (M+H)$^+$=412.

Example 204—3-(1-methyl-5-(4-methylcyclohexyl)-1,2,3,6-tetrahydropyridin-4-yl)-5-(6-(thiazole-4-carboxamido)pyridin-3-yl)thiophene-2-carboxylic acid

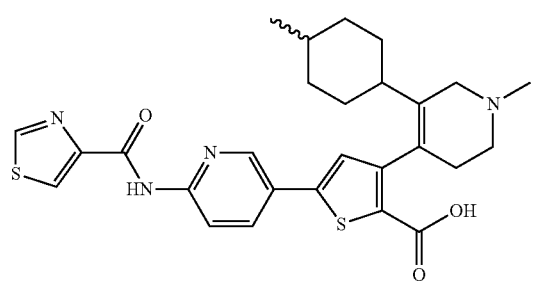

1,3-Thiazole-4-carboxylic acid (20 mg) was dissolved in DMF (3 mL). HATU (65 mg) and DIPEA (0.06 mL) were added and the reaction mixture was stirred at RT for 15 min. 203 (41 mg, 0.1 mmol) was added and the reaction mixture was stirred at RT for 1 hr. The mixture was evaporated in vacuo and the residue was dissolved in DCM. The resulting mixture was washed with saturated NaHCO$_3$ solution (2×) followed by 2 N HCl (2×). The DCM was separated and concentrated to obtain the compound as a brown oil, which was purified by column chromatography to give 204. MS calcd: (M+H)$^+$=523. MS found: (M+H)$^+$=523.

Example 205—3-(5-Cyclohexyl-1-methyl-1,2,3,6-tetrahydro-pyridin-4-yl)-5-{4-[(thiazole-4-carbonyl)-amino]-phenyl}-thiophene-2-carboxylic acid

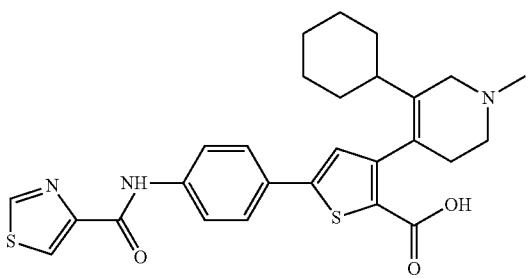

205 was prepared according to the following scheme:

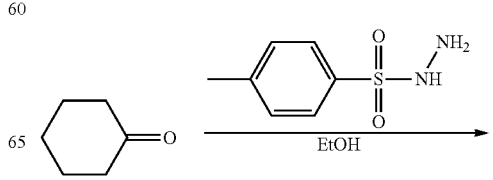

-continued

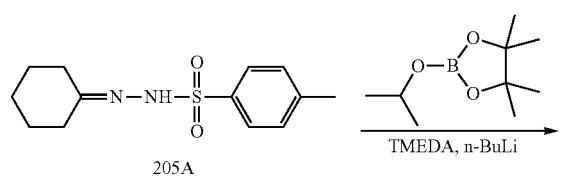
205A

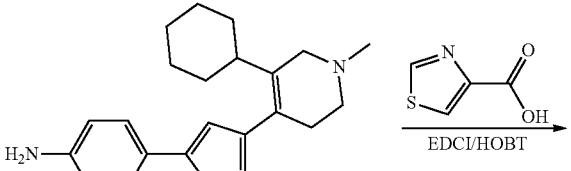
205G

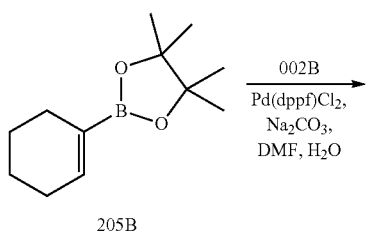
205B

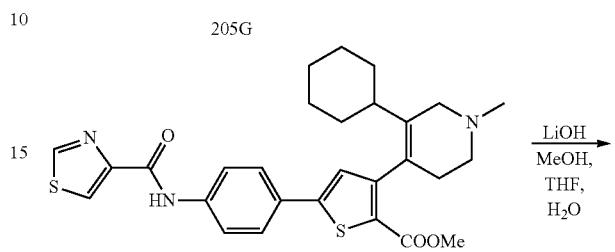
205H

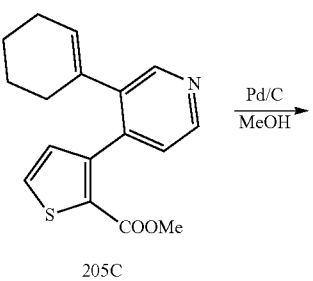
205C

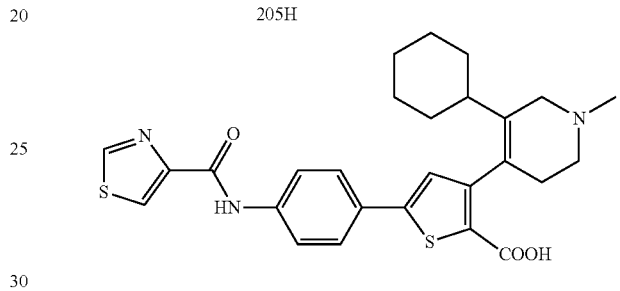
205

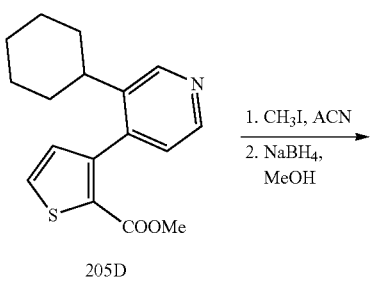
205D

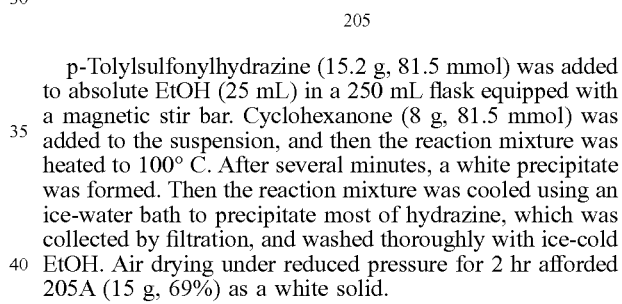

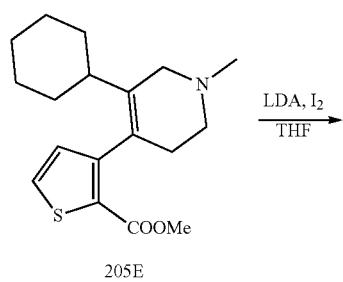
205E

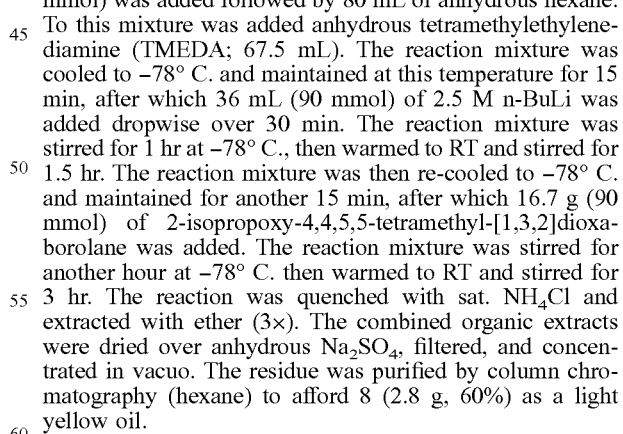

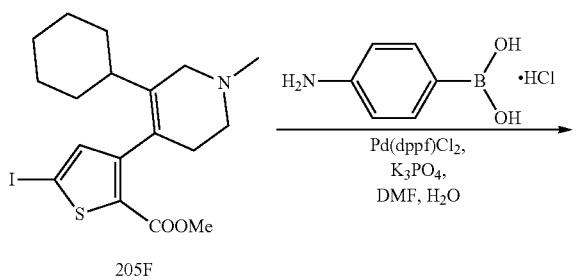
205F p-Tolylsulfonylhydrazine (15.2 g, 81.5 mmol) was added to absolute EtOH (25 mL) in a 250 mL flask equipped with a magnetic stir bar. Cyclohexanone (8 g, 81.5 mmol) was added to the suspension, and then the reaction mixture was heated to 100° C. After several minutes, a white precipitate was formed. Then the reaction mixture was cooled using an ice-water bath to precipitate most of hydrazine, which was collected by filtration, and washed thoroughly with ice-cold EtOH. Air drying under reduced pressure for 2 hr afforded 205A (15 g, 69%) as a white solid.

To a flame-dried 500-mL round-bottom flask equipped with a magnetic stir bar and rubber septum, 205A (6 g, 22.5 mmol) was added followed by 80 mL of anhydrous hexane. To this mixture was added anhydrous tetramethylethylenediamine (TMEDA; 67.5 mL). The reaction mixture was cooled to −78° C. and maintained at this temperature for 15 min, after which 36 mL (90 mmol) of 2.5 M n-BuLi was added dropwise over 30 min. The reaction mixture was stirred for 1 hr at −78° C., then warmed to RT and stirred for 1.5 hr. The reaction mixture was then re-cooled to −78° C. and maintained for another 15 min, after which 16.7 g (90 mmol) of 2-isopropoxy-4,4,5,5-tetramethyl-[1,3,2]dioxaborolane was added. The reaction mixture was stirred for another hour at −78° C. then warmed to RT and stirred for 3 hr. The reaction was quenched with sat. NH$_4$Cl and extracted with ether (3×). The combined organic extracts were dried over anhydrous Na$_2$SO$_4$, filtered, and concentrated in vacuo. The residue was purified by column chromatography (hexane) to afford 8 (2.8 g, 60%) as a light yellow oil.

A mixture of 002B (0.5 g, 1.68 mmol), 205B (0.538 g, 2.52 mmol) and Na$_2$CO$_3$ (0.533 g, 5.04 mmol) in DMF/H$_2$O (5 mL/1 mL) was degassed and placed under argon atmosphere (Ar). Pd(dppf)Cl$_2$ (61 mg, 168 μmol) was added under Ar. The mixture was stirred at 80° C. for 3 hr. The reaction mixture was cooled to RT, diluted in EtOAc and washed with H$_2$O. The combined organic layers were washed with brine, dried over Na$_2$SO$_4$, filtered and concentrated to give the crude product which was purified by column chromatography to give 205C (0.36 g, 68%) as a yellow solid.

A mixture of 205C (250 mg, 83.6 mmol) and 10% Pd/C (wet, 330 mg) in MeOH (8 mL) was stirred for 6 days at RT under $H_2$ (0.5 MPa). When the reaction finished, the mixture was filtered to remove the catalyst and the filtrate was concentrated to give 205D (200 mg, 79%) as a yellow oil.

A mixture of 205D (125 mg, 0.417 mmol) and $CH_3I$ (0.592 mg, 4.17 mmol) in ACN (15 mL) was refluxed at 80° C. The resultant reaction mixture was concentrated in vacuo to give the quaternary ammonium salt, which was then dissolved in MeOH (15 mL). The resulting solution was cooled to 0° C., and $NaBH_4$ (158 mg, 4.17 mmol) was added. Then the reaction mixture was allowed to warm to RT and heated to 80° C. for 6 hr. When TLC analysis indicated no further consumption of the quaternary ammonium salt, the solvent was removed and the residue was purified by column chromatography to give 205E (94 mg, 71%) as a yellow oil.

n-BuLi (187 μL, 469.54 μmol) was added dropwise to diisopropylamine (54.8 μL, 391.28 μmol) in THF (6 mL) at −20° C. under Ar, and the mixture was stirred for 1 hr at −20° C. 205E (50 mg, 156.51 μmol) in THF (10 mL) was added to the lithium diisopropylamide (LDA) mixture at −78° C. and stirred for 2.5 hr. $I_2$ (119.17 mg, 469.54 μmol) in THF (10 mL) was added to the solution and stirred for 1.5 hr at −78° C., then allowed to warm to RT and stirred overnight. The reaction mixture was quenched with sat. $NH_4Cl$, diluted in 5% $Na_2S_2O_3$, extracted with EtOAc, washed with brine, dried over $Na_2SO_4$, and concentrated to afford the crude product 205F (71 mg), which was used without further purification.

A mixture of 205F (50 mg, 112 μmol), (4-aminophenyl) boronic acid hydrochloride (29.06 mg, 168 μmol) and $K_3PO_4$ (71.5 mg, 336.81 μmol) in $DMF/H_2O$ (1 mL/0.2 mL) was degassed and placed under Ar. $Pd(dppf)Cl_2$ (4.1 mg, 5.6 μmol) was added under Ar. The mixture was stirred at 88° C. for 4 hr. The reaction mixture was cooled to RT, diluted in EtOAc and washed with $H_2O$. The combined organic layers were washed with brine, dried over $Na_2SO_4$, filtered and concentrated to give the crude product, which was purified by prep-TLC to give 205G (40 mg, 86.9%) as a brown oil.

A mixture of 205G (40 mg, 97.43 μmol), thiazole-4-carboxylic acid (18.87 mg, 146.14 μmol), EDCI (28 mg, 146.14 μmol) and hydroxybenzotriazole (HOBT; 19.75 mg, 146.14 μmol) in DCM (5 mL) was stirred at RT overnight. The reaction mixture was diluted in DCM and washed with $H_2O$. The combined organic layers were washed with brine, dried over $Na_2SO_4$, filtered and concentrated to give the crude product which was purified by prep-TLC to give 205H (12 mg, 23.6%) as a yellow solid.

A mixture of 205H (12 mg, 23 μmol), LiOH (1 N, 100 μL), MeOH (0.6 mL), $H_2O$ (0.1 mL) and THF (0.3 mL) was stirred for 3 days at RT. The reaction mixture was concentrated, and then diluted in 5 mL $H_2O$ and extracted with ether. Then aqueous phase was acidified by the addition of 1 N HCl to pH 3-4, then extracted with EtOAc, washed with brine, dried over $Na_2SO_4$ and concentrated to give the title compound (6.8 mg, 58.1%) as a yellow oil. MS calcd: $(M+H)^+=508.7$. MS found: $(M+H)^+=508.7$.

Example 206—3-(5-Cycloheptyl-1-methyl-1,2,3,6-tetrahydro-pyridin-4-yl)-5-phenyl-thiophene-2-carboxylic acid

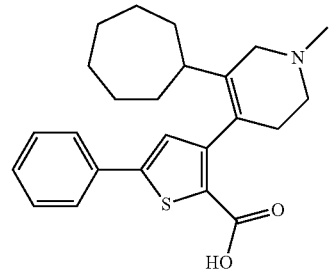

206

206 was prepared according to the following scheme.

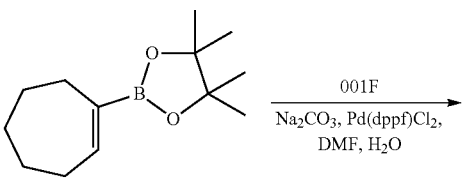

206A

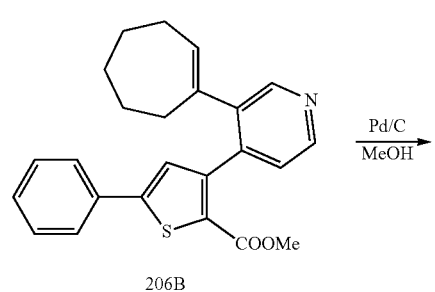

206B

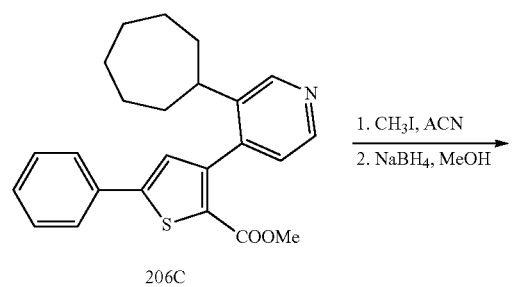

206C

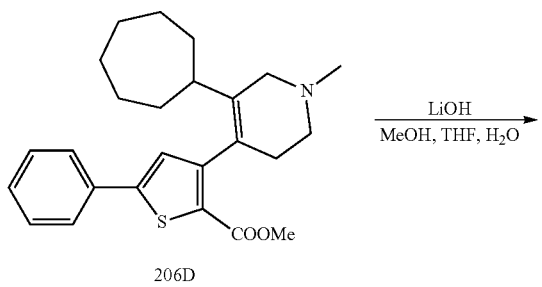

206D

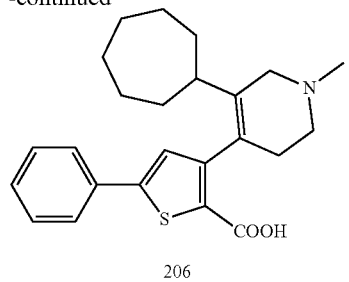

206

206A was prepared by the same method as 205B, using cycloheptanone instead of cyclohexanone.

A mixture of 001F (40 mg, 107.2 μmol), 206A (119.1 mg, 536.2 μmol) and Na$_2$CO$_3$ (34.1 mg, 321.6 μmol) in DMF/H$_2$O (2 mL/0.6 mL) was degassed and placed under Ar atmosphere. Pd(dppf)Cl$_2$ (3.9 mg, 5.36 μmol) was added under Ar atmosphere. The mixture was stirred for 3 hr at 80° C. The reaction mixture was cooled to RT, diluted in EtOAc and washed with H$_2$O. The combined organic layers were washed with brine, dried over Na$_2$SO$_4$, filtered and concentrated to give the crude product which was purified by column chromatography to give 206B (36.9 mg, 88.5%) as a yellow solid.

A mixture of 206B (36.9 mg, 94.8 μmol) and 10% Pd/C (wet, 107 mg) in MeOH (2 mL) was stirred for 6 days at RT under H$_2$ (0.5 MPa). When the reaction finished, the mixture was filtered to remove the catalyst, and the filtrate was concentrated to give 206C (18.2 mg, 49%).

A mixture of 206C (18.2 mg, 46.5 μmol) and CH$_3$I (26.4 mg, 186.1 μmol) in ACN (2 mL) was refluxed at 80° C. When TLC analysis indicated total consumption of the starting material, the solvent and the remaining CH$_3$I which were removed in vacuo to give quaternary ammonium salt. The quaternary ammonium salt was dissolved by MeOH (2 mL). The resulting solution was cooled to 0° C. and NaBH$_4$ (17.6 mg, 465 μmol) was added to the solution. Then the reaction mixture was brought to RT and heated to 80° C. for 6 hr. When TLC analysis indicated no further consumption of the salt, the solvent was removed and the residue was purified by column chromatography to give 206D (18 mg, 95%) as a yellow oil.

A mixture of 206D (18 mg, 43.9 μmol), LiOH (2 N, 100 μL), MeOH (0.6 mL), H$_2$O (0.1 mL) and THF (0.3 mL) was stirred for 4 days at RT. The reaction mixture was concentrated, and then diluted in 5 mL H$_2$O and extracted with ether. Then aqueous phase was acidified by adding 1 N HCl to pH 3-4, then extracted with EtOAc, washed with brine, dried over Na$_2$SO$_4$ and concentrated to give 206 (17 mg, 88.5%) as a yellow solid. MS calcd: (M+H)$^+$=396.6. MS found: (M+H)$^+$=396.6.

Example 207—3-(5-Cyclopentyl-1-methyl-1,2,3,6-tetrahydro-pyridin-4-yl)-5-phenyl-thiophene-2-carboxylic acid

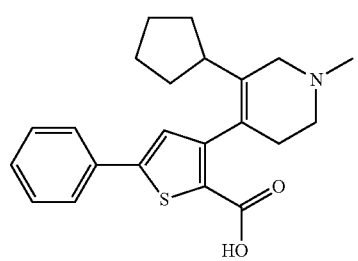

207

207 was prepared by the same method as 206, using cyclopentanone instead of cycloheptanone. MS calcd: (M+H)$^+$=368.5. MS found: (M+H)$^+$=368.5.

Example 208—3-[5-(4-Chloro-phenyl)-1-methyl-1,2,3,6-tetrahydro-pyridin-4-yl]-5-phenyl-thiophene-2-carboxylic acid

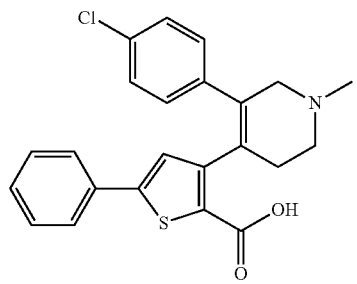

208

208 was prepared according to the following scheme.

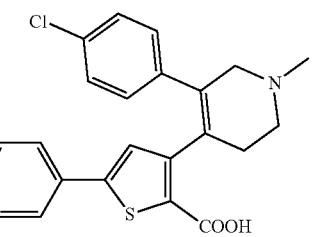

208

A mixture of 001F (30 mg, 80.16 μmol), (4-chlorophenyl)boronic acid (18.8 mg, 120.24 μmol), and Na$_2$CO$_3$ (22.6 mg, 240.48 µmol), in DMF/H₂O (1.5 mL/0.4 mL) was degassed and placed under Ar. Pd(dppf)Cl₂ (5.8 mg, 8.016 µmol) was added under Ar. The mixture was stirred at 80° C. for 3 hr. The mixture was cooled to RT, diluted in EtOAc and washed with H₂O. The combined organic layers were washed with brine, dried over Na₂SO₄, filtered and concentrated to give the crude product, which was purified by column chromatography to give 208A (32.5 mg, 100%) as a solid.

A mixture of 208A (32.5 mg, 80 µmol) and CH₃I (113.5 mg, 800 µmol) in ACN (5 mL) was refluxed at 80° C. When TLC analysis indicated no further consumption of the starting material, solvent and remaining CH₃I were removed in vacuo to give the quaternary ammonium salt. The salt was dissolved by MeOH (5 mL). The resulting solution was cooled to 0° C. and NaBH₄ (30.74 mg, 800 µmol) was added. Then the mixture was allowed to warm to RT and then heated at 80° C. for 6 hr. When TLC analysis indicated no further consumption of the quaternary ammonium salt, the solvent was removed and the residue was purified by column chromatography to give 208B (37 mg).

A mixture of 208B (37 mg, 87.4 µmol), LiOH (2 N, 300 µL), MeOH (0.6 mL), H₂O (0.1 mL) and THF (0.3 mL) was stirred for 4 days at RT. The reaction mixture was concentrated, and then diluted in 5 m, H₂O and extracted with ether. Then aqueous phase was acidified by adding 1 N HCl to pH 3-4, then extracted with EtOAc, washed with brine, dried over Na₂SO₄, and concentrated to give 208 (17 mg, 51.7%) as a solid. MS calcd: (M+H)⁺=410.9. MS found: (M+H)⁺=410.9.

Example 209—3-(1-Methyl-5-pentyl-1,2,3,6-tetrahydro-pyridin-4-yl)-5-phenyl-thiophene-2-carboxylic acid

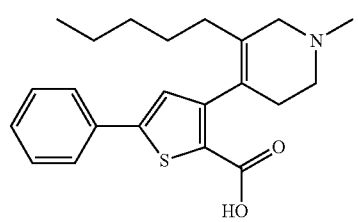

209

209 was prepared according to the following scheme.

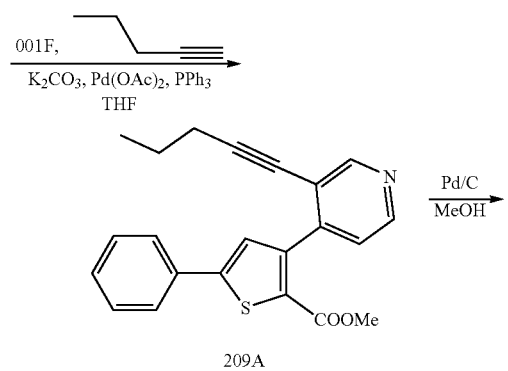

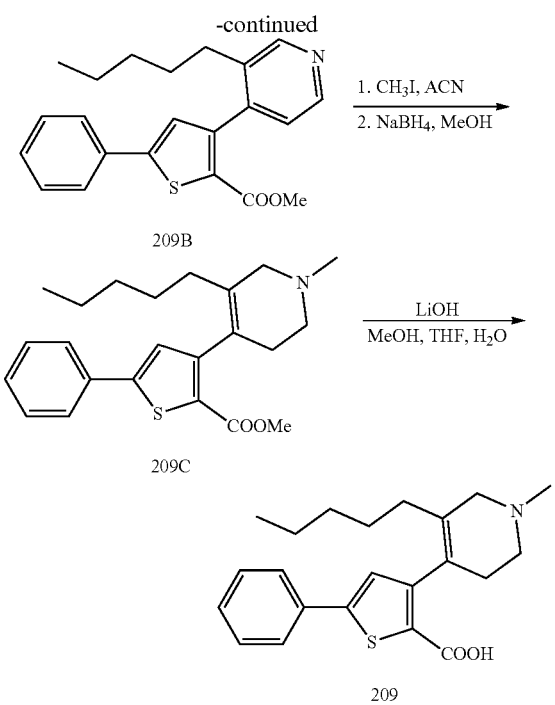

A mixture of 001F (30 mg, 80.4 µmol), pent-1-yne (27.3 mg, 402 µmol), K₂CO₃ (33.3 mg, 241.2 µmol), Pd(OAc)₂ (1.8 mg, 24.1 µmol) and PPh₃ (2.1 mg, 24.1 µmol) in THF (2 mL) was degassed and placed under Ar. The mixture was stirred at 70° C. overnight. The reaction mixture was cooled to RT, concentrated in vacuo, diluted in EtOAc, and washed with H₂O. The combined organic layers were washed with brine, dried over Na₂SO₄, filtered, and concentrated to give the crude product, which was purified by prep-TLC to give 209A (18 mg, 62%) as a light yellow solid.

A mixture of 209A (18 mg, 94.8 µmol) and 10% Pd/C (dry, 18 mg) in MeOH (2 mL) was stirred at RT under H₂ (0.5 MPa) for 2 days. When the reaction finished, the mixture was filtered to remove the catalyst, and the filtrate was concentrated to give 209B (12 mg, 60%).

A mixture of 209B (12 mg, 32.9 µmol) and CH₃I (46.6 mg, 329 µmol) in ACN (2 mL) was refluxed at 60° C. When TLC analysis indicated no further consumption of the starting material, the solvent and CH₃I which had not been consumed were removed in vacuo to give quaternary ammonium salt. The salt was dissolved in MeOH (2 mL), and the resulting solution was cooled to 0° C., and NaBH₄ (12.4 mg, 329 µmol) was added. Then the mixture was allowed to rise to RT and was then heated at 80° C. for 6 hr. When TLC analysis indicated no further consumption of the salt, the solvent was removed and the residue was purified by prep-TLC to give 209C (9.8 mg, 78%) as an oil.

A mixture of 209C (9.8 mg, 25.6 µmol), LiOH (2 N, 80 µL), MeOH (0.6 mL), H₂O (0.1 mL) and THF (0.3 mL) was stirred for 5 days at RT. The reaction mixture was concentrated, and then diluted in 3 mL H₂O and extracted with ether. The aqueous phase was acidified by adding 1 N HCl to pH 3-4, then extracted with EtOAc, washed with brine, dried over Na₂SO₄ and concentrated to give 209 (7.5 mg, 79.8%) as a light brown oil. MS calcd: (M+H)⁺=370.5. MS found: (M+H)⁺=370.5.

Example 210—3-(4-Cyclohexyl-1-methyl-1,2,5,6-tetrahydro-pyridin-3-yl)-5-{4-[(thiazole-4-carbonyl)-amino]-phenyl}-thiophene-2-carboxylic acid

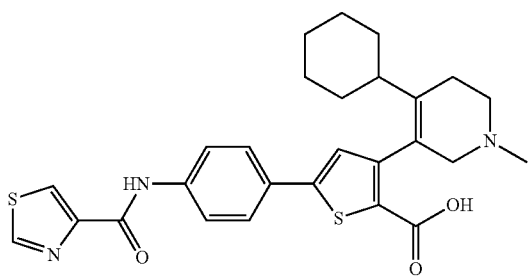

210 was prepared according to the following scheme.

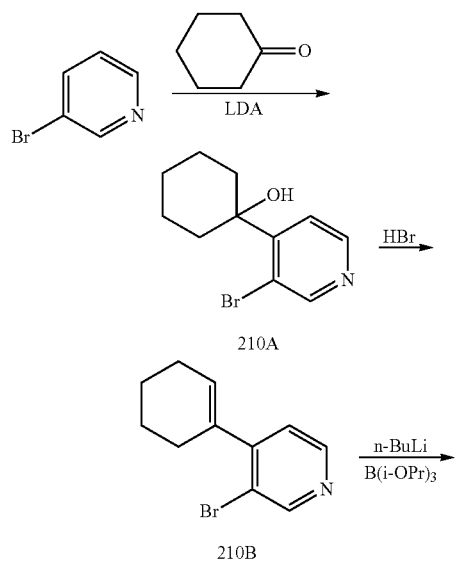

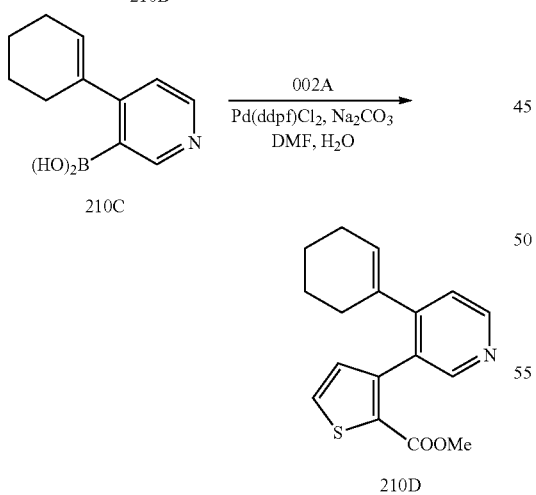

n-BuLi (2.5 M, 45.9 mL, 114.7 mmol) was added to diisopropylamine (16 mL, 114.7 μmol) in anhydrous ether (80 mL) at −20° C. under Ar atmosphere, the mixture was stirred at −20° C. for 1.5 hr. 3-Bromo-pyridine (15 g, 95.6 mmol) in anhydrous ether (30 mL) was added drop wise to the mixture at −78° C. and stirred for another 1.5 hr, after which cyclohexanone (12.9 g, 114.7 mmol) in anhydrous ether (30 mL) was added, and the solution was stirred for 1 hr at −78° C., and then allowed to warm to RT. The reaction mixture was quenched with sat. NH$_4$Cl, diluted in EtOAc, washed with water and brine, dried over Na$_2$SO$_4$, concentrated and purified to afford 3 (3.68 g, 15.3%) as a white solid.

A mixture of 210A (3.68 g, 14.4 mmol) in HBr (40%, 45 mL) was refluxed at 100° C. overnight. The pH was adjusted to around 9 by progressively adding solid Na$_2$CO$_3$ in ice-bath, extracted with EtOAc, concentrated and purified by column chromatography to afford 210B (2.6 g, 76.5%) as a yellow solid.

n-BuLi (2.5 M, 6.3 mL, 15.8 mmol) was added dropwise to 210B (2.5 g, 10.5 mmol) in THF (20 mL) at −78° C. under Ar, and then the mixture was stirred at −78° C. for 1 hr. Triisopropyl borate (3.7 mL, 15.8 mmol) in THF (10 mL) was added dropwise to the mixture at −78° C. and the reaction mixture was stirred for 2 hr and then allowed to warm to RT and stirred overnight. The reaction mixture was quenched with sat. NaH$_2$PO$_4$ and stirred 30 min, extracted using EtOAc, washed with brine, dried over Na$_2$SO$_4$, concentrated to afford 210C (3 g) as a light brown oil. Crude product was used for next step directly.

A mixture of 210C (3 g, 14.8 mmol), 002A (3.95 g, 14.8 mmol) and Na$_2$CO$_3$ (4.7 g, 44.4 mmol) in DMF/H$_2$O (25 mL/5 mL) was degassed and placed under Ar atmosphere. Pd(dppf)Cl$_2$ (541 mg, 740 μmol) was added under Ar. The mixture was stirred at 80° C. for 3 hr. The reaction mixture was cooled to RT, diluted in EtOAc and washed with H$_2$O. The combined organic layers were washed with brine, dried over Na$_2$SO$_4$, filtered and concentrated to give the crude product which was purified by column chromatography to give 210D (2.15 g, 48.5%) as a brown solid.

210 was then prepared using the same method as 205, using 210D instead of 205C. MS calcd: (M+H)$^+$=508.7. MS found: (M+H)$^+$=508.7.

Example 211—3-(5-Cyclohexyl-1-methyl-1,2,3,6-tetrahydro-pyridin-4-yl)-5-(3,3-dimethyl-but-1-ynyl)-thiophene-2-carboxylic acid

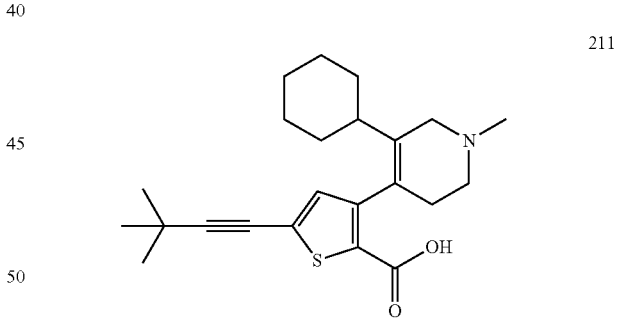

211 was prepared by the following scheme:

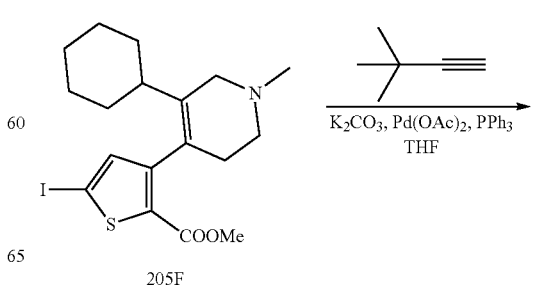

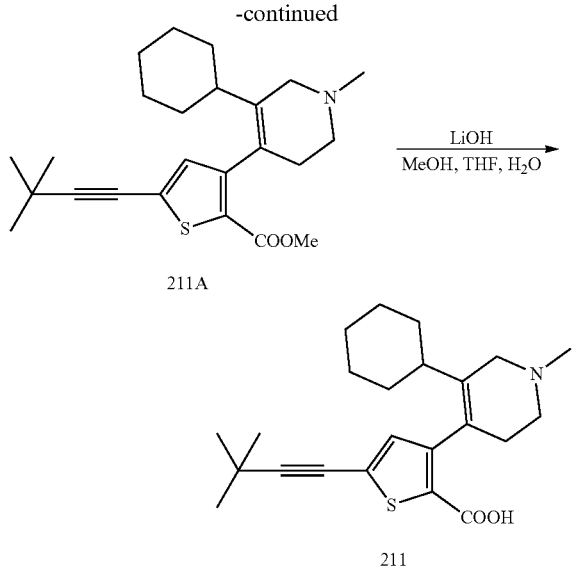

A mixture of 205F (40 mg, 90 µmol), 3,3-dimethyl-but-1-yne (73.8 mg, 900 µmol), $K_2CO_3$ (37.2 mg, 270 µmol), Pd(OAc)$_2$ (2.4 mg, 9 µmol) and PPh$_3$ (2 mg, 9 µmol) in THF (2 mL) was degassed and placed under Ar atmosphere. The mixture was stirred at 70° C. overnight. The reaction mixture was cooled to RT, removed solution, diluted in EtOAc, and washed with $H_2O$. The combined organic layers were washed with brine, dried over $Na_2SO_4$, filtered and concentrated to give the crude product which was purified by prep-TLC to give 211A (11.2 mg, 31%) as an oil.

A mixture of 211A (11.2 mg, 28 µmol), LiOH (2 N, 80 µL), MeOH (0.6 mL), $H_2O$ (0.1 mL) and THF (0.3 mL) was stirred for 5 days at RT. The reaction mixture was concentrated, and then diluted in 6 mL $H_2O$ and extracted with ether. Then aqueous phase was acidified by adding 1 N HCl to pH 3-4, then extracted with EtOAc, washed with brine, dried over $Na_2SO_4$ and concentrated to give 1976 (8.7 mg, 80.5%) as a light brown oil. MS calcd: $(M+H)^+=386.6$. MS found: $(M+H)^+=386.6$.

Example 212—RNA-Dependent RNA HCV NS5B (Polymerase) Assay and IC$_{50}$ Determination In vitro RNA-dependent RNA polymerase activity was determined in a reaction mixture (50 µL) containing 50 mM Tris-HCl, pH 7.5, 5 mM MgCl$_2$, 1 mM dithiothreitol, 0.5% Triton® X-100, 10 µM of UTP, 0.1-0.5 µCi of $\alpha$-$^{32}$P UTP (Perkin Elmer Life Sciences), 1 µg of polyA:U16 (Midland Oligo), and 0.6 µg of purified HCV1b NS5B polymerase delta 21. Different concentrations of compounds were added to the reaction mixtures. The reaction was carried out at RT (23° C.) for 60 min and then stopped by the addition of 100 µL of 50 mM EDTA. The reaction mixtures were filtered through either a DE81 membrane or a positively charged nylon membrane, and the membranes were then extensively washed with 30 mM sodium citrate, pH 7.0 and 300 mM NaCl. The radiolabeled RNA products were quantitated using a Storm™ PhosphorImager™ (GE life Sciences). IC$_{50}$ values were calculated using GraFit 6 and GraphPad Prism 5 from triplicate assays. Data (IC$_{50}$) obtained for compounds of the invention are summarized in Tables 1 and 2.

Example 213—HCV Replicon Assay and EC$_{50}$ Determination

The antiviral activity of compounds against hepatitis C virus was determined by a hepatitis C virus replicon reporter cell line developed by Bartenschlager (Lohmann et al., Science 1999, 285:110-113; Bartenschlager et al., Antiviral Res 2003, 60:91-102). This cell-based assay utilized a liver cell carcinoma (Huh-7) cell line stably transformed with an HCV1b replicon containing a luciferase reporter gene. Varied concentrations of compounds were added to the reporter cell line, and further incubated at 37° C. for 72 hr in DMEM supplemented with 10% FCS. The inhibitory effects of experimental compounds or the reference compound, interferon alpha (INFα), on HCV replication were measured by luciferase activity using the Britelite™ plus luminescence reporter gene kit (Perkin Elmer, Shelton, Conn.). The Britelite plus reagent was added to the 96-well plates containing the HCV reporter cells, and luminescence was measured within 15 min using a Wallac 1450 Microbeta® Trilux liquid scintillation counter. EC$_{50}$ values were calculated using GraFit 6 and GraphPad Prism 5 from triplicate HCV replicon assays. Data (EC$_{50}$) obtained for compounds of the invention are summarized in Tables 1 and 2.

In Table 1, representative IC$_{50}$ data obtained using the biochemical assay of Example 212 and representative EC$_{50}$ data obtained using the cellular assay of Example 213 are presented as follows: +++<3 µM; 3 µM≤++≤10 µM; +>10 µM; and ND=no data.

TABLE 1

| Compound | IC$_{50}$ | EC$_{50}$ |
|---|---|---|
| 178 | ND | +++ |
| 179 | +++ | ND |
| 180 | ND | +++ |
| 181 | +++ | ND |
| 183 | ND | +++ |
| 184 | +++ | ND |
| 185 | ND | +++ |
| 187 | +++ | ND |
| 196 | ND | +++ |
| 197 | ND | +++ |
| 199 | +++ | ND |
| 200 | +++ | ++ |
| 201 | ND | +++ |
| 202 | ND | +++ |
| 203 | +++ | ND |
| 204 | ND | +++ |
| 206 | +++ | ND |
| 208 | + | ND |
| 209 | ++ | ND |

TABLE 2

| Compound | IC$_{50}$ | EC$_{50}$ |
|---|---|---|
| 182 | +++ | ND |
| 186 | +++ | ND |
| 188 | ND | +++ |
| 189 | +++ | ND |
| 190 | +++ | +++ |
| 191 | ND | +++ |
| 192 | ND | +++ |
| 193 | ND | +++ |
| 194 | ND | +++ |
| 195 | ND | +++ |
| 198 | +++ | ND |
| 205 | ND | +++ |
| 207 | ++ | ND |
| 210 | +++ | ND |
| 211 | +++ | ND |

All publications, including but not limited to patents and patent applications, cited in this specification are incorporated by reference herein for all that they disclose, as if each individual publication were specifically and individually set forth in its entirety.

While a number of aspects and embodiments of this invention have been described, it is apparent that the basic examples and general formulas and schemata may be altered to provide other embodiments that utilize the compounds and methods of this invention. Therefore, it will be appreciated that the scope of this invention is to be defined by the appended claims rather than by the specific embodiments that have been represented by way of example.

What is claimed is:

1. A compound according to Formula I:

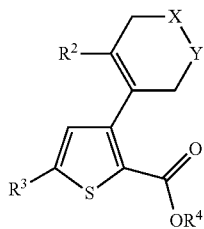

I or a pharmaceutically acceptable salt thereof, wherein:

X is —$CH_2$— and Y is —$NR^1$—;

$R^1$ is —$C_{5-6}$hydroxyalkyl, —$S(O)_2$—$C_{0-4}$alkyl-$R^O$, —$C_{0-4}$alkyl-$R^O$, —$C_{0-3}$alkyl-C(O)—$C_{0-4}$alkyl-$R^O$, —$C_{0-3}$alkyl-C(O)O—$C_{0-4}$alkyl-$R^O$;

wherein:

$R^M$ and $R^N$ are independently hydrogen, —$C_{1-4}$alkyl, or $R^M$ and $R^N$ together with the atoms to which they are attached can form a 4- to 6-membered ring; and $R^O$ is (a) a 5- to 7-membered cycloalkyl, substituted with a —$C_{1-3}$alkyl, aryl, —O-aryl, or —$NR^MR^N$ moiety, (b) a 7-membered cycloalkyl optionally substituted with a hydroxyl, or (c) a 6- to 10-membered aryl, monocyclic or bicyclic, and substituted with one to three moieties independently selected from —$C_{1-4}$alkyl, halogen, —$NR^MR^N$, —$C_{1-4}$haloalkyl, —$C_{1-4}$alkoxy, —$C_{1-4}$hydroxyalkyl, cyano, —O-aryl, and aryl, provided that at least one such substitution is —$C_{1-4}$alkoxy, —$C_{1-4}$hydroxyalkyl, cyano, or —O-aryl;

$R^2$ is —$C_{1-5}$alkyl optionally substituted with 1-5 halogens, —$C_{1-5}$alkoxy, —$C_{5-7}$cycloalkyl-$C_{0-3}$alkyl in which the alkyl is optionally substituted with 1-3 halogens, —$C_{1-4}$alkyl-$C_{3-5}$cycloalkyl, or phenyl optionally substituted with 1 or 2 halogens or —$C_{1-3}$ alkyl groups optionally substituted with 1-3 halogens;

$R^3$ is —$R^A$—$R^B$;

wherein $R^A$ is a phenyl moiety optionally substituted with one or two Z, in which each Z is independently halogen, —$C_{1-3}$alkyl, —$C_{1-3}$haloalkyl, —$C_{1-3}$alkoxy, or cyano; and wherein $R^B$ is —$N(R^U)C(O)$—$R^Q$;

wherein $R^Q$ is a thiazolyl, optionally substituted with one or two $R^Z$, in which each $R^Z$ is independently —$C_{1-3}$ alkyl, —$C_{1-3}$alkoxy, or —$NR^MR^N$;

$R^S$ and $R^T$ are each independently hydrogen or —$C_{1-4}$ alkyl, or one of $R^S$ and $R^T$ is hydrogen and the other is —C(O)-5- to 9-membered aryl; and $R^U$ is hydrogen or —$C_{1-4}$alkyl;

provided that, when $R^A$ is phenyl, then $R^B$ appears at the para or meta position relative to the thiophene moiety; and $R^4$ is hydrogen, —$C_{1-4}$alkyl, —$C_{1-4}$alkyl-OC(O)O—$C_{1-4}$alkyl, —$C_{1-4}$alkyl-OC(O)—$C_{1-4}$alkyl, —$C_{1-4}$alkyl-OC(O)O—$C_{3-6}$cycloalkyl, 5-methyl-2-oxo-[1,3]dioxol-4-ylmethyl-, —$C_{0-3}$alkyl-$C_{5-6}$aryl, or —$C_{1-4}$alkyl-$NR^VR^W$; and $R^V$ and $R^W$ are independently hydrogen or —$C_{1-4}$alkyl.

2. A compound according to claim 1, wherein $R^A$ is phenyl substituted with one or two Z.

3. A compound according to claim 2, wherein $R^B$ appears at the para position relative to the thiophene moiety.

4. A compound according to claim 3, wherein $R^B$ is —NHC(O)—$R^Q$.

5. A compound according to claim 1, wherein $R^2$ is —$C_{5-6}$cycloalkyl-$C_{1-3}$alkyl.

6. A compound according to claim 1, wherein:

$R^1$ is hydrogen, —$C_{1-4}$alkyl, —$C_{1-3}$alkyl-$C_{3-6}$cycloalkyl, —$C_{1-4}$hydroxyalkyl, —$C_{2-4}$alkyl-$NR^MR^N$, —$C_{1-4}$alkyl ester, or —$C_{1-3}$alkyl-$C_{6-10}$aryl; and $R^M$ and $R^N$ are independently hydrogen or —$C_{1-4}$alkyl.

7. A compound according to claim 1, wherein $R^1$ is —$C_{1-4}$alkyl, —$C_{1-3}$alkyl-$C_{3-6}$cycloalkyl, —$C_{1-4}$hydroxyalkyl, or —$C_{2-4}$alkyl-$NR^MR^N$.

8. A compound according to claim 1, wherein $R^4$ is hydrogen.

* * * * *